(12) United States Patent
Cunningham et al.

(10) Patent No.: US 11,629,139 B2
(45) Date of Patent: Apr. 18, 2023

(54) SMALL MOLECULE INHIBITORS OF EBOLA AND LASSA FEVER VIRUSES AND METHODS OF USE

(71) Applicants: **President and Fellows of

(51) Int. Cl.
*C07D 209/14* (2006.01)
*C07D 211/16* (2006.01)
*C07D 211/62* (2006.01)
*C07D 213/647* (2006.01)
*C07D 213/68* (2006.01)
*C07D 213/75* (2006.01)
*C07D 215/12* (2006.01)
*C07D 231/56* (2006.01)
*C07D 295/185* (2006.01)

(52) U.S. Cl.
CPC .......... *C07D 211/16* (2013.01); *C07D 211/62* (2013.01); *C07D 213/647* (2013.01); *C07D 213/68* (2013.01); *C07D 213/75* (2013.01); *C07D 215/12* (2013.01); *C07D 231/56* (2013.01); *C07D 295/185* (2013.01); *C07B 2200/05* (2013.01)

(56) References Cited

FOREIGN PATENT DOCUMENTS

| WO | WO-2006/062898 A2 | 6/2006 |
| WO | WO-2007/011623 A1 | 1/2007 |
| WO | WO-2008/147474 A2 | 12/2008 |
| WO | WO-2012/031090 A2 | 3/2012 |
| WO | WO-2012/103081 A1 | 8/2012 |

OTHER PUBLICATIONS

Van der Linden, ACS infect Dis, vol. 2(3), 173-179, 2016. (Year: 2016).*
Assimon, Me d Chem Comm, vol. 6, 912-918, 2015. (Year: 2015).*
Cote, Nature, VOl 477, 2011, 344-350. (Year: 2011).*
CAS Registry No. 1278381-27-3, entered into CA Registry File on Apr. 11, 2011, supplied by FCH Group.
CAS Registry No. 1295233-84-9, entered into CA Registry File on May 15, 2011, supplied by FCH Group.
CAS Registry No. 1299938-25-2, entered into CA Registry File on May 24, 2011, supplied by FCH Group.
International Search Report and Written Opinion dated Feb. 20, 2013, from PCT/US2012/046677.
International Search Report and Written Opinion for International Application No. PCT/US2018/050238 dated Jan. 8, 2019.
Liu et al., "Identification of Potent Ebola Virus Entry Inhibitors with Suitable Properties for in Vivo Studies," Journal of Medicinal Chemistry, 61(14):6293-6307 (2018).
PubChemCompound, datasheet retrieved from the Internet: <http//pubchem.ncbi.nlm.nih.gov/search/search.cgi> See CID 37198024, CID 31111847, CID 31678675, CID 37351054, CID 9041503, CID 9162573, CID 24654219, CID 2993072, CID 7964476, CID 9105639, etc. (2013).

* cited by examiner

Fig. 1

SMALL MOLECULE INHIBITORS OF EBOLA AND LASSA FEVER VIRUSES AND METHODS OF USE

RELATED APPLICATION

This application is the U.S. National Stage of International Patent Application No. PCT/US2018/050238, filed Sep. 10, 2018, which claims the benefit of priority to U.S. Provisional Patent Application Ser. No. 62/556,066, filed Sep. 8, 2017. The contents of each of which are hereby incorporated by reference in their entirety.

GOVERNMENT SUPPORT

This invention was made with government support under AI109740 awarded by the National Institutes of Health. The government has certain rights in the invention.

BACKGROUND

Ebola virus (EboV) is a highly pathogenic enveloped virus that causes outbreaks of zoonotic infection in Africa. EboV is transmitted by close contact and virus levels increase by 75-fold/day for several days after initial infection. The clinical symptoms are manifestations of the massive production of pro-inflammatory cytokines in response to infection and in many outbreaks, mortality exceeds 75%. The endothelial cell dysfunction associated with "cytokine storm" results in capillary leak, hypovolemic shock, disseminated intravascular coagulation and inadequate perfusion of major organs. The unpredictable onset, ease of transmission, rapid progression of disease, high mortality and lack of effective vaccine or therapy have created a high level of public concern about EboV. Current therapy is supportive; there is no effective anti-EboV vaccine or therapy. Therefore, development of anti-EboV drugs is a high priority.

Screening of a small molecule library against infection by vesicular stomatitis virus (VSV) particles engineered to express the EboV GP and to encode luciferase marker has identified a novel benzylpiperazine adamantane diamide, 3.0, that inhibits infection of Vero cells by vesicular stomatitis virus particles (VSV) pseudotyped with EboV Zaire GP, but not with VSV G or Lassa fever virus (LFV) GP.

3.0

SAR around the 3.0 series identified other compounds, including 3.47, with increased potency against EboV GP-dependent infection.

3.47

Studies of compounds 3.0 and 3.47 established that they are effective anti-Ebola agents as they target host protein Niemann-Pick C1 (NPC1), a multi-span protein that resides in lysosomes and mediates transport of cholesterol into cells and binds to the Ebola virus (EboV) glycoprotein, which is essential for infection. Thus, 3.0/3.47 and related compounds are candidate anti-EboV agents (see, for example, US Patent Application publication number 2014329834 to Cunningham, J. et al.).

SUMMARY

One aspect disclosed herein are compounds represented by formula I:

I or a pharmaceutically acceptable salt, solvate, hydrate, prodrug, chemically-protected form, enantiomer or stereoisomer thereof; wherein, independently for each occurrence, wherein A, E, Z, $R^1$, $R^2$, $R^3$, and $R^8$ are as defined in the specification.

In another aspect, the invention relates to compounds represented by formula II

II or a pharmaceutically acceptable salt, solvate, hydrate, prodrug, chemically-protected form, enantiomer or stereoisomer thereof; wherein, independently for each occurrence, wherein $R^a$, $R^b$, $R^c$, $R^5$, $R^6$, and $R^7$ are as defined in the specification.

In some embodiments, the invention relates to pharmaceutical compositions of a compound of Formula (I) or Formula (II), and a pharmaceutically acceptable carrier.

The invention further relates to methods of treating or preventing a viral infection in a subject comprising administering to the subject a compound of the invention.

The invention still further relates to methods of treating or preventing a disease (e.g., cancer, obesity, HIV/AIDS) in a subject comprising administering to the subject a compound of the invention.

BRIEF DESCRIPTION OF THE FIGURES

Figure 1:
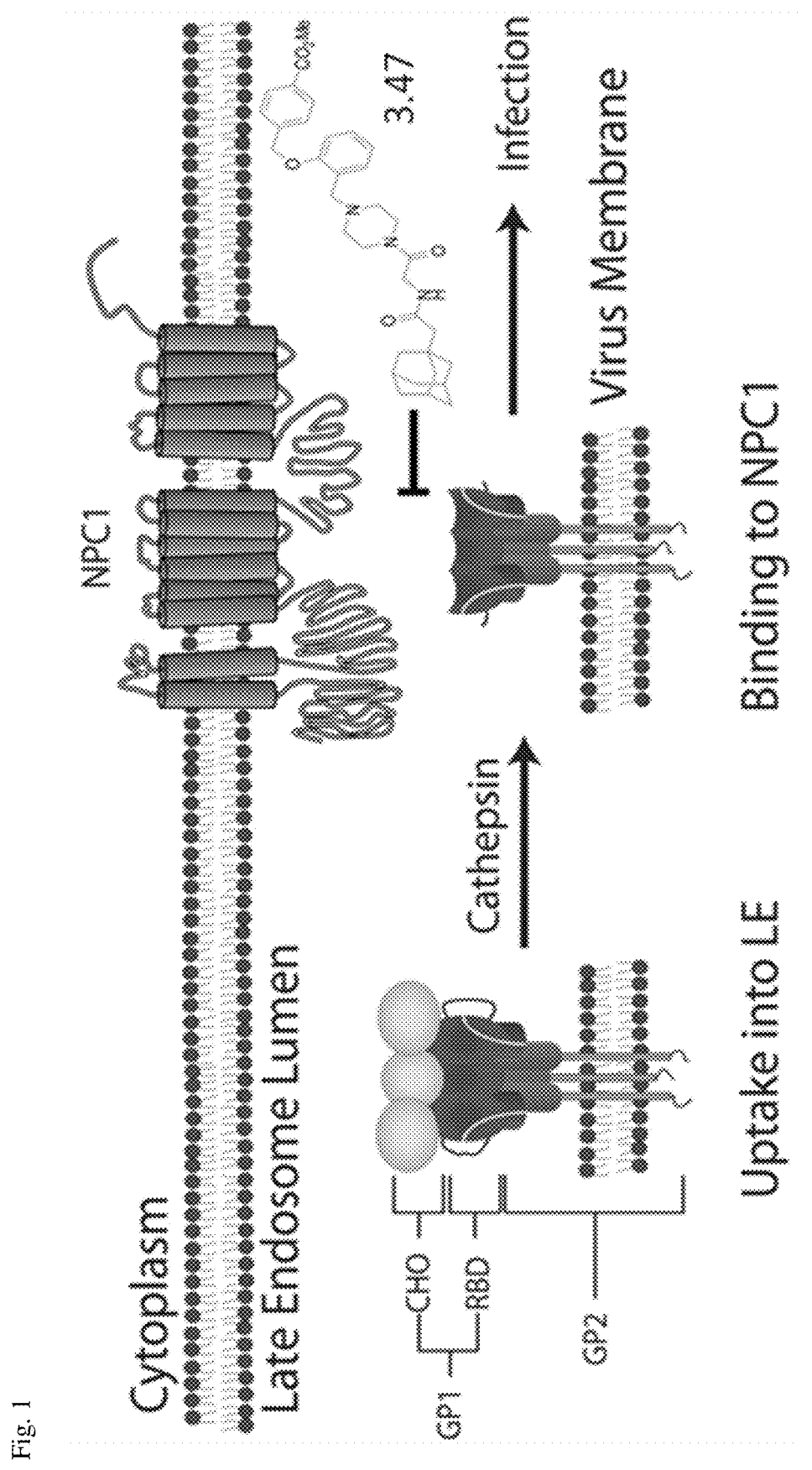

FIG. 1 depicts a possible model of 3.47 targeting NPC1 and inhibiting EboV binding and infection.

DETAILED DESCRIPTION

Overview

Figure 2:
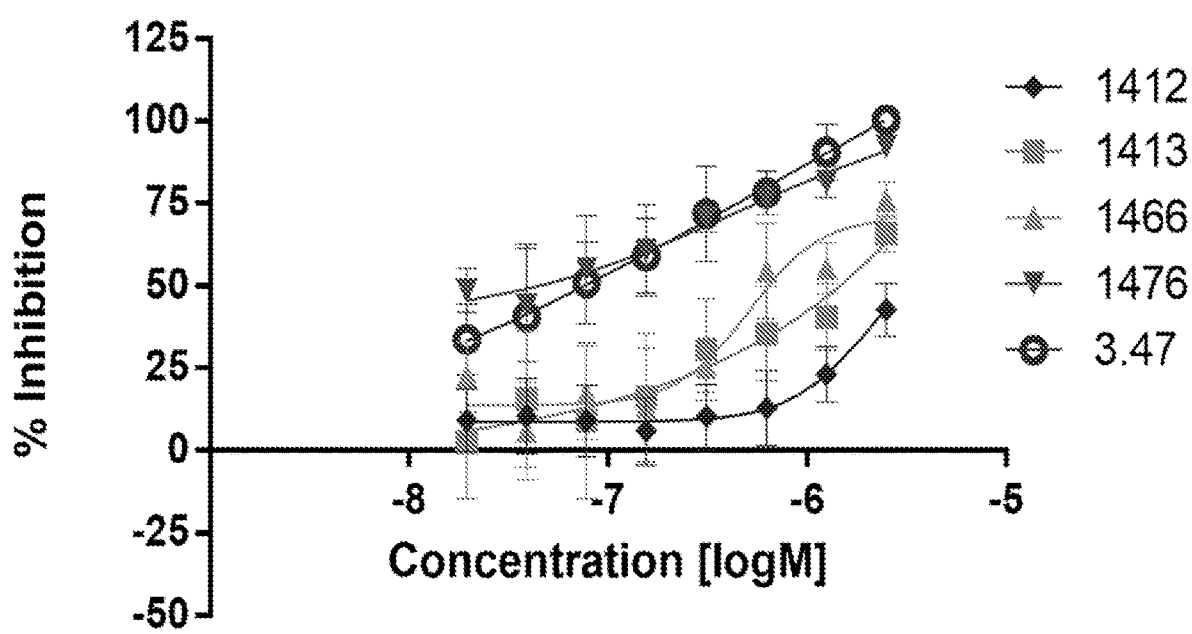
FIG. 2 depicts a dose response curve showing the inhibition of Ebola virus (Kikwit) by certain compounds disclosed herein (1412, 1413, 1466, 1476). Compound 1466 is also referred to herein as the (−)-entantiomer of 1413 (i.e., (−)-1413).
Figure 3:
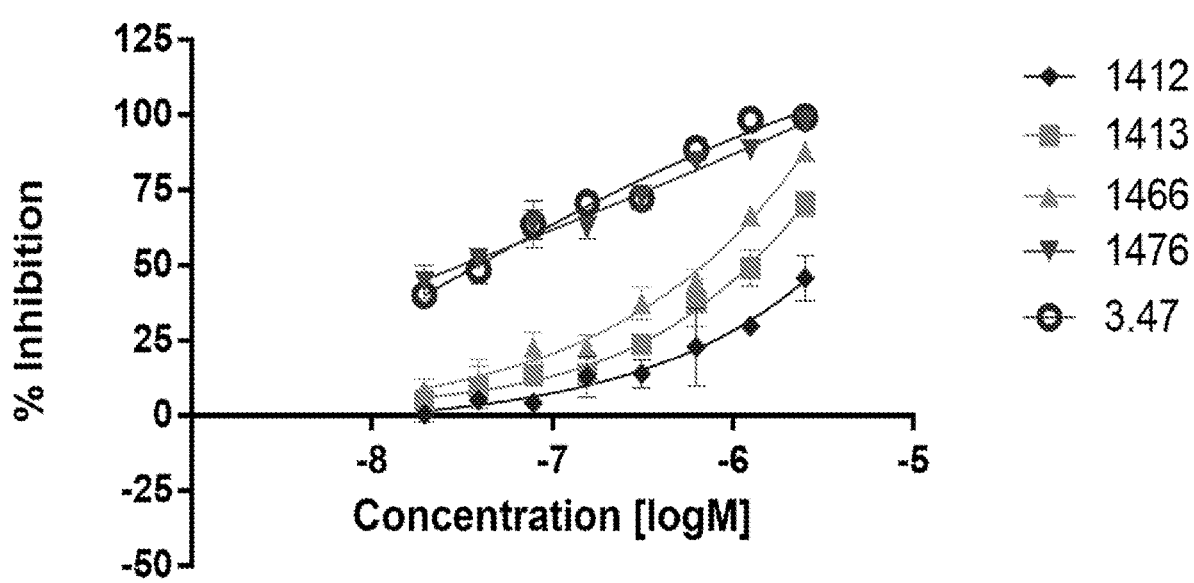
FIG. 3 depicts a dose response curve showing the inhibition of Ebola virus (Makona) by certain compounds disclosed herein (1412, 1413, 1466, 1476). Compound 1466 is also referred to herein as the (−)-entantiomer of 1413 (i.e., (−)-1413).
Figure 4:
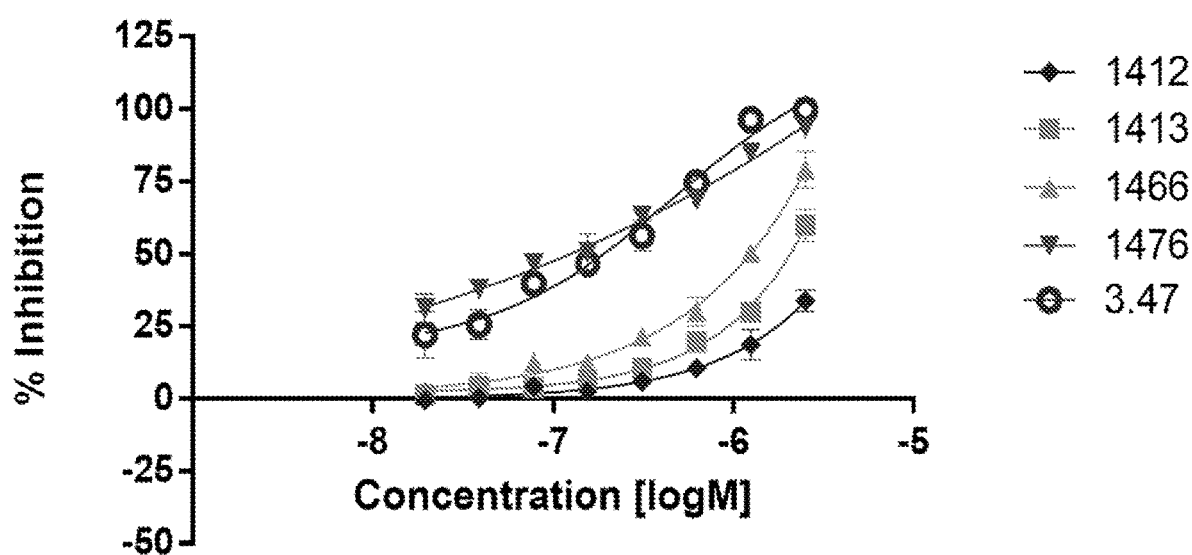
FIG. 4 depicts a dose response curve showing the inhibition of Ebola virus (Mayinga) by certain compounds disclosed herein (1412, 1413, 1466, 1476). Compound 1466 is also referred to herein as the (−)-entantiomer of 1413 (i.e., (−)-1413).
Figure 5:
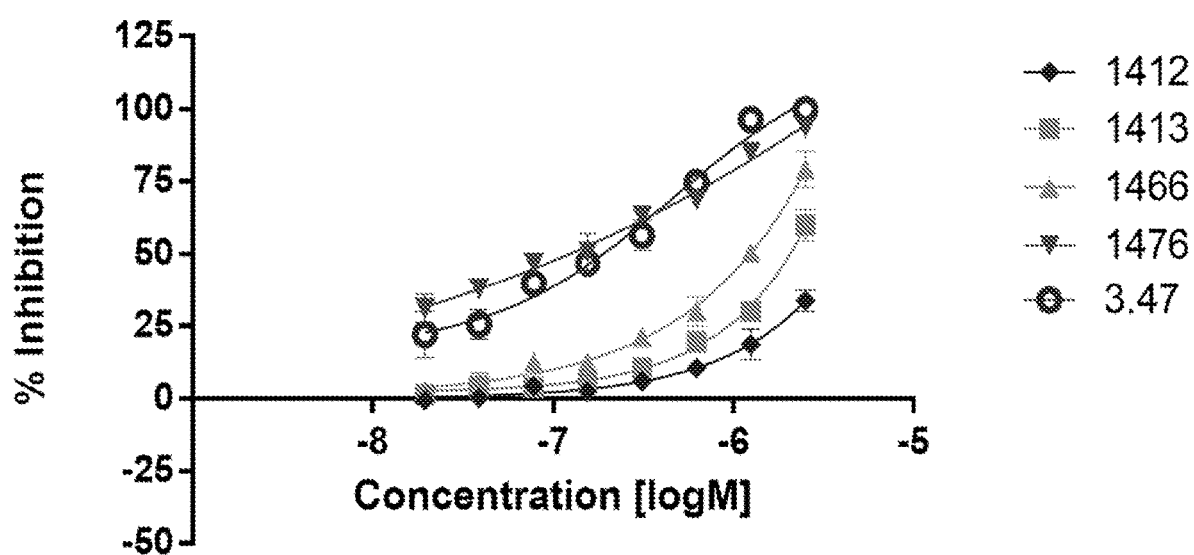
FIG. 5 depicts a dose response curve showing the inhibition of Ebola virus (Kikwit) by certain compounds disclosed herein (1477, 1478).
Figure 6:
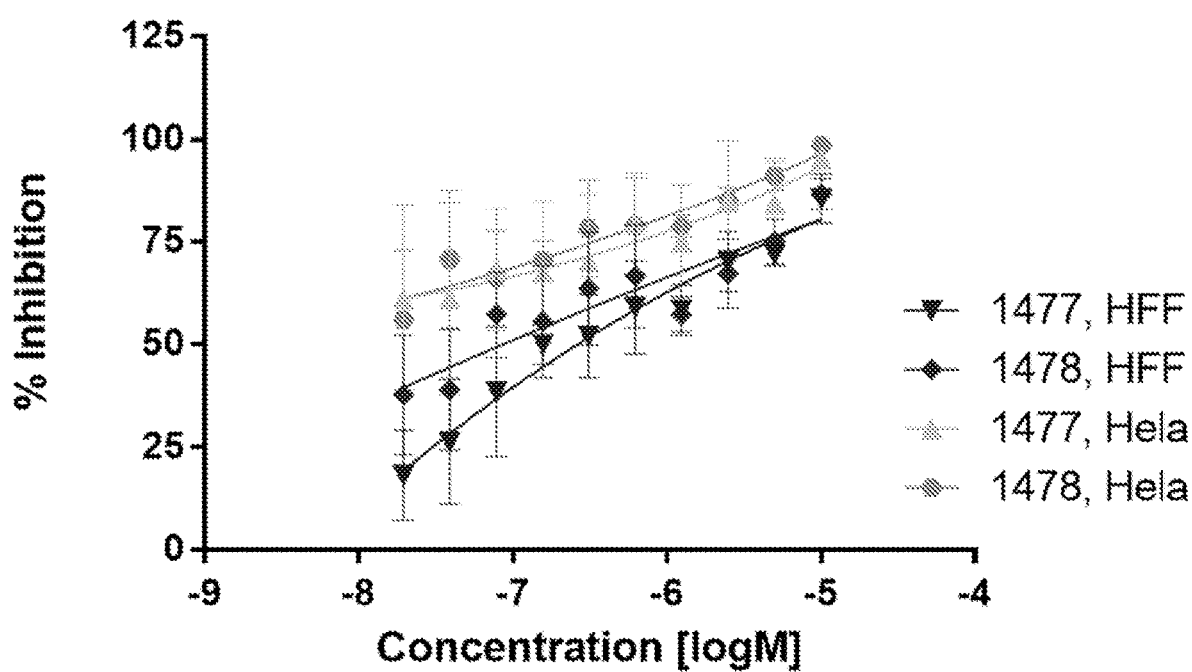
FIG. 6 depicts a dose response curve showing the inhibition of Ebola virus (Makona) by certain compounds disclosed herein (1477, 1478).
Figure 7:
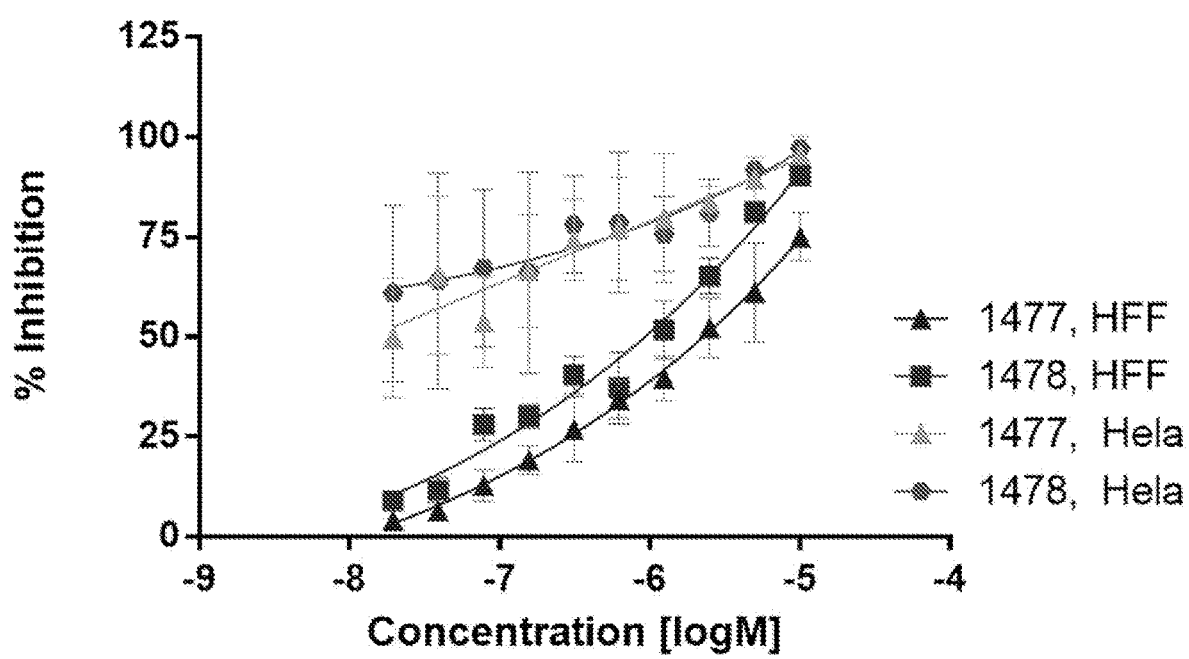
FIG. 7 depicts a dose response curve showing the inhibition of Ebola virus (Makona) by certain compounds disclosed herein (1477, 1478).

In certain aspects, the invention provides substituted piperazine and piperidine compounds, and pharmaceutical compositions thereof. In particular, such compounds can be used as anti-viral agents, anti-cancer agents or anti-obesity agents.

Definitions

The articles "a" and "an" are used herein to refer to one or to more than one (i.e., to at least one) of the grammatical object of the article. By way of example, "an element" means one element or more than one element.

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e., "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

The definition of each expression, e.g., alkyl, m, n, and the like, when it occurs more than once in any structure, is intended to be independent of its definition elsewhere in the same structure.

The term "substituted" refers to moieties having substituents replacing a hydrogen on one or more carbons of the backbone. It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, etc. As used herein, the term "substituted" is contemplated to include all permissible substituents of organic compounds. In a broad aspect, the permissible substituents include acyclic and cyclic, branched and unbranched, carbocyclic and heterocyclic, aromatic and non-aromatic substituents of organic compounds. The permissible substituents can be one or more and the same or different for appropriate organic compounds. For purposes of this invention, the heteroatoms such as nitrogen may have hydrogen substituents and/or any permissible substituents of organic compounds described herein which satisfy the valences of the heteroatoms. Substituents can include any substituents described herein, for example, a halogen, a hydroxyl, a carbonyl (such as a carboxyl, an alkoxycarbonyl, a formyl, or an acyl), a thiocarbonyl (such as a thioester, a thioacetate, or a thioformate), an alkoxyl, a phosphoryl, a phosphate, a phosphonate, a phosphinate, an amino, an amido, an amidine, an imine, a cyano, a nitro, an azido, a sulfhydryl, an alkylthio, a sulfate, a sulfonate, a sulfamoyl, a sulfonamido, a sulfonyl, a heterocyclyl, an aralkyl, or an aromatic or heteroaromatic moiety. It will be understood by those skilled in the art that substituents can themselves be substituted, if appropriate. Unless specifically stated as "unsubstituted," references to chemical moieties herein are understood to include substituted variants. For example, reference to an "aryl" group or moiety implicitly includes both substituted and unsubstituted variants.

The term "lower" when appended to any of the groups listed below indicates that the group contains less than seven carbons (i.e. six carbons or less). For example "lower alkyl" refers to an alkyl group containing 1-6 carbons, and "lower alkenyl" refers to an alkenyl group containing 2-6 carbons.

The term "saturated," as used herein, pertains to compounds and/or groups which do not have any carbon-carbon double bonds or carbon-carbon triple bonds.

The term "unsaturated," as used herein, pertains to compounds and/or groups which have at least one carbon-carbon double bond or carbon-carbon triple bond.

The term "aliphatic," as used herein, pertains to compounds and/or groups which are linear or branched, but not cyclic (also known as "acyclic" or "open-chain" groups).

The term "cyclic," as used herein, pertains to compounds and/or groups which have one ring, or two or more rings (e.g., spiro, fused, bridged).

The term "aromatic" refers to a planar or polycyclic structure characterized by a cyclically conjugated molecular moiety containing 4n+2 electrons, wherein n is the absolute value of an integer. Aromatic molecules containing fused, or joined, rings also are referred to as bicyclic aromatic rings. For example, bicyclic aromatic rings containing heteroatoms in a hydrocarbon ring structure are referred to as bicyclic heteroaryl rings.

The term "hydrocarbon" as used herein refers to an organic compound consisting entirely of hydrogen and carbon.

The term "heteroatom" as used herein refers to an atom of any element other than carbon or hydrogen. Illustrative heteroatoms include boron, nitrogen, oxygen, phosphorus, sulfur and selenium.

The term "alkyl" means an aliphatic or cyclic hydrocarbon radical containing from 1 to 12 carbon atoms. Representative examples of alkyl include, but are not limited to, methyl, ethyl, n-propyl, iso-propyl, n-butyl, sec-butyl, isobutyl, tert-butyl, n-pentyl, isopentyl, neopentyl, n-hexyl, 2-methylcyclopentyl, and 1-cyclohexylethyl.

In some instances, the number of carbon atoms in a hydrocarbon substituent (i.e., alkyl, cycloalkyl, etc.) is indicated by the prefix "Cx-Cy-" or "Cx-y", wherein x is the minimum and y is the maximum number of carbon atoms in the substituent. For example, the term "Cx-yalkyl" refers to substituted or unsubstituted saturated hydrocarbon groups, including straight-chain alkyl and branched-chain alkyl groups that contain from x to y carbons in the chain, including haloalkyl groups such as trifluoromethyl and 2,2, 2-trifluoroethyl, etc. Thus, for example, "C1-C6-alkyl" or "C1-6 alkyl" refers to an alkyl substituent containing from 1 to 6 carbon atoms. Illustrating further, C3-C6-cycloalkyl or C3-6-cycloalkyl refers to saturated cycloalkyl containing from 3 to 6 carbon ring atoms. The terms "C2-yalkenyl" and "C2-yalkynyl" refer to substituted or unsubstituted unsaturated aliphatic groups analogous in length and possible substitution to the alkyls described above, but that contain at least one double or triple bond respectively.

The term "alkylene" is art-recognized, and as used herein pertains to a bidentate moiety obtained by removing a hydrogen atom from an alkyl group, as defined above.

The term "alkenyl" as used herein means a straight or branched chain hydrocarbon radical containing from 2 to 10 carbons and containing at least one carbon-carbon double bond formed by the removal of two hydrogens. Representative examples of alkenyl include, but are not limited to, ethenyl, 2-propenyl, 2-methyl-2-propenyl, 3-butenyl, 4-pentenyl, 5-hexenyl, 2-heptenyl, 2-methyl-1-heptenyl, and 3-decenyl.

The term "alkenyl", as used herein, refers to an aliphatic group containing at least one double bond and is intended to include both "unsubstituted alkenyls" and "substituted alkenyls", the latter of which refers to alkenyl moieties having substituents replacing a hydrogen on one or more carbons of the alkenyl group. Such substituents may occur on one or more carbons that are included or not included in one or more double bonds. Moreover, such substituents include all those contemplated for alkyl groups, as discussed below, except where stability is prohibitive. For example, substitution of alkenyl groups by one or more alkyl, carbocyclyl, aryl, heterocyclyl, or heteroaryl groups is contemplated.

The term "alkynyl" as used herein means a straight or branched chain hydrocarbon radical containing from 2 to 10 carbon atoms and containing at least one carbon-carbon triple bond. Representative examples of alkynyl include, but are not limited, to acetylenyl, 1-propynyl, 2-propynyl, 3-butynyl, 2-pentynyl, and 1-butynyl.

The term "aryl" as used herein include substituted or unsubstituted single-ring aromatic groups in which each atom of the ring is carbon. Preferably the ring is a 5- to 7-membered ring, more preferably a 6-membered ring. The term "aryl" also includes polycyclic ring systems having two or more cyclic rings in which two or more carbons are common to two adjoining rings wherein at least one of the rings is aromatic, e.g., the other cyclic rings can be cycloalkyls, cycloalkenyls, cycloalkynyls, aryls, heteroaryls, and/or heterocyclyls. Aryl groups include phenyl, naphthyl or anthracenyl group. The aryl groups of the present invention may be substituted with 1, 2, 3, 4 or 5 substituents independently selected from the group consisting of deutero, alkyl, alkenyl, alkynyl, halo, haloalkyl, fluoroalkyl, hydroxy, alkoxy, alkenyloxy, alkynyloxy, carbocyclyloxy, heterocyclyloxy, haloalkoxy, fluoroalkyloxy, sulfhydryl, alkylthio, haloalkylthio, fluoroalkylthio, alkenylthio, alkynylthio, sulfonic acid, alkylsulfonyl, haloalkylsulfonyl, fluoroalkylsulfonyl, alkenylsulfonyl, alkynylsulfonyl, alkoxysulfonyl, haloalkoxysulfonyl, fluoroalkoxysulfonyl, alkenyloxysulfonyl, alkynyloxysulfony, aminosulfonyl, sulfinic acid, alkylsulfinyl, haloalkylsulfinyl, fluroralkylsulfinyl, alkenylsulfinyl, alkynylsulfinyl, alkoxysulfinyl, haloalkoxysulfinyl, fluroralkoxysulfinyl, alkenyloxysulfinyl, alkynyloxysulfiny, aminosulfinyl, formyl, alkylcarbonyl, haloalkylcarbonyl, fluoroalkylcarbonyl, alkenylcarbonyl, alkynylcarbonyl, carboxy, alkoxycarbonyl, haloalkoxycarbonyl, fluoroalkoxycarbonyl, alkenyloxycarbonyl, alkynyloxycarbonyl, alkylcarbonyloxy, haloalkylcarbonyloxy, fluoroalkylcarbonyloxy, alkenylcarbonyloxy, alkynylcarbonyloxy, alkylsulfonyloxy, haloalkylsulfonyloxy, fluoroalkylsulfonyloxy, alkenylsulfonyloxy, alkynylsulfonyloxy, haloalkoxysulfonyloxy, fluoroalkoxysulfonyloxy, alkenyloxysulfonyloxy, alkynyloxysulfonyloxy, alkylsulfinyloxy, haloalkylsulfinyloxy, fluoroalkylsulfinyloxy, alkenylsulfinyloxy, alkynylsulfinyloxy, alkoxysulfinyloxy, haloalkoxysulfinyloxy, fluoroalkoxysulfinyloxy, alkenyloxysulfinyloxy, alkynyloxysulfinyloxy, aminosulfinyloxy, amino, amido, aminosulfonyl, aminosulfinyl, cyano, nitro, azido, phosphinyl, phosphoryl including phosphine oxide and phosphonate, silyl, silyloxy, cyclic acetal, and any of said substituents bound to the heterocyclyl group through an alkylene moiety (e.g. methylene).

The term "carbocyclyl" as used herein means monocyclic or multicyclic (e.g., bicyclic, tricyclic, etc.) hydrocarbon radical containing from 3 to 12 carbon atoms that is completely saturated or has one or more unsaturated bonds, and for the avoidance of doubt, the degree of unsaturation does not result in an aromatic ring system (e.g. phenyl). Examples of carbocyclyl groups include 1-cyclopropyl, 1-cyclobutyl, 2-cyclopentyl, 1-cyclopentenyl, 3-cyclohexyl, 1-cyclohexenyl and 2-cyclopentenylmethyl. The carbocyclyl groups of the invention may be substituted 1, 2, 3, 4 or 5 substituents independently selected from the group consisting of deutero, alkyl, alkenyl, alkynyl, halo, haloalkyl, fluoroalkyl, hydroxy, alkoxy, alkenyloxy, alkynyloxy, carbocyclyloxy, heterocyclyloxy, haloalkoxy, fluoroalkyloxy, sulfhydryl, alkylthio, haloalkylthio, fluoroalkylthio, alkenylthio, alkynylthio, sulfonic acid, alkylsulfonyl, haloalkylsulfonyl, fluoroalkylsulfonyl, alkenylsulfonyl, alkynylsulfonyl, alkoxysulfonyl, haloalkoxysulfonyl, fluoroalkoxysulfonyl, alkenyloxysulfonyl, alkynyloxysulfony, aminosulfonyl, sulfinic acid, alkylsulfinyl, haloalkylsulfinyl, fluroralkylsulfinyl, alkenylsulfinyl, alkynylsulfinyl, alkoxysulfinyl, haloalkoxysulfinyl, fluroralkoxysulfinyl, alkenyloxysulfinyl, alkynyloxysulfiny, aminosulfinyl, formyl, alkylcarbonyl, haloalkylcarbonyl, fluoroalkylcarbonyl, alkenylcarbonyl, alkynylcarbonyl, carboxy, alkoxycarbonyl, haloalkoxycarbonyl, fluoroalkoxycarbonyl, alkenyloxycarbonyl, alkynyloxycarbonyl, alkylcarbonyloxy, haloalkylcarbonyloxy, fluoroalkylcarbonyloxy, alkenylcarbonyloxy, alkynylcarbonyloxy, alkylsulfonyloxy, haloalkylsulfonyloxy, fluoroalkylsulfonyloxy, alkenylsulfonyloxy, alkynylsulfonyloxy, haloalkoxysulfonyloxy, fluoroalkoxysulfonyloxy, alkenyloxysulfonyloxy, alkynyloxysulfonyloxy, alkylsulfinyloxy, haloalkylsulfinyloxy, fluoroalkylsulfinyloxy, alkenylsulfinyloxy, alkynylsulfinyloxy, alkoxysulfinyloxy, haloalkoxysulfinyloxy, fluoroalkoxysulfinyloxy, alkenyloxysulfinyloxy, alkynyloxysulfinyloxy, aminosulfinyloxy, amino, amido, aminosulfonyl, aminosulfinyl, cyano, nitro, azido, phosphinyl, phosphoryl including phosphine oxide and phosphonate, silyl, silyloxy, and any of said substituents bound to the heterocyclyl group through an alkylene moiety (e.g. methylene).

The term "arylene," is art-recognized, and as used herein pertains to a bidentate moiety obtained by removing a hydrogen atom from an aryl ring, as defined above.

The term "arylalkyl" or "aralkyl" as used herein means an aryl group, as defined herein, appended to the parent molecular moiety through an alkyl group, as defined herein. Representative examples of aralkyl include, but are not limited to, benzyl, 2-phenylethyl, 3-phenylpropyl, and 2-naphth-2-ylethyl.

The term "arylalkenyl" embraces aryl-substituted alkenyl radicals. Preferable arylalkenyl radicals are "lower arylalkenyl" radicals having aryl radicals attached to alkenyl radicals having two to six carbon atoms. Examples of such radicals include phenylethenyl. The aryl in said arylalkenyl may be additionally substituted with halo, alkyl, alkoxy, haloalkyl and haloalkoxy.

The term "arylalkynyl" embraces aryl-substituted alkynyl radicals. Preferable arylalkynyl radicals are "lower arylalkynyl radicals having aryl radicals attached to alkynyl radicals having two to six carbon atoms. Examples of such radicals include phenylethynyl. The aryl in said aralkyl may be additionally substituted with halo, alkyl, alkoxy, haloalkyl and haloalkoxy. The terms benzyl and phenylmethyl are interchangeable.

The term "cycloalkenyl" includes carbocyclic groups have one or more carbon-carbon double bonds. Preferred cycloalkenyl groups include C3-C6 rings. For example, cyclopentenyl, cyclopentadienyl, cyclohexenyl and cycloheptadienyl.

The term "heterocyclyl", as used herein refers to a radical of a non-aromatic, ring systems, including, but not limited to, monocyclic, bicyclic and tricyclic rings, which can be completely saturated or which can contain one or more units of unsaturation, for the avoidance of doubt, the degree of unsaturation does not result in an aromatic ring system, and have 3 to 12 atoms including at least one heteroatom, such as nitrogen, oxygen, or sulfur. For purposes of exemplification, which should not be construed as limiting the scope of this invention, the following are examples of heterocyclic rings: azepines, azetidinyl, morpholinyl, oxopiperidinyl, oxopyrrolidinyl, piperazinyl, piperidinyl, pyrrolidinyl, quinicludinyl, thiomorpholinyl, tetrahydropyranyl and tetrahydrofuranyl. The heterocyclyl groups of the invention are substituted with 0, 1, 2, 3, 4 or 5 substituents independently selected from the group consisting of deutero, alkyl, alkenyl, alkynyl, halo, haloalkyl, fluoroalkyl, hydroxy, alkoxy, alkenyloxy, alkynyloxy, carbocyclyloxy, heterocyclyloxy, haloalkoxy, fluoroalkyloxy, sulfhydryl, alkylthio, haloalkylthio, fluoroalkylthio, alkenylthio, alkynylthio, sulfonic acid, alkylsulfonyl, haloalkylsulfonyl, fluoroalkylsulfonyl, alkenylsulfonyl, alkynylsulfonyl, alkoxysulfonyl, haloalkoxysulfonyl, fluoroalkoxysulfonyl, alkenyloxysulfonyl, alkynyloxysulfony, aminosulfonyl, sulfinic acid, alkylsulfinyl, haloalkylsulfinyl, fluroralkylsulfinyl, alkenylsulfinyl, alkynylsulfinyl, alkoxysulfinyl, haloalkoxysulfinyl, fluroralkoxysulfinyl, alkenyloxysulfinyl, alkynyloxysulfiny, aminosulfinyl, formyl, alkylcarbonyl, haloalkylcarbonyl, fluoroalkylcarbonyl, alkenylcarbonyl, alkynylcarbonyl, carboxy, alkoxycarbonyl, haloalkoxycarbonyl, fluoroalkoxycarbonyl, alkenyloxycarbonyl, alkynyloxycarbonyl, alkylcarbonyloxy, haloalkylcarbonyloxy, fluoroalkylcarbonyloxy, alkenylcarbonyloxy, alkynylcarbonyloxy, alkylsulfonyloxy, haloalkylsulfonyloxy, fluoroalkylsulfonyloxy, alkenylsulfonyloxy, alkynylsulfonyloxy, haloalkoxysulfonyloxy, fluoroalkoxysulfonyloxy, alkenyloxysulfonyloxy, alkynyloxysulfonyloxy, alkylsulfinyloxy, haloalkylsulfinyloxy, fluoroalkylsulfinyloxy, alkenylsulfinyloxy, alkynylsulfinyloxy, alkoxysulfinyloxy, haloalkoxysulfinyloxy, fluoroalkoxysulfinyloxy, alkenyloxysulfinyloxy, alkynyloxysulfinyloxy, aminosulfinyloxy, amino, amido, aminosulfonyl, aminosulfinyl, cyano, nitro, azido, phosphinyl, phosphoryl including phosphine oxide and phosphonate, silyl, silyloxy, and any of said substituents bound to the heterocyclyl group through an alkylene moiety (e.g. methylene).

The term "heterocycloalkyl", as used herein, refers to an alkyl group substituted with a heterocycle group.

The term "cyclic acetal" refers to a bidentate moiety represented by —O-alkylene-O—. Representative examples of cyclic acetals include, but are not limited to, methylenedioxy, ethylenedioxy, propylenedioxy, butylenedioxy;

The term "heteroaryl" as used herein refers to a radical of an aromatic ring, including, but not limited to, monocyclic, bicyclic and tricyclic rings, which has 3 to 12 atoms including at least one heteroatom, such as nitrogen, oxygen, or sulfur. For purposes of exemplification, which should not be construed as limiting the scope of this invention: azaindolyl, benzo(b)thienyl, benzimidazolyl, benzofuranyl, benzoxazolyl, benzothiazolyl, benzothiadiazolyl, benzotriazolyl, benzoxadiazolyl, furanyl, imidazolyl, imidazopyridinyl, indolyl, indolinyl, indazolyl, isoindolinyl, isoxazolyl, isothiazolyl, isoquinolinyl, oxadiazolyl, oxazolyl, purinyl, pyranyl, pyrazinyl, pyrazolyl, pyridinyl, pyrimidinyl, pyrrolyl, pyrrolo[2,3-d]pyrimidinyl, pyrazolo[3,4-d]pyrimidinyl, quinolinyl, quinazolinyl, triazolyl, thiazolyl, thiophenyl, tetrahydroindolyl, tetrazolyl, thiadiazolyl, thienyl, thiomorpholinyl, triazolyl or tropanyl. The heteroaryl groups of the invention may be substituted with 1, 2, 3, 4 or 5 substituents independently selected from the group consisting of deutero, alkyl, alkenyl, alkynyl, halo, haloalkyl, fluoroalkyl, hydroxy, alkoxy, alkenyloxy, alkynyloxy, carbocyclyloxy, heterocyclyloxy, haloalkoxy, fluoroalkyloxy, sulfhydryl, alkylthio, haloalkylthio, fluoroalkylthio, alkenylthio, alkynylthio, sulfonic acid, alkylsulfonyl, haloalkylsulfonyl, fluoroalkylsulfonyl, alkenylsulfonyl, alkynylsulfonyl, alkoxysulfonyl, haloalkoxysulfonyl, fluoroalkoxysulfonyl, alkenyloxysulfonyl, alkynyloxysulfony, aminosulfonyl, sulfinic acid, alkylsulfinyl, haloalkylsulfinyl, flluroralkylsulfinyl, alkenylsulfinyl, alkynylsulfinyl, alkoxysulfinyl, haloalkoxysulfinyl, fluroralkoxysulfinyl, alkenyloxysulfinyl, alkynyloxysulfiny, aminosulfinyl, formyl, alkylcarbonyl, haloalkylcarbonyl, fluoroalkylearbonyl, alkenylcarbonyl, alkynylcarbonyl, carboxy, alkoxycarbonyl, haloalkoxycarbonyl, fluoroalkoxycarbonyl, alkenyloxycarbonyl, alkynyloxycarbonyl, alkylcarbonyloxy, haloalkylcarbonyloxy, fluoroalkylcarbonyloxy, alkenylcarbonyloxy, alkynylcarbonyloxy, alkylsulfonyloxy, haloalkylsulfonyloxy, fluoroalkylsulfonyloxy, alkenylsulfonyloxy, alkynylsulfonyloxy, haloalkoxysulfonyloxy, fluoroalkoxysulfonyloxy, alkenyloxysulfonyloxy, alkynyloxysulfonyloxy, alkylsulfinyloxy, haloalkylsulfinyloxy, fluoroalkylsulfinyloxy, alkenylsulfinyloxy, alkynylsulfinyloxy, alkoxysulfinyloxy, haloalkoxysulfinyloxy, fluoroalkoxysulfinyloxy, alkenyloxysulfinyloxy, alkynyloxysulfinyloxy, aminosulfinyloxy, amino, amido, aminosulfonyl, aminosulfinyl, cyano, nitro, azido, phosphinyl, phosphoryl including phosphine oxide and phosphonate, silyl, silyloxy, and any of said substituents bound to the heteroaryl group through an alkylene moiety (e.g. methylene).

The term "heteroarylene," is art-recognized, and as used herein pertains to a bidentate moiety obtained by removing a hydrogen atom from a heteroaryl ring, as defined above.

The term "heteroarylalkyl" or "heteroaralkyl" as used herein means a heteroaryl, as defined herein, appended to the parent molecular moiety through an alkyl group, as defined herein. Representative examples of heteroarylalkyl include, but are not limited to, pyridin-3-ylmethyl and 2-(thien-2-yl)ethyl.

The term "halo" or "halogen" means —Cl, —Br, —I or —F.

The term "haloalkyl" means an alkyl group, as defined herein, wherein at least one hydrogen is replaced with a halogen, as defined herein. Representative examples of haloalkyl include, but are not limited to, chloromethyl, 2-fluoroethyl, trifluoromethyl, pentafluoroethyl, and 2-chloro-3-fluoropentyl.

The term "fluoroalkyl" means an alkyl group, as defined herein, wherein all the hydrogens are replaced with fluorines.

The term "hydroxyalkyl" embraces linear or branched alkyl radicals having one to about ten carbon atoms any one of which may be substituted with one or more hydroxyl radicals. More preferred hydroxyalkyl radicals are "lower hydroxyalkyl" radicals having one to six carbon atoms and one or more hydroxyl radicals. Examples of such radicals include hydroxymethyl, hydroxyethyl, hydroxypropyl, hydroxybutyl and hydroxyhexyl. Even more preferred are lower hydroxyalkyl radicals having one to three carbon atoms.

The term "hydroxy" as used herein means an —OH group.

The term "oxy" refers to a —O— group.

The term "alkoxy" as used herein means an alkyl group, as defined herein, appended to the parent molecular moiety through an oxygen atom. Representative examples of alkoxy include, but are not limited to, methoxy, ethoxy, propoxy, 2-propoxy, butoxy, tert-butoxy, pentyloxy, and hexyloxy. The terms "alkenyloxy", "alkynyloxy", "carbocyclyloxy", and "heterocyclyloxy" are likewise defined.

The term "cycloalkyloxy" refers to a cycloakyl group having an oxygen attached thereto.

The term "haloalkoxy" as used herein means an alkoxy group, as defined herein, wherein at least one hydrogen is replaced with a halogen, as defined herein. Representative examples of haloalkoxy include, but are not limited to, chloromethoxy, 2-fluoroethoxy, trifluoromethoxy, and pentafluoroethoxy. The term "fluoroalkyloxy" is likewise defined.

The term "aryloxy" as used herein means an aryl group, as defined herein, appended to the parent molecular moiety through an oxygen.

The term "heteroaryloxy" as used herein means a heteroaryl group, as defined herein, appended to the parent molecular moiety through an oxygen. The terms "heteroaryloxy" is likewise defined.

The term "arylalkoxy" or "arylalkyloxy" as used herein means an arylalkyl group, as defined herein, appended to the parent molecular moiety through an oxygen. The term "heteroarylalkoxy" is likewise defined. Representative examples of aryloxy and heteroarylalkoxy include, but are not limited to, 2-chlorophenylmethoxy, 3-trifluoromethylphenylethoxy, and 2,3-dimethylpyridinylmethoxy.

The term "sulfhydryl" or "thio" as used herein means a —SH group.

The term "alkylthio" as used herein means an alkyl group, as defined herein, appended to the parent molecular moiety through a sulfur. Representative examples of alkylthio include, but are not limited, methylthio, ethylthio, tert-butylthio, and hexylthio. The terms "haloalkylthio", "fluoroalkylthio", "alkenylthio", "alkynylthio", "carbocyclylthio", and "heterocyclylthio" are likewise defined.

The term "arylthio" as used herein means an aryl group, as defined herein, appended to the parent molecular moiety through an sulfur. The term "heteroarylthio" is likewise defined.

The term "arylalkylthio" or "aralkylthio" as used herein means an arylalkyl group, as defined herein, appended to the parent molecular moiety through an sulfur. The term "heteroarylalkylthio" is likewise defined.

The term "sulfonyl" as used herein refers to —S(=O)$_2$— group.

The term "sulfonic acid" as used herein refers to —S(=O)$_2$OH.

The term "alkylsulfonyl" as used herein means an alkyl group, as defined herein, appended to the parent molecular moiety through a sulfonyl group, as defined herein. Representative examples of alkylsulfonyl include, but are not limited to, methylsulfonyl and ethylsulfonyl. The terms "haloalkylsulfonyl", "fluoroalkylsulfonyl", "alkenylsulfonyl", "alkynylsulfonyl", "carbocyclylsulfonyl", "heterocyclylsulfonyl", "arylsulfonyl", "aralkylsulfonyl", "heteroarylsulfonyl" and "heteroaralkylsulfonyl" are likewise defined.

The term "alkoxysulfonyl" as used herein means an alkoxy group, as defined herein, appended to the parent molecular moiety through a sulfonyl group, as defined herein. Representative examples of alkoxysulfonyl include, but are not limited to, methoxysulfonyl, ethoxysulfonyl and propoxysulfonyl. The terms "haloalkoxysulfonyl", "fluoroalkoxysulfonyl", "alkenyloxysulfonyl", "alkynyloxysulfonyl", "carbocyclyloxysulfonyl", "heterocyclyloxysulfonyl", "aryloxysulfonyl", "aralkyloxysulfonyl", "heteroaryloxysulfonyl" and "heteroaralkyloxysulfonyl" are likewise defined.

The term "aminosulfonyl" as used herein means an amino group, as defined herein, appended to the parent molecular moiety through a sulfonyl group.

The term "alkylaminosulfonyl" includes "N-alkylaminosulfonyl" and "N,N-dialkylaminosulfonyl" where sulfamyl radicals are independently substituted, respectively, with one alkyl radical, or two alkyl radicals. More preferred alkylaminosulfonyl radicals are "lower alkylaminosulfonyl" radicals having one to six carbon atoms. Even more preferred are lower alkylaminosulfonyl radicals having one to three carbon atoms. Examples of such lower alkylaminosulfonyl radicals include N-methylaminosulfonyl, N-ethylaminosulfonyl and N-methyl-N-ethylaminosulfonyl.

The terms "N-arylaminosulfonyl" and "N-alkyl-N-arylaminosulfonyl" denote sulfamyl radicals substituted, respectively, with one aryl radical, or one alkyl and one aryl radical. More preferred N-alkyl-N-arylaminosulfonyl radicals are "lower N-alkyl-N-arylsulfonyl" radicals having alkyl radicals of one to six carbon atoms. Even more preferred are lower N-alkyl-N-arylsulfonyl radicals having one to three carbon atoms. Examples of such lower N-alkylN-aryl-aminosulfonyl radicals include N-methyl-N-phenylaminosulfonyl and N-ethyl-N-phenylaminosulfonyl. Examples of such N-aryl-aminosulfonyl radicals include N-phenylaminosulfonyl.

The term "arylalkylaminosulfonyl" embraces aralkyl radicals as described above, attached to an aminosulfonyl radical. More preferred are lower arylalkylaminosulfonyl radicals having one to three carbon atoms.

The term "heterocyclylaminosulfonyl" embraces heterocyclyl radicals as described above, attached to an aminosulfonyl radical.

The term "sulfinyl" as used herein refers to —S(=O)— group. Sulfinyl groups are as defined above for sulfonyl groups. The term "sulfinic acid" as used herein refers to —S(=O)OH.

The term "carbonyl" as used herein means a —C(=O)— group.

The term "alkylcarbonyl" as used herein means an alkyl group, as defined herein, appended to the parent molecular moiety through a carbonyl group, as defined herein. Representative examples of alkylcarbonyl include, but are not limited to, acetyl, 1-oxopropyl, 2,2-dimethyl-1-oxopropyl, 1-oxobutyl, and 1-oxopentyl. The terms "haloalkylcarbonyl", "fluoroalkylcarbonyl", "alkenylcarbonyl", "alkynylcarbonyl", "carbocyclylcarbonyl", "heterocyclylcarbonyl", "arylcarbonyl", "aralkylcarbonyl", "heteroarylcarbonyl", and "heteroaralkylcarbonyl" are likewise defined.

The terms "arylcarbonyl" denotes carbonyl radicals substituted with an aryl radical.

The terms "heteroarylcarbonyl" denotes carbonyl radicals substituted with a heteroaryl radical.

The terms "cycloalkylcarbonyl" denotes carbonyl radicals substituted with a cycloalkyl radical.

The terms "heterocyclylcarbonyl" denotes carbonyl radicals substituted with a heterocyclyl radical.

The term "aminocarbonyl" when used by itself or with other terms such as "aminocarbonylalkyl", "N-alkylaminocarbonyl", "N-arylaminocarbonyl", "N,N-dialkylaminocarbonyl", "N-alkyl-N-arylaminocarbonyl", "N-alkyl-N-hydroxyaminocarbonyl" and "N-alkyl-N-hydroxyaminocarbonylalkyl", denotes an amide group of the formula H2NC (=O)—.

The terms "N-alkylaminocarbonyl" and "N,N-dialkylaminocarbonyl" denote aminocarbonyl radicals which have been substituted with one alkyl radical and independently with two alkyl radicals, respectively. More preferred are "lower alkylaminocarbonyl" having lower alkyl radicals as described above attached to an aminocarbonyl radical.

The terms "N-arylaminocarbonyl" and "N-alkyl-N-arylaminocarbonyl" denote aminocarbonyl radicals substituted, respectively, with one aryl radical, or one alkyl and one aryl radical.

The term "thiocarbonyl" as used herein means a —C(=S)— group.

The term "formyl" as used herein means a —C(=O)H group.

The term "carboxy" as used herein means a —CO₂H group.

The term "alkoxycarbonyl" as used herein means an alkoxy group, as defined herein, appended to the parent molecular moiety through a carbonyl group, as defined herein. Representative examples of alkoxycarbonyl include, but are not limited to, methoxycarbonyl, ethoxycarbonyl, and tert-butoxycarbonyl. The terms "haloalkoxycarbonyl", "fluoroalkoxycarbonyl", "alkenyloxycarbonyl", "alkynyloxycarbonyl", "carbocyclyloxycarbonyl", "heterocyclyloxycarbonyl", "aryloxycarbonyl", "aralkyloxycarbonyl", "heteroaryloxycarbonyl", and "heteroaralkyloxycarbonyl" are likewise defined.

The term "alkylcarbonyloxy" as used herein means an alkylcarbonyl group, as defined herein, appended to the parent molecular moiety through an oxygen atom. Representative examples of alkylcarbonyloxy include, but are not limited to, acetyloxy, ethylcarbonyloxy, and tert-butylcarbonyloxy. The terms "haloalkylcarbonyloxy", "fluoroalkylcarbonyloxy", "alkenylcarbonyloxy", "alkynylcarbonyloxy", "carbocyclylcarbonyloxy", "heterocyclylcarbonyloxy", "arylcarbonyloxy", "aralkylcarbonyloxy", "heteroarylcarbonyloxy", and "heteroaralkylcarbonyloxy" are likewise defined.

The term "alkylsulfonyloxy" as used herein means an alkylsulfonyl group, as defined herein, appended to the parent molecular moiety through an oxygen atom. The terms "haloalkylsulfonyloxy", "fluoroalkylsulfonyloxy", "alkenylsulfonyloxy", "alkynylsulfonyloxy", "carbocyclylsulfonyloxy", "heterocyclylsulfonyloxy", "arylsulfonyloxy", "aralkylsulfonyloxy", "heteroarylsulfonyloxy", "heteroaralkylsulfonyloxy", "haloalkoxysulfonyloxy", "fluoroalkoxysulfonyloxy", "alkenyloxysulfonyloxy", "alkynyloxysulfonyloxy", "carbocyclyloxysulfonyloxy", "heterocyclyloxysulfonyloxy", "aryloxysulfonyloxy", "aralkyloxysulfonyloxy", "heteroaryloxysulfonyloxy" and "heteroaralkyloxysulfonyloxy", The term "amide", as used herein, refers to a group

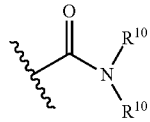

wherein each $R^{10}$ independently represent a hydrogen or hydrocarbyl group, or two $R^{10}$ are taken together with the N atom to which they are attached complete a heterocycle having from 4 to 8 atoms in the ring structure.

The terms "amine" and "amino" are art-recognized and refer to both unsubstituted and substituted amines and salts thereof, e.g., a moiety that can be represented by

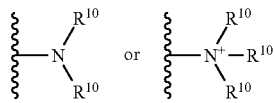

wherein each $R^{10}$ independently represents a hydrogen or a hydrocarbyl group, alkyl, haloalkyl, fluoroalkyl, alkenyl, alkynyl, carbocyclyl, heterocyclyl, aryl, aralkyl, heteroaryl, heteroaralkyl, alkylcarbonyl, haloalkylcarbonyl, fluoroalkylcarbonyl, alkenylcarbonyl, alkynylcarbonyl, carbocyclylcarbonyl, heterocyclylcarbonyl, arylcarbonyl, aralkylcarbonyl, heteroarylcarnbonyl, heteroaralkylcarbonyl, the sufonyl, sulfinyl groups defined above; or two $R^{10}$ are taken together with the N atom to which they are attached complete a heterocycle having from 4 to 8 atoms in the ring structure. Representative examples include, but are not limited to methylamino, acetylamino, and dimethylamino The term "cycloalkylamino", as used herein refers to an amino group substituted with a cycloalkyl group.

The term "aminoalkyl", as used herein, refers to an alkyl group substituted with an amino group. More preferred aminoalkyls include "lower aminoalkyl" having one to six carbon atoms and one or more amino radicals. Examples include aminomethyl, aminoethyl, aminopropyl, aminobutyl and aminohexyl.

The term "alkylamino", as used herein, refers to an amino group substituted with at least one alkyl group, e.g., N-alkylamino and N, N-dialkylamino. Examples include N-methylamino, N-ethylamino, N, N-dimethylamino, N, N-diethylamino and the like.

The term "arylamino" denotes amino groups which have been substituted with one or two aryl groups, such as N-phenylamino. The "arylamino" radicals may be further substituted on the aryl group as defined herein.

The term "heteroarylamino" denotes amino groups which have been substituted with at least one heteroaryl group, such as N-thienylamino. The"heteroarylamino" may be further substituted on the heteroaryl group as defined herein.

The term "aralkylamino" denotes amino groups which have been substituted with at least one aralkyl group. Examples include N-benzylamino. The "aralkylamino" radicals may be further substituted on the aryl ring portion of the radical.

The terms "N-aralkyl-N-alkylamino" and "N-alkyl-N-arylamino" denote amino groups which have been substituted with one aralkyl and one alkyl, or one aryl and one alkyl, respectively.

The term "cyano" as used herein means a —C≡N group.

The term "nitro" as used herein means a —NO$_2$ group.

The term "azido" as used herein means a —N$_3$ group.

The term "phosphinyl" as used herein includes —PH$_3$ and substituted derivatives thereof wherein one, two or three of the hydrogens are independently replaced with substituents selected from the group consisting of alkyl, haloalkyl, fluoroalkyl, alkenyl, alkynyl, carbocyclyl, heterocyclyl, aryl, aralkyl, heteroaryl, heteroaralkyl, alkoxy, haloalkoxy, fluoroalkyloxy, alkenyloxy, alkynyloxy, carbocyclyloxy, heterocyclyloxy, aryloxy, aralkyloxy, heteroaryloxy, heteroaralkyloxy, and amino.

The term "phosphine oxide" as used herein includes —P(O)R$_2$, wherein R is alkyl, aryl, heteroaryl.

The term "phosphoryl" as used herein refers to —P(=O)OH$_2$ and substituted derivatives thereof wherein one or both of the hydroxyls are independently replaced with substituents selected from the group consisting of alkyl, haloalkyl, fluoroalkyl, alkenyl, alkynyl, carbocyclyl, heterocyclyl, aryl, aralkyl, heteroaryl, heteroaralkyl, alkoxy, haloalkoxy, fluoroalkyloxy, alkenyloxy, alkynyloxy, carbocyclyloxy, heterocyclyloxy, aryloxy, aralkyloxy, heteroaryloxy, heteroaralkyloxy, and amino.

The term "sulfate" is art-recognized and refers to the group —OSO$_3$H, or a pharmaceutically acceptable salt thereof.

The term "sulfonamide" is art-recognized and refers to the group represented by the general formulae

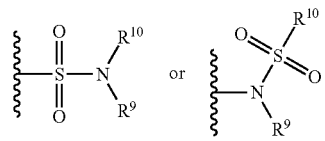

wherein $R^9$ and $R^{10}$ independently represents hydrogen or hydrocarbyl, such as alkyl, or $R^9$ and $R^{10}$ taken together with the intervening atom(s) complete a heterocycle having from 4 to 8 atoms in the ring structure.

The term "sulfoxide" is art-recognized and refers to the group —S(O)—R$^{10}$, wherein R$^{10}$ represents a hydrocarbyl.

The term "sulfonate" is art-recognized and refers to the group SO$_3$H, or a pharmaceutically acceptable salt thereof.

The term "sulfone" is art-recognized and refers to the group —S(O)$_2$—R$^{10}$, wherein R$^{10}$ represents a hydrocarbyl.

The terms triflyl, tosyl, mesyl, and nonaflyl are art-recognized and refer to trifluoromethanesulfonyl, p-toluenesulfonyl, methanesulfonyl, and nonafluorobutanesulfonyl groups, respectively. The terms triflate, tosylate, mesylate, and nonaflate are art-recognized and refer to trifluoromethanesulfonate ester, p-toluenesulfonate ester, methanesulfonate ester, and nonafluorobutanesulfonate ester functional groups and molecules that contain said groups, respectively.

The term "silyl" as used herein includes H$_3$Si— and substituted derivatives thereof wherein one, two or three of the hydrogens are independently replaced with substituents selected from alkyl, haloalkyl, fluoroalkyl, alkenyl, alkynyl, carbocyclyl, heterocyclyl, aryl, aralkyl, heteroaryl, and heteroaralkyl. Representative examples include trimethylsilyl (TMS), tert-butyldiphenylsilyl (TBDPS), tert-butyldimethylsilyl (TBS/TBDMS), triisopropylsilyl (TIPS), and [2-(trimethylsilyl)ethoxy]methyl (SEM).

The term "silyloxy" as used herein means a silyl group, as defined herein, is appended to the parent molecule through an oxygen atom.

In the compounds of this invention any atom not specifically designated as a particular isotope is meant to represent any stable isotope of that atom. Unless otherwise stated, when a position is designated specifically as "H" or "hydrogen", the position is understood to have hydrogen at its natural abundance isotopic composition. Also unless otherwise stated, when a position is designated specifically as "D" or "deuterium", the position is understood to have deuterium at an abundance that is at least 3340 times greater than the natural abundance of deuterium, which is 0.015% (i.e., at least 50.1% incorporation of deuterium). For example, it is understood that the carbons in the following moieties may be bound to any stable isotope of hydrogen is exemplary representations such as

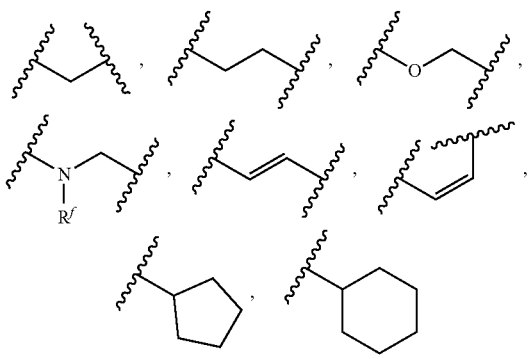

and the like.

The abbreviations Me, Et, Ph, Bn, Tf, Nf, Ts, and Ms represent methyl, ethyl, phenyl, benzyl, trifluoromethanesulfonyl, nonafluorobutanesulfonyl, p-toluenesulfonyl and methanesulfonyl, respectively. A more comprehensive list of the abbreviations utilized by organic chemists of ordinary skill in the art appears in the first issue of each volume of the *Journal of Organic Chemistry*; this list is typically presented in a table entitled Standard List of Abbreviations.

The term "viral infection" as used herein refers to infection by a viral pathogen wherein there is clinical evidence of the infection based on symptoms or based on the demonstration of the presence of the viral pathogen in a biological sample from the individual. As used herein an "individual" refers to an animal, preferably a mammal, including both non-human mammals and humans, and more preferably, refers to a human.

The expression "effective amount" when used to describe therapy to an individual suffering from a viral infection refers to the amount of a compound that results in a therapeutically useful effect on the symptoms of the viral infection and/or a reduction in viral load.

As used herein, a therapeutic that "prevents" a disorder or condition refers to a compound that, in a statistical sample, reduces the occurrence of the disorder or condition in the treated sample relative to an untreated control sample, or delays the onset or reduces the severity of one or more symptoms of the disorder or condition relative to the untreated control sample.

The term "treating" includes prophylactic and/or therapeutic treatments. The term "prophylactic or therapeutic" treatment is art-recognized and includes administration to the host of one or more of the subject compositions. If it is administered prior to clinical manifestation of the unwanted condition (e.g., disease or other unwanted state of the host animal) then the treatment is prophylactic (i.e., it protects the host against developing the unwanted condition), whereas if it is administered after manifestation of the unwanted condition, the treatment is therapeutic, (i.e., it is intended to diminish, ameliorate, or stabilize the existing unwanted condition or side effects thereof). For example, treating a viral infection encompasses alleviating, reducing the frequency of, or eliminating one or more symptoms of the infection and/or a reducing the viral load.

Exemplary Compounds

One aspect of the invention relates to a compound represented by formula (I):

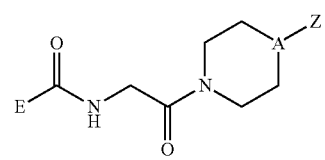

or a pharmaceutically acceptable salt, solvate, hydrate, prodrug, chemically-protected form, enantiomer or stereoisomer thereof; wherein, independently for each occurrence, wherein A is N or $CR^8$;

Z is

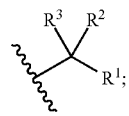

E is selected from optionally substituted alkyl, cycloalkyl, arylalkyl, cycloalkylalkyl, amino, alkoxy, cyclcoalkyloxy, and cycloalkylamino;

$R^1$ is selected from optionally substituted aryl and heteroaryl, $R^2$ and $R^3$ are independently selected from H, deutero, optionally substituted alkyl, haloalkyl, or $R^2$ and $R^3$, together with the carbon to which they are bound, combine to form a carbonyl; and $R^8$ is selected from H, deutero, halo, hydroxyl, cyano, amino, alkyl, alkoxy, carboxy, alkoxycarbonyl, and aminocarbonyl;

provided that E is not

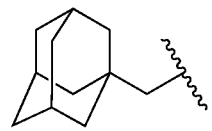

In some embodiments, A is N.
In some embodiments, E is

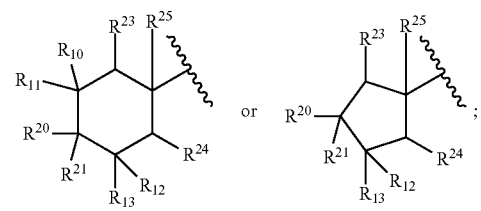

$R^{10}$, $R^{11}$, $R^{12}$, $R^{13}$, and $R^{14}$ are each independently H or halo; or $R^{10}$ and $R^{12}$ combine to form a 3-4-, or 5-membered ring.
and
$R^{20}$, $R^{21}$, $R^{23}$, $R^{24}$, and $R^{25}$ are each independently H, halo, or alkyl; or
$R^{23}$ and $R^{24}$ combine to form a 3-, 4-, or 5-membered ring.

In some embodiments, $R^{23}$ and $R^{24}$ combine to form a 3-membered ring. In some embodiments, $R^{20}$ and $R^{21}$ are each halo, e.g., F.

In some embodiments, E is

In some embodiments, E is and
$Y^1$ is selected from O, $NR^{27}$, and $CR^{28}R^{29}$;
$Y^2$ is selected from O, $NR^{30}$, and $CR^{31}R^{32}$;
$R^{26}$, $R^{28}$, $R^{29}$, $R^{31}$, and $R^{32}$ are each independently H, halo, optionally substituted alkyl or haloalkyl;
$R^{27}$ is selected from H and alkyl;
$R^{30}$ is selected from H, $R^d$ is selected from alkyl, cycloalkyl, heterocyclyl, aryl, or heteroaryl; or
$R^{26}$ and $R^{29}$ combine to form a 3-, 4-, or 5-membered ring.

In some embodiments, $R^d$ is methyl. In some embodiments, $R^{26}$ and $R^{29}$ combine to form a 3-membered ring. In some embodiments, $R^{31}$ and $R^{32}$ are each halo. In some embodiments, $R^{31}$ and $R^{32}$ are each F.

In some embodiments, E is

In some embodiments, E is and
$R^{33}$, $R^{34}$, and $R^{35}$ are each independently H, halo, optionally substituted alkyl, haloalkyl or optionally substituted aryl; or $R^{33}$ and $R^{34}$ combine to form a an optionally substituted 3-, 4-, 5-, or 6-membered ring.

In some embodiments, the 3-, 4-, 5-, or 6-membered ring is substituted with one to four substitutents selected from halo, alkyl, and haloalkyl.

In some embodiments, $R^{33}$ and $R^{34}$ combine to form a 4- or 5-membered ring. In some embodiments, $R^{33}$ and $R^{34}$ are each halo (e.g., F).

In some embodiments, E is

-continued

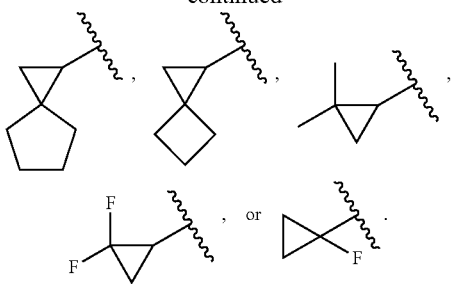

In some embodiments, E is

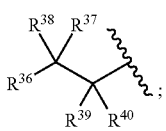

and
$R^{36}$, $R^{37}$, $R^{38}$, $R^{39}$, and $R^{40}$ are each independently H, halo, alkyl, haloalkyl, or aryl; or $R^{37}$ and $R^{38}$ combine to form an optionally substituted 3-, 4-, 5-, or 6-membered ring.

In some embodiments, said 3-, 4-, 5-, or 6-membered ring is substituted with one to four substitutents selected from halo, alkyl, and haloalkyl. In some embodiments, $R^{38}$ and $R^{39}$ are each alkyl. In some embodiments, $R^{38}$ and $R^{39}$ are each methyl.

In some embodiments, E is

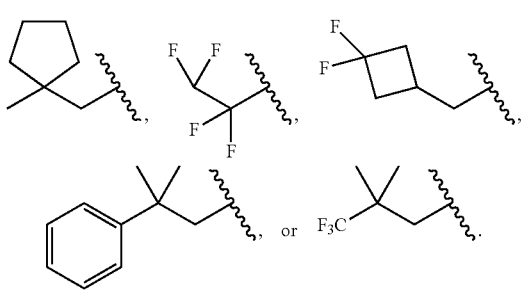

In some embodiments, E is

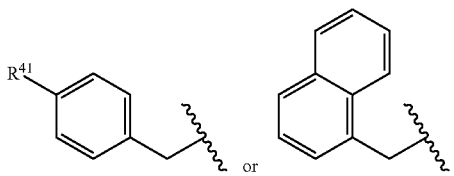

and $R^{41}$ is H, halo, or alkyl.

In some embodiments, $R^1$ is substituted with one or more groups selected from halo, hydroxyl, amino, amido, nitro, carboxy, aminocarbonyl, cyano, azido, aminosulfonyl, optionally substituted alkyl, optionally substituted cycloalkyl, optionally substituted alkoxy, haloalkoxy, optionally substituted alkynyl, optionally substituted cycloalkyloxy, optionally substituted aryl and optionally substituted heteroaryl.

In some embodiments, $R^1$ is

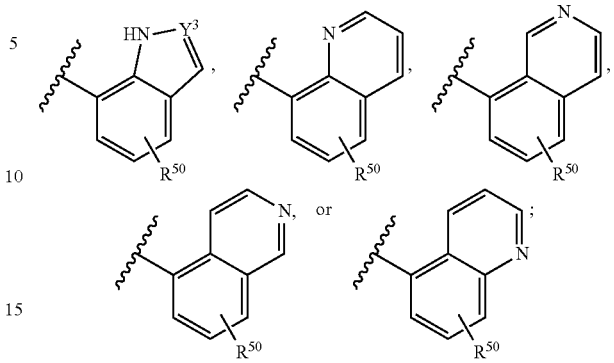

and
$Y^3$ is N or CH and $R^{50}$ is H, halo, or alkyl.

In some embodiments, $R^1$ is

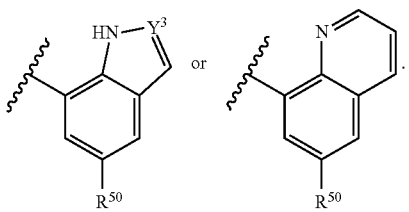

In some embodiments, $R^{50}$ is halo.

In some embodiments, Z is

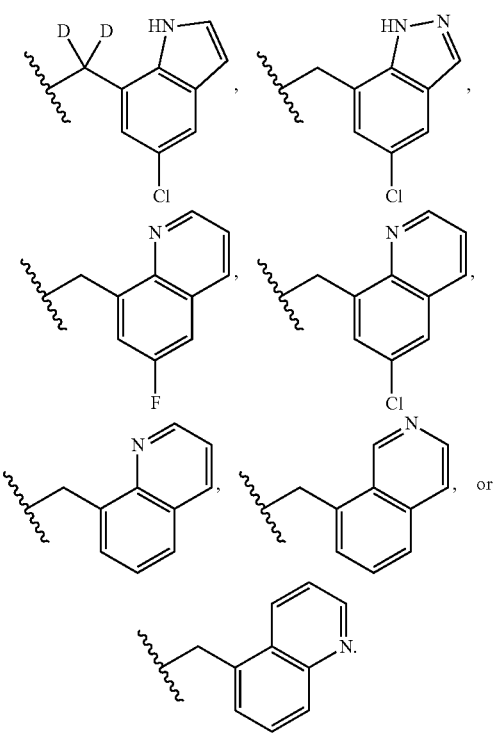

In some embodiments, $R^1$ is

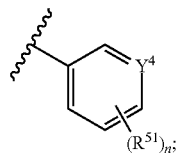

$R^{51}$ is H, deutero, halo, cyano, azido, alkyl, haloalkyl, fluoroalkyl, cycloalkyl, hydroxyl, alkoxy, haloalkoxy, carbocyclylalkoxy, heterocyclylalkoxy, aryloxy, heteroaryloxy, amino, alkylamino, carbocyclylamino, heterocyclylamino, arylamino, heteroarylamino, amido, alkenyl, alkynyl, carbocyclyl, aryl, heteroaryl, or carbocyclylalkoxy;

$Y^4$ is N or CH; and n is an integer selected from 1, 2, or 3.

In some embodiments, $R^1$ is phenyl, pyridin-1-yl, pyridin-2-yl, or pyridin-3-yl, optionally substituted with one, two, or three substituents selected from H, deutero, halo, cyano, azido, alkyl, haloalkyl, fluoroalkyl, cycloalkyl, hydroxyl, alkoxy, haloalkoxy, carbocyclylalkoxy, heterocyclylalkoxy, aryloxy, heteroaryloxy, amino, alkylamino, carbocyclylamino, heterocyclylamino, arylamino, heteroarylamino, amido, alkenyl, alkynyl, carbocyclyl, aryl, heteroaryl, and carbocyclylalkoxy.

In some embodiments, n is 2 or 3.

In some embodiments, $R^1$ is

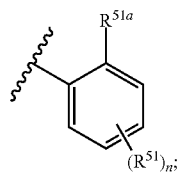

$R^{51a}$ is H, deutero, halo, cyano, azido, alkyl, haloalkyl, fluoroalkyl, cycloalkyl, hydroxyl, alkoxy, haloalkoxy, carbocyclylalkoxy, heterocyclylalkoxy, aryloxy, heteroaryloxy, amino, alkylamino, carbocyclylamino, heterocyclylamino, arylamino, heteroarylamino, amido, alkenyl, alkynyl, carbocyclyl, aryl, heteroaryl, or carbocyclylalkoxy; and n is an integer selected from 0, 1 or 2.

In some embodiments, $R^1$ is

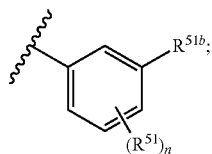

$R^{51b}$ is H, deutero, halo, cyano, azido, alkyl, haloalkyl, fluoroalkyl, cycloalkyl, hydroxyl, alkoxy, haloalkoxy, carbocyclylalkoxy, heterocyclylalkoxy, aryloxy, heteroaryloxy, amino, alkylamino, carbocyclylamino, heterocyclylamino, arylamino, heteroarylamino, amido, alkenyl, alkynyl, carbocyclyl, aryl, heteroaryl, or carbocyclylalkoxy; and n is an integer selected from 0, 1, or 2.

In some embodiments, $R^1$ is

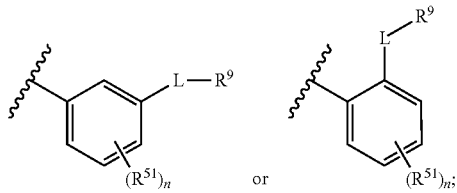

L is

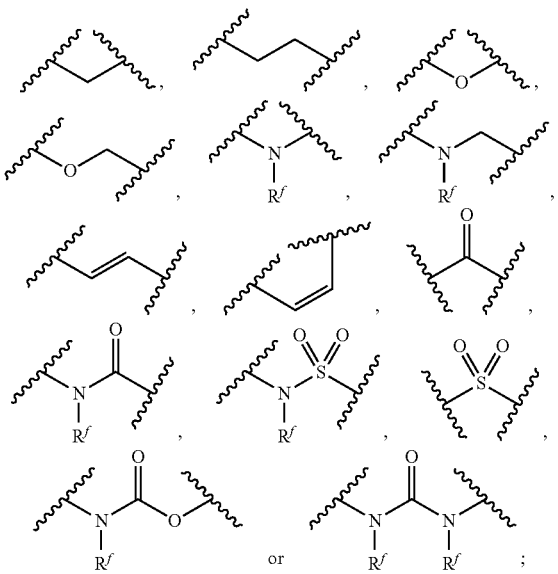

$R^f$ are each independently selected from H, alkyl, and cycloalkyl.

$R^9$ is selected from H, optionally substituted alkyl, amino, cycloamino, cycloalkyl, heterocyclyl, aryl, and heteroaryl; and n is an integer selected from 0, 1 or 2.

In some embodiments, $R^9$ is phenyl or pyridinyl optionally substituted with deutero, alkyl, alkenyl, alkynyl, halo, haloalkyl, fluoroalkyl, hydroxy, alkoxy, alkenyloxy, alkynyloxy, carbocyclyloxy, heterocyclyloxy, haloalkoxy, hydroxyalkyl, aminoalkyl fluoroalkyloxy, sulfhydryl, alkylthio, haloalkylthio, fluoroalkylthio, alkenylthio, alkynylthio, sulfonic acid, alkylsulfonyl, haloalkylsulfonyl, arylsulfonyl, fluoroalkylsulfonyl, alkenylsulfonyl, alkynylsulfonyl, alkoxysulfonyl, haloalkoxysulfonyl, fluoroalkoxysulfonyl, alkenyloxysulfonyl, alkynyloxysulfony, aminosulfonyl, alkylaminosulfonyl, arylaminosulfonyl, heteroarylaminosulfonyl, aralkylaminosulfonyl, N-alkyl-N-arylaminosulfonyl, N-aralkyl-N-alkylamino sulfonyl, sulfinic acid, alkylsulfinyl, haloalkylsulfinyl, fluroralkylsulfinyl, alkenylsulfinyl, alkynylsulfinyl, alkoxysulfinyl, haloalkoxysulfinyl, fluroralkoxysulfinyl, alkenyloxysulfinyl, alkynyloxysulfiny, aminosulfinyl, formyl, alkylcarbonyl, haloalkylcarbonyl, fluoroalkylcarbonyl, alkenylcarbonyl, alkynylcarbonyl, carboxy, alkoxycarbonyl, haloalkoxycarbonyl, fluoroalkoxycarbonyl, alkenyloxycarbonyl, alkynyloxycarbonyl, alkylcarbonyloxy, haloalkylcarbonyloxy, fluoroalkylcarbonyloxy, alkenylcarbonyloxy, alkynylcarbonyloxy, alkylsulfonyloxy, haloalkylsulfonyloxy, fluoroalkylsulfonyloxy, alkenylsulfonyloxy, alkynylsulfonyloxy, haloalkoxysulfonyloxy, fluoroalkoxysulfonyloxy, alkenyloxysulfonyloxy, alkynyloxysulfonyloxy, alkylsulfinyloxy, haloalkylsulfinyloxy, fluoroalkylsulfinyloxy, alkenylsulfinyloxy, alkynylsulfinyloxy, alkoxysulfinyloxy, haloalkoxysulfinyloxy, fluoroalkoxysulfinyloxy, alkenyloxysulfinyloxy, alkynyloxysulfinyloxy, aminosulfinyloxy, amino, alkylsulfonylamino, arylsulfonylamino, heteroarylsulfonylamino, aralkylsulfonylamino, alkylcarbonylamino, arylcarbonylamino, heteroarylcarbonylamino, aralkylcarbonylamino, aminocarbonyl, alkylaminocarbonyl, arylaminocarbonyl, heteroarylaminocarbonyl, aralkylaminocarbonyl, N-alkyl-N-arylaminocarbonyl, N-aralkyl-N-alkylamino carbonyl cyano, nitro, azido, phosphinyl, phosphine oxide and phosphonate, silyl, silyloxy, cyclic acetal, aryl, heteroaryl.

In some embodiments, $R^9$ is phenyl or pyridinyl optionally substituted with halo, amino, amide, cyano, carboxy, alkoxycarbonyl, lower cycloalkyl, sulfanamide, phosphine oxide, phosphoryl, sulfoxide, sulfone, alkyl, or lower cycloalkyl. In some embodiments, wherein $R^9$ is phenyl.

In some embodiments, $R^9$ is

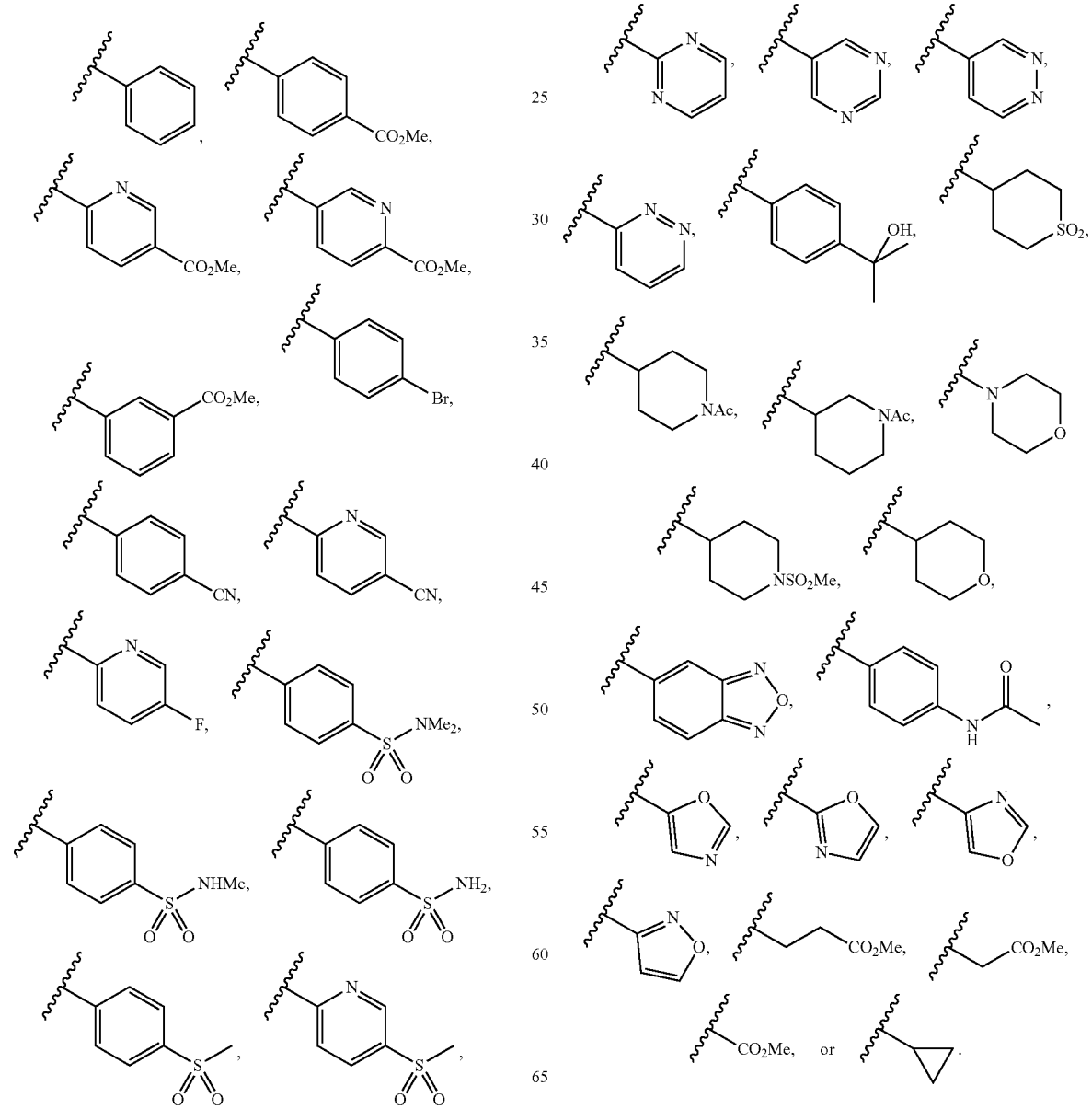

In some embodiments, Z is
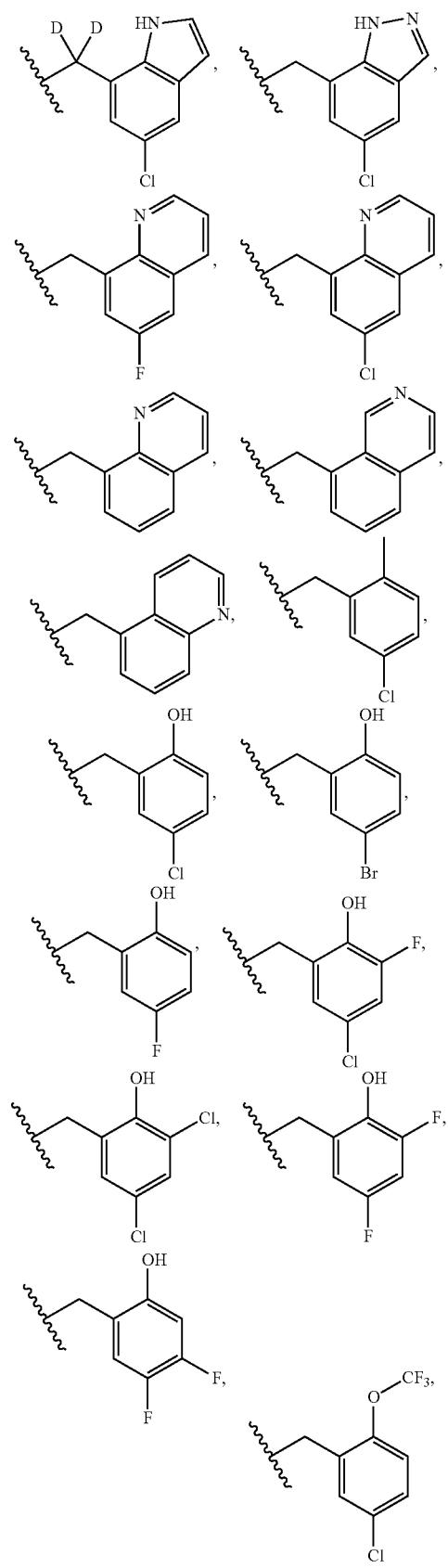
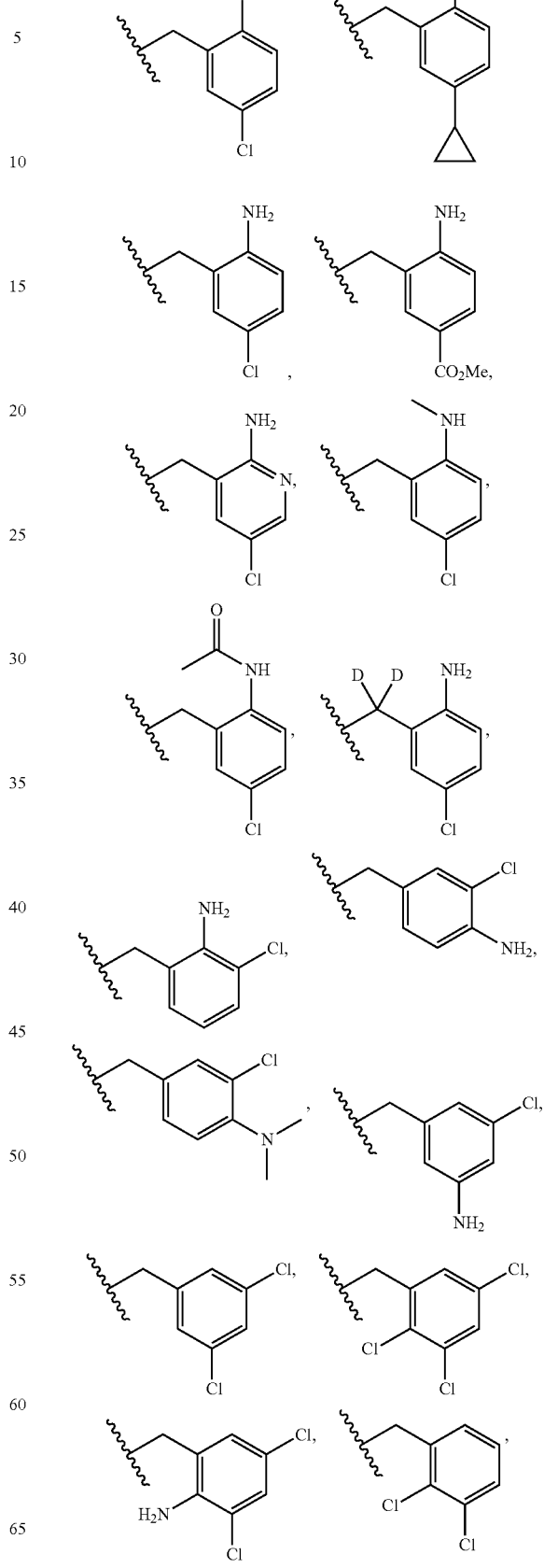

-continued
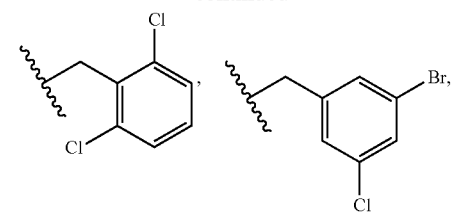
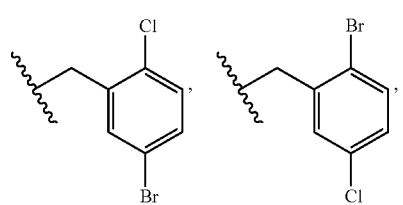
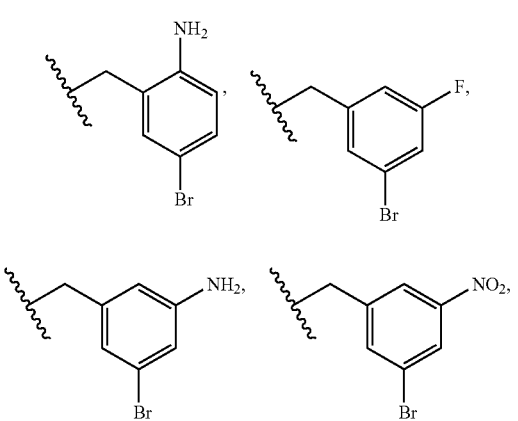
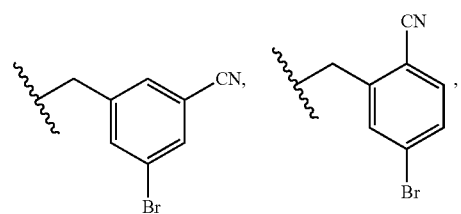
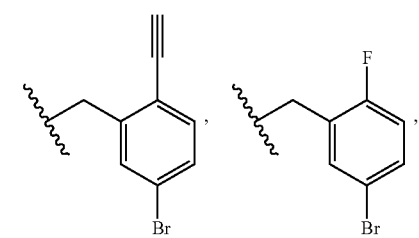
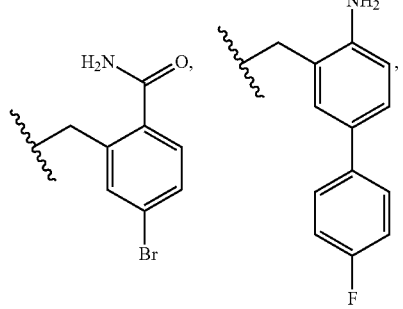
-continued
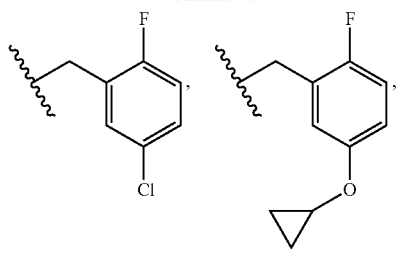
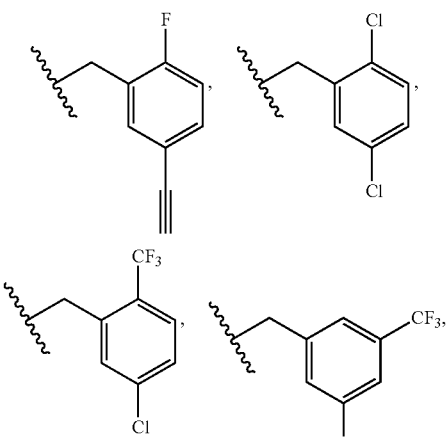
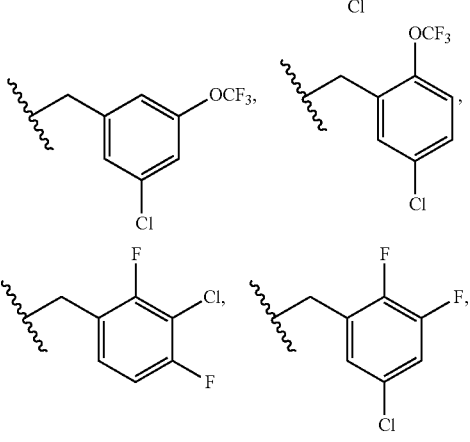
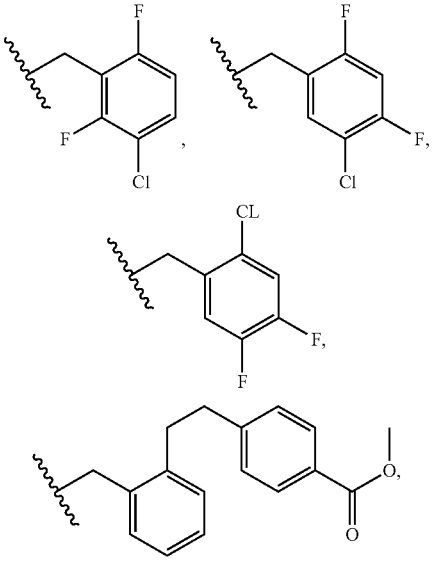

-continued
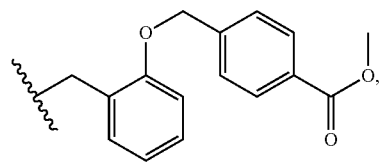
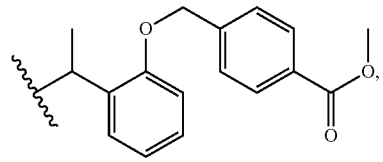
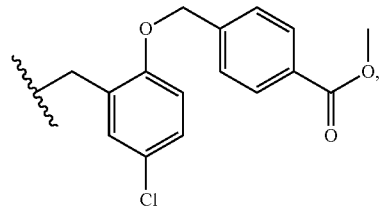
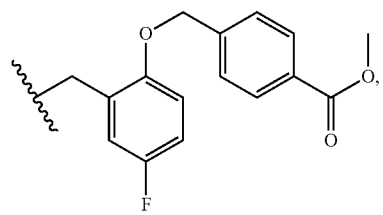
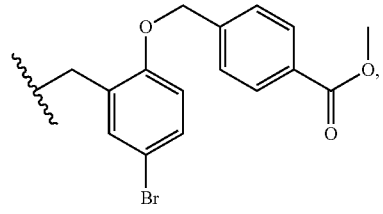
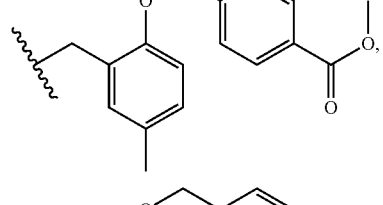
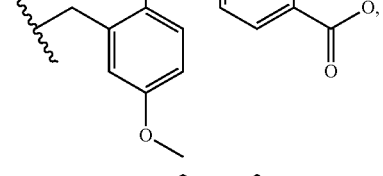
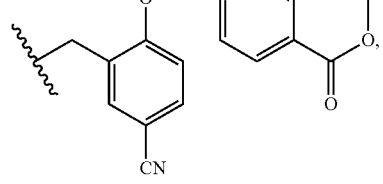
-continued
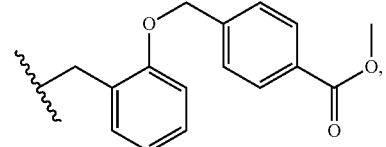
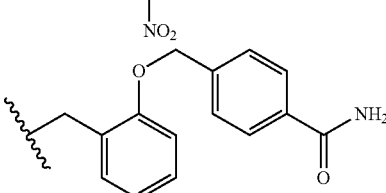
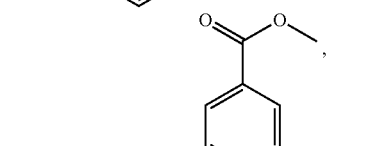
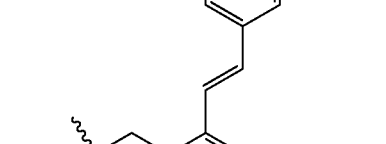
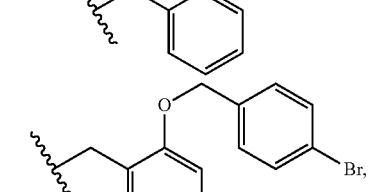
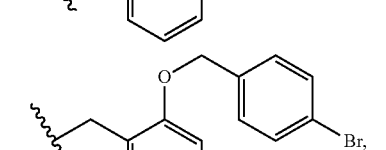
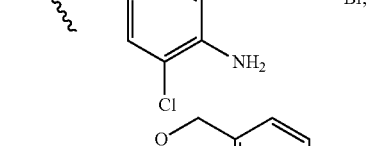
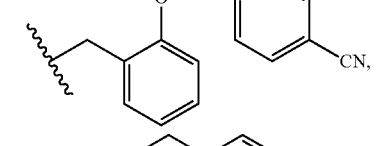
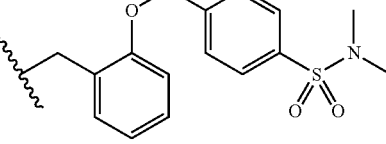
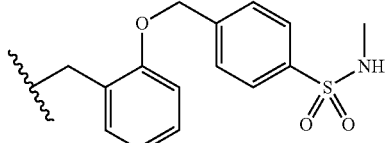
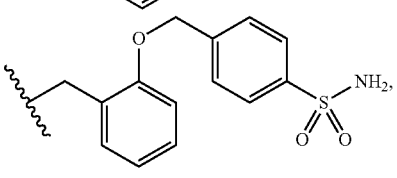

-continued
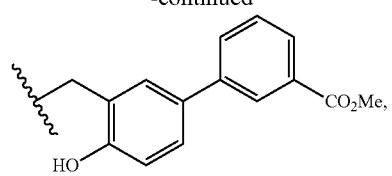
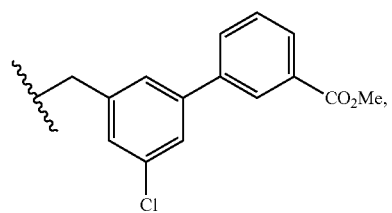
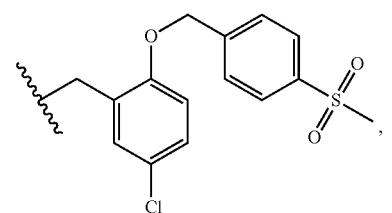
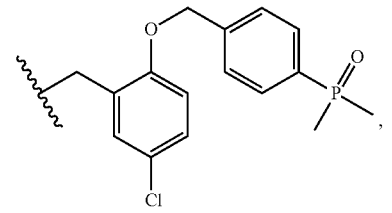
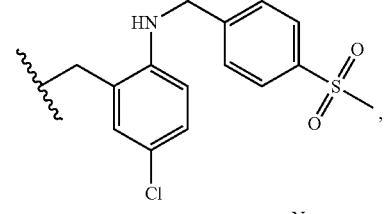
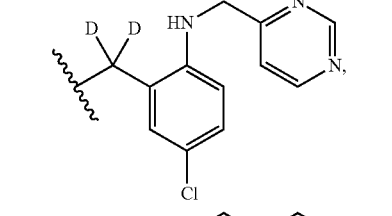
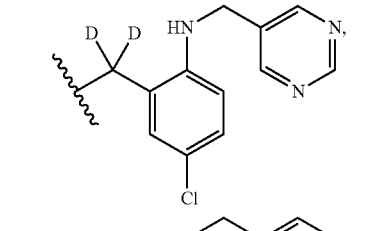
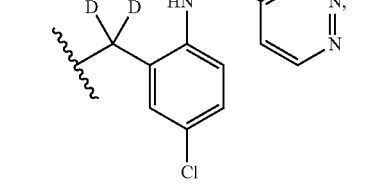
-continued
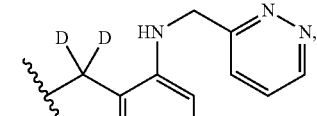
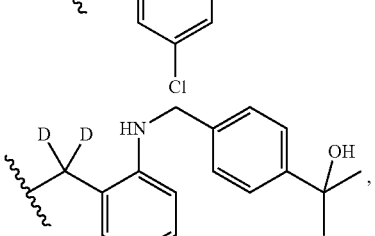
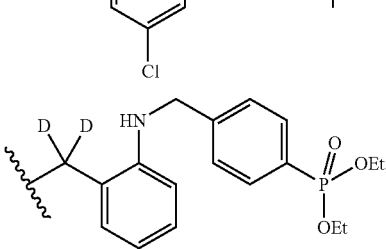
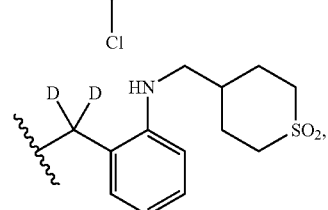
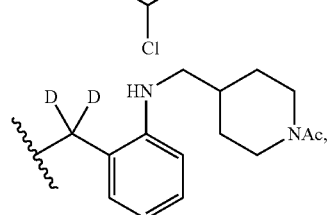
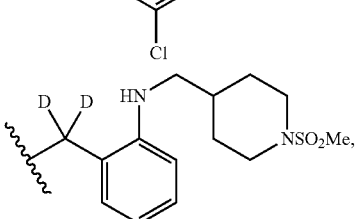
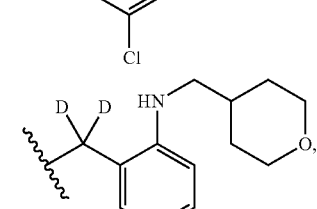
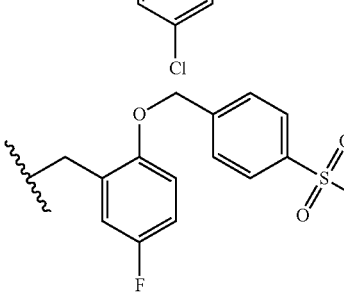

33
-continued
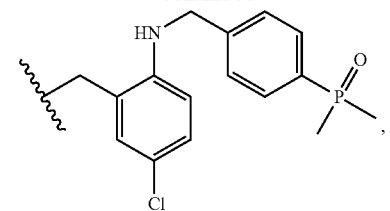
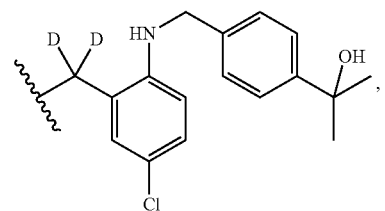
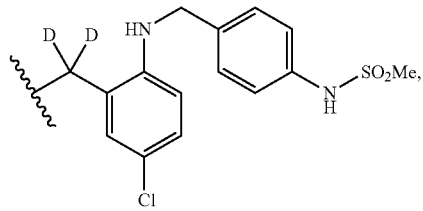
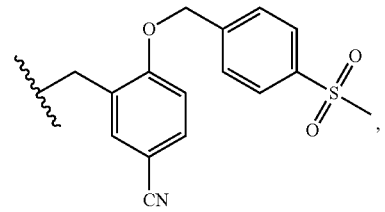
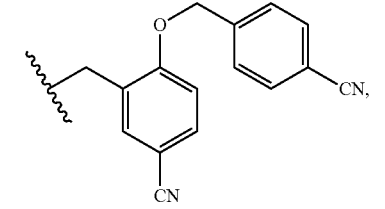
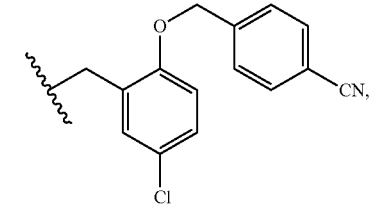
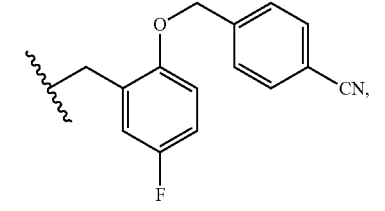
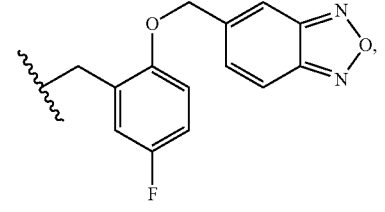
34
-continued
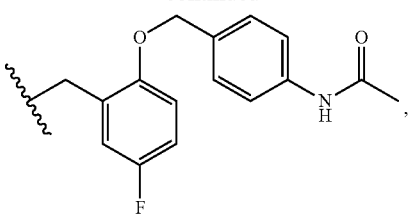
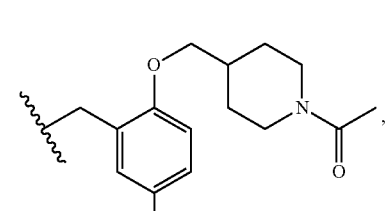
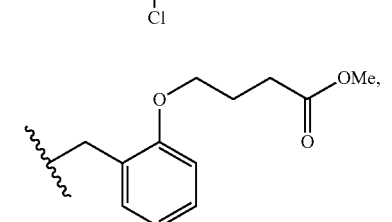
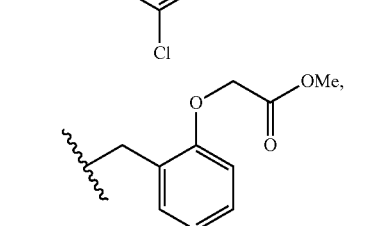
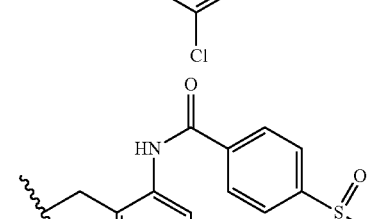
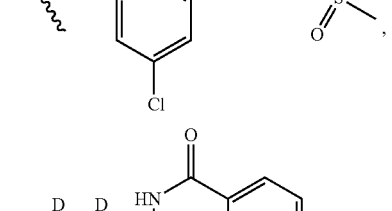
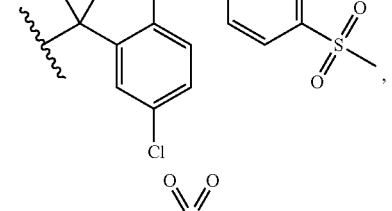
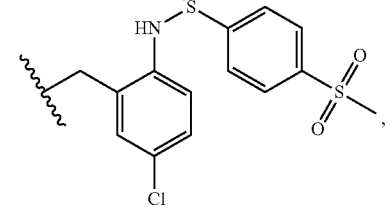

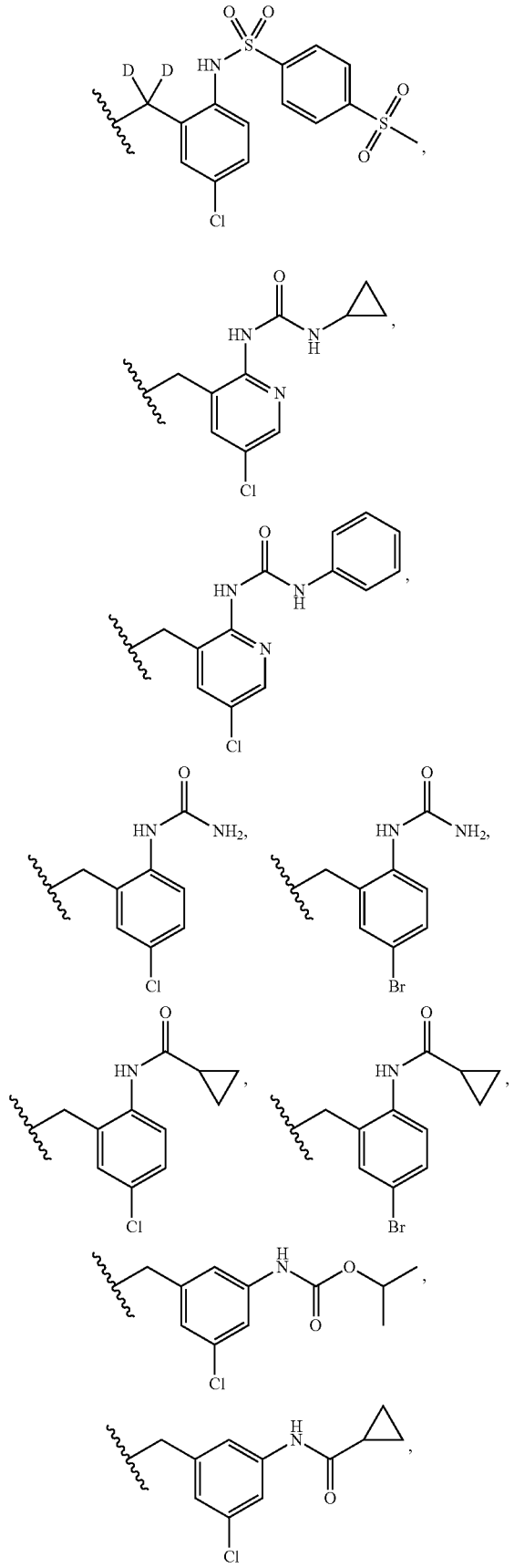
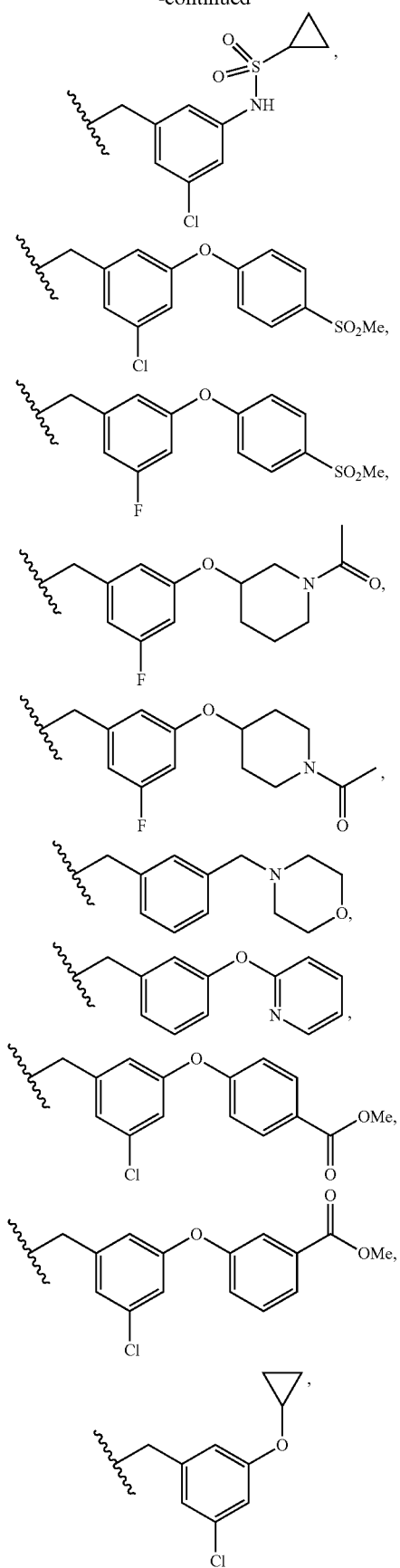

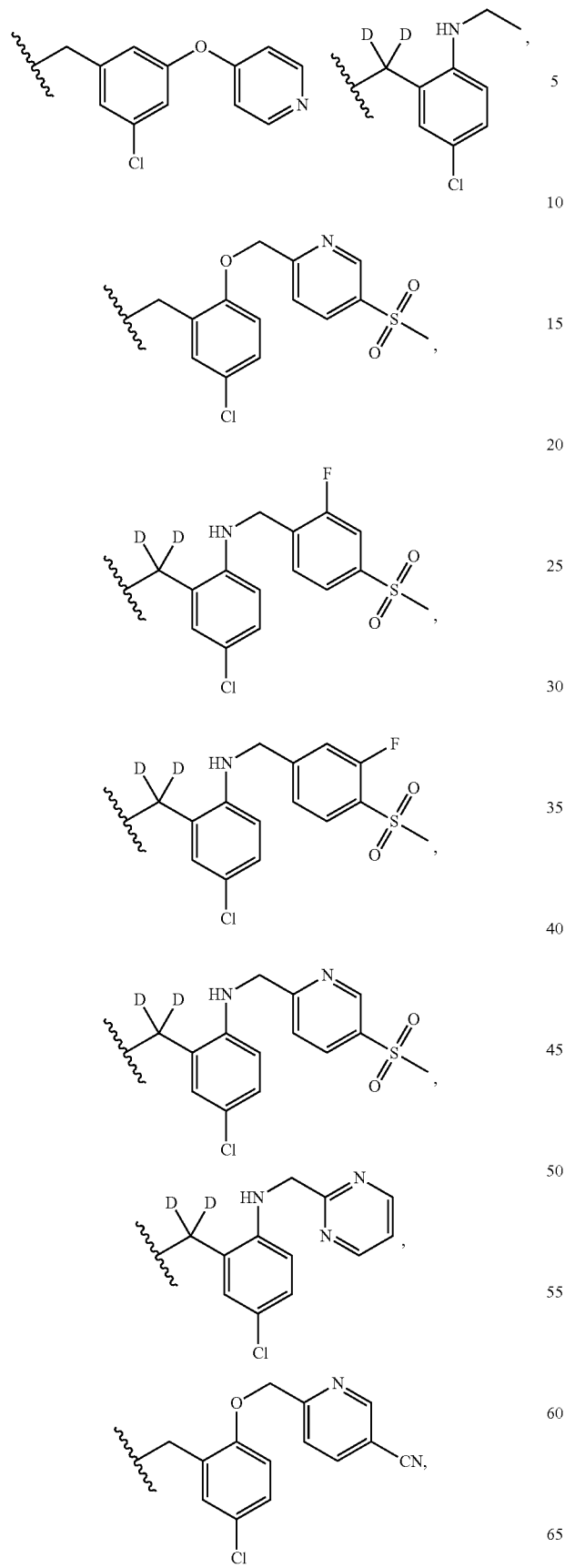
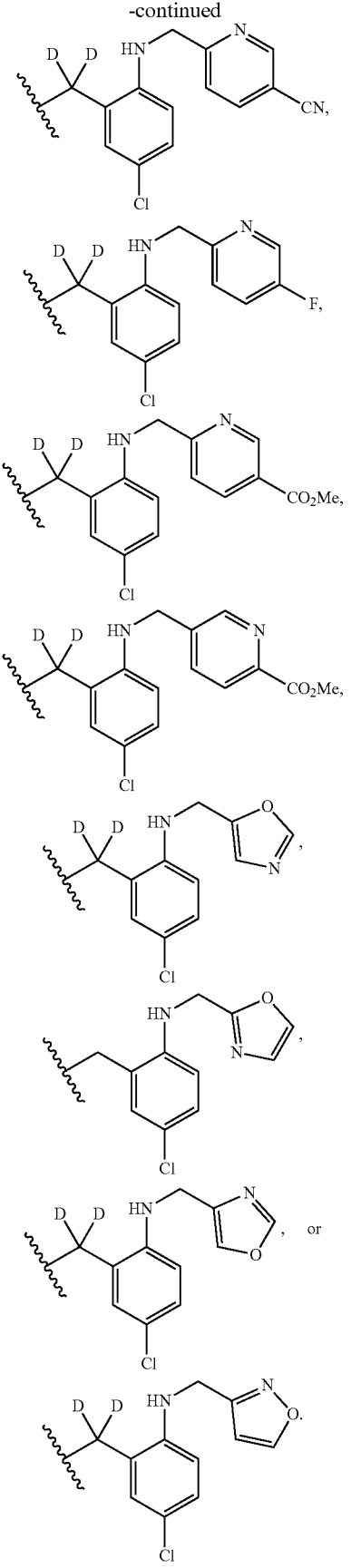

In certain other aspects the invention relates to compounds represented by formula (II)

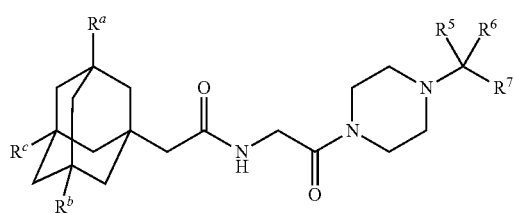

or a pharmaceutically acceptable salt, solvate, hydrate, prodrug, chemically-protected form, enantiomer or stereoisomer thereof; wherein, independently for each occurrence, wherein $R^a$, $R^b$, and $R^c$ are independently selected from H, halo, hydroxy, optionally substituted alkyl, optionally substituted alkoxy, optionally substituted aryl, and optionally substituted heteroaryl;

$R^5$ and $R^6$ are independently selected from H, deutero, and alkyl, or $R^5$ and $R^6$, together with the carbon to which they are bound, combine to form a carbonyl; and $R^7$ is

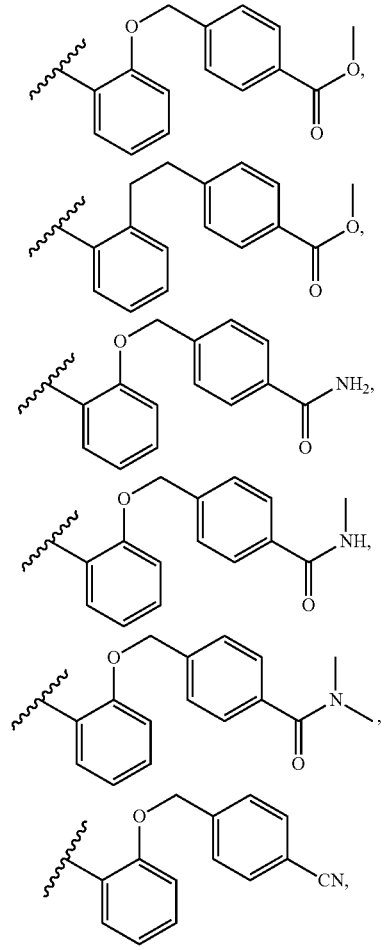

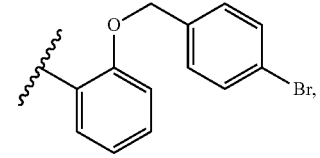

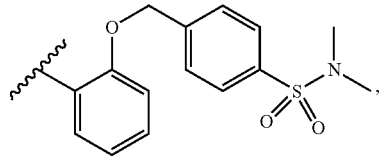

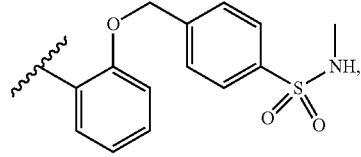

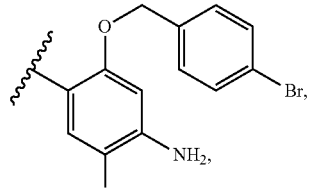

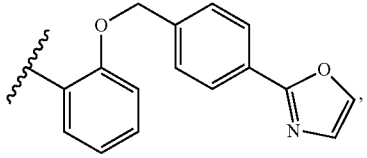

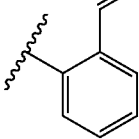 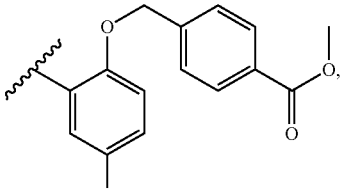

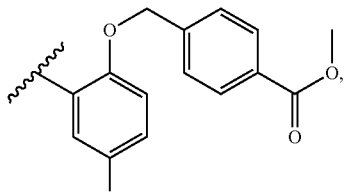

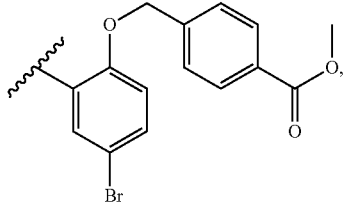

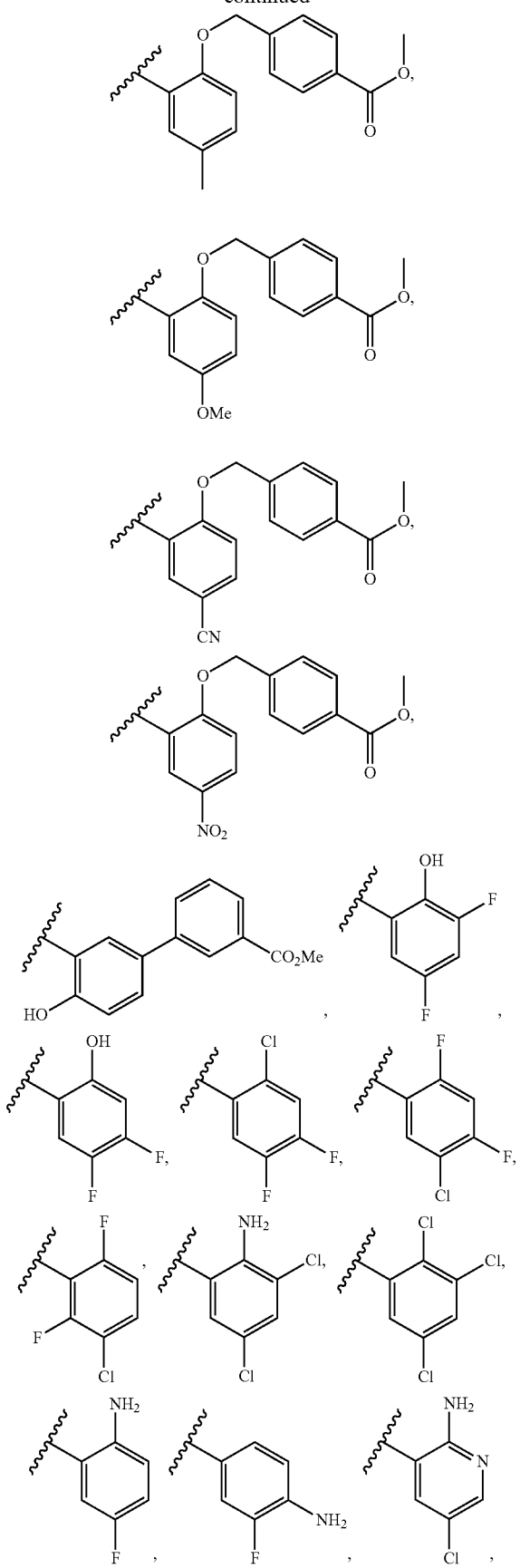
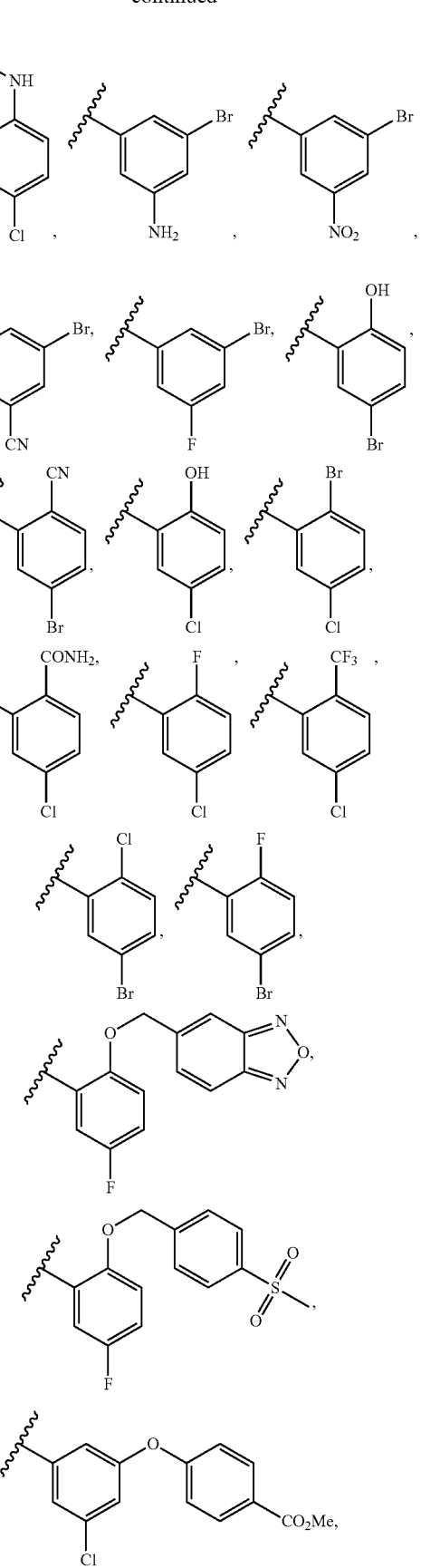

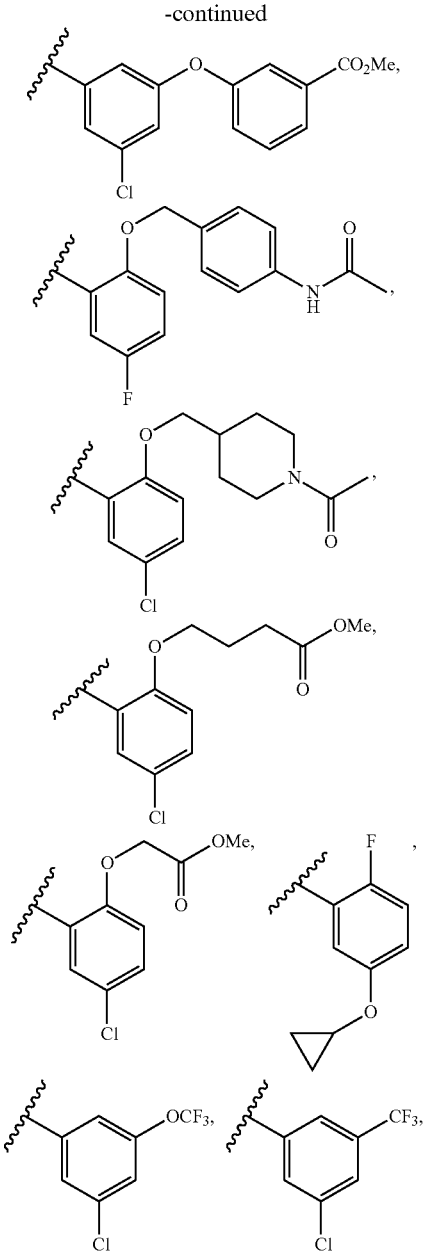

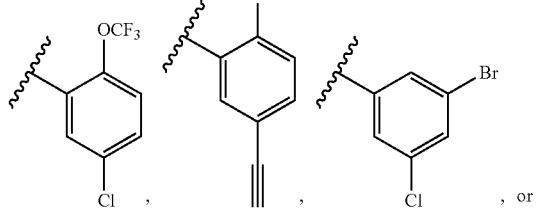

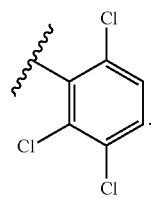

In some embodiments, $R^a$, $R^b$, and $R^c$ are each halo. In some embodiments, $R^b$ and $R^c$ are each H. In some embodiments, one of $R^a$, $R^b$, and $R^c$ is

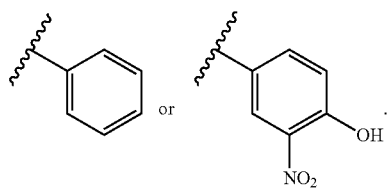 [SMILES: *c1ccccc1 ; *c1ccc(O)c([N+](=O)[O-])c1]

Exemplary compounds of Formula I and Formula II are depicted in the examples and Table 1. The compounds disclosed in the examples and Table 1 are understood to encompass both the free base and the conjugate acid. For example, the compounds in the examples and Table 1 may be depicted as complexes or salts with trifluoroacetic acid or hydrochloric acid, but the compounds in their corresponding free base forms or as salts with other acids are equally within the scope of the invention. Compounds may be isolated in either the free base form, as a salt (e.g., a hydrochloride salt) or in both forms. In the chemical structures shown below, standard chemical abbreviations are sometimes used.

TABLE 1

| Compound number | Structure | IC50(uM) |
|---|---|---|
| 1433 | (structure shown) | >5 |

Expemplary compounds of Formula I and Formula II.

TABLE 1-continued
Expemplary compounds of Formula I and Formula II.
| Compound number | Structure | IC50(uM) |
|---|---|---|
| 1429 | 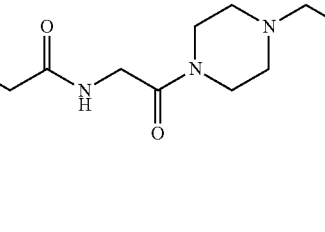 | 0.95 |
| 1427 | 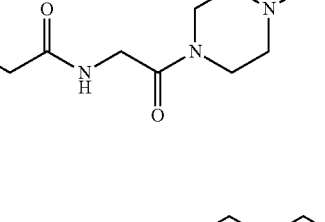 | 2.45 |
| 1428 | 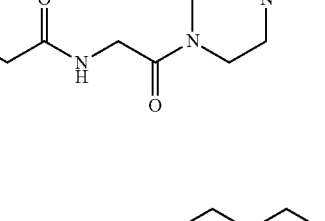 | >5 |
| 1424 | 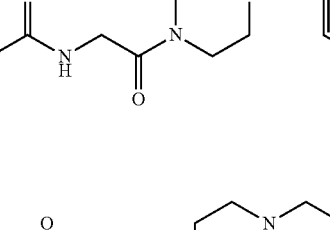 | 2.8 |
| 1422 | 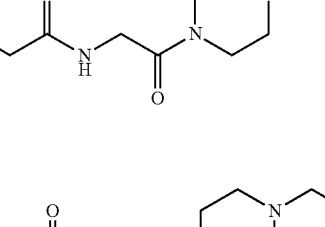 | 0.36 |
| 1421 | 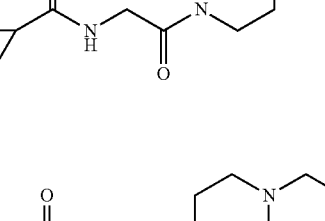 | >5 |
| 1420 | 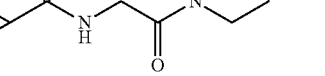 | 0.49 |

TABLE 1-continued

Exemplary compounds of Formula I and Formula II.

| Compound number | Structure | IC50(uM) |
|---|---|---|
| 1406 | 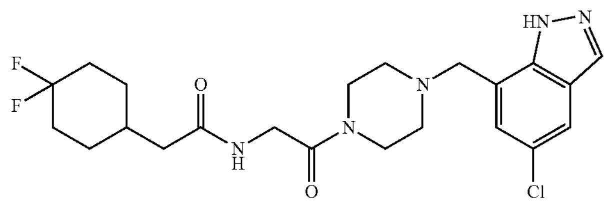 [SMILES: O=C(CC1CCC(F)(F)CC1)NCC(=O)N1CCN(Cc2cc(Cl)cc3cn[nH]c23)CC1] | 0.46 |
| 1405 | 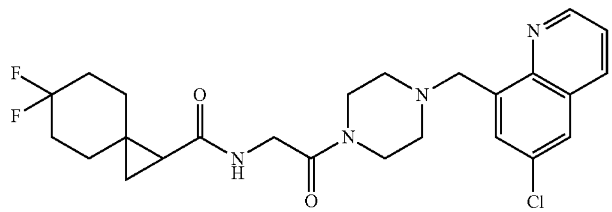 [SMILES: O=C(NCC(=O)N1CCN(Cc2cc(Cl)cc3cccnc23)CC1)C1CC12CCC(F)(F)CC2] | 0.07-0.26 |
| 1431 | 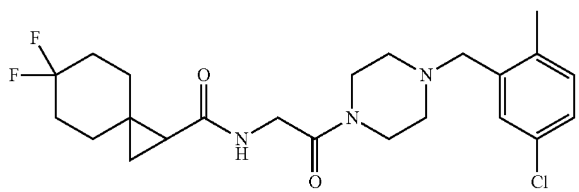 [SMILES: Cc1ccc(Cl)cc1CN1CCN(C(=O)CNC(=O)C2CC23CCC(F)(F)CC3)CC1] | 0.55 |
| 1425 | 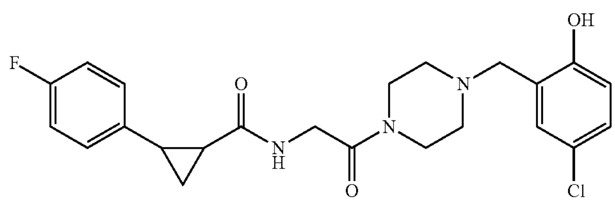 [SMILES: O=C(NCC(=O)N1CCN(Cc2cc(Cl)ccc2O)CC1)C1CC1c1ccc(F)cc1] | 3.4 |
| 1372 | 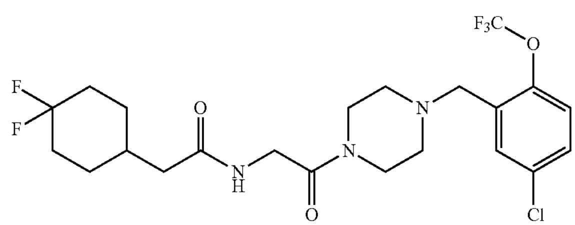 [SMILES: O=C(CC1CCC(F)(F)CC1)NCC(=O)N1CCN(Cc2cc(Cl)ccc2OC(F)(F)F)CC1] | >2 |
| 1384 | 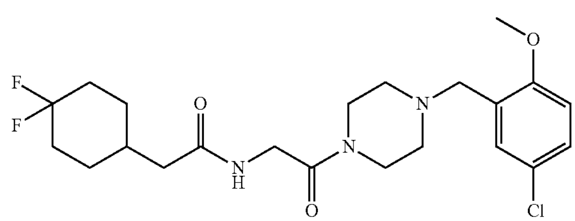 [SMILES: COc1ccc(Cl)cc1CN1CCN(C(=O)CNC(=O)CC2CCC(F)(F)CC2)CC1] | 0.33 |
| 1404 | 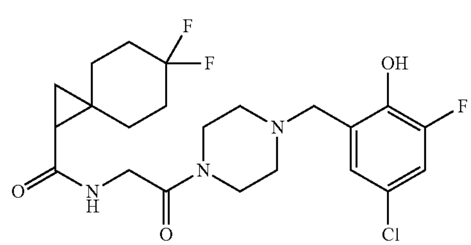 [SMILES: O=C(NCC(=O)N1CCN(Cc2cc(Cl)cc(F)c2O)CC1)C1CC12CCC(F)(F)CC2] | 0.63 |

TABLE 1-continued
Exemplary compounds of Formula I and Formula II.
| Compound number | Structure | IC50(uM) |
|---|---|---|
| 1403 | 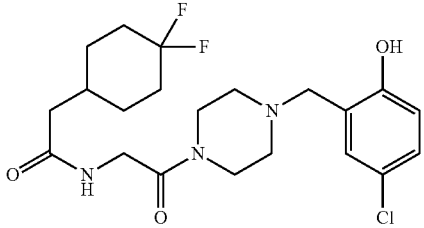 | 0.19-0.73 |
| 1402 | 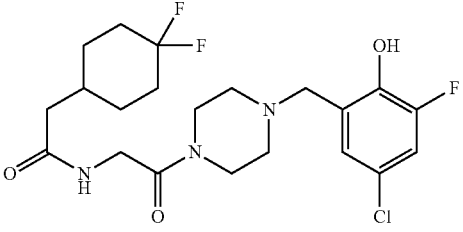 [SMILES: O=C(CC1CCC(F)(F)CC1)NCC(=O)N1CCN(Cc2cc(Cl)cc(F)c2O)CC1] | 2.9 |
| 1401 | 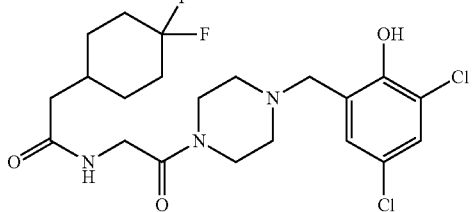 | 3.7 |
| 1400 | 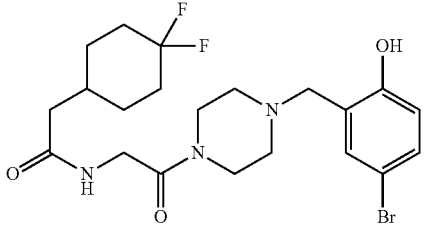 | 0.67 |
| 1399 | 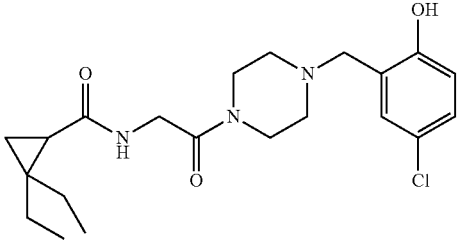 [SMILES: CCC1(CC)CC1C(=O)NCC(=O)N1CCN(Cc2cc(Cl)ccc2O)CC1] | 0.22 |
| 1398 | 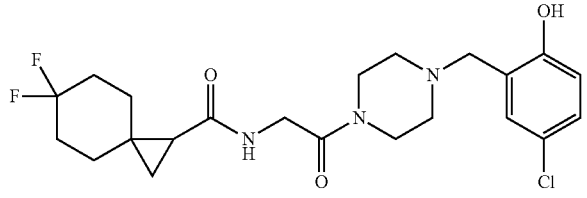 [SMILES: O=C(NCC(=O)N1CCN(Cc2cc(Cl)ccc2O)CC1)C1CC12CCC(F)(F)CC2] | 0.075-0.32 |

TABLE 1-continued
Exemplary compounds of Formula I and Formula II.
| Compound number | Structure | IC50(uM) |
|---|---|---|
| 1397 | 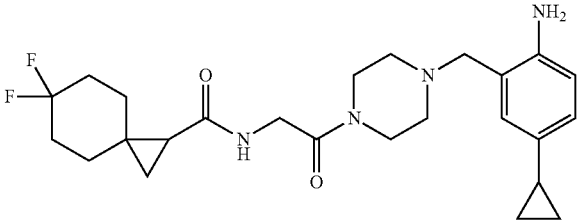 [SMILES: Nc1ccc(C2CC2)cc1CN1CCN(C(=O)CNC(=O)C2CC23CCC(F)(F)CC3)CC1] | 2.4-4.2 |
| 1413 | 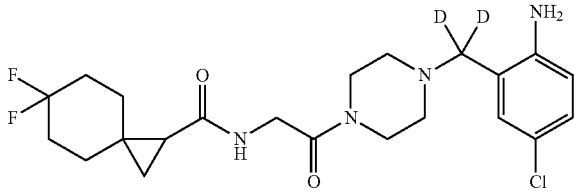 [SMILES: [2H]C([2H])(c1cc(Cl)ccc1N)N1CCN(C(=O)CNC(=O)C2CC23CCC(F)(F)CC3)CC1] | 0.068 |
| 1412 | 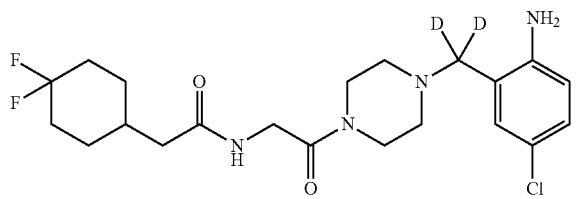 [SMILES: [2H]C([2H])(c1cc(Cl)ccc1N)N1CCN(C(=O)CNC(=O)CC2CCC(F)(F)CC2)CC1] | 0.13 |
| 1391 | 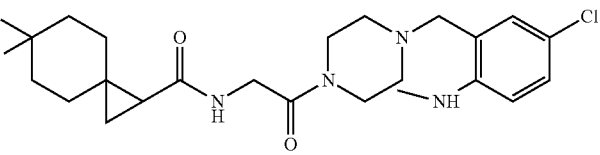 | 0.08-0.26 |
| 1411 | 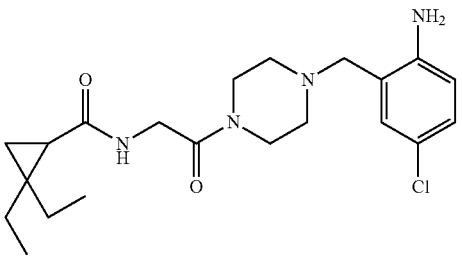 [SMILES: CCC1(CC)CC1C(=O)NCC(=O)N1CCN(Cc2cc(Cl)ccc2N)CC1] | 0.14 |
| 1410 | 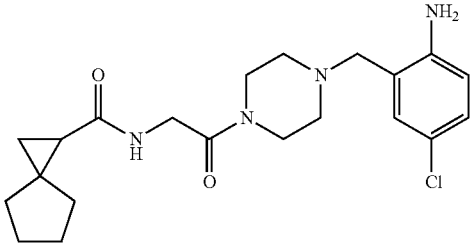 [SMILES: Nc1ccc(Cl)cc1CN1CCN(C(=O)CNC(=O)C2CC23CCCC3)CC1] | 0.22-0.49 |

TABLE 1-continued

Exemplary compounds of Formula I and Formula II.

| Compound number | Structure | IC50(uM) |
|---|---|---|
| 1409 | 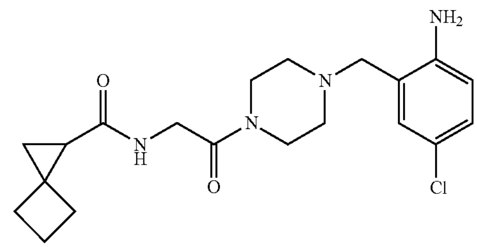 [SMILES: Nc1ccc(Cl)cc1CN1CCN(C(=O)CNC(=O)C2CC23CCC3)CC1] | 2.9 |
| 1474 | 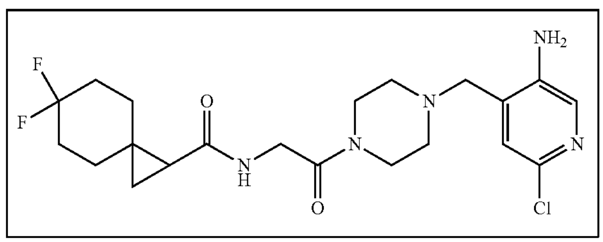 [SMILES: Nc1cnc(Cl)cc1CN1CCN(C(=O)CNC(=O)C2CC23CCC(F)(F)CC3)CC1] | |
| 1407 | 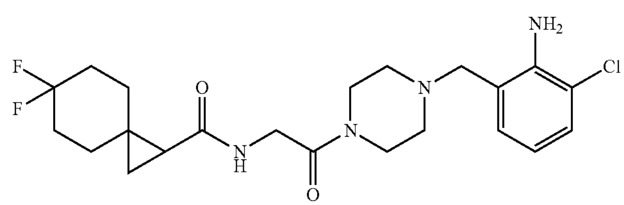 [SMILES: Nc1c(Cl)cccc1CN1CCN(C(=O)CNC(=O)C2CC23CCC(F)(F)CC3)CC1] | 0.23-0.5 |
| 1390 | 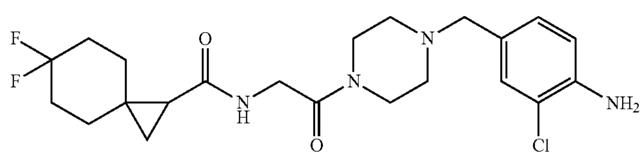 [SMILES: Nc1ccc(CN2CCN(C(=O)CNC(=O)C3CC34CCC(F)(F)CC4)CC2)cc1Cl] | 1.1 |
| 1388 | 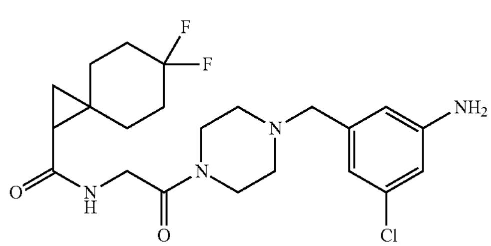 [SMILES: Nc1cc(Cl)cc(CN2CCN(C(=O)CNC(=O)C3CC34CCC(F)(F)CC4)CC2)c1] | 0.5 |
| 1387 | 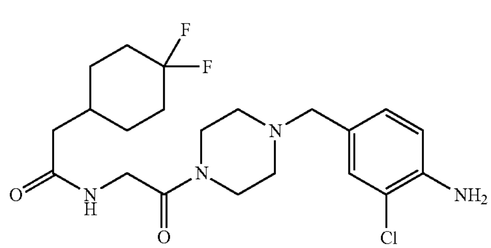 [SMILES: Nc1ccc(CN2CCN(C(=O)CNC(=O)CC3CCC(F)(F)CC3)CC2)cc1Cl] | >5 |

TABLE 1-continued

Exemplary compounds of Formula I and Formula II.

| Compound number | Structure | IC50(uM) |
|---|---|---|
| 1386 | 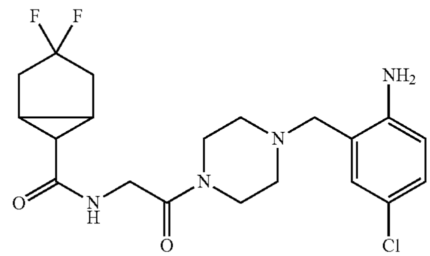 [SMILES: Nc1ccc(Cl)cc1CN1CCN(C(=O)CNC(=O)C2C3CC(F)(F)CC32)CC1] | 4.4 |
| 1385 | 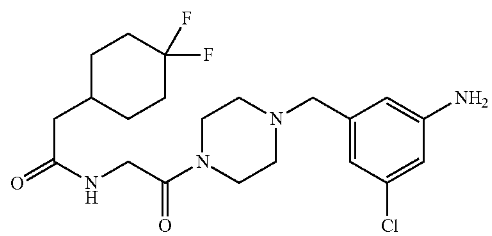 [SMILES: Nc1cc(Cl)cc(CN2CCN(C(=O)CNC(=O)CC3CCC(F)(F)CC3)CC2)c1] | 2.2 |
| 1381 | 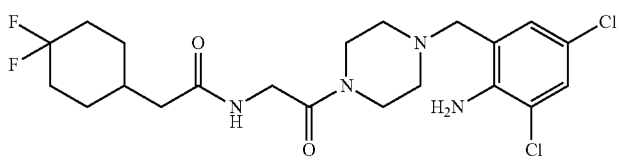 [SMILES: Nc1c(Cl)cc(Cl)cc1CN1CCN(C(=O)CNC(=O)CC2CCC(F)(F)CC2)CC1] | >2 |
| 1359 | 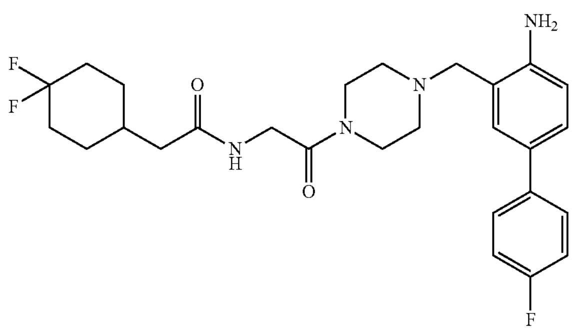 [SMILES: Nc1ccc(-c2ccc(F)cc2)cc1CN1CCN(C(=O)CNC(=O)CC2CCC(F)(F)CC2)CC1] | >2 |
| 1373 | 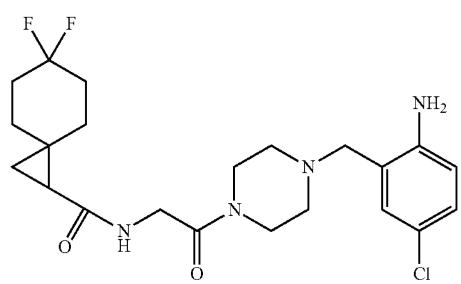 [SMILES: Nc1ccc(Cl)cc1CN1CCN(C(=O)CNC(=O)C2CC23CCC(F)(F)CC3)CC1] | 0.1 |
| 1408 | 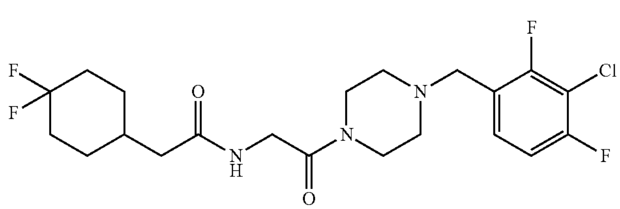 [SMILES: O=C(CC1CCC(F)(F)CC1)NCC(=O)N1CCN(Cc2ccc(F)c(Cl)c2F)CC1] | 4 |

TABLE 1-continued

Exemplary compounds of Formula I and Formula II.

| Compound number | Structure | IC50(uM) |
|---|---|---|
| 1383 | 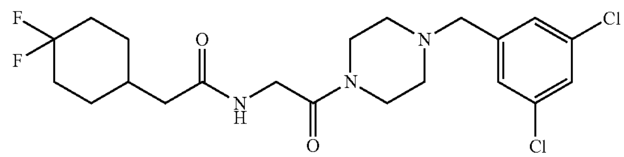 [SMILES: O=C(CC1CCC(F)(F)CC1)NCC(=O)N1CCN(Cc2cc(Cl)cc(Cl)c2)CC1] | >2 |
| 1382 | 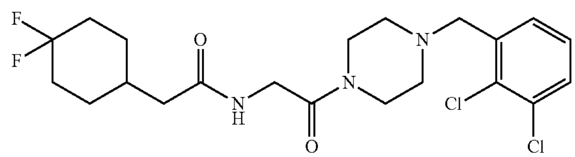 [SMILES: O=C(CC1CCC(F)(F)CC1)NCC(=O)N1CCN(Cc2cccc(Cl)c2Cl)CC1] | >2 |
| 1374 | 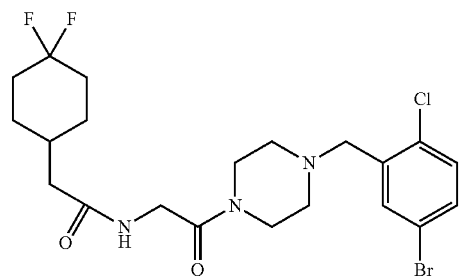 [SMILES: O=C(CC1CCC(F)(F)CC1)NCC(=O)N1CCN(Cc2cc(Br)ccc2Cl)CC1] | >2 |
| 1371 | 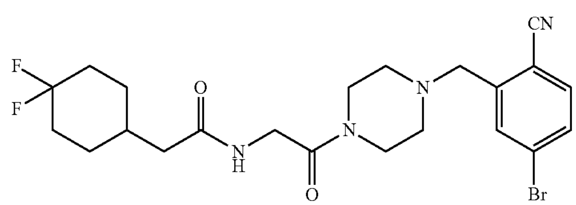 [SMILES: N#Cc1ccc(Br)cc1CN1CCN(C(=O)CNC(=O)CC2CCC(F)(F)CC2)CC1] | >2 |
| 1370 | 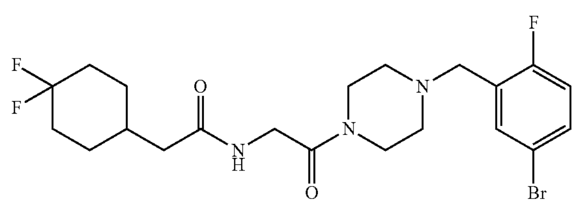 [SMILES: O=C(CC1CCC(F)(F)CC1)NCC(=O)N1CCN(Cc2cc(Br)ccc2F)CC1] | ~2.2 |
| 1369 | 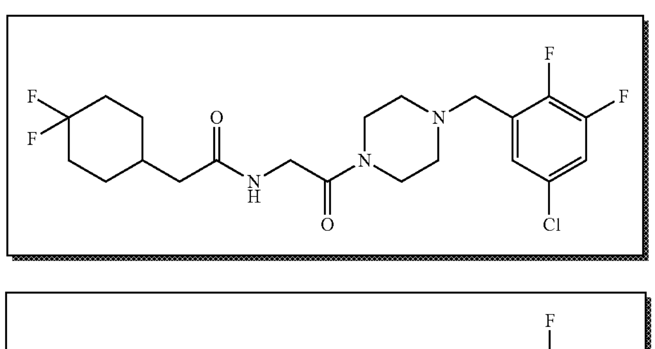 | >2 |
| 1368 | 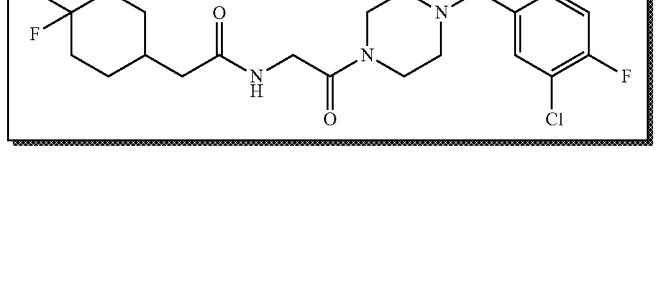 | >2 |

TABLE 1-continued

Exemplary compounds of Formula I and Formula II.

| Compound number | Structure | IC50(uM) |
|---|---|---|
| 1367 | 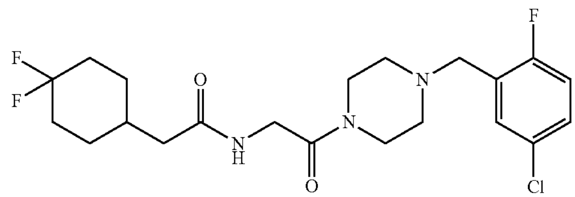 [SMILES: O=C(CC1CCC(F)(F)CC1)NCC(=O)N1CCN(Cc2cc(Cl)ccc2F)CC1] | >2 |
| 1366 | 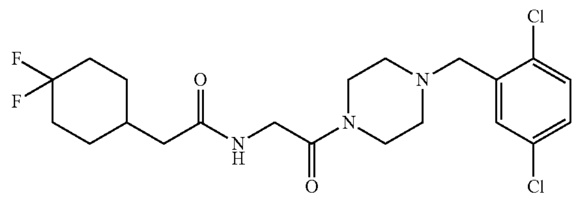 [SMILES: O=C(CC1CCC(F)(F)CC1)NCC(=O)N1CCN(Cc2cc(Cl)ccc2Cl)CC1] | >2 |
| 1358 | 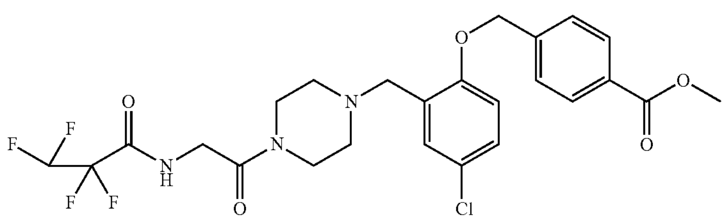 [SMILES: COC(=O)c1ccc(COc2ccc(Cl)cc2CN2CCN(C(=O)CNC(=O)C(F)(F)C(F)F)CC2)cc1] | 0.2 |
| 1357 | 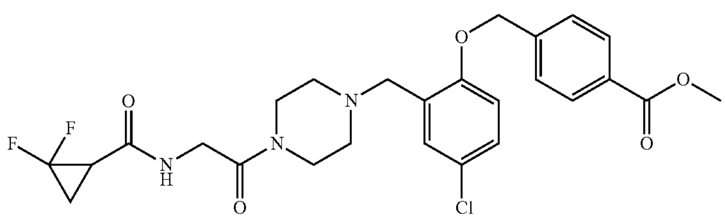 [SMILES: COC(=O)c1ccc(COc2ccc(Cl)cc2CN2CCN(C(=O)CNC(=O)C3CC3(F)F)CC2)cc1] | 0.5 |
| 1356 | 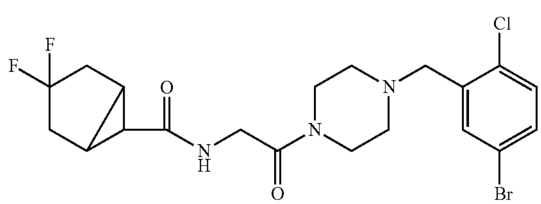 [SMILES: O=C(NCC(=O)N1CCN(Cc2cc(Br)ccc2Cl)CC1)C1C2CC(F)(F)CC21] | >2 |
| 1346 | 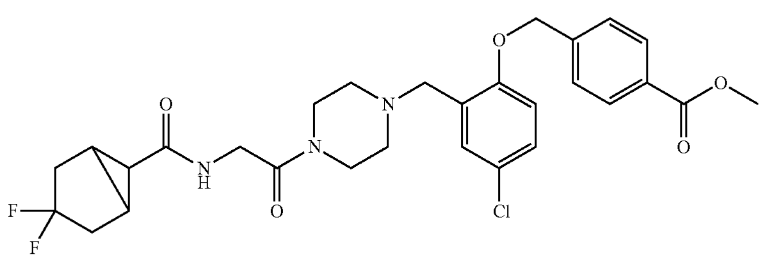 [SMILES: COC(=O)c1ccc(COc2ccc(Cl)cc2CN2CCN(C(=O)CNC(=O)C3C4CC(F)(F)CC43)CC2)cc1] | 0.2 |

TABLE 1-continued

Exemplary compounds of Formula I and Formula II.

| Compound number | Structure | IC50(uM) |
|---|---|---|
| 1344 | 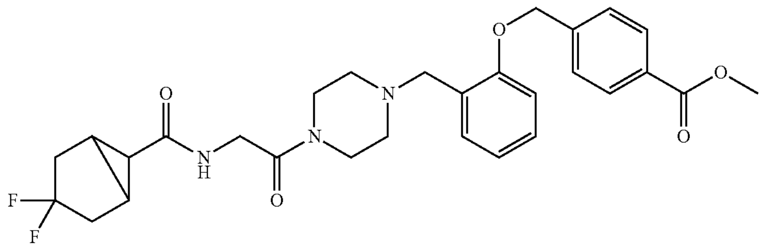 [SMILES: COC(=O)c1ccc(COc2ccccc2CN2CCN(C(=O)CNC(=O)C3C4CC(F)(F)CC43)CC2)cc1] | 0.17 |
| 1328 | 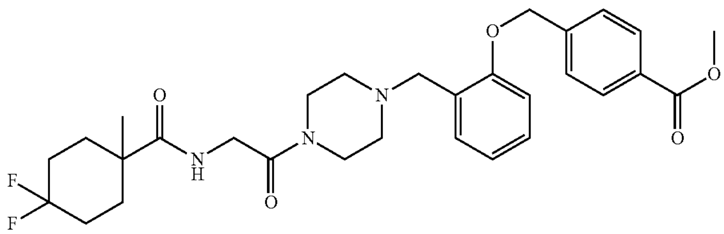 [SMILES: COC(=O)c1ccc(COc2ccccc2CN2CCN(C(=O)CNC(=O)C3(C)CCC(F)(F)CC3)CC2)cc1] | 0.25 |
| 1298 | 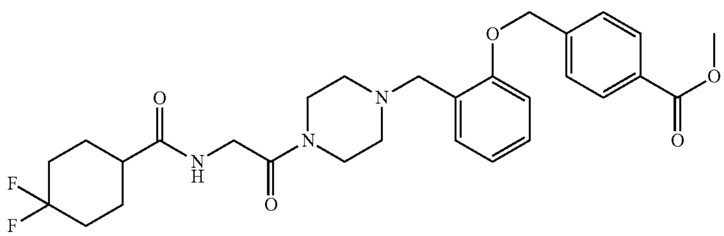 [SMILES: COC(=O)c1ccc(COc2ccccc2CN2CCN(C(=O)CNC(=O)C3CCC(F)(F)CC3)CC2)cc1] | 1.5 |
| 1362 | 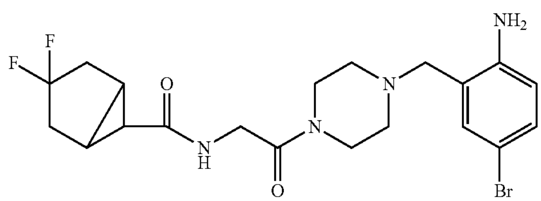 [SMILES: Nc1ccc(Br)cc1CN1CCN(C(=O)CNC(=O)C2C3CC(F)(F)CC32)CC1] | >2 |
| 1355 | 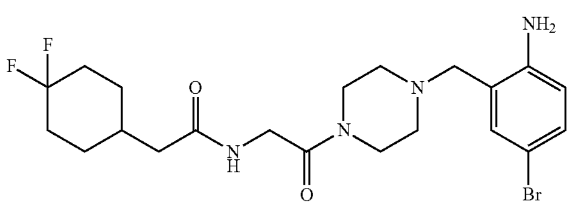 | 1.74 |
| 1343 | 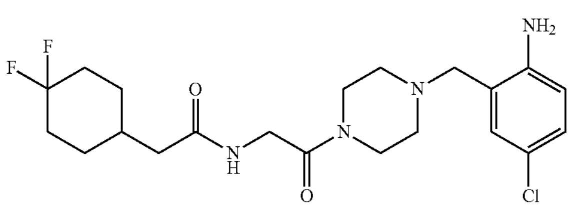 | 0.32 |

TABLE 1-continued

Exemplary compounds of Formula I and Formula II.

| Compound number | Structure | IC50(uM) |
|---|---|---|
| 1336 | 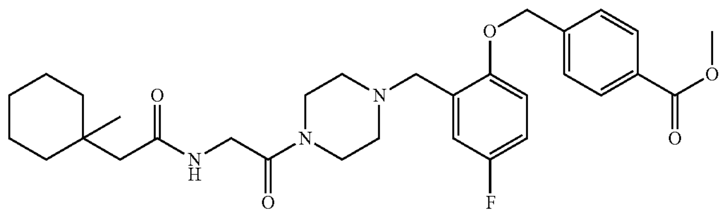 [SMILES: COC(=O)c1ccc(COc2ccc(F)cc2CN2CCN(C(=O)CNC(=O)CC3(C)CCCCC3)CC2)cc1] | 0.051 |
| 1335 | 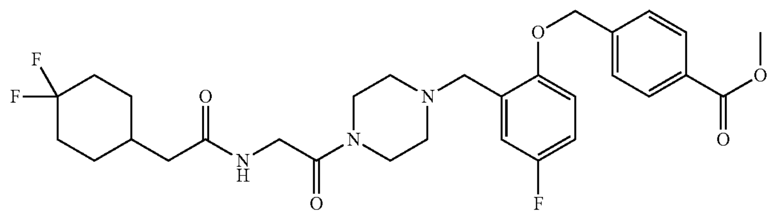 [SMILES: COC(=O)c1ccc(COc2ccc(F)cc2CN2CCN(C(=O)CNC(=O)CC3CCC(F)(F)CC3)CC2)cc1] | 0.018 |
| 1334 | 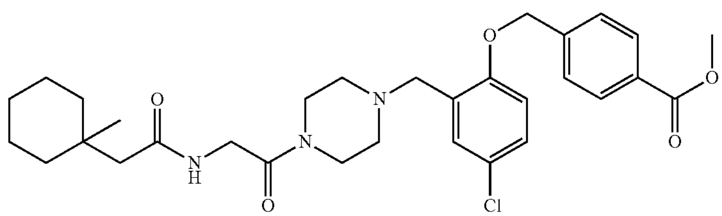 | 0.019 |
| 1333 | 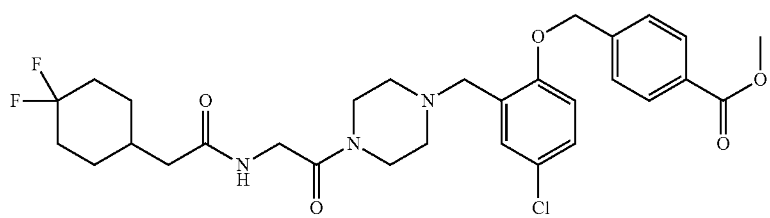 [SMILES: COC(=O)c1ccc(COc2ccc(Cl)cc2CN2CCN(C(=O)CNC(=O)CC3CCC(F)(F)CC3)CC2)cc1] | 0.015 |
| 1320 | 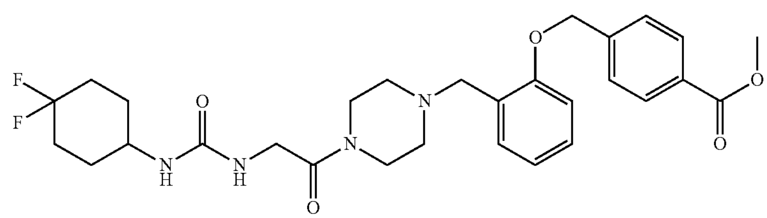 [SMILES: COC(=O)c1ccc(COc2ccccc2CN2CCN(C(=O)CNC(=O)NC3CCC(F)(F)CC3)CC2)cc1] | >2 |
| 1319 | 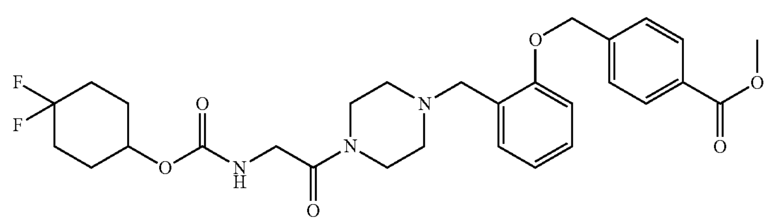 [SMILES: COC(=O)c1ccc(COc2ccccc2CN2CCN(C(=O)CNC(=O)OC3CCC(F)(F)CC3)CC2)cc1] | 0.31 |
| 1317 | 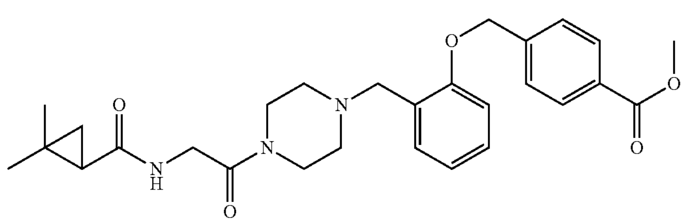 | 0.4 |

TABLE 1-continued
Exemplary compounds of Formula I and Formula II.
| Compound number | Structure | IC50(uM) |
|---|---|---|
| 1376 | 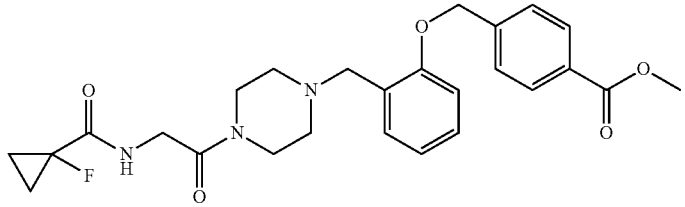 [SMILES: COC(=O)c1ccc(COc2ccccc2CN2CCN(C(=O)CNC(=O)C3(F)CC3)CC2)cc1] | >2 |
| 1316 | 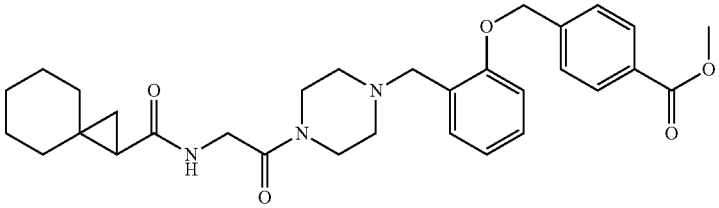 [SMILES: COC(=O)c1ccc(COc2ccccc2CN2CCN(C(=O)CNC(=O)C3CC34CCCCC4)CC2)cc1] | 0.07 |
| 1315 | 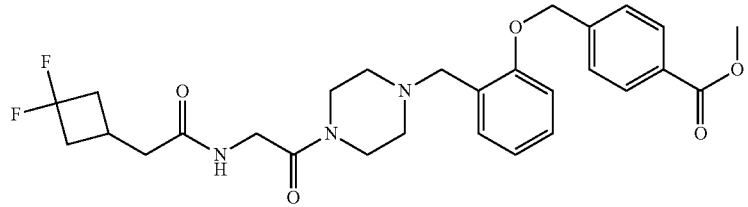 [SMILES: COC(=O)c1ccc(COc2ccccc2CN2CCN(C(=O)CNC(=O)CC3CC(F)(F)C3)CC2)cc1] | 0.4 |
| 1311 | 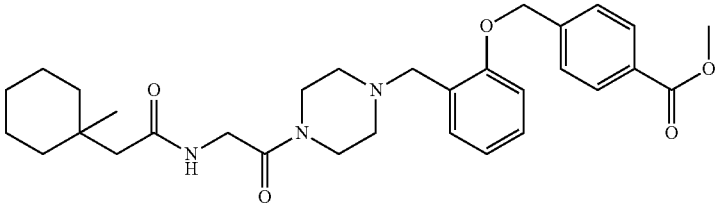 [SMILES: COC(=O)c1ccc(COc2ccccc2CN2CCN(C(=O)CNC(=O)CC3(C)CCCCC3)CC2)cc1] | 0.08 |
| 1142 | 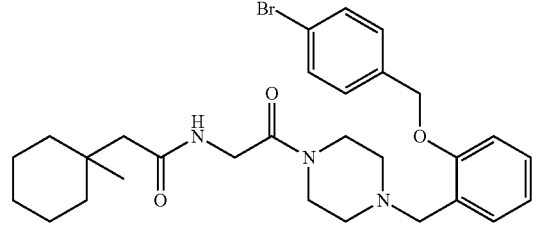 [SMILES: CC1(CC(=O)NCC(=O)N2CCN(Cc3ccccc3OCc3ccc(Br)cc3)CC2)CCCCC1] | 0.52 |
| 1275 | 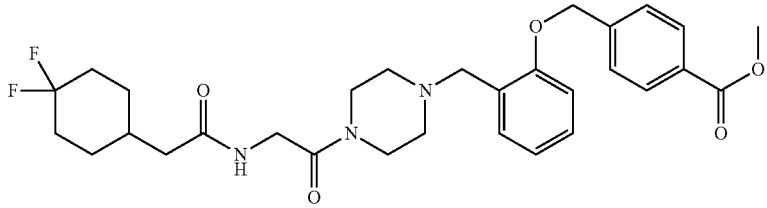 [SMILES: COC(=O)c1ccc(COc2ccccc2CN2CCN(C(=O)CNC(=O)CC3CCC(F)(F)CC3)CC2)cc1] | 0.05 |

TABLE 1-continued
Exemplary compounds of Formula I and Formula II.
| Compound number | Structure | IC50(uM) |
|---|---|---|
| 1138 | 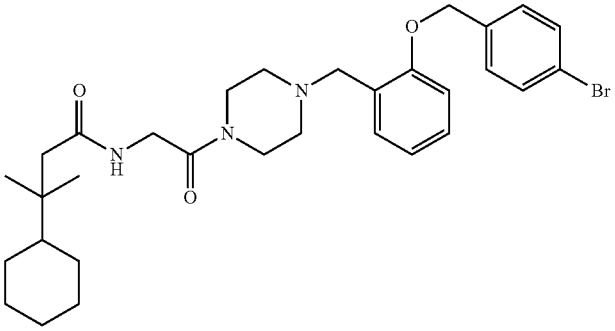 [SMILES: CC(C)(CC(=O)NCC(=O)N1CCN(Cc2ccccc2OCc2ccc(Br)cc2)CC1)C1CCCCC1] | >2 |
| 1279 | 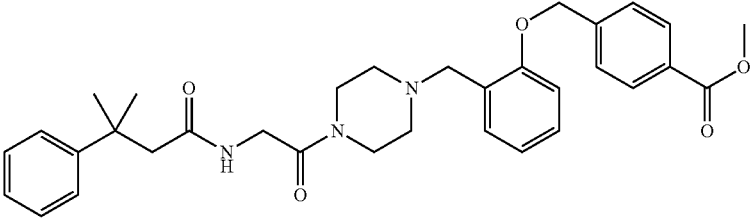 [SMILES: COC(=O)c1ccc(COc2ccccc2CN2CCN(C(=O)CNC(=O)CC(C)(C)c3ccccc3)CC2)cc1] | 1.5 |
| 1278 | 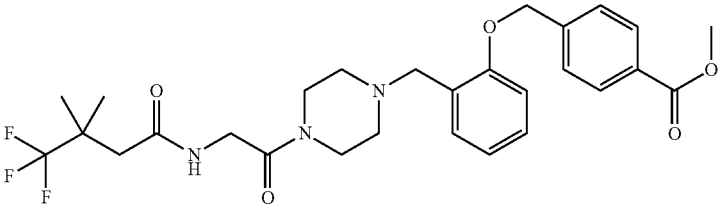 [SMILES: COC(=O)c1ccc(COc2ccccc2CN2CCN(C(=O)CNC(=O)CC(C)(C)C(F)(F)F)CC2)cc1] | >2 |
| 1312 | 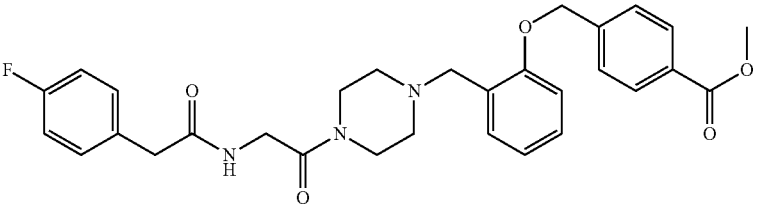 [SMILES: COC(=O)c1ccc(COc2ccccc2CN2CCN(C(=O)CNC(=O)Cc3ccc(F)cc3)CC2)cc1] | 0.6 |
| 1136 | 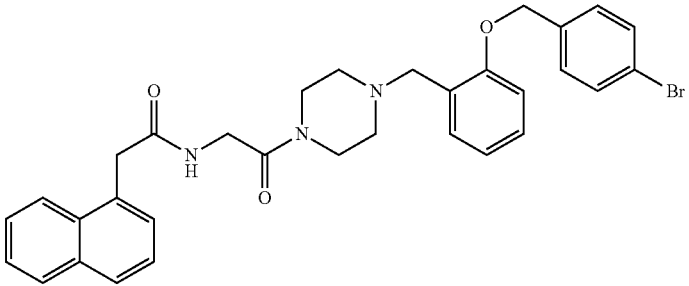 [SMILES: O=C(Cc1cccc2ccccc12)NCC(=O)N1CCN(Cc2ccccc2OCc2ccc(Br)cc2)CC1] | >2 |
| 1277 | 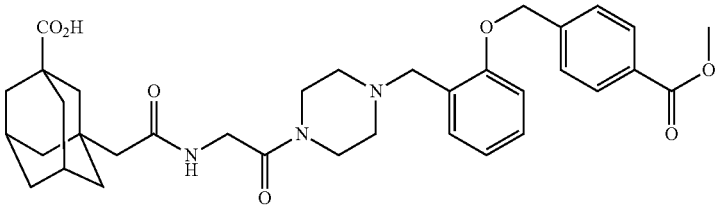 [SMILES: COC(=O)c1ccc(COc2ccccc2CN2CCN(C(=O)CNC(=O)CC34CC5CC(C3)CC(C(=O)O)(C5)C4)CC2)cc1] | >2 |

TABLE 1-continued

Exemplary compounds of Formula I and Formula II.

| Compound number | Structure | IC50(uM) |
|---|---|---|
| 1246 | 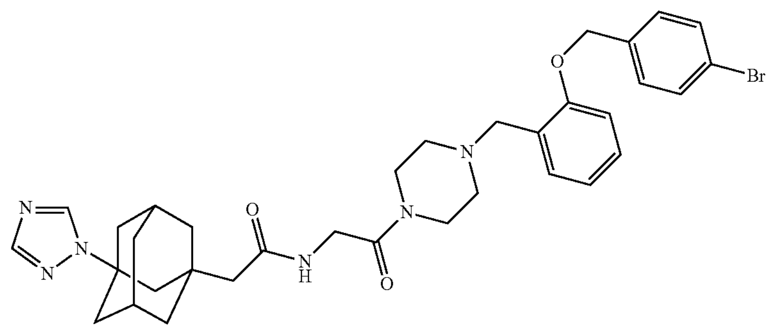 [SMILES: O=C(CC12CC3CC(C1)CC(n1cncn1)(C3)C2)NCC(=O)N1CCN(Cc2ccccc2OCc2ccc(Br)cc2)CC1] | <2 |
| 1141 | 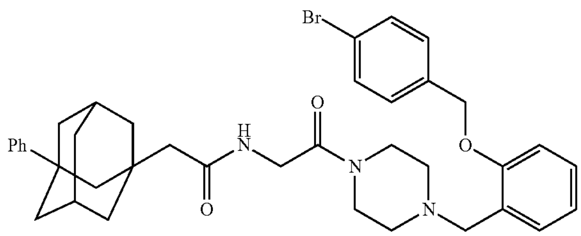 [SMILES: O=C(CC12CC3CC(C1)CC(c1ccccc1)(C3)C2)NCC(=O)N1CCN(Cc2ccccc2OCc2ccc(Br)cc2)CC1] | 0.7 |
| 1245 | 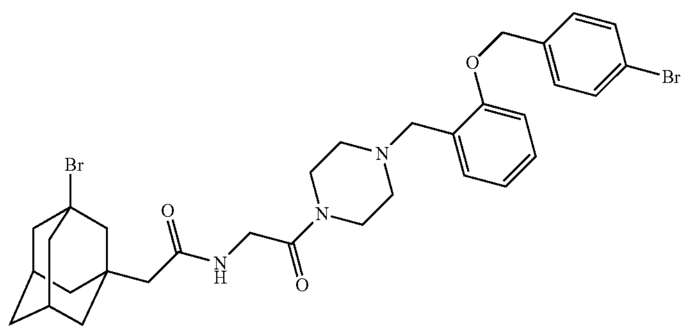 | 0.6 |
| 1244 | 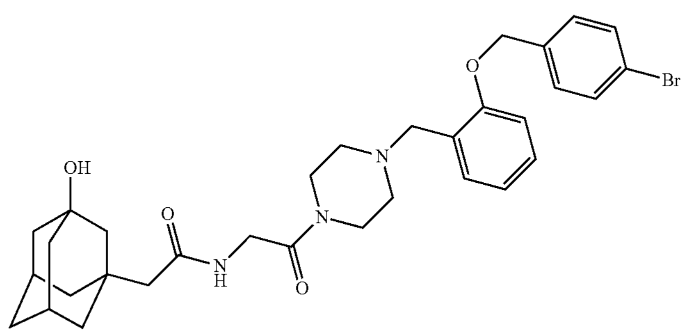 [SMILES: O=C(CC12CC3CC(CC(O)(C3)C1)C2)NCC(=O)N1CCN(Cc2ccccc2OCc2ccc(Br)cc2)CC1] | 0.5 |
| 1243 | 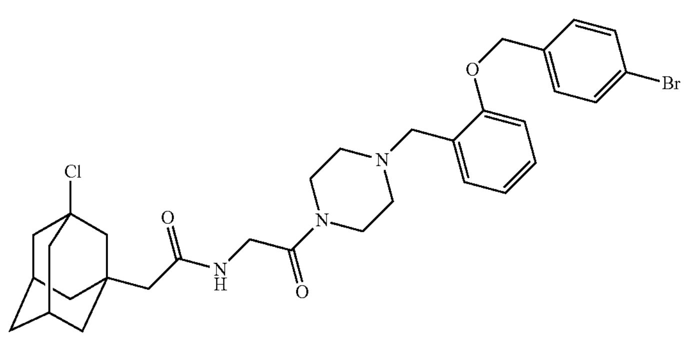 [SMILES: O=C(CC12CC3CC(CC(Cl)(C3)C1)C2)NCC(=O)N1CCN(Cc2ccccc2OCc2ccc(Br)cc2)CC1] | 0.5 |

TABLE 1-continued

Expemplary compounds of Formula I and Formula II.

| Compound number | Structure | IC50(uM) |
|---|---|---|
| 1255 | 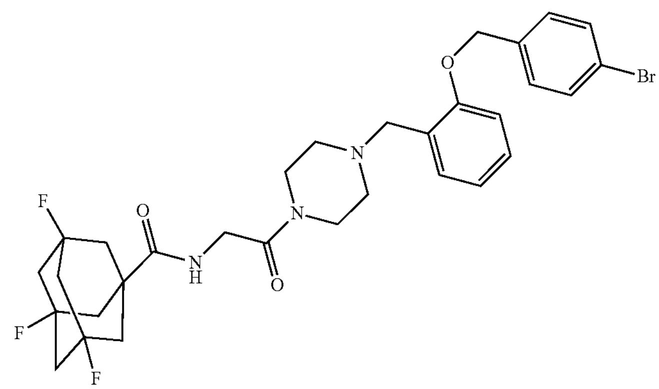 [SMILES: O=C(CNC(=O)C12CC3(F)CC(F)(CC(F)(C3)C1)C2)N1CCN(Cc2ccccc2OCc2ccc(Br)cc2)CC1] | 0.4 |
| 1254 | 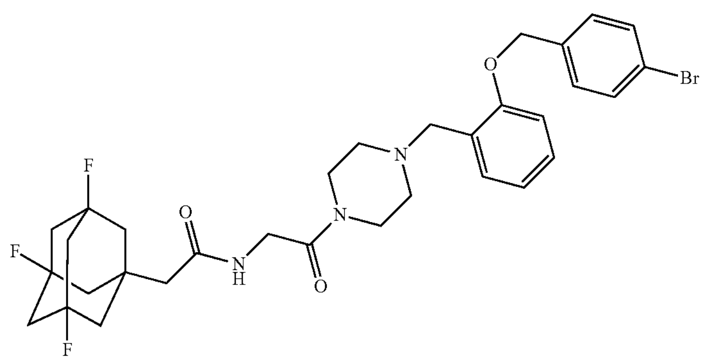 [SMILES: O=C(CC12CC3(F)CC(F)(CC(F)(C3)C1)C2)NCC(=O)N1CCN(Cc2ccccc2OCc2ccc(Br)cc2)CC1] | 0.2 |
| 1253 | 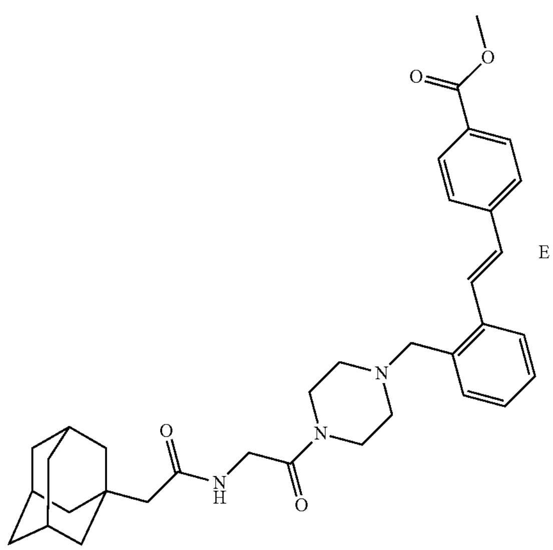 [SMILES: COC(=O)c1ccc(/C=C/c2ccccc2CN2CCN(C(=O)CNC(=O)CC34CC5CC(CC(C5)C3)C4)CC2)cc1] | 1.5 |

TABLE 1-continued

Exemplary compounds of Formula I and Formula II.

| Compound number | Structure | IC50(uM) |
|---|---|---|
| 1123 | 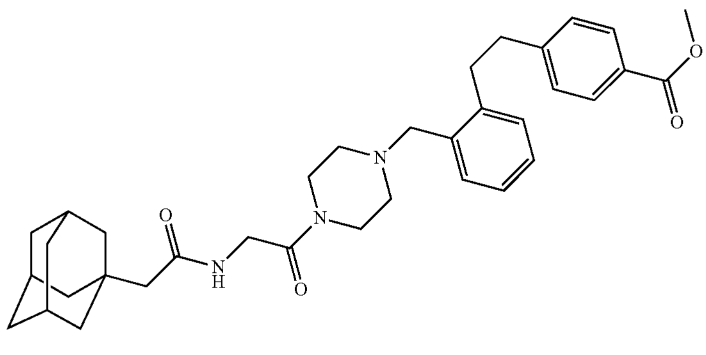 [SMILES: COC(=O)c1ccc(CCc2ccccc2CN2CCN(C(=O)CNC(=O)CC34CC5CC(CC(C5)C3)C4)CC2)cc1] | 0.02 |
| 1112 | 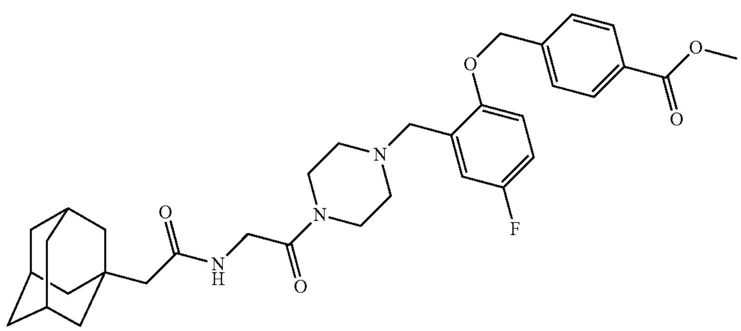 | <2 |
| 1118 | 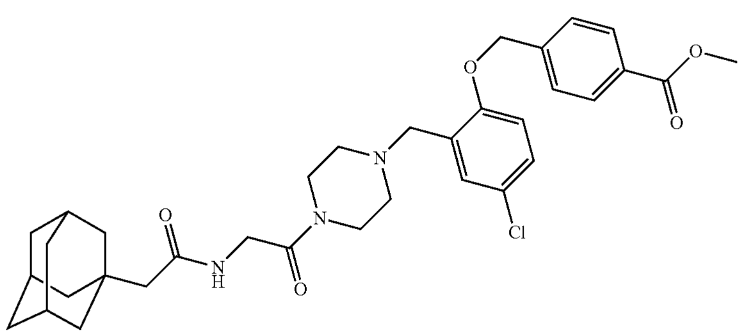 [SMILES: COC(=O)c1ccc(COc2ccc(F)cc2CN2CCN(C(=O)CNC(=O)CC34CC5CC(CC(C5)C3)C4)CC2)cc1] | 0.001 |
| 1111 | 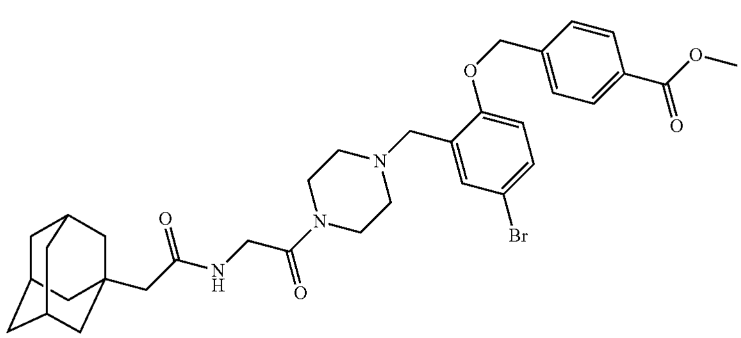 [SMILES: COC(=O)c1ccc(COc2ccc(Br)cc2CN2CCN(C(=O)CNC(=O)CC34CC5CC(CC(C5)C3)C4)CC2)cc1] | 0.013 |

TABLE 1-continued
Exemplary compounds of Formula I and Formula II.
| Compound number | Structure | IC50(uM) |
|---|---|---|
| 1114 | 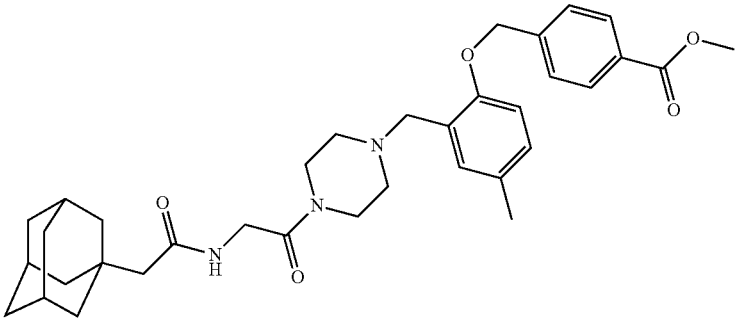 | <2 |
| 1115 | 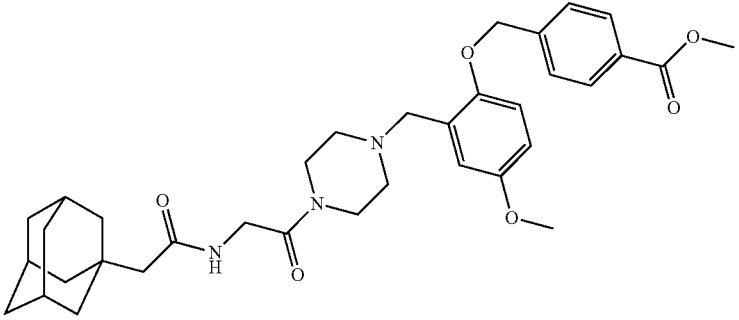 [SMILES: COC(=O)c1ccc(COc2ccc(OC)cc2CN2CCN(C(=O)CNC(=O)CC34CC5CC(CC(C5)C3)C4)CC2)cc1] | 1.4 |
| 1117 | 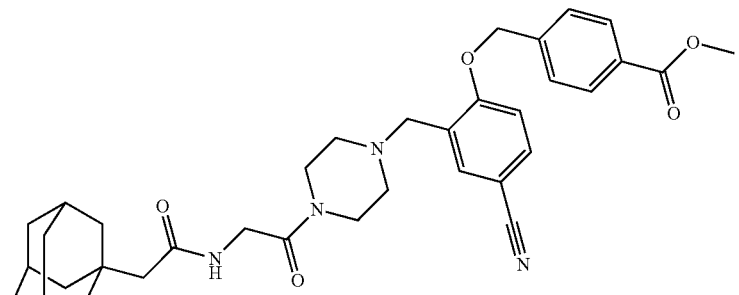 | 0.05 |
| 1113 | 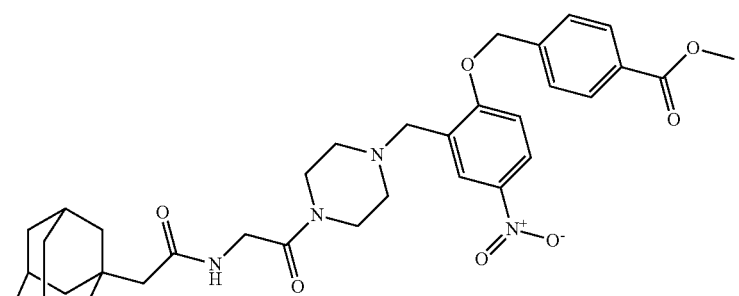 | <2 |
| 1310 | 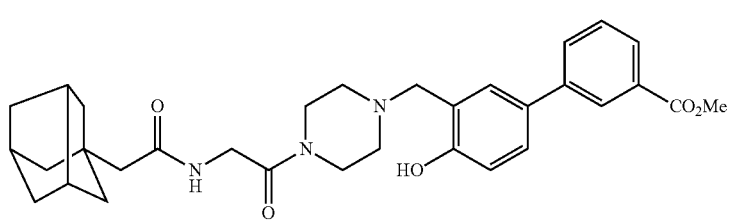 [SMILES: COC(=O)c1cccc(-c2ccc(O)c(CN3CCN(C(=O)CNC(=O)CC45CC6CC(C4)C(C6)C5)CC3)c2)c1] | 0.31 |

TABLE 1-continued
Exemplary compounds of Formula I and Formula II.
| Compound number | Structure | IC50(uM) |
|---|---|---|
| 1325 | 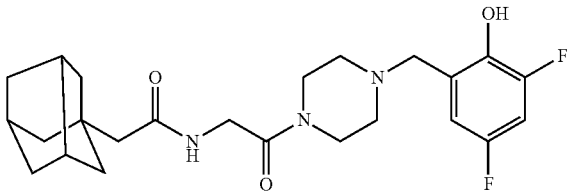 [SMILES: O=C(CC12CC3CC(C1)C(C3)C2)NCC(=O)N1CCN(Cc2cc(F)cc(F)c2O)CC1] | 1 |
| 1324 | 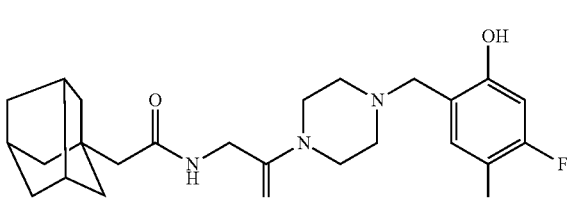 | 1.5 |
| 1349 | 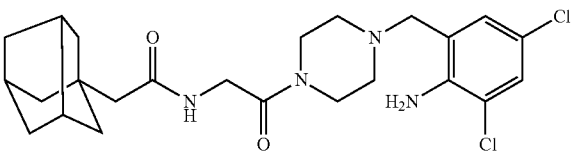 | 0.5 |
| 1321 | 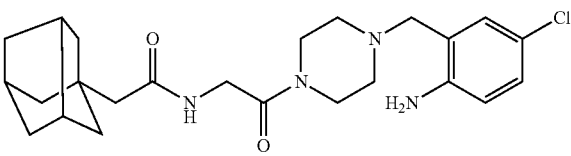 [SMILES: Nc1ccc(Cl)cc1CN1CCN(C(=O)CNC(=O)CC23CC4CC(C2)C(C4)C3)CC1] | 0.09 |
| 1342 | 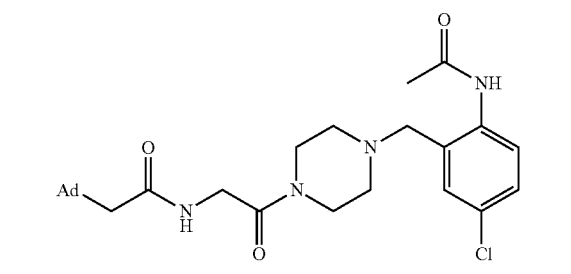 | 1.1 |
| 1341 | 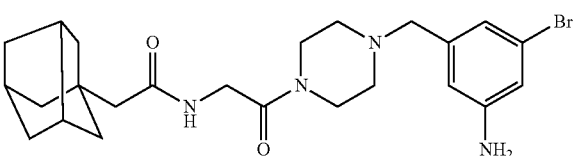 | 0.32 |
| 1340 | 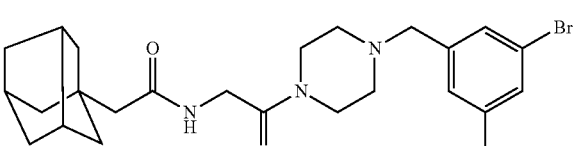 | 1.27 |

TABLE 1-continued

Exemplary compounds of Formula I and Formula II.

| Compound number | Structure | IC50(uM) |
|---|---|---|
| 1026 | 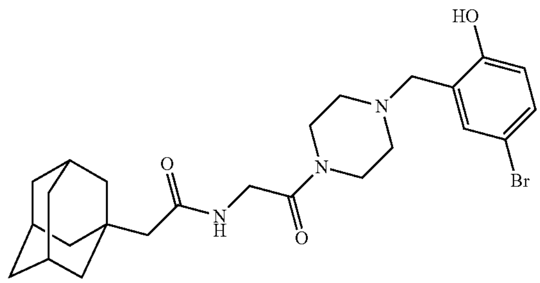 | 0.3-0.5 |
| 1249 | 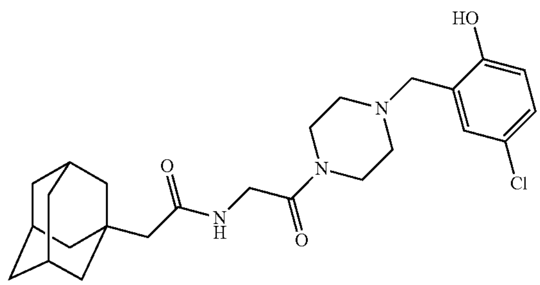 [SMILES: O=C(CC12CC3CC(CC(C3)C1)C2)NCC(=O)N1CCN(Cc2cc(Cl)ccc2O)CC1] | 0.2 |
| 1304 | 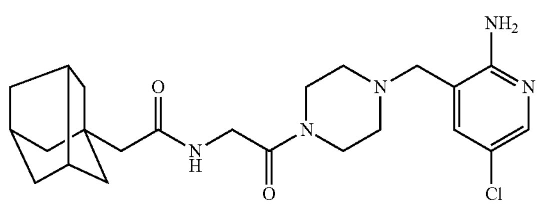 [SMILES: Nc1ncc(Cl)cc1CN1CCN(C(=O)CNC(=O)CC23CC4CC(C2)C(C4)C3)CC1] | >1.5 |
| 1252 | 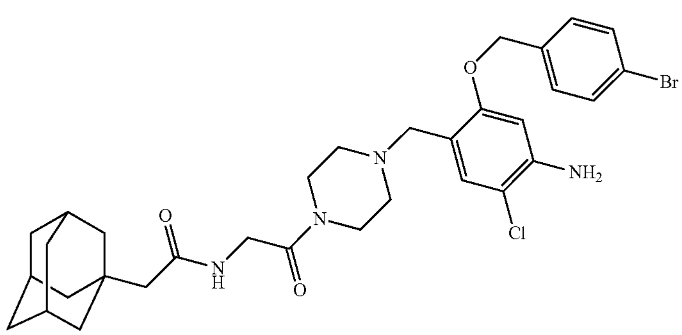 [SMILES: Nc1cc(OCc2ccc(Br)cc2)c(CN2CCN(C(=O)CNC(=O)CC34CC5CC(CC(C5)C3)C4)CC2)cc1Cl] | 0.8 |
| 1251 | 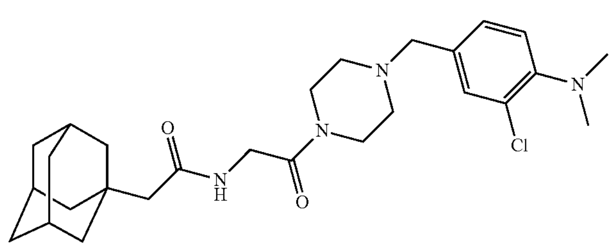 [SMILES: CN(C)c1ccc(CN2CCN(C(=O)CNC(=O)CC34CC5CC(CC(C5)C3)C4)CC2)cc1Cl] | 1.7 |

TABLE 1-continued

Exemplary compounds of Formula I and Formula II.

| Compound number | Structure | IC50(uM) |
|---|---|---|
| 1250 | 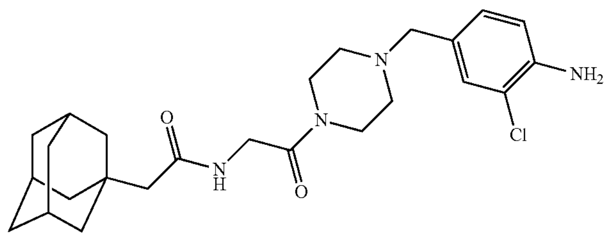 [SMILES: Nc1ccc(CN2CCN(C(=O)CNC(=O)CC34CC5CC(CC(C5)C3)C4)CC2)cc1Cl] | 0.8 |
| 1122 | 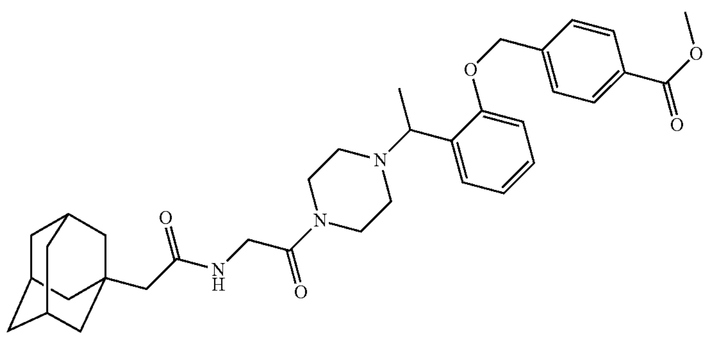 [SMILES: COC(=O)c1ccc(COc2ccccc2C(C)N2CCN(C(=O)CNC(=O)CC34CC5CC(CC(C5)C3)C4)CC2)cc1] | ~2 |
| 1260 | 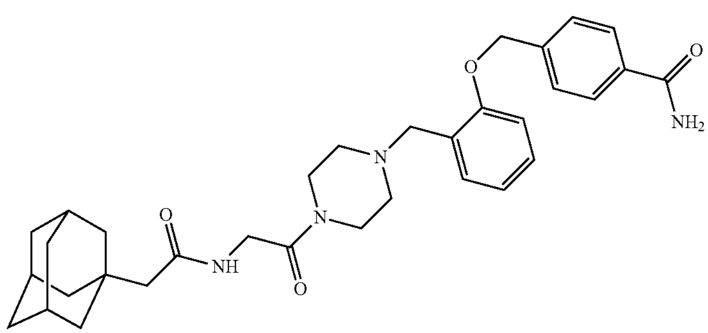 [SMILES: NC(=O)c1ccc(COc2ccccc2CN2CCN(C(=O)CNC(=O)CC34CC5CC(CC(C5)C3)C4)CC2)cc1] | 0.7 |
| 1259 | 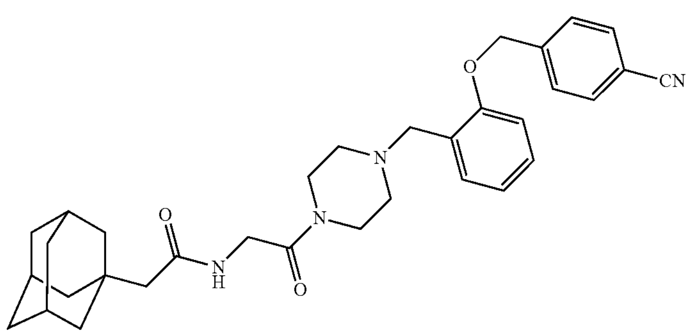 [SMILES: N#Cc1ccc(COc2ccccc2CN2CCN(C(=O)CNC(=O)CC34CC5CC(CC(C5)C3)C4)CC2)cc1] | 0.7 |

TABLE 1-continued

Expemplary compounds of Formula I and Formula II.

| Compound number | Structure | IC50(uM) |
|---|---|---|
| 1258 | 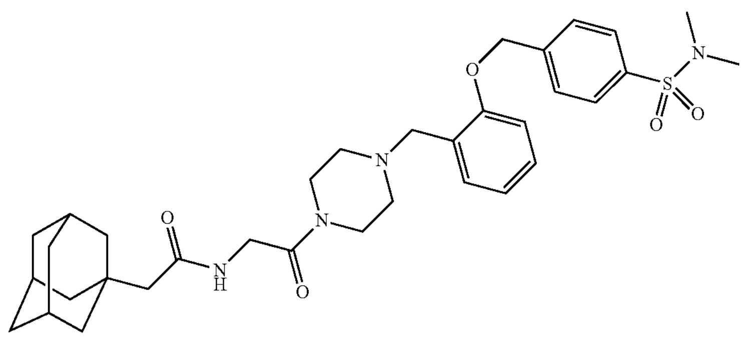 [SMILES: CN(C)S(=O)(=O)c1ccc(COc2ccccc2CN2CCN(C(=O)CNC(=O)CC34CC5CC(CC(C5)C3)C4)CC2)cc1] | 0.4 |
| 1257 | 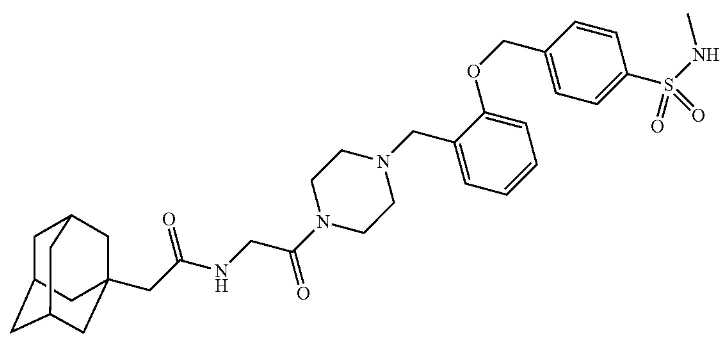 [SMILES: CNS(=O)(=O)c1ccc(COc2ccccc2CN2CCN(C(=O)CNC(=O)CC34CC5CC(CC(C5)C3)C4)CC2)cc1] | 0.3 |
| 1256 | 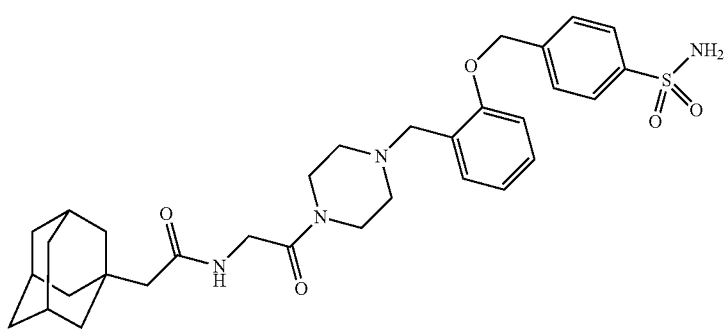 [SMILES: NS(=O)(=O)c1ccc(COc2ccccc2CN2CCN(C(=O)CNC(=O)CC34CC5CC(CC(C5)C3)C4)CC2)cc1] | |
| 1444 | 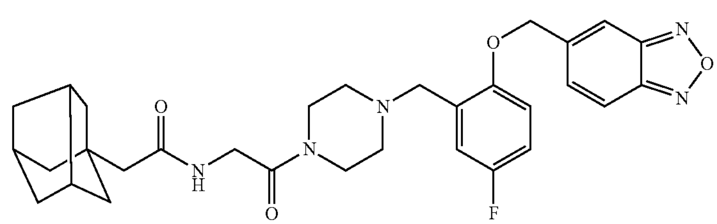 [SMILES: O=C(CC12CC3CC(C1)C(C3)C2)NCC(=O)N1CCN(Cc2cc(F)ccc2OCc2ccc3nonc3c2)CC1] | 0.025 |
| 1443 | 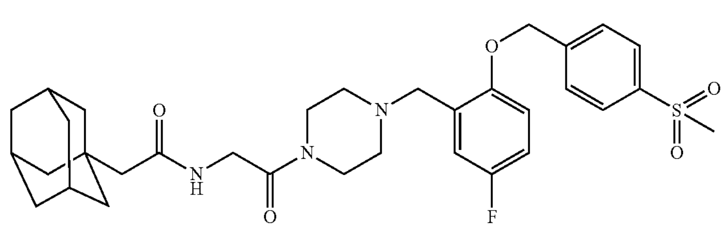 [SMILES: CS(=O)(=O)c1ccc(COc2ccc(F)cc2CN2CCN(C(=O)CNC(=O)CC34CC5CC(CC(C5)C3)C4)CC2)cc1] | 0.0045 |

TABLE 1-continued
Exemplary compounds of Formula I and Formula II.
| Compound number | Structure | IC50(uM) |
|---|---|---|
| 1441 | 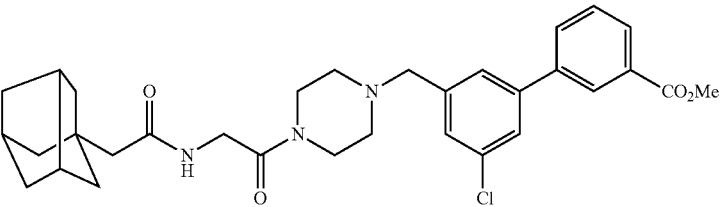 [SMILES: COC(=O)c1cccc(-c2cc(Cl)cc(CN3CCN(C(=O)CNC(=O)CC45CC6CC(C4)C(C6)C5)CC3)c2)c1] | 0.248 |
| 1445 | 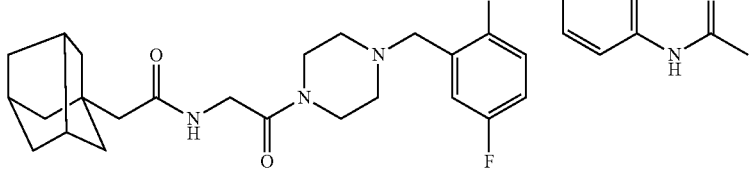 | 0.71 |
| 1323 | 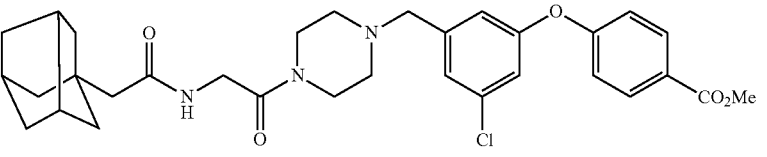 [SMILES: COC(=O)c1ccc(Oc2cc(Cl)cc(CN3CCN(C(=O)CNC(=O)CC45CC6CC(C4)C(C6)C5)CC3)c2)cc1] | 0.015 |
| 1322 | 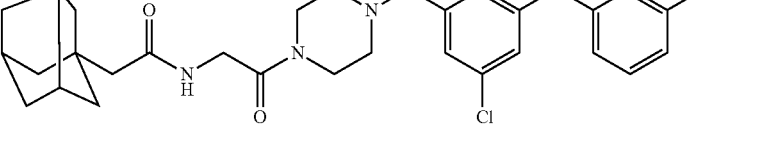 | 0.011 |
| 1301 | 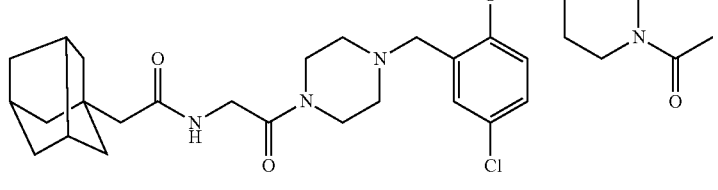 | 0.4 |
| 1303 | 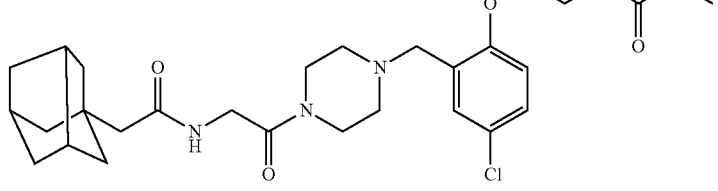 | ~2 |
| 1302 | 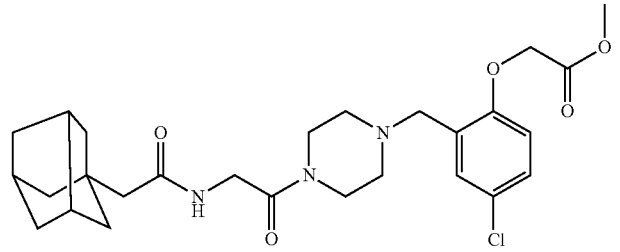 [SMILES: COC(=O)COc1ccc(Cl)cc1CN1CCN(C(=O)CNC(=O)CC23CC4CC(C2)C(C4)C3)CC1] | >2 |

TABLE 1-continued
Expemplary compounds of Formula I and Formula II.
| Compound number | Structure | IC50(uM) |
|---|---|---|
| 1354 | 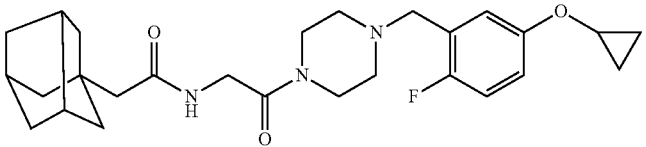 [SMILES: O=C(CC12CC3CC(C1)C(C3)C2)NCC(=O)N1CCN(Cc2cc(OC3CC3)ccc2F)CC1] | >2 |
| 1330 | 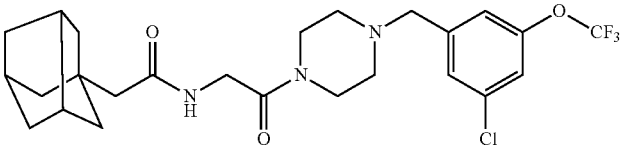 [SMILES: O=C(CC12CC3CC(C1)C(C3)C2)NCC(=O)N1CCN(Cc2cc(Cl)cc(OC(F)(F)F)c2)CC1] | 1.51 |
| 1309 | 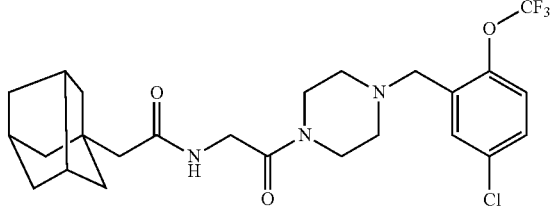 [SMILES: O=C(CC12CC3CC(C1)C(C3)C2)NCC(=O)N1CCN(Cc2cc(Cl)ccc2OC(F)(F)F)CC1] | 0.42 |
| 1352 | 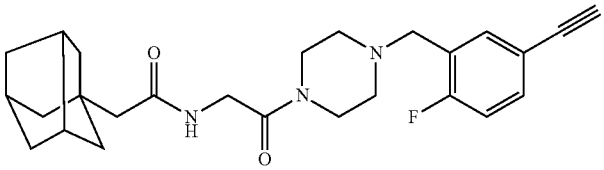 [SMILES: C#Cc1ccc(F)c(CN2CCN(C(=O)CNC(=O)CC34CC5CC(C3)C(C5)C4)CC2)c1] | 1.7 |
| 1332 | 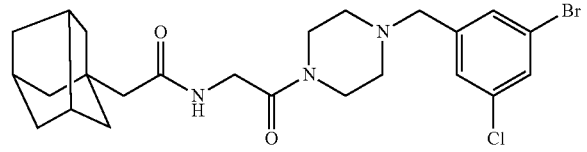 [SMILES: O=C(CC12CC3CC(C1)C(C3)C2)NCC(=O)N1CCN(Cc2cc(Cl)cc(Br)c2)CC1] | 0.9 |
| 1329 | 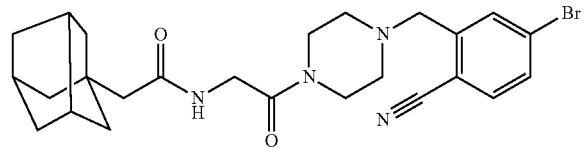 [SMILES: N#Cc1ccc(Br)cc1CN1CCN(C(=O)CNC(=O)CC23CC4CC(C2)C(C4)C3)CC1] | 0.31 |
| 1327 | 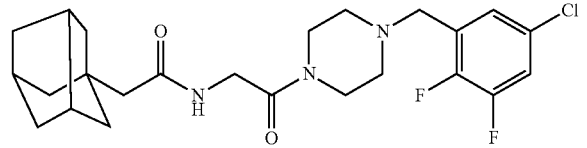 [SMILES: O=C(CC12CC3CC(C1)C(C3)C2)NCC(=O)N1CCN(Cc2cc(Cl)cc(F)c2F)CC1] | 0.67 |
| 1326 | 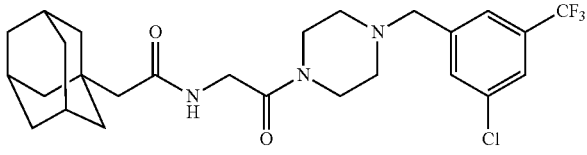 [SMILES: O=C(CC12CC3CC(CC(C3)C1)C2)NCC(=O)N1CCN(Cc2cc(Cl)cc(C(F)(F)F)c2)CC1] | 0.92 |

TABLE 1-continued
Exemplary compounds of Formula I and Formula II.
| Compound number | Structure | IC50(uM) |
|---|---|---|
| 1363 | 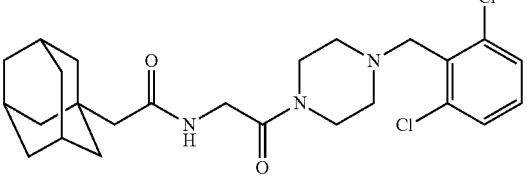 | 1.0 |
| 1353 | 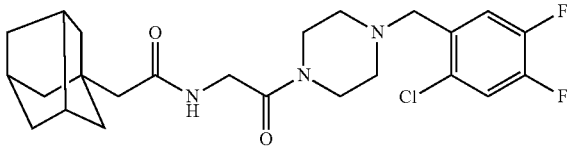 [SMILES: O=C(CC12CC3CC(C1)C(C3)C2)NCC(=O)N1CCN(Cc2cc(F)c(F)cc2Cl)CC1] | 1.5 |
| 1351 | 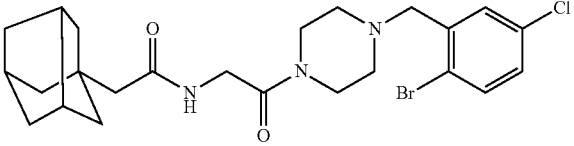 [SMILES: O=C(CC12CC3CC(C1)C(C3)C2)NCC(=O)N1CCN(Cc2cc(Cl)ccc2Br)CC1] | 1.1 |
| 1350 | 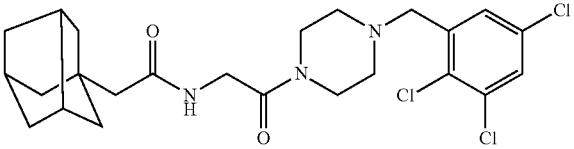 [SMILES: O=C(CC12CC3CC(C1)C(C3)C2)NCC(=O)N1CCN(Cc2cc(Cl)cc(Cl)c2Cl)CC1] | 0.8 |
| 1348 | 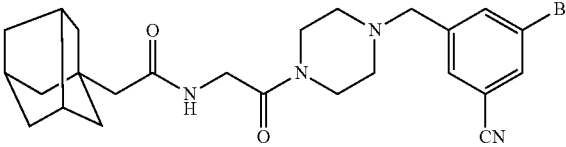 | 1.3 |
| 1339 | 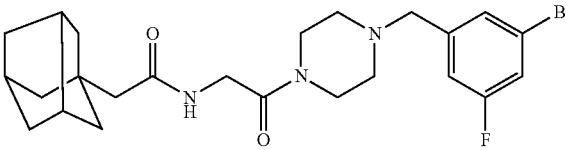 | 1.4 |
| 1338 | 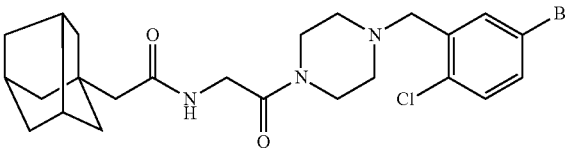 | 0.082 |
| 1337 | 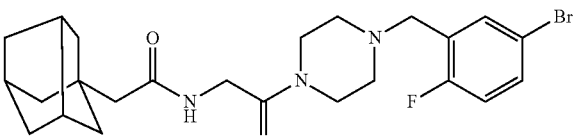 | 1.2 |
| 1308 | 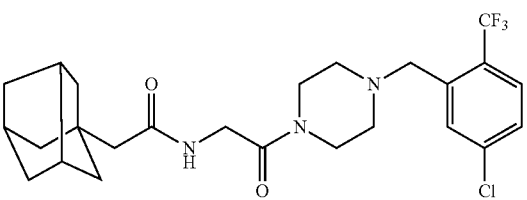 [SMILES: O=C(CC12CC3CC(C1)C(C3)C2)NCC(=O)N1CCN(Cc2cc(Cl)ccc2C(F)(F)F)CC1] | >2 |

TABLE 1-continued

Exemplary compounds of Formula I and Formula II.

| Compound number | Structure | IC50(uM) |
|---|---|---|
| 1307 | 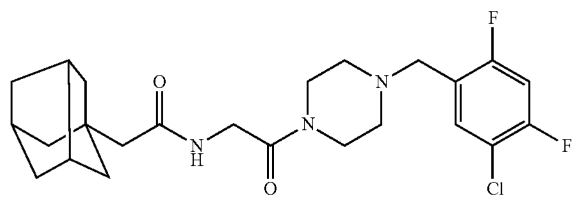 [SMILES: O=C(CC12CC3CC(C1)C(C3)C2)NCC(=O)N1CCN(Cc2cc(Cl)c(F)cc2F)CC1] | 0.37 |
| 1306 | 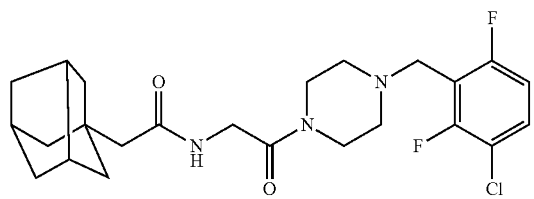 [SMILES: O=C(CC12CC3CC(C1)C(C3)C2)NCC(=O)N1CCN(Cc2c(F)ccc(Cl)c2F)CC1] | 1.35 |
| 1305 | 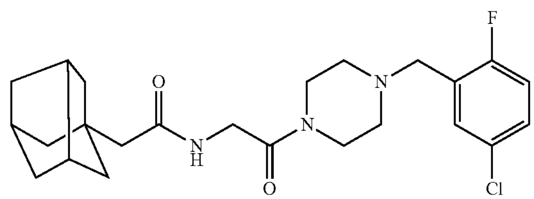 [SMILES: O=C(CC12CC3CC(C1)C(C3)C2)NCC(=O)N1CCN(Cc2cc(Cl)ccc2F)CC1] | 0.36 |
| 1364 | 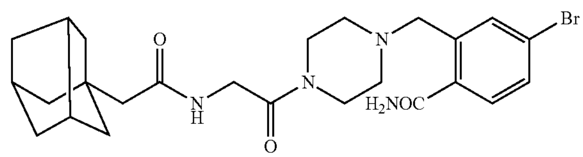 [SMILES: NC(=O)c1ccc(Br)cc1CN1CCN(C(=O)CNC(=O)CC23CC4CC(C2)C(C4)C3)CC1] | 1.9 |
| 1512 | 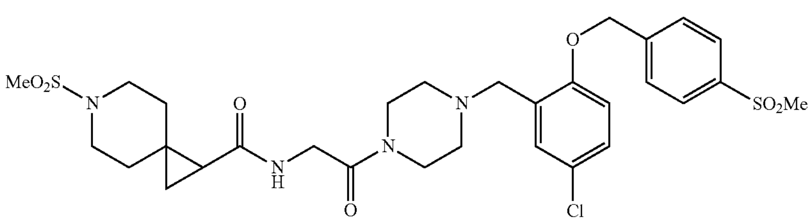 [SMILES: CS(=O)(=O)c1ccc(COc2ccc(Cl)cc2CN2CCN(C(=O)CNC(=O)C3CC34CCN(S(C)(=O)=O)CC4)CC2)cc1] | |
| 1511 | 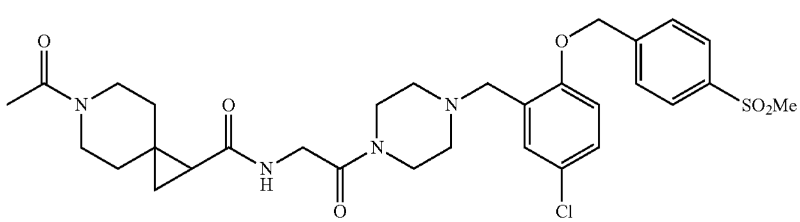 [SMILES: CC(=O)N1CCC2(CC1)CC2C(=O)NCC(=O)N1CCN(Cc2cc(Cl)ccc2OCc2ccc(S(C)(=O)=O)cc2)CC1] | |
| 1508 | 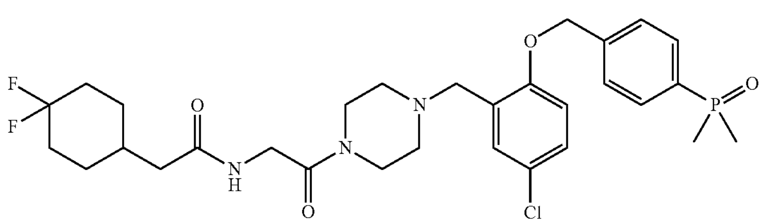 [SMILES: CP(C)(=O)c1ccc(COc2ccc(Cl)cc2CN2CCN(C(=O)CNC(=O)CC3CCC(F)(F)CC3)CC2)cc1] | |

TABLE 1-continued

Exemplary compounds of Formula I and Formula II.

| Compound number | Structure | IC50(uM) |
|---|---|---|
| 1507 | 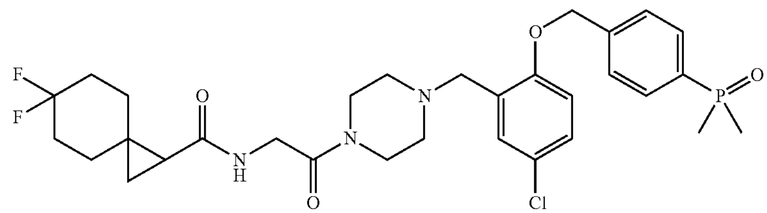 [SMILES: CP(C)(=O)c1ccc(COc2ccc(Cl)cc2CN2CCN(C(=O)CNC(=O)C3CC34CCC(F)(F)CC4)CC2)cc1] | |
| 1506 | 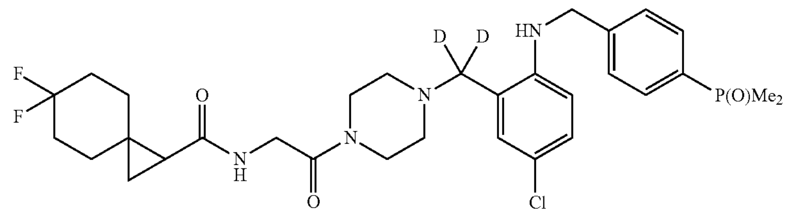 | |
| 1503 | 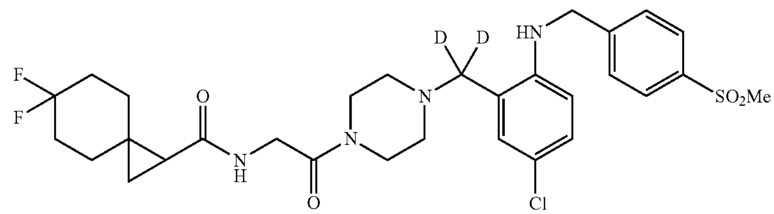 [SMILES: [2H]C([2H])(c1cc(Cl)ccc1NCc1ccc(S(C)(=O)=O)cc1)N1CCN(C(=O)CNC(=O)C2CC23CCC(F)(F)CC3)CC1] | |
| 1496 | 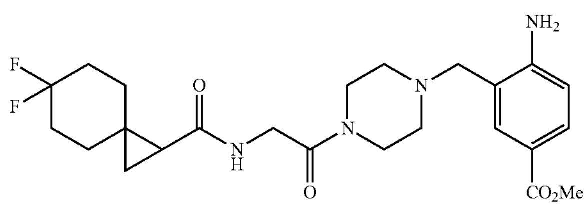 [SMILES: COC(=O)c1ccc(N)c(CN2CCN(C(=O)CNC(=O)C3CC34CCC(F)(F)CC4)CC2)c1] | |
| 1488 | 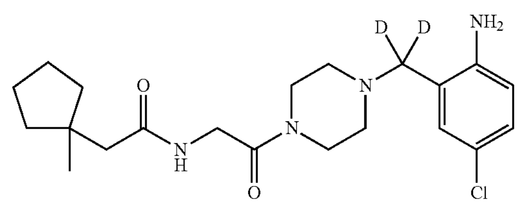 [SMILES: [2H]C([2H])(c1cc(Cl)ccc1N)N1CCN(C(=O)CNC(=O)CC2(C)CCCC2)CC1] | |
| 1478 | 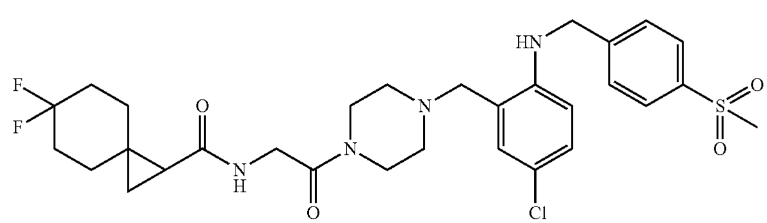 [SMILES: CS(=O)(=O)c1ccc(CNc2ccc(Cl)cc2CN2CCN(C(=O)CNC(=O)C3CC34CCC(F)(F)CC4)CC2)cc1] | |
| 1477 | 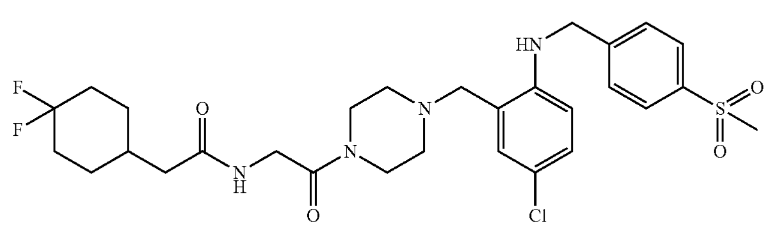 [SMILES: CS(=O)(=O)c1ccc(CNc2ccc(Cl)cc2CN2CCN(C(=O)CNC(=O)CC3CCC(F)(F)CC3)CC2)cc1] | |

TABLE 1-continued

Exemplary compounds of Formula I and Formula II.

| Compound number | Structure | IC50(uM) |
|---|---|---|
| 1476 | 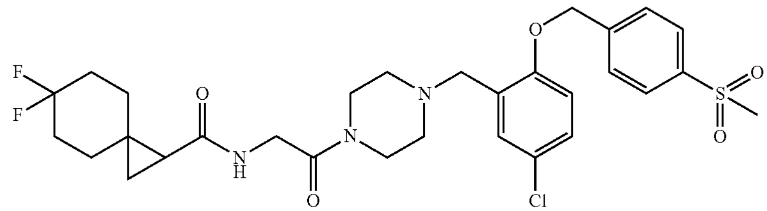 | |
| 1475 | 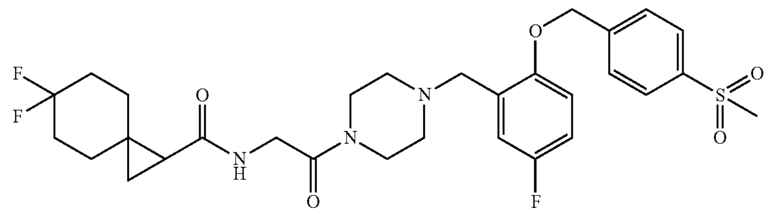 [SMILES: CS(=O)(=O)c1ccc(COc2ccc(F)cc2CN2CCN(C(=O)CNC(=O)C3CC34CCC(F)(F)CC4)CC2)cc1] | |
| 1473 | 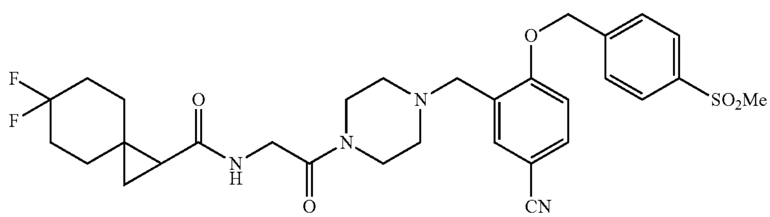 [SMILES: CS(=O)(=O)c1ccc(COc2ccc(C#N)cc2CN2CCN(C(=O)CNC(=O)C3CC34CCC(F)(F)CC4)CC2)cc1] | |
| 1472 | 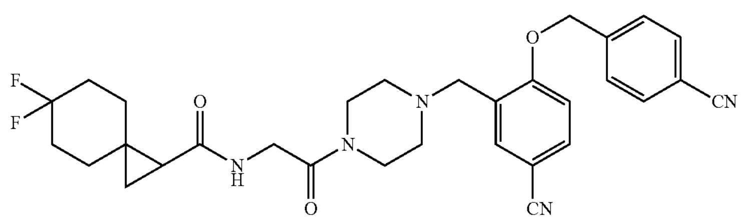 [SMILES: N#Cc1ccc(COc2ccc(Cl)cc2CN2CCN(C(=O)CNC(=O)C3CC34CCC(F)(F)CC4)CC2)cc1] | |
| 1471 | 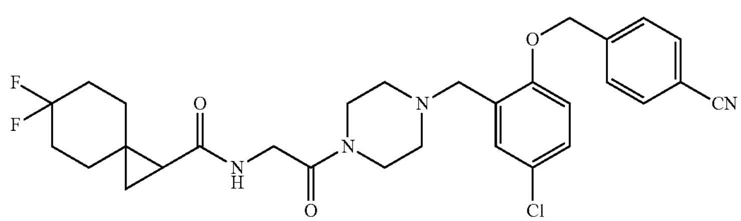 | |
| 1470 | 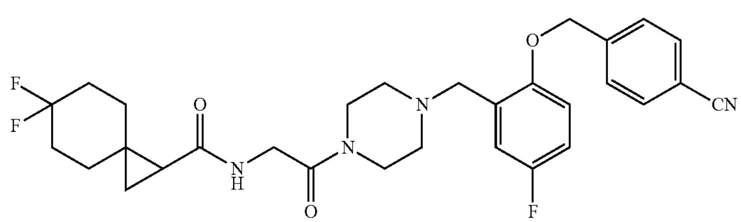 [SMILES: N#Cc1ccc(COc2ccc(F)cc2CN2CCN(C(=O)CNC(=O)C3CC34CCC(F)(F)CC4)CC2)cc1] | |
| 1465 | 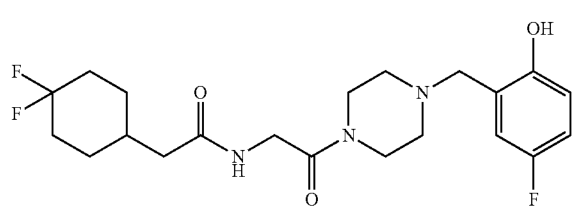 [SMILES: O=C(CC1CCC(F)(F)CC1)NCC(=O)N1CCN(Cc2cc(F)ccc2O)CC1] | |

TABLE 1-continued

Exemplary compounds of Formula I and Formula II.

| Compound number | Structure | IC50(uM) |
|---|---|---|
| 1462 | 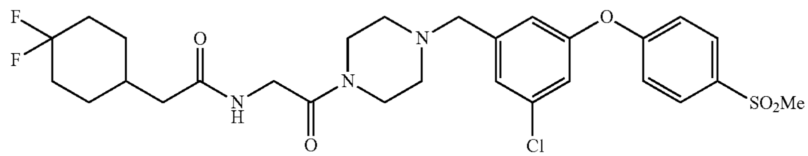 [SMILES: CS(=O)(=O)c1ccc(Oc2cc(Cl)cc(CN3CCN(C(=O)CNC(=O)CC4CCC(F)(F)CC4)CC3)c2)cc1] | >1 |
| 1461 | 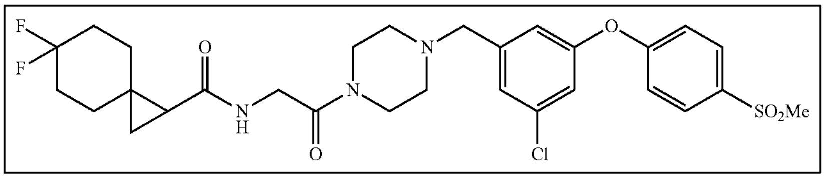 [SMILES: CS(=O)(=O)c1ccc(Oc2cc(Cl)cc(CN3CCN(C(=O)CNC(=O)C4CC45CCC(F)(F)CC5)CC3)c2)cc1] | 0.15 |
| 1460 | 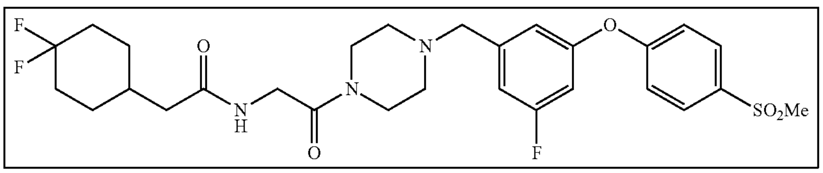 [SMILES: CS(=O)(=O)c1ccc(Oc2cc(F)cc(CN3CCN(C(=O)CNC(=O)CC4CCC(F)(F)CC4)CC3)c2)cc1] | >1 |
| 1459 | 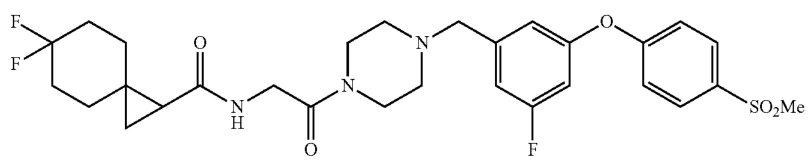 [SMILES: CS(=O)(=O)c1ccc(Oc2cc(F)cc(CN3CCN(C(=O)CNC(=O)C4CC45CCC(F)(F)CC5)CC3)c2)cc1] | 0.2 |
| 1365 | 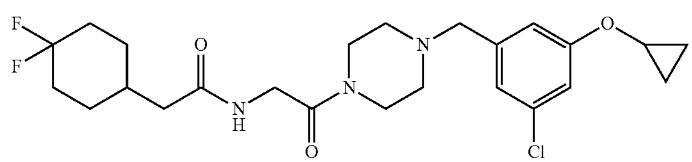 [SMILES: O=C(CC1CCC(F)(F)CC1)NCC(=O)N1CCN(Cc2cc(Cl)cc(OC3CC3)c2)CC1] | 1.6 |
| 1432 | 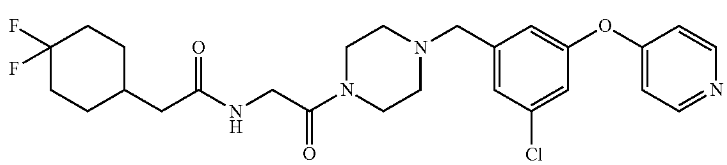 [SMILES: O=C(CC1CCC(F)(F)CC1)NCC(=O)N1CCN(Cc2cc(Cl)cc(Oc3ccncc3)c2)CC1] | 0.185 |
| 1458 | 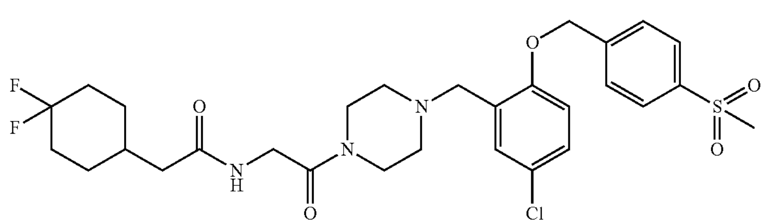 | 0.009 |
| 1456 | 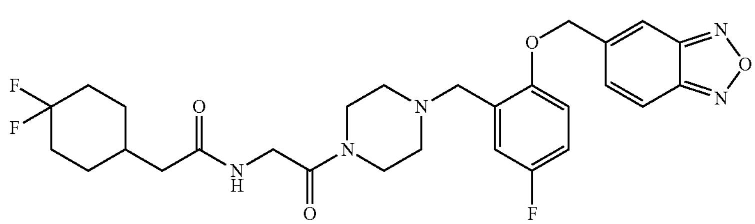 [SMILES: O=C(CC1CCC(F)(F)CC1)NCC(=O)N1CCN(Cc2cc(F)ccc2OCc2ccc3nonc3c2)CC1] | 0.19 |

TABLE 1-continued

Exemplary compounds of Formula I and Formula II.

| Compound number | Structure | IC50(uM) |
|---|---|---|
| 1455 | 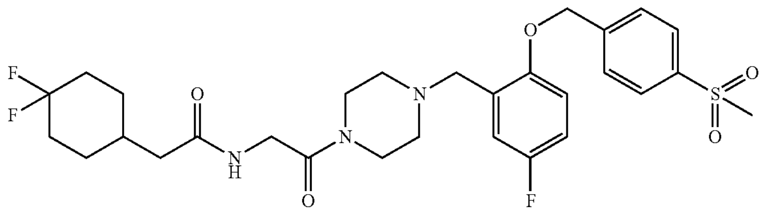 [SMILES: CS(=O)(=O)c1ccc(COc2ccc(F)cc2CN2CCN(C(=O)CNC(=O)CC3CCC(F)(F)CC3)CC2)cc1] | 0.04 |
| 1453 | 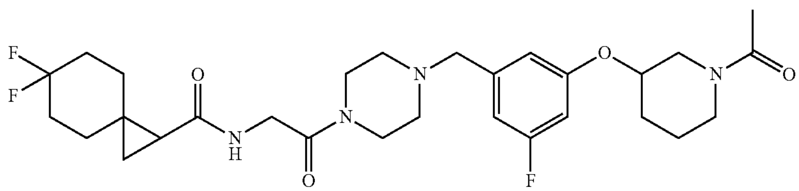 [SMILES: CC(=O)N1CCCC(Oc2cc(F)cc(CN3CCN(C(=O)CNC(=O)C4CC45CCC(F)(F)CC5)CC3)c2)C1] | >5 |
| 1451 | 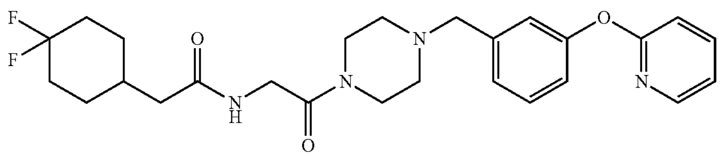 [SMILES: O=C(CC1CCC(F)(F)CC1)NCC(=O)N1CCN(Cc2cccc(Oc3ccccn3)c2)CC1] | >5 |
| 1442 | 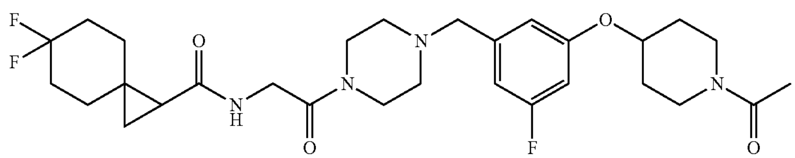 [SMILES: CC(=O)N1CCC(Oc2cc(F)cc(CN3CCN(C(=O)CNC(=O)C4CC45CCC(F)(F)CC5)CC3)c2)CC1] | 0.6 |
| 1505 | 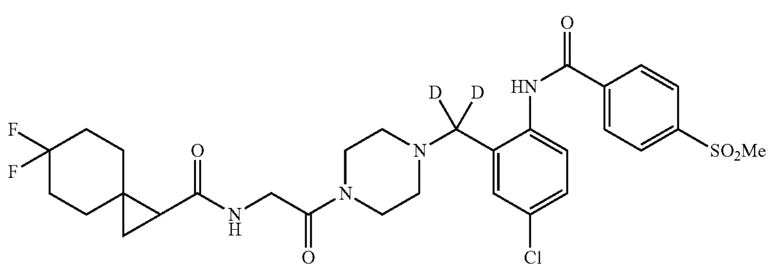 [SMILES: [2H]C([2H])(c1cc(Cl)ccc1NC(=O)c1ccc(S(C)(=O)=O)cc1)N1CCN(C(=O)CNC(=O)C2CC23CCC(F)(F)CC3)CC1] | |
| 1504 | 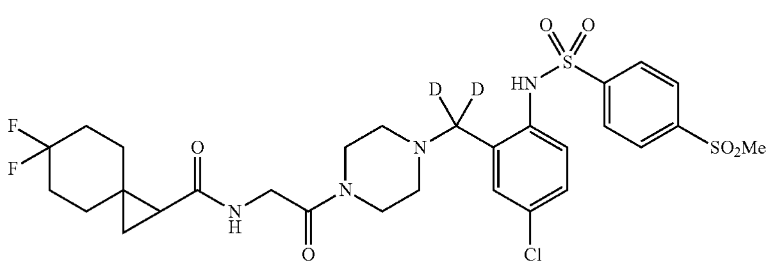 [SMILES: [2H]C([2H])(c1cc(Cl)ccc1NS(=O)(=O)c1ccc(S(C)(=O)=O)cc1)N1CCN(C(=O)CNC(=O)C2CC23CCC(F)(F)CC3)CC1] | |
| 1393 | 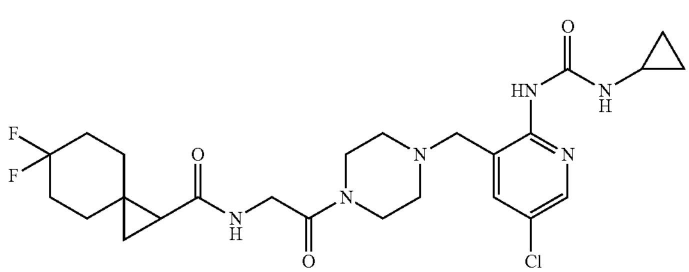 [SMILES: O=C(Nc1ncc(Cl)cc1CN1CCN(C(=O)CNC(=O)C2CC23CCC(F)(F)CC3)CC1)NC1CC1] | >5 |

TABLE 1-continued

Exemplary compounds of Formula I and Formula II.

| Compound number | Structure | IC50(uM) |
|---|---|---|
| 1392 | 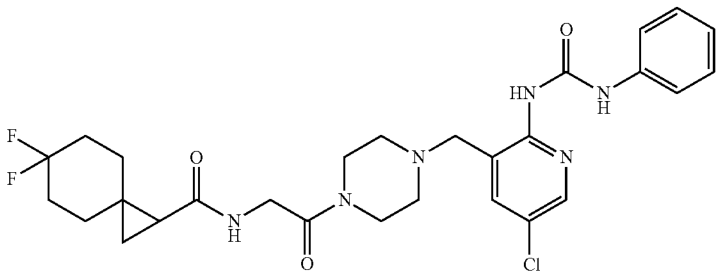 [SMILES: O=C(Nc1ccccc1)Nc1ncc(Cl)cc1CN1CCN(C(=O)CNC(=O)C2CC23CCC(F)(F)CC3)CC1] | 1 |
| 1389 | 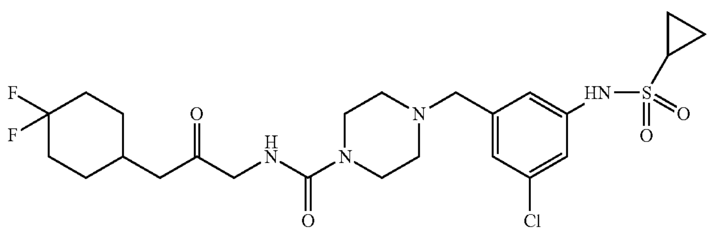 [SMILES: O=C(CNC(=O)N1CCN(Cc2cc(Cl)cc(NS(=O)(=O)C3CC3)c2)CC1)CC1CCC(F)(F)CC1] | |
| 1361 | 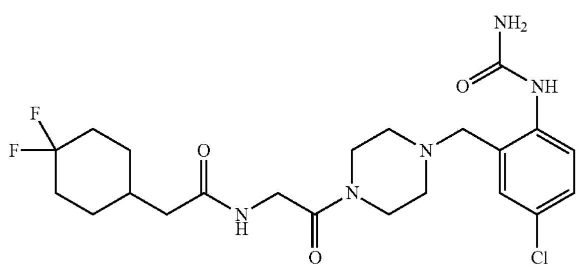 [SMILES: NC(=O)Nc1ccc(Cl)cc1CN1CCN(C(=O)CNC(=O)CC2CCC(F)(F)CC2)CC1] | >2 |
| 1360 | 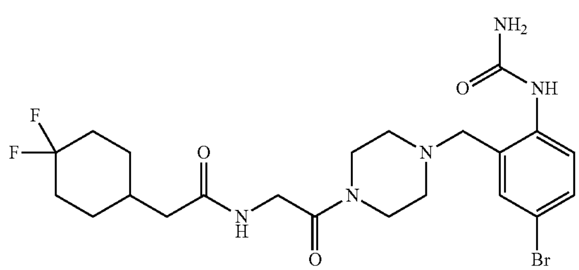 [SMILES: NC(=O)Nc1ccc(Br)cc1CN1CCN(C(=O)CNC(=O)CC2CCC(F)(F)CC2)CC1] | >2 |
| 1379 | 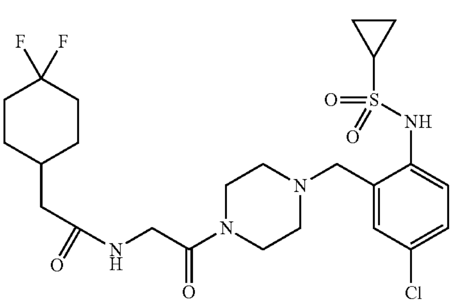 [SMILES: O=C(CC1CCC(F)(F)CC1)NCC(=O)N1CCN(Cc2cc(Cl)ccc2NS(=O)(=O)C2CC2)CC1] | ~2.2 |

TABLE 1-continued

Exemplary compounds of Formula I and Formula II.

| Compound number | Structure | IC50(uM) |
|---|---|---|
| 1378 | 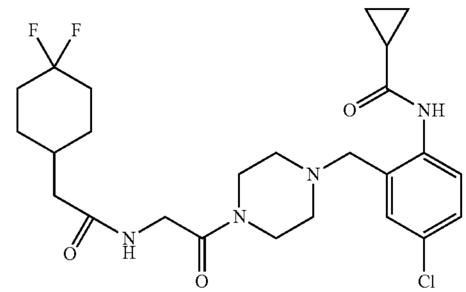 | >2 |
| 1375 | 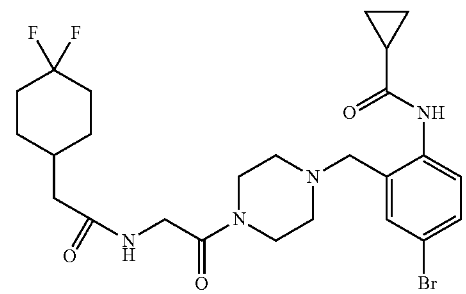 | >2 |
| 1440 | 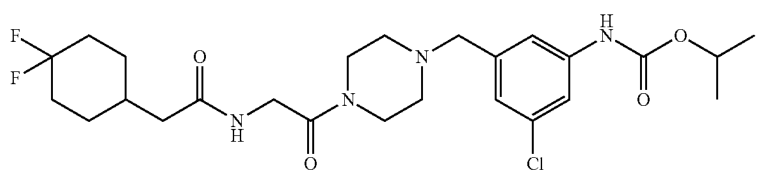 [SMILES: CC(C)OC(=O)Nc1cc(Cl)cc(CN2CCN(C(=O)CNC(=O)CC3CCC(F)(F)CC3)CC2)c1] | |
| 1439 | 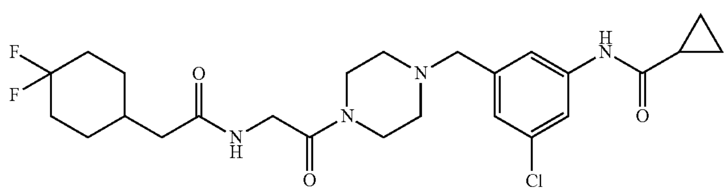 [SMILES: O=C(CC1CCC(F)(F)CC1)NCC(=O)N1CCN(Cc2cc(Cl)cc(NC(=O)C3CC3)c2)CC1] | |
| 1518 | 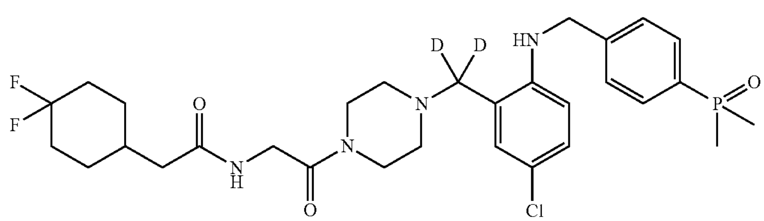 [SMILES: [2H]C([2H])(c1cc(Cl)ccc1NCc1ccc(P(C)(C)=O)cc1)N1CCN(C(=O)CNC(=O)CC2CCC(F)(F)CC2)CC1] | |
| 1517 | 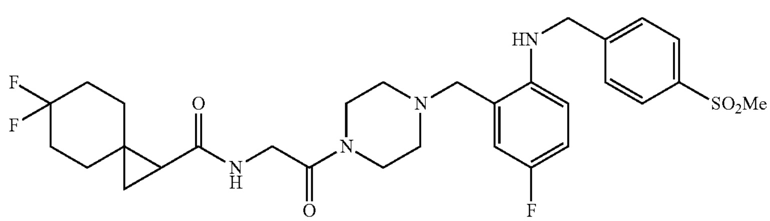 [SMILES: CS(=O)(=O)c1ccc(CNc2ccc(F)cc2CN2CCN(C(=O)CNC(=O)C3CC34CCC(F)(F)CC4)CC2)cc1] | |

TABLE 1-continued

Exemplary compounds of Formula I and Formula II.

| Compound number | Structure | IC50(uM) |
|---|---|---|
| 1516 | 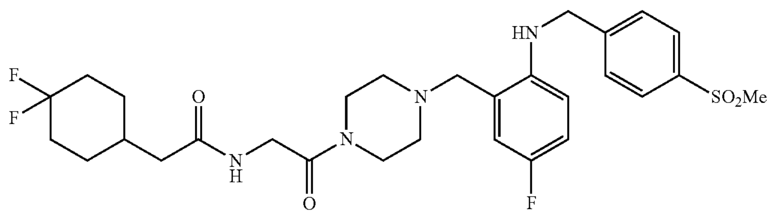 [SMILES: CS(=O)(=O)c1ccc(CNc2ccc(F)cc2CN2CCN(C(=O)CNC(=O)CC3CCC(F)(F)CC3)CC2)cc1] | |
| 1515 | 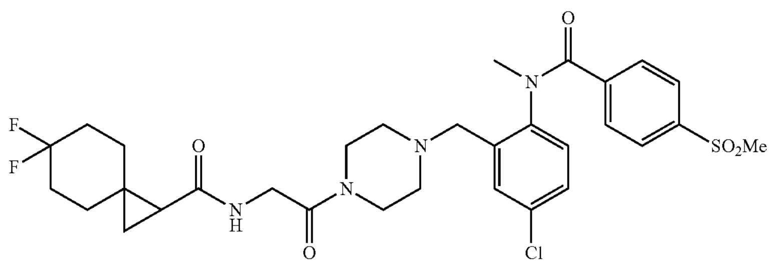 [SMILES: CN(C(=O)c1ccc(S(C)(=O)=O)cc1)c1ccc(Cl)cc1CN1CCN(C(=O)CNC(=O)C2CC23CCC(F)(F)CC3)CC1] | |
| 1530 | 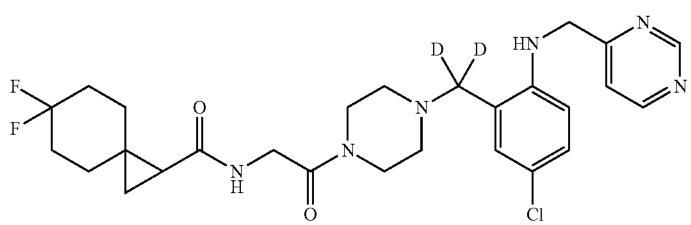 [SMILES: [2H]C([2H])(c1cc(Cl)ccc1NCc1ccncn1)N1CCN(C(=O)CNC(=O)C2CC23CCC(F)(F)CC3)CC1] | |
| 1529 | 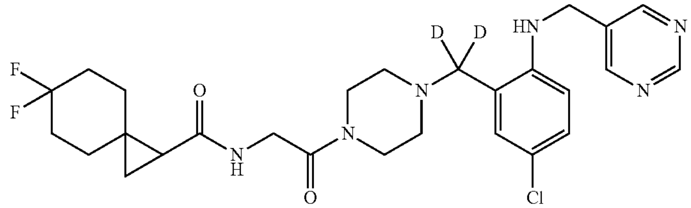 [SMILES: [2H]C([2H])(c1cc(Cl)ccc1NCc1cncnc1)N1CCN(C(=O)CNC(=O)C2CC23CCC(F)(F)CC3)CC1] | |
| 1528 | 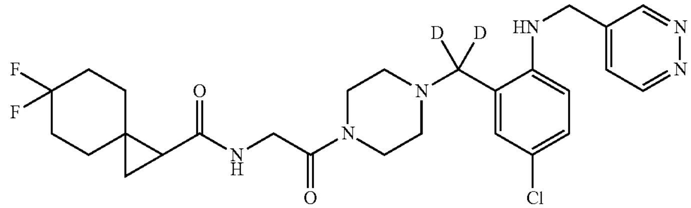 [SMILES: [2H]C([2H])(c1cc(Cl)ccc1NCc1ccnnc1)N1CCN(C(=O)CNC(=O)C2CC23CCC(F)(F)CC3)CC1] | |
| 1527 | 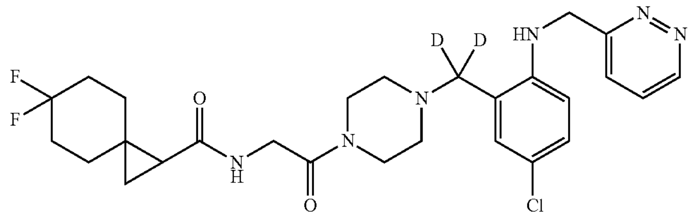 [SMILES: [2H]C([2H])(c1cc(Cl)ccc1NCc1cccnn1)N1CCN(C(=O)CNC(=O)C2CC23CCC(F)(F)CC3)CC1] | |

TABLE 1-continued

Exemplary compounds of Formula I and Formula II.

| Compound number | Structure | IC50(uM) |
|---|---|---|
| 1526 | 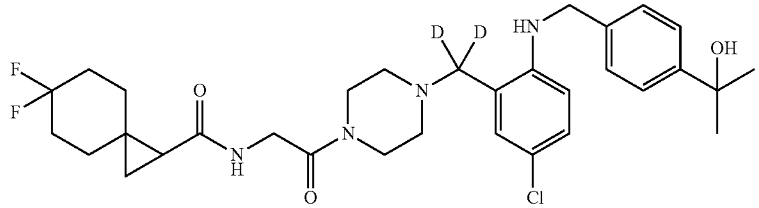 [SMILES: [2H]C([2H])(c1cc(Cl)ccc1NCc1ccc(C(C)(C)O)cc1)N1CCN(C(=O)CNC(=O)C2CC23CCC(F)(F)CC3)CC1] | |
| 1525 | 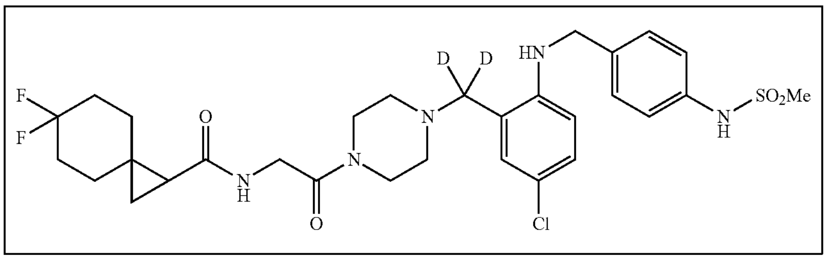 [SMILES: [2H]C([2H])(c1cc(Cl)ccc1NCc1ccc(NS(C)(=O)=O)cc1)N1CCN(C(=O)CNC(=O)C2CC23CCC(F)(F)CC3)CC1] | |
| 1524 | 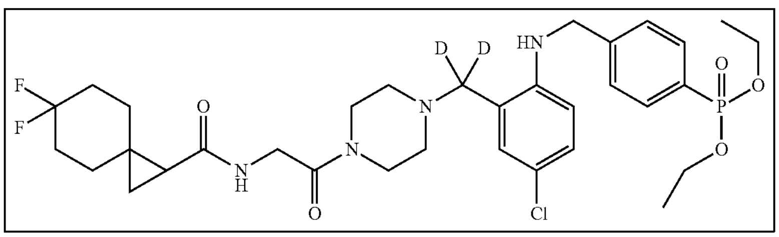 [SMILES: [2H]C([2H])(c1cc(Cl)ccc1NCc1ccc(P(=O)(OCC)OCC)cc1)N1CCN(C(=O)CNC(=O)C2CC23CCC(F)(F)CC3)CC1] | |
| 1523 | 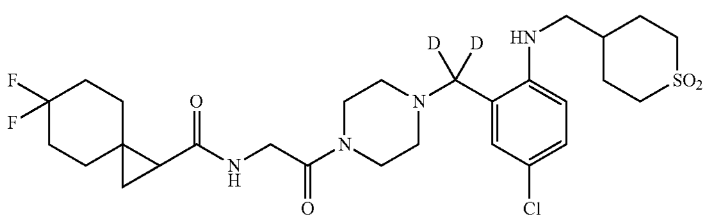 [SMILES: [2H]C([2H])(c1cc(Cl)ccc1NCC1CCS(=O)(=O)CC1)N1CCN(C(=O)CNC(=O)C2CC23CCC(F)(F)CC3)CC1] | |
| 1522 | 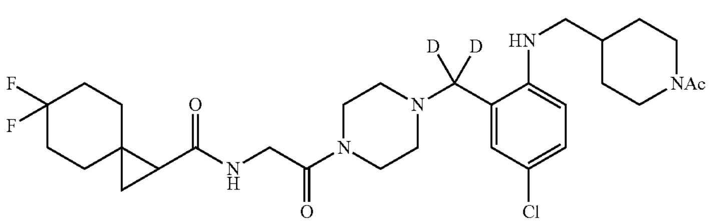 | |
| 1521 | 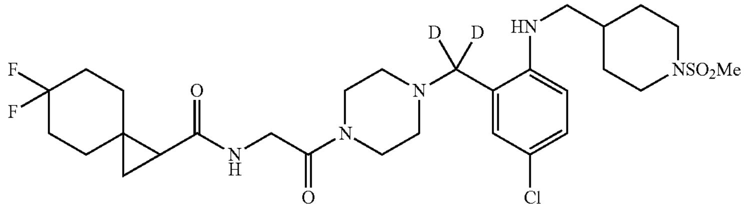 | |

TABLE 1-continued

Exemplary compounds of Formula I and Formula II.

| Compound number | Structure | IC50(uM) |
|---|---|---|
| 1520 | 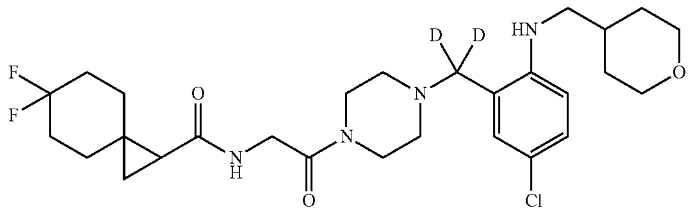 [SMILES: [2H]C([2H])(c1cc(Cl)ccc1NCC1CCOCC1)N1CCN(C(=O)CNC(=O)C2CC23CCC(F)(F)CC3)CC1] | |
| 1622 | 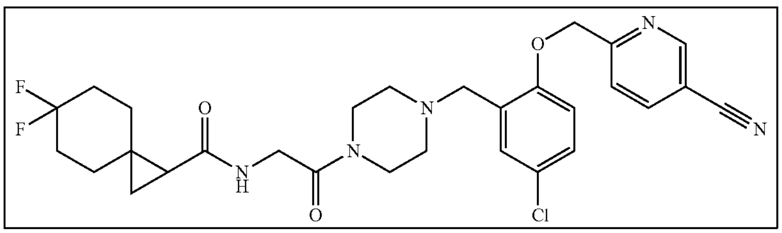 [SMILES: N#Cc1ccc(COc2ccc(Cl)cc2CN2CCN(C(=O)CNC(=O)C3CC34CCC(F)(F)CC4)CC2)nc1] | 0.019 |
| 1621 | 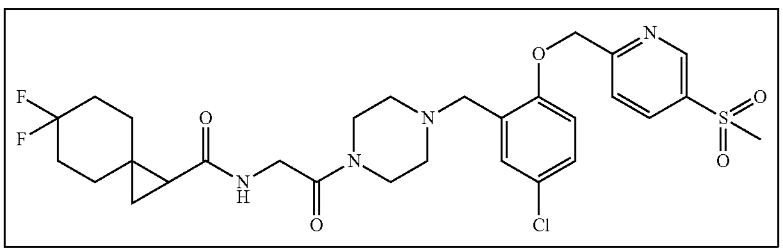 [SMILES: CS(=O)(=O)c1ccc(COc2ccc(Cl)cc2CN2CCN(C(=O)CNC(=O)C3CC34CCC(F)(F)CC4)CC2)nc1] | 0.030 |
| 1586 | 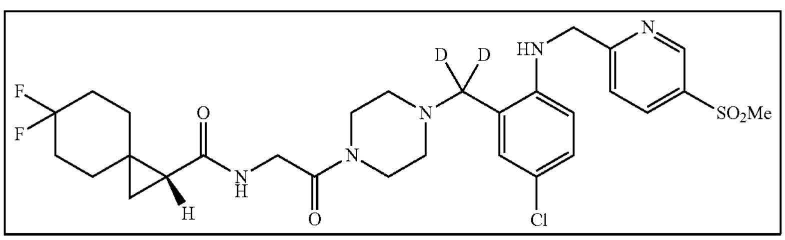 [SMILES: [2H]C([2H])(c1cc(Cl)ccc1NCc1ccc(S(C)(=O)=O)cn1)N1CCN(C(=O)CNC(=O)[C@@H]2CC23CCC(F)(F)CC3)CC1] | 0.045 |
| 1584 | 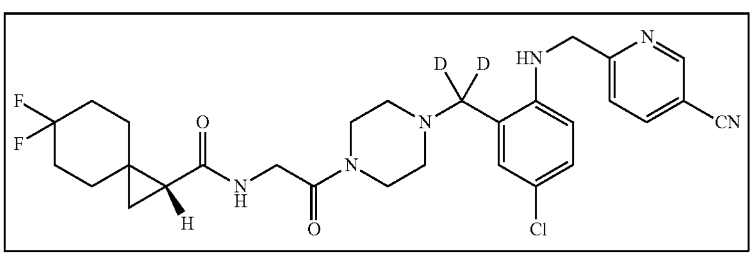 [SMILES: [2H]C([2H])(c1cc(Cl)ccc1NCc1ccc(C#N)cn1)N1CCN(C(=O)CNC(=O)[C@@H]2CC23CCC(F)(F)CC3)CC1] | 0.03 |
| 1582 | 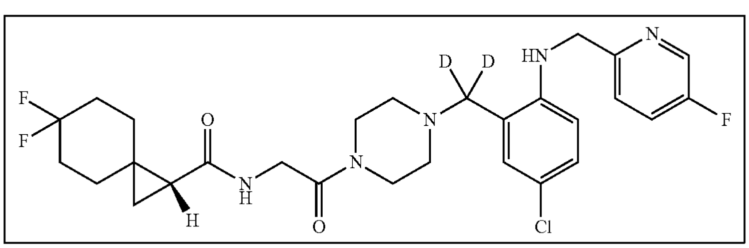 [SMILES: [2H]C([2H])(c1cc(Cl)ccc1NCc1ccc(F)cn1)N1CCN(C(=O)CNC(=O)[C@@H]2CC23CCC(F)(F)CC3)CC1] | 0.24 |

TABLE 1-continued
Exemplary compounds of Formula I and Formula II.
| Compound number | Structure | IC50(uM) |
|---|---|---|
| 1549 | 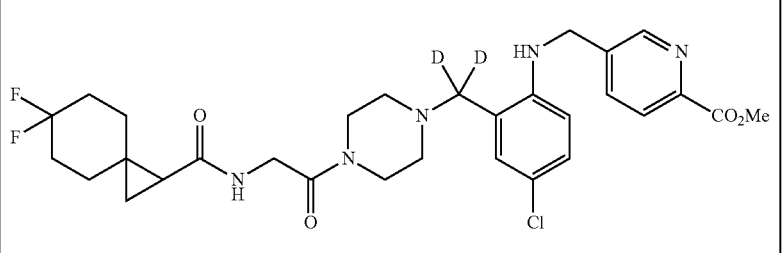 | 0.05 |
| 1548 | 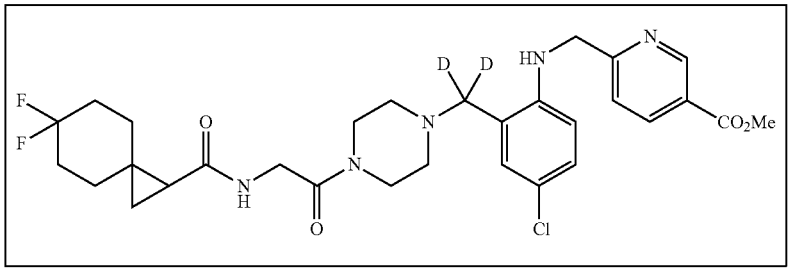 [SMILES: [2H]C([2H])(c1cc(Cl)ccc1NCc1ccc(C(=O)OC)cn1)N1CCN(C(=O)CNC(=O)C2CC23CCC(F)(F)CC3)CC1] | 0.007 |
| 1580 | 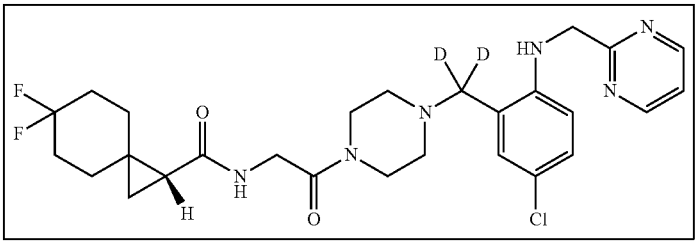 [SMILES: [2H]C([2H])(c1cc(Cl)ccc1NCc1ncccn1)N1CCN(C(=O)CNC(=O)[C@@H]2CC23CCC(F)(F)CC3)CC1] | 0.70 |
| 1587 | 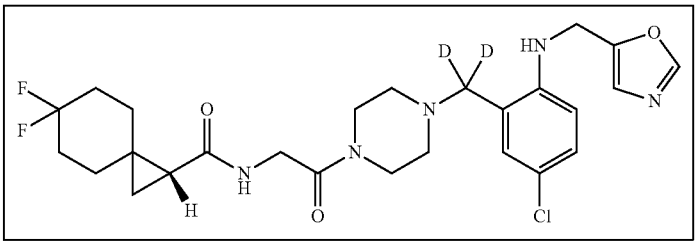 [SMILES: [2H]C([2H])(c1cc(Cl)ccc1NCc1cnco1)N1CCN(C(=O)CNC(=O)[C@@H]2CC23CCC(F)(F)CC3)CC1] | 0.13 |
| 1585 | 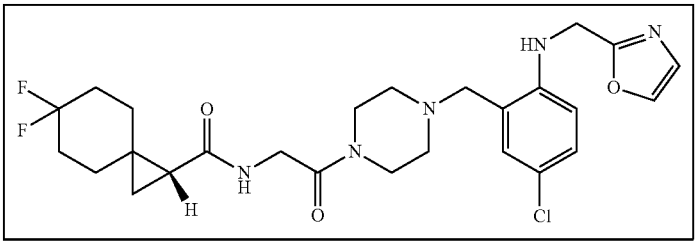 [SMILES: O=C(NCC(=O)N1CCN(Cc2cc(Cl)ccc2NCc2ncco2)CC1)[C@@H]1CC12CCC(F)(F)CC2] | 1.3 |

TABLE 1-continued

Exemplary compounds of Formula I and Formula II.

| Compound number | Structure | IC50(uM) |
|---|---|---|
| 1583 | 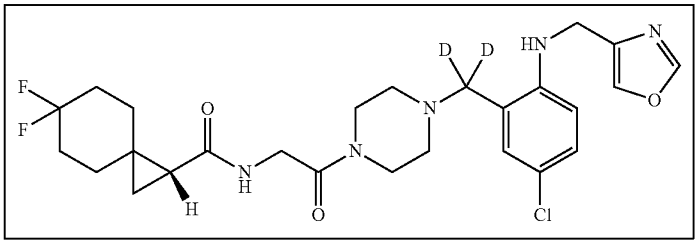 [SMILES: [2H]C([2H])(c1cc(Cl)ccc1NCc1cocn1)N1CCN(C(=O)CNC(=O)[C@@H]2CC23CCC(F)(F)CC3)CC1] | 0.15 |
| 1581 | 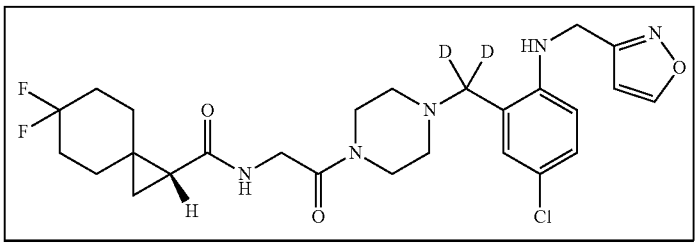 [SMILES: [2H]C([2H])(c1cc(Cl)ccc1NCc1ccon1)N1CCN(C(=O)CNC(=O)[C@@H]2CC23CCC(F)(F)CC3)CC1] | 0.47 |
| 1560 | 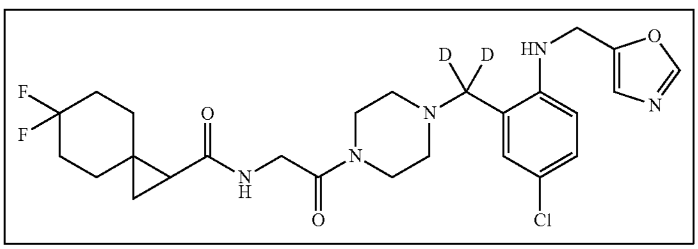 [SMILES: [2H]C([2H])(c1cc(Cl)ccc1NCc1cnco1)N1CCN(C(=O)CNC(=O)C2CC23CCC(F)(F)CC3)CC1] | 0.04 |
| 1562 | 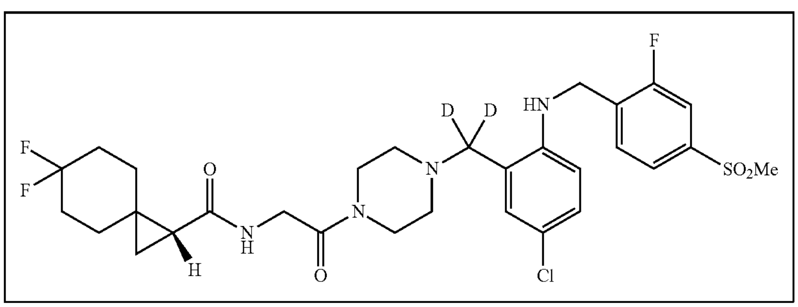 [SMILES: [2H]C([2H])(c1cc(Cl)ccc1NCc1ccc(S(C)(=O)=O)cc1F)N1CCN(C(=O)CNC(=O)[C@@H]2CC23CCC(F)(F)CC3)CC1] | 0.013 |
| 1561 | 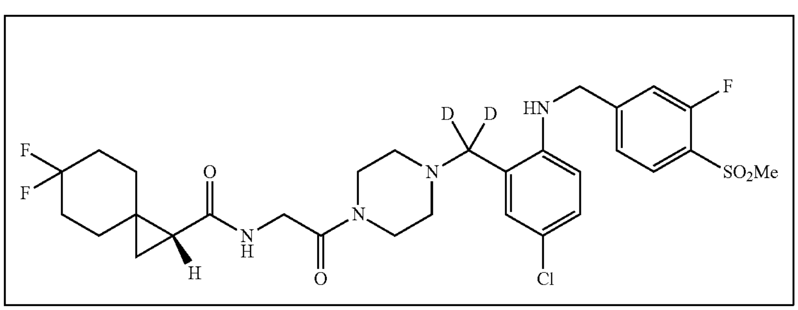 [SMILES: [2H]C([2H])(c1cc(Cl)ccc1NCc1ccc(S(C)(=O)=O)c(F)c1)N1CCN(C(=O)CNC(=O)[C@@H]2CC23CCC(F)(F)CC3)CC1] | 0.008 |

TABLE 1-continued

Exemplary compounds of Formula I and Formula II.

| Compound number | Structure | IC50(uM) |
|---|---|---|
| 1539 | 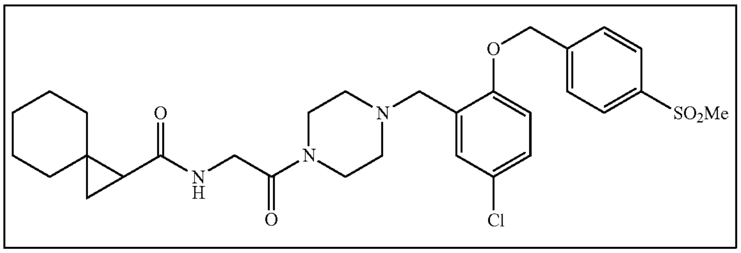 [SMILES: CS(=O)(=O)c1ccc(COc2ccc(Cl)cc2CN2CCN(C(=O)CNC(=O)C3CC34CCCCC4)CC2)cc1] | 0.1 |
| 1534 | 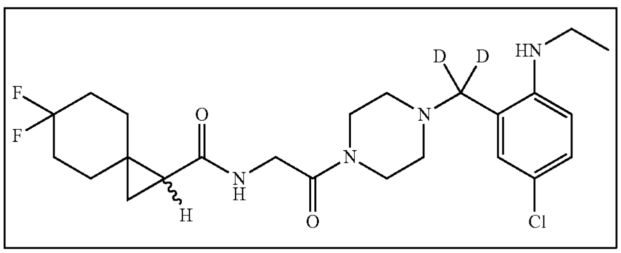 [SMILES: [2H]C([2H])(c1cc(Cl)ccc1NCC)N1CCN(C(=O)CNC(=O)C2CC23CCC(F)(F)CC3)CC1] | 0.2 |
| 1801 | 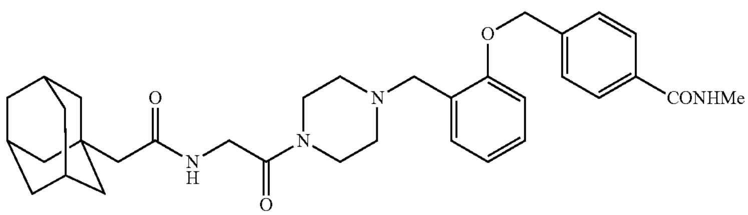 | 2.1 |
| 1802 | 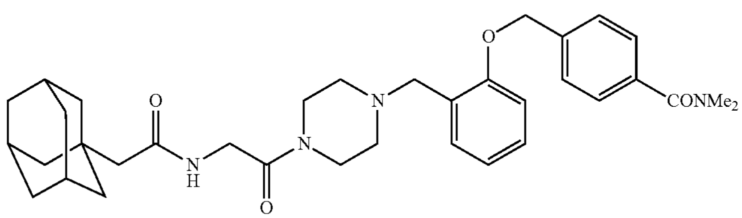 | 3.3 |
| 1803 | 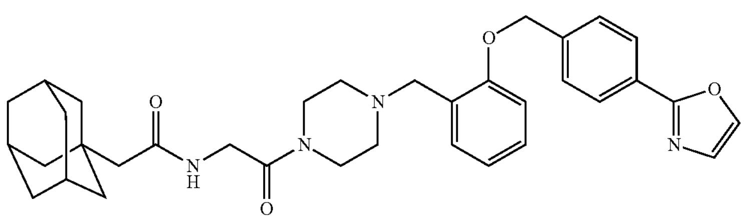 [SMILES: O=C(CC12CC3CC(CC(C3)C1)C2)NCC(=O)N1CCN(Cc2ccccc2OCc2ccc(-c3ncco3)cc2)CC1] | 0.27 |
| 1804 | 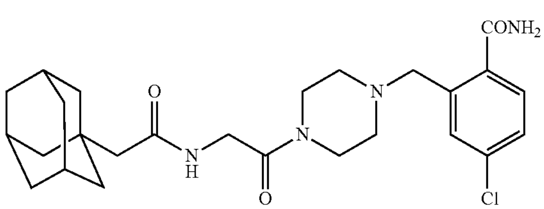 [SMILES: NC(=O)c1ccc(Cl)cc1CN1CCN(C(=O)CNC(=O)CC23CC4CC(CC(C4)C2)C3)CC1] | 1.9 |

TABLE 1-continued

Exemplary compounds of Formula I and Formula II.

| Compound number | Structure | IC50(uM) |
|---|---|---|
| 1805 | 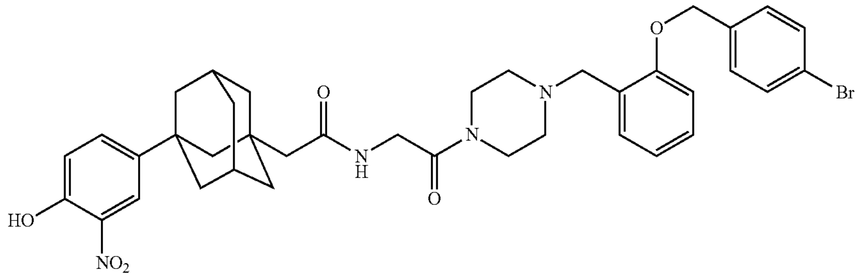 [SMILES: O=C(CC12CC3CC(C1)CC(c1ccc(O)c([N+](=O)[O-])c1)(C3)C2)NCC(=O)N1CCN(Cc2ccccc2OCc2ccc(Br)cc2)CC1] | 0.6 |
| 1806 | 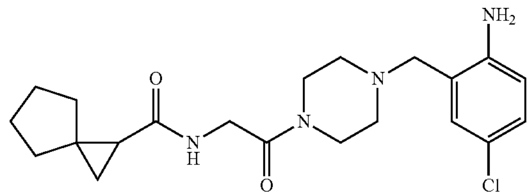 [SMILES: Nc1ccc(Cl)cc1CN1CCN(C(=O)CNC(=O)C2CC23CCCC3)CC1] | 0.24 |
| 1807 | 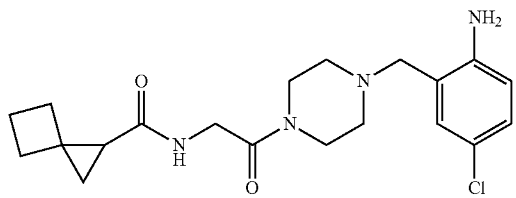 [SMILES: Nc1ccc(Cl)cc1CN1CCN(C(=O)CNC(=O)C2CC23CCC3)CC1] | 2.5 |
| 1808 | 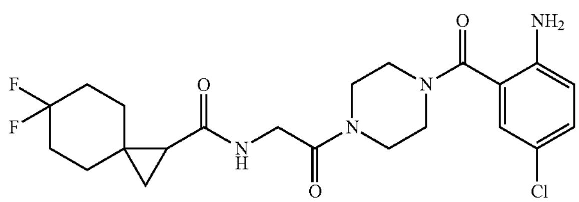 [SMILES: Nc1ccc(Cl)cc1C(=O)N1CCN(C(=O)CNC(=O)C2CC23CCC(F)(F)CC3)CC1] | |

Compounds of the invention may be provided as salts with pharmaceutically compatible counterions (i.e., pharmaceutically acceptable salts). A "pharmaceutically acceptable salt" means any non-toxic salt that, upon administration to a recipient, is capable of providing, either directly or indirectly, a compound or a prodrug of a compound of this invention. A "pharmaceutically acceptable counterion" is an ionic portion of a salt that is not toxic when released from the salt upon administration to a recipient. Pharmaceutically compatible salts may be formed with many acids, including but not limited to hydrochloric, sulfuric, acetic, lactic, tartaric, malic, succinic, etc. Salts tend to be more soluble in aqueous or other protonic solvents than are the corresponding free base forms.

Acids commonly employed to form pharmaceutically acceptable salts include inorganic acids such as hydrogen bisulfide, hydrochloric, hydrobromic, hydroiodic, sulfuric and phosphoric acid, as well as organic acids such as para-toluenesulfonic, salicylic, tartaric, bitartaric, ascorbic, maleic, besylic, fumaric, gluconic, glucuronic, formic, glutamic, methanesulfonic, ethanesulfonic, benzenesulfonic, lactic, oxalic, para-bromophenylsulfonic, carbonic, succinic, citric, benzoic and acetic acid, and related inorganic and organic acids. Such pharmaceutically acceptable salts thus include sulfate, pyrosulfate, bisulfate, sulfite, bisulfite, phosphate, monohydrogenphosphate, dihydrogenphosphate, metaphosphate, pyrophosphate, chloride, bromide, iodide, acetate, propionate, decanoate, caprylate, acrylate, formate, isobutyrate, caprate, heptanoate, propiolate, oxalate, malonate, succinate, suberate, sebacate, fumarate, maleate, butyne-1,4-dioate, hexyne-1,6-dioate, benzoate, chlorobenzoate, methylbenzoate, dinitrobenzoate, hydroxybenzoate, methoxybenzoate, phthalate, terephathalate, sulfonate, xylenesulfonate, phenylacetate, phenylpropionate, phenylbutyrate, citrate, lactate, s-hydroxybutyrate, glycolate, maleate, tartrate, methanesulfonate, propanesulfonate, naphthalene-1-sulfonate, naphthalene-2-sulfonate, mandelate and the like salts. Preferred pharmaceutically acceptable acid addition salts include those formed with mineral acids such as hydrochloric acid and hydrobromic acid, and especially those formed with organic acids such as maleic acid.

Suitable bases for forming pharmaceutically acceptable salts with acidic functional groups include, but are not limited to, hydroxides of alkali metals such as sodium, potassium, and lithium; hydroxides of alkaline earth metal such as calcium and magnesium; hydroxides of other metals, such as aluminum and zinc; ammonia, and organic amines, such as unsubstituted or hydroxy-substituted mono-, di-, or trialkylamines; dicyclohexylamine; tributyl amine; pyridine; N-methyl,N-ethylamine; diethylamine; triethylamine; mono-, bis-, or tris-(2-hydroxy-lower alkyl amines), such as mono-, bis-, or tris-(2-hydroxyethyl)amine, 2-hydroxy-tert-butylamine, or tris-(hydroxymethyl)methylamine, N,N-di-lower alkyl-N-(hydroxy lower alkyl)-amines, such as N,N-dimethyl-N-(2-hydroxyethyl)amine, or tri-(2-hydroxyethyl) amine; N-methyl-D-glucamine; and amino acids such as arginine, lysine, and the like.

Certain compounds of the invention and their salts may exist in more than one crystal form and the present invention includes each crystal form and mixtures thereof.

Certain compounds of the invention and their salts may also exist in the form of solvates, for example hydrates, and the present invention includes each solvate and mixtures thereof.

Certain compounds of the invention may contain one or more chiral centers, and exist in different optically active forms. When compounds of the invention contain one chiral center, the compounds exist in two enantiomeric forms and the present invention includes both enantiomers and mixtures of enantiomers, such as racemic mixtures. The enantiomers may be resolved by methods known to those skilled in the art, for example by formation of diastereoisomeric salts which may be separated, for example, by crystallization; formation of diastereoisomeric derivatives or complexes which may be separated, for example, by crystallization, gas-liquid or liquid chromatography; selective reaction of one enantiomer with an enantiomer-specific reagent, for example enzymatic esterification; or gas-liquid or liquid chromatography in a chiral environment, for example on a chiral support for example silica with a bound chiral ligand or in the presence of a chiral solvent. It will be appreciated that where the desired enantiomer is converted into another chemical entity by one of the separation procedures described above, a further step may be used to liberate the desired enantiomeric form. Alternatively, specific enantiomers may be synthesized by asymmetric synthesis using optically active reagents, substrates, catalysts or solvents, or by converting one enantiomer into the other by asymmetric transformation.

When a compound of the invention contains more than one chiral center, it may exist in diastereoisomeric forms. The diastereoisomeric compounds may be separated by methods known to those skilled in the art, for example chromatography or crystallization and the individual enantiomers may be separated as described above. The present invention includes each diastereoisomer of compounds of the invention and mixtures thereof.

Certain compounds of the invention may exist in different tautomeric forms or as different geometric isomers, and the present invention includes each tautomer and/or geometric isomer of compounds of the invention and mixtures thereof.

Certain compounds of the invention may exist in different stable conformational forms which may be separable. Torsional asymmetry due to restricted rotation about an asymmetric single bond, for example because of steric hindrance or ring strain, may permit separation of different conformers. The present invention includes each conformational isomer of compounds of the invention and mixtures thereof.

Certain compounds of the invention may exist in zwitterionic form and the present invention includes each zwitterionic form of compounds of the invention and mixtures thereof.

The present invention also includes pro-drugs. As used herein the term "pro-drug" refers to an agent that is converted into the parent drug in vivo by some physiological chemical process (e.g., a prodrug on being brought to the physiological pH is converted to the desired drug form). Pro-drugs are often useful because, in some situations, they may be easier to administer than the parent drug. They may, for instance, be bioavailable by oral administration whereas the parent drug is not. The prodrug may also have improved solubility in pharmacological compositions over the parent drug. An example, without limitation, of a pro-drug would be a compound of the present invention wherein it is administered as an ester (the "pro-drug") to facilitate transmittal across a cell membrane where water solubility is not beneficial, but then it is metabolically hydrolyzed to the carboxylic acid once inside the cell where water solubility is beneficial. Pro-drugs have many useful properties. For example, a pro-drug may be more water soluble than the ultimate drug, thereby facilitating intravenous administration of the drug. A pro-drug may also have a higher level of oral bioavailability than the ultimate drug. After administration, the prodrug is enzymatically or chemically cleaved to deliver the ultimate drug in the blood or tissue.

Exemplary pro-drugs upon cleavage release the corresponding free acid, and such hydrolyzable ester-forming residues of the compounds of this invention include but are not limited to carboxylic acid substituents (e.g., $—C(O)_2H$ or a moiety that contains a carboxylic acid) wherein the free hydrogen is replaced by $(C_1-C_4)$alkyl, $(C_2-C_{12})$alkanoyloxymethyl, $(C_4-C_9)$1-(alkanoyloxy)ethyl, 1-methyl-1-(alkanoyloxy)-ethyl having from 5 to 10 carbon atoms, alkoxycarbonyloxymethyl having from 3 to 6 carbon atoms, 1-(alkoxycarbonyloxy)ethyl having from 4 to 7 carbon atoms, 1-methyl-1-(alkoxycarbonyloxy)ethyl having from 5 to 8 carbon atoms, N-(alkoxycarbonyl)aminomethyl having from 3 to 9 carbon atoms, 1-(N-(alkoxycarbonyl)amino) ethyl having from 4 to 10 carbon atoms, 3-phthalidyl, 4-crotonolactonyl, gamma-butyrolacton-4-yl, di-N,N—$(C_1$-$C_2)$alkylamino$(C_2$-$C_3)$alkyl (such as β-dimethylaminoethyl), carbamoyl-$(C_1$-$C_2)$alkyl, N,N-di$(C_1$-$C_2)$-alkylcarbamoyl-$(C_1$-$C_2)$alkyl and piperidino-, pyrrolidino- or morpholino$(C_2$-$C_3)$alkyl.

Other exemplary pro-drugs release an alcohol or amine of a compound of the invention wherein the free hydrogen of a hydroxyl or amine substituent is replaced by $(C_1$-$C_6)$ alkanoyloxymethyl, 1-$((C_1$-$C_6)$alkanoyloxy)ethyl, 1-methyl-1-$((C_1$-$C_6)$alkanoyloxy)ethyl, $(C_1$-$C_6)$alkoxycarbonyl-oxymethyl, N—$(C_1$-$C_6)$alkoxycarbonylaminomethyl, succinoyl, $(C_1$-$C_6)$alkanoyl, α-amino$(C_1$-$C_4)$alkanoyl, arylactyl and α-aminoacyl, or α-aminoacyl-α-aminoacyl wherein said α-aminoacyl moieties are independently any of the naturally occurring L-amino acids found in proteins, $—P(O)(OH)_2$, $—P(O)(O(C_1$-$C_6)$alkyl$)_2$ or glycosyl (the radical resulting from detachment of the hydroxyl of the hemiacetal of a carbohydrate).

The phrase "protecting group" as used herein means temporary substituents which protect a potentially reactive functional group from undesired chemical transformations. Examples of such protecting groups include esters of carboxylic acids, silyl ethers of alcohols, and acetals and ketals of aldehydes and ketones, respectively. The field of protecting group chemistry has been reviewed (Greene, T. W.; Wuts, P. G. M. *Protective Groups in Organic Synthesis*, $2^{nd}$ ed.; Wiley: New York, 1991). Protected forms of the inventive compounds are included within the scope of this invention.

The term "chemically protected form," as used herein, pertains to a compound in which one or more reactive functional groups are protected from undesirable chemical reactions, that is, are in the form of a protected or protecting group (also known as a masked or masking group). It may be convenient or desirable to prepare, purify, and/or handle the active compound in a chemically protected form.

By protecting a reactive functional group, reactions involving other unprotected reactive functional groups can be performed, without affecting the protected group; the protecting group may be removed, usually in a subsequent step, without substantially affecting the remainder of the molecule. See, for example, Protective Groups in Organic Synthesis (T. Green and P. Wuts, Wiley, 1991), and Protective Groups in Organic Synthesis (T. Green and P. Wuts; 3rd Edition; John Wiley and Sons, 1999).

For example, a hydroxy group may be protected as an ether (—OR) or an ester (—OC(=O)R), for example, as: a t-butyl ether; a benzyl, benzhydryl (diphenylmethyl), or trityl (triphenylmethyl) ether; a trimethylsilyl or t-butyldimethylsilyl ether; or an acetyl ester (—OC(=O)CH$_3$, —OAc).

For example, an aldehyde or ketone group may be protected as an acetal or ketal, respectively, in which the carbonyl group (C(=O)) is converted to a diether (C(OR)$_2$), by reaction with, for example, a primary alcohol. The aldehyde or ketone group is readily regenerated by hydrolysis using a large excess of water in the presence of acid.

For example, an amine group may be protected, for example, as an amide (—NRC(=O)R) or a urethane (—NRC(=O)OR), for example, as: a methyl amide (—NHC(=O)CH$_3$); a benzyloxy amide (—NHC(=O)OCH$_2$C$_6$H$_5$NHCbz); as a t-butoxy amide (—NHC=(=O)OC(CH$_3$)$_3$, —NHBoc); a 2-biphenyl-2-propoxy amide (—NHC(=O)OC(CH$_3$)$_2$C$_6$H$_4$C$_6$H$_5$NHBoc), as a 9-fluorenylmethoxy amide (—NHFmoc), as a 6-nitroveratryloxy amide (—NHNvoc), as a 2-trimethylsilylethyloxy amide (—NHTeoc), as a 2,2,2-trichloroethyloxy amide (—NHTroc), as an allyloxy amide (—NHAlloc), as a 2-(phenylsulfonyl)ethyloxy amide (—NHPsec); or, in suitable cases (e.g., cyclic amines), as a nitroxide radical.

For example, a carboxylic acid group may be protected as an ester or an amide, for example, as: a benzyl ester; a t-butyl ester; a methyl ester; or a methyl amide.

For example, a thiol group may be protected as a thioether (—SR), for example, as: a benzyl thioether; or an acetamidomethyl ether (—SCH$_2$NHC(=O)CH$_3$).

The compounds described herein are isolated molecules. An isolated molecule is a molecule that is substantially pure and is free of other substances with which it is ordinarily found in nature or in vivo systems to an extent practical and appropriate for its intended use. In particular, the molecular species are sufficiently pure and are sufficiently free from other biological constituents of host cells so as to be useful in, for example, producing pharmaceutical preparations or sequencing if the molecular species is a nucleic acid, peptide, or polysaccharide. Because an isolated molecular species of the invention may be admixed with a pharmaceutically-acceptable carrier in a pharmaceutical preparation or be mixed with some of the components with which it is associated in nature, the molecular species may comprise only a small percentage by weight of the preparation. The molecular species is nonetheless substantially pure in that it has been substantially separated from the substances with which it may be associated in living systems.

Methods

In certain aspects, the invention provides methods of treating a disease or infection in a subject, comprising administering to a subject a compound of Formula I or Formula II, e.g., in a therapeutically effective amount.

In some embodiments, the disease or infection is cancer, obesity, HIV/AIDS, a viral infection (e.g, by Ebola, Lassa fever, Marburg, Nipah, Hendra, and avian-derived influenza viruses), hemorrhagic fever, Ebola Hemorrhagic Fever (EHF).

In some embodiments, the invention provides for methods of inhibiting Niemann-Pick C1 (NPC1) activity.

Several viruses produce a syndrome referred to as hemorrhagic fever following infection of humans. Although the viruses are not structurally similar, they produce this syndrome in humans, which is characterized by an exaggerated immune response. Often the viruses which produce this type of systemic inflammatory response resulting in hemorrhagic fever have transferred from a different species to humans. Examples of viruses that fall into this category include Ebola, Lassa fever, Marburg, Nipah, Hendra, and avian-derived influenza. The methods of the invention are particularly useful for treating Ebola viruses.

The methods of the invention are useful for treating a subject in need thereof. A subject in need thereof is a subject having or at risk of having an enveloped virus infection. In its broadest sense, the terms "treatment" or "to treat" refer to both therapeutic and prophylactic treatments. If the subject in need of treatment is experiencing a condition (i.e., has or is having a particular condition), then "treating the condition" refers to ameliorating, reducing or eliminating one or more symptoms arising from the condition. If the subject in need of treatment is one who is at risk of having a condition, then treating the subject refers to reducing the risk of the subject having the condition or, in other words, decreasing the likelihood that the subject will develop an infectious disease to the virus, as well as to a treatment after the subject has been infected in order to fight the infectious disease, e.g., reduce or eliminate it altogether or prevent it from becoming worse.

Thus the invention encompasses the use of the inhibitors described herein alone or in combination with other therapeutics for the treatment of a subject having or at risk of having a viral infection, e.g., an enveloped viral infection. A "subject having an enveloped viral infection" is a subject that has had contact with a virus. Thus the virus has invaded the body of the subject. The word "invade" as used herein refers to contact by the virus with an external surface of the subject, e.g., skin or mucosal membranes and/or refers to the penetration of the external surface of the subject by the virus. A subject at risk of having an enveloped virus infection is one that has been exposed to or may become exposed to an enveloped virus or a geographical area in which an enveloped viral infection has been reported. Further risks include close contact with a human or non-human primate or their tissues infected with the virus. Such persons include laboratory or quarantine facility workers who handle non-human primates that have been associated with the disease. In addition, hospital staff and family members who care for patients with the disease are at risk if they do not use proper barrier nursing techniques.

As used herein, a subject includes humans and non-human animals such as non-human primates, dogs, cats, sheep, goats, cows, pigs, horses and rodents.

The compositions are delivered in effective amounts. The term "effective amount" refers to the amount necessary or sufficient to realize a desired biologic effect. Combined with the teachings provided herein, by choosing among the various active compounds and weighing factors such as potency, relative bioavailability, patient body weight, severity of adverse side-effects and preferred mode of administration, an effective prophylactic or therapeutic treatment regimen can be planned which does not cause substantial toxicity and yet is effective to treat the particular subject. In addition, based on testing, toxicity of the inhibitor is expected to be low. The effective amount for any particular application can vary depending on such factors as the disease or condition being treated, the particular inhibitor being administered, the size of the subject, or the severity of the disease or condition. One of ordinary skill in the art can empirically determine the effective amount of a particular inhibitor and/or other therapeutic agent without necessitating undue experimentation. It is preferred generally that a maximum dose be used, that is, the highest safe dose according to some medical judgment. Multiple doses per day may be contemplated to achieve appropriate systemic levels of compounds. Appropriate systemic levels can be determined by, for example, measurement of the patient's peak or sustained plasma level of the drug. "Dose" and "dosage" are used interchangeably herein.

For any compound described herein, the therapeutically effective amount can be initially determined from preliminary in vitro studies and/or animal models. A therapeutically effective dose can also be determined from human data for inhibitors which have been tested in humans and for compounds which are known to exhibit similar pharmacological activities, such as other related active agents. The applied dose can be adjusted based on the relative bioavailability and potency of the administered compound. Adjusting the dose to achieve maximal efficacy based on the methods described above and other methods well-known in the art, is well within the capabilities of the ordinarily skilled artisan.

In certain embodiments, the methods of the invention are useful for treating infection with enveloped viruses. Viruses are small infectious agents which contain a nucleic acid core and a protein coat, but are not independently living organisms. A virus cannot multiply in the absence of a living cell within which it can replicate. Viruses enter specific living cells either by transfer across a membrane or direct injection and multiply, causing disease. The multiplied virus can then be released and infect additional cells. Some viruses are DNA-containing viruses and others are RNA-containing viruses. The genomic size, composition and organization of viruses show tremendous diversity.

As used herein, an "enveloped" virus is a virus which possesses a membrane or 'envelope', which is a lipid bilayer containing viral proteins. The envelope proteins of a virus play a pivotal role in its lifecycle. They participate in the assembly of the infectious particle and also play a crucial role in virus entry by binding to a receptor present on the host cell and inducing fusion between the viral envelope and a membrane of the host cell. Enveloped viruses can be either spherical or filamentous (rod-shaped) and include but are not limited to filoviruses, such as Ebola virus or Marburg virus, Lassa virus, Arboroviruses such as Togaviruses, flaviviruses (such as hepatitis-C virus), bunyaviruses, and Arenaviruses, Orthomyxoviridae, Paramyxoviridae, poxvirus, herpesvirus, hepadnavirus, Rhabdovirus, Bornavirus, and Arterivirus.

In some embodiments, the invention provides for methods of treating infection by Ebola virus. Five species of Ebola virus have been identified: Cote d'Ivoire (CI), Sudan (S), Zaire (Z), and Reston (R), Bundibugyo (B), The Reston subtype is the only known filovirus that is not known to cause fatal disease in humans; however, it can be fatal in monkeys. In some embodiments, the compounds of the invention may selectively inhibit Ebola infection.

Infection by Ebola virus leads to Ebola Hemorrhagic Fever (EHF), the clinical manifestations of which are severe. The incubation period varies between four and sixteen days. The initial symptoms are generally a severe frontal and temporal headache, generalized aches and pains, malaise, and by the second day the victim will often have a fever. Later symptoms include watery diarrhea, abdominal pain, nausea, vomiting, a dry sore throat, and anorexia. By day seven of the symptoms, the patient will often have a maculopapular (small slightly raised spots) rash. At the same time the person may develop thrombocytopenia and hemorrhagic manifestations, particularly in the gastrointestinal tract, and the lungs, but it can occur from any orifice, mucous membrane or skin site. Ebola causes lesions in almost every organ, although the liver and spleen are the most noticeably affected. Both are darkened and enlarged with signs of necrosis. The cause of death (>75% in most outbreaks) is normally shock, associated with fluid and blood loss into the tissues. The hemorrhagic and connective tissue complications of the disease are not well understood, but may be related to onset of disseminated intravascular coagulation.

As used herein, the term "Marburg virus" refers to the filovirus that causes Marburg hemorrhagic fever. Marburg hemorrhagic fever is a rare, severe type of hemorrhagic fever which affects both humans and non-human primates. The case-fatality rate for Marburg hemorrhagic fever is 70% in recent Angola outbreak. After an incubation period of 5-10 days, the onset of the disease is sudden and is marked by fever, chills, headache, and myalgia. Around the fifth day after the onset of symptoms, a maculopapular rash, most prominent on the trunk (chest, back, stomach), may occur. Nausea, vomiting, chest pain, a sore throat, abdominal pain, and diarrhea then may appear. Symptoms become increasingly severe and may include jaundice, inflammation of the pancreas, severe weight loss, delirium, shock, liver failure, massive hemorrhaging, and multi-organ dysfunction.

The family Orthomyxoviridae includes, without limitation, influenza A virus, influenza B virus, influenza C virus, Thogotovirus, Dhori virus, and infectious salmon anemia virus.

Influenza type A viruses are divided into subtypes based on two proteins on the surface of the virus. These proteins are called hemagglutinin (HA) and neuraminidase (NA). There are 15 different HA subtypes and 9 different NA subtypes. Subtypes of influenza A virus are named according to their HA and NA surface proteins, and many different combinations of HA and NA proteins are possible. For example, an "H7N2 virus" designates an influenza A subtype that has an HA 7 protein and an NA 2 protein. Similarly an "H5N1" virus has an HA 5 protein and an NA 1 protein. Only some influenza A subtypes (i.e., H1N1, H2N2, and H3N2) are currently in general circulation among people. Other subtypes such as H5N1 are found most commonly in other animal species and in a small number of humans, where it is highly pathogenic. For example, H7N7 and H3N8 viruses cause illness in horses. Humans can be infected with influenza types A, B, and C. However, the only subtypes of influenza A virus that normally infect people are influenza A subtypes H1N1, H2N2, and H3N2 and recently, H5N1.

The family Paramyxoviridae includes, without limitation, human parainfluenza virus, human respiratory syncytial virus (RSV), Sendai virus, Newcastle disease virus, mumps virus, rubeola (measles) virus, Hendra virus, Nipah virus, avian pneumovirus, and canine distemper virus. The family Filoviridae includes, without limitation, Marburg virus and Ebola virus. The family Rhabdoviridae includes, without limitation, rabies virus, vesicular stomatitis virus (VSV), Mokola virus, Duvenhage virus, European bat virus, salmon infectious hematopoietic necrosis virus, viral hemorrhagic septicaemia virus, spring viremia of carp virus, and snakehead rhabdovirus. The family Bornaviridae includes, without limitation, Borna disease virus. The family Bunyaviridae includes, without limitation, Bunyamwera virus, Hantaan virus, Crimean Congo virus, California encephalitis virus, Rift Valley fever virus, and sandfly fever virus. The family Arenaviridae includes, without limitation, Old World Arenaviruses, such as Lassa virus (Lassa fever), Ippy virus, Lymphocytic choriomeningitis virus (LCMV), Mobala virus, and Mopeia virus and New World Arenaviruses, such as Junin virus (Argentine hemorrhagic fever), Sabia (Brazilian hemorrhagic fever), Amapari virus, Flexal virus, Guanarito virus (Venezuela hemorrhagic fever), Machupo virus (Bolivian hemorrhagic fever), Latino virus, Boliveros virus, Parana virus, Pichinde virus, Pirital virus, Tacaribe virus, Tamiami virus, and Whitewater Arroyo virus. The Arenaviridae associated with specific diseases include Lymphocytic choriomeningitis virus (meningitis), Lassa virus (hemorrhagic fever), Junin Virus (Argentine hemorrhagic fever), Machupo Virus (Bolivian hemorrhagic fever), Sabia virus (Brazilian hemorrhagic fever), and Guanarito (Venezuelan Hemorrhagic fever).

The arboviruses are a large group (more than 400) of enveloped RNA viruses that are transmitted primarily (but not exclusively) by arthropod vectors (mosquitoes, sandflies, fleas, ticks, lice, etc). More recently, the designated Arborviruses have been split into four virus families, including the togaviruses, flaviviruses, arenaviruses and bunyaviruses.

As used herein, the term "togavirus" refers to members of the family Togaviridae, which includes the genuses Alphavirus (e.g. Venezuela equine encephalitis virus, Sindbis virus, which causes a self-limiting febrile viral disease characterized by sudden onset of fever, rash, arthralgia or arthritis, lassitude, headache and myalgia) and Rubivirus (e.g. Rubella virus, which causes Rubella in vertebrates).

Rubella virus infections in adults are frequently subclinical. A characteristic pink, continuous maculopapular rash appears in 95% of adolescent patients 14-25 days after infection, and the patient is infectious for most of this time. After early viremia, rubella virus multiplies in many organs, particularly lymph nodes (lymphadenopathy), including the placenta, but symptoms in adults are rare. In children Rubella virus causes a mild febrile illness. The virus crosses placenta and multiplies in the fetus. Up to 85% of infants infected in the first trimester of pregnancy get congenital rubella syndrome (CRS), characterized by low birth weight, deafness, CNS involvement, and possibly abortion, with symptoms worse the earlier in pregnancy they occur.

Flaviviridae is a member of the family of (+)-sense RNA enveloped viruses. Flaviviridae includes flavivirus, Pestivirus, and Hepacivirus. Flavivirus genus including yellow fever virus, dengue fever virus, and Japanese encaphilitis (JE) virus. The Pestivirus genus includes the three serotypes of bovine viral diarrhea, but no known human pathogens. Genus Hepacivirus consists of hepatitis C virus and hepatitis C-like viruses.

A yellow fever virus infection is characterized by an incubation period of 3 to 6 days, during which 5% to 50% of infected people develop disease. Yellow fever begins with a nonspecific 1- to 3-day febrile illness, followed by a brief remission, and then by a life-threatening toxic syndrome accompanied by epistaxis, other hemorrhagic phenomena, jaundice, and disseminated intravascular coagulation. Mortality rates for yellow fever are approximately 20%.

There are four serotypes of dengue fever virus, all transmitted by mosquitos. Dengue fever virus infection may be asymptomatic or may result in dengue fever. This is generally a self-limiting febrile illness which occurs after a 4-8 day incubation period. It has symptoms such as fever, aches and arthralgia (pain in the joints) which can progress to arthritis (inflammation of the joints), myositis (inflammation of muscle tissue) and a discrete macular or maculopapular rash. In this situation clinical differentiation from other viral illnesses may not be possible, recovery is rapid, and need for supportive treatment is minimal. Dengue haemorrhagic fever (DHF) is a potentially deadly complication. Dengue hemorrhagic fever commences with high fever and many of the symptoms of dengue fever, but with extreme lethargy and drowsiness. The patient has increased vascular permeability and abnormal homeostasis that can lead to hypovolemia and hypotension, and in severe cases, result in hypovolemic shock often complicated by severe internal bleeding.

The Japanese encephalitis antigenic complex includes Alfuy, Japanese encephalitis, Kokobera, Koutango, Kunjin, Murray Valley encephalitis, St. Louis encephalitis, Stratford, Usutu, and West Nile viruses. These viruses are transmissible by mosquitoes and many of them can cause febrile, sometimes fatal, illnesses in humans. West Nile virus is the most widespread of the flaviviruses, with geographic distribution including Africa and Eurasia. West Nile virus RNA has been detected in overwintering mosquitoes in New York City & the geographic range of the virus is increasing in the USA.

The genus Pestivirus has been divided into bovine viral diarrhea virus (BVDV), classical swine fever virus (CSFV), and border disease virus (BDV). Infection with BVDV results in a variety of diseases ranging from subclinical to highly fatal. Many BVDV viruses cause only clinically mild disease in nonpregnant adult cattle. Prenatal infection can cause congenital malformations and/or fetal death.

The Hepacivirus genus includes the hepatitis C virus (HCV). The majority of cases of HCV infection give rise to an acute illness, where up to 85% of infections may develop into chronic hepatitis. Almost all patients develop a vigorous antibody and cell-mediated immune response which fails to clear the infection but may contribute towards liver damage.

Arenaviridae is a member of the family of (−) sense RNA viruses. As used herein, the term "Arenavirus" refers to members of the genus Arenavirus, a family of viruses whose members are generally associated with rodent-transmitted disease in humans, including Lymphocytic choriomeningitis virus (LCMV), Lassa virus, Junin virus, which causes Argentine hemorrhagic fever, Machupo virus, which causes Bolivian hemorrhagic fever, Guanarito virus, which causes Venezuelan hemorrhagic fever, and Sabia, which causes Brazilian hemorrhagic fever. LCMV causes which causes lymphocytic choriomeningitis, a mild disease that is occasionally severe with hemorrhaging. Infection by LCMV is rare in humans. Lassa virus causes Lassa fever in humans. Signs and symptoms of Lassa fever typically occur 1-3 weeks after the patient comes into contact with the virus. These include fever, retrosternal pain, sore throat, back pain, cough, abdominal pain, vomiting, diarrhea, conjunctivitis, facial swelling, proteinuria, and mucosal bleeding. Neurological problems have also been described, including hearing loss, tremors, and encephalitis.

Bunyaviridae is a family of (−)-sense RNA viruses. As used herein, "bunyavirus" refers to members of the Bunyaviridae family and includes the genuses Orthobunyavirus, Hantavirus, Phlebovirus, and Nairovirus.

Hantavirus infection is spread from rodents (reservoir) to man by aerosolized feces, not insect vector, causing hantavirus pulmonary syndrome (HPS). Patients with HPS typically present in with a relatively short febrile prodrome lasting 3-5 days. In addition to fever and myalgias, early symptoms include headache, chills, dizziness, non-productive cough, nausea, vomiting, and other gastrointestinal symptoms. Malaise, diarrhea, and lightheadedness are reported by approximately half of all patients, with less frequent reports of arthralgias, back pain, and abdominal pain. Patients may report shortness of breath, (respiratory rate usually 26-30 times per minute). Typical findings on initial presentation include fever, tachypnea and tachycardia. The physical examination is usually otherwise normal.

In man, the Phlebovirus Rift valley fever virus produces an acute, flu-like illness and is transmitted by mosquitoes from animal reservoirs (e.g. sheep) to man. Sand fly fever is transmitted to man by Phlebotomous flies (sand-flies) and causes an acute, febrile illness characterized by fever, malaise, eye pain, and headache.

Hendra and Nipah virus in the Henipavirus genus of the subfamily Paramyxovirinae are distinguished by fatal disease in both animal and human hosts. In particular, the high mortality and person-to-person transmission associated with the most recent Nipah virus outbreak.

Combination Therapy

The compounds of the invention may be used in combination with other therapeutic agents to treat a disease or infection disclosed herein. The compound and other therapeutic agent may be administered simultaneously or sequentially. When the other therapeutic agents are administered simultaneously they can be administered in the same or separate formulations, but are administered at the same time. The other therapeutic agents are administered sequentially with one another and with the inhibitors, when the administration of the other therapeutic agents and the inhibitors is temporally separated. The separation in time between the administration of these compounds may be a matter of minutes or it may be longer. Other therapeutic agents include but are not limited to anti-viral vaccines and anti-viral agents, inhibitors of metabolizing enzymes, e.g., liver enzymes, that normally metabolize said anti-viral agents and/or compounds of the invention. In some instances the inhibitors are administered with multiple therapeutic agents, e.g., 2, 3, 4 or even more different anti-viral agents.

An anti-viral vaccine is a formulation composed of one or more viral antigens and one or more adjuvants. The viral antigens include proteins or fragments thereof as well as whole killed virus. Adjuvants are well known to those of skill in the art.

Antiviral agents are compounds which prevent infection of cells by viruses or replication of the virus within the cell. There are many fewer antiviral drugs than antibacterial drugs because viruses are more dependent on host cell factors than bacteria. There are several stages within the process of viral infection which can be blocked or inhibited by antiviral agents. These stages include, attachment of the virus to the host cell (immunoglobulin or binding peptides), membrane penetration inhibitors, e.g. T-20, uncoating of the virus (e.g. amantadine), synthesis or translation of viral mRNA (e.g. interferon), replication of viral RNA or DNA (e.g. nucleotide analogues), maturation of new virus proteins (e.g. protease inhibitors), and budding and release of the virus.

Nucleotide analogues are synthetic compounds which are similar to nucleotides, but which have an incomplete or abnormal deoxyribose or ribose group. Once the nucleotide analogues are in the cell, they are phosphorylated, producing the triphosphate formed which competes with normal nucleotides for incorporation into the viral DNA or RNA. Once the triphosphate form of the nucleotide analogue is incorporated into the growing nucleic acid chain, it causes irreversible association with the viral polymerase and thus chain termination. Nucleotide analogues include, but are not limited to, acyclovir (used for the treatment of herpes simplex virus and varicella-zoster virus), gancyclovir (useful for the treatment of cytomegalovirus), idoxuridine, ribavirin (useful for the treatment of respiratory syncitial virus), dideoxyinosine, dideoxycytidine, zidovudine (azidothymidine), imiquimod, and resimiquimod.

The interferons are cytokines which are secreted by virus-infected cells as well as immune cells. The interferons function by binding to specific receptors on cells adjacent to the infected cells, causing the change in the cell which protects it from infection by the virus. $\alpha$- and $\beta$-interferon also induce the expression of Class I and Class II MHC molecules on the surface of infected cells, resulting in increased antigen presentation for host immune cell recognition. $\alpha$- and $\beta$-interferons are available as recombinant forms and have been used for the treatment of chronic hepatitis B and C infection. At the dosages which are effective for anti-viral therapy, interferons have severe side effects such as fever, malaise and weight loss.

Anti-viral agents which may be useful in combination with the inhibitors of the invention include but are not limited to immunoglobulins, amantadine, interferons, nucleotide analogues, and other protease inhibitors (other than the papain-like cysteine protease inhibitors—although combinations of papain-like cysteine protease inhibitors are also useful). Specific examples of anti-viral agents include but are not limited to Acemannan; Acyclovir; Acyclovir Sodium; Adefovir; Alovudine; Alvircept Sudotox; Amantadine Hydrochloride; Aranotin; Arildone; Atevirdine Mesylate; Avridine; Cidofovir; Cipamfylline; Cytarabine Hydrochloride; Delavirdine Mesylate; Desciclovir; Didanosine; Disoxaril; Edoxudine; Enviradene; Enviroxime; Famciclovir; Famotine Hydrochloride; Fiacitabine; Fialuridine; Fosarilate; Foscarnet Sodium; Fosfonet Sodium; Ganciclovir; Ganciclovir Sodium; Idoxuridine; Kethoxal; Lamivudine; Lobucavir; Memotine Hydrochloride; Methisazone; Nevirapine; Penciclovir; Pirodavir; Ribavirin; Rimantadine Hydrochloride; Saquinavir Mesylate; Somantadine Hydrochloride; Sorivudine; Statolon; Stavudine; Tilorone Hydrochloride; Trifluridine; Valacyclovir Hydrochloride; Vidarabine; Vidarabine Phosphate; Vidarabine Sodium Phosphate; Viroxime; Zalcitabine; Zidovudine; and Zinviroxime.

Immunoglobulin therapy is used for the prevention of viral infection. Immunoglobulin therapy for viral infections is different than bacterial infections, because rather than being antigen-specific, the immunoglobulin therapy functions by binding to extracellular virions and preventing them from attaching to and entering cells which are susceptible to the viral infection. The therapy is useful for the prevention of viral infection for the period of time that the antibodies are present in the host. In general there are two types of immunoglobulin therapies, normal immunoglobulin therapy and hyper-immunoglobulin therapy. Normal immune globulin therapy utilizes a antibody product which is prepared from the serum of normal blood donors and pooled. This pooled product contains low titers of antibody to a wide range of human viruses, such as hepatitis A, parvovirus, enterovirus (especially in neonates). Hyper-immune globulin therapy utilizes antibodies which are prepared from the serum of individuals who have high titers of an antibody to a particular virus. Those antibodies are then used against a specific virus. Another type of immunoglobulin therapy is active immunization. This involves the administration of antibodies or antibody fragments to viral surface proteins.

Pharmaceutical Compositions

In certain embodiments, the present invention provides pharmaceutical compositions comprising a compound of Formula I or II and a pharmaceutically acceptable carrier.

The formulations of the invention are administered in pharmaceutically acceptable solutions, which may routinely contain pharmaceutically acceptable concentrations of salt, buffering agents, preservatives, compatible carriers, adjuvants, and optionally other therapeutic ingredients.

For use in therapy, an effective amount of the inhibitor can be administered to a subject by any mode that delivers the inhibitor to the desired surface. Administering the pharmaceutical composition of the present invention may be accomplished by any means known to the skilled artisan. Preferred routes of administration include but are not limited to oral, intrathecal, intra-arterial, direct bronchial application, parenteral (e.g. intravenous), intramuscular, intranasal, sublingual, intratracheal, inhalation, ocular, vaginal, and rectal, e.g., using a suppository.

For oral administration, the compounds (i.e., inhibitors, and other therapeutic agents) can be formulated readily by combining the active compound(s) with pharmaceutically acceptable carriers well known in the art. Such carriers enable the compounds of the invention to be formulated as tablets, pills, dragees, capsules, liquids, gels, syrups, slurries, suspensions and the like, for oral ingestion by a subject to be treated. Pharmaceutical preparations for oral use can be obtained as solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate. Optionally the oral formulations may also be formulated in saline or buffers, i.e. EDTA for neutralizing internal acid conditions or may be administered without any carriers.

Also specifically contemplated are oral dosage forms of the above component or components. The component or components may be chemically modified or mixed with other components so that oral delivery of the derivative is efficacious. Generally, the chemical modification or mixture contemplated permits (a) longer half-lives; and (b) uptake into the blood stream from the stomach or intestine. Also desired is the increase in overall stability of the component or components and increase in circulation time in the body. Examples of such moieties or other compounds include: polyethylene glycol, copolymers of ethylene glycol and propylene glycol, carboxymethyl cellulose, dextran, polyvinyl alcohol, polyvinyl pyrrolidone and polyproline. Abuchowski and Davis, 1981, "Soluble Polymer-Enzyme Adducts" In: Enzymes as Drugs, Hocenberg and Roberts, eds., Wiley-Interscience, New York, N.Y., pp. 367-383; Newmark, et al., 1982, J. Appl. Biochem. 4:185-189. Other polymers that could be used are poly-1,3-dioxolane and poly-1,3,6-tioxocane. Preferred for pharmaceutical usage, as indicated above, are polyethylene glycol moieties.

For the component (or derivative) the location of release may be the stomach, the small intestine (the duodenum, the jejunum, or the ileum), or the large intestine. One skilled in the art has available formulations which will not dissolve in the stomach, yet will release the material in the duodenum or elsewhere in the intestine. Preferably, the release will avoid the deleterious effects of the stomach environment, either by protection of the inhibitor (or derivative) or by release of the biologically active material beyond the stomach environment, such as in the intestine.

To ensure full gastric resistance a coating impermeable to at least pH 5.0 is essential. Examples of the more common inert ingredients that are used as enteric coatings are cellulose acetate trimellitate (CAT), hydroxypropylmethylcellulose phthalate (HPMCP), HPMCP 50, HPMCP 55, polyvinyl acetate phthalate (PVAP), Eudragit L30D, Aquateric, cellulose acetate phthalate (CAP), Eudragit L, Eudragit S, and Shellac. These coatings may be used as mixed films.

A coating or mixture of coatings can also be used on tablets, which are not intended for protection against the stomach. This can include sugar coatings, or coatings which make the tablet easier to swallow. Capsules may consist of a hard shell (such as gelatin) for delivery of dry therapeutic i.e. powder; for liquid forms, a soft gelatin shell may be used. The shell material of cachets could be thick starch or other edible paper. For pills, lozenges, molded tablets or tablet triturates, moist massing techniques can be used.

The therapeutic can be included in the formulation as fine multi-particulates in the form of granules or pellets of particle size about 1 mm. The formulation of the material for capsule administration could also be as a powder, lightly compressed plugs or even as tablets. The therapeutic could be prepared by compression.

Colorants and flavoring agents may all be included. For example, the inhibitor (or derivative) may be formulated (such as by liposome or microsphere encapsulation) and then further contained within an edible product, such as a refrigerated beverage containing colorants and flavoring agents.

One may dilute or increase the volume of the therapeutic with an inert material. These diluents could include carbohydrates, especially mannitol, α-lactose, anhydrous lactose, cellulose, sucrose, modified dextrans and starch. Certain inorganic salts may be also be used as fillers including calcium triphosphate, magnesium carbonate and sodium chloride. Some commercially available diluents are Fast-Flo, Emdex, STA-Rx 1500, Emcompress and Avicell.

Disintegrants may be included in the formulation of the therapeutic into a solid dosage form. Materials used as disintegrates include but are not limited to starch, including the commercial disintegrant based on starch, Explotab. Sodium starch glycolate, Amberlite, sodium carboxymethylcellulose, ultramylopectin, sodium alginate, gelatin, orange peel, acid carboxymethyl cellulose, natural sponge and bentonite may all be used. Another form of the disintegrants are the insoluble cationic exchange resins. Powdered gums may be used as disintegrants and as binders and these can include powdered gums such as agar, Karaya or tragacanth. Alginic acid and its sodium salt are also useful as disintegrants. Binders may be used to hold the therapeutic agent together to form a hard tablet and include materials from natural products such as acacia, tragacanth, starch and gelatin. Others include methyl cellulose (MC), ethyl cellulose (EC) and carboxymethyl cellulose (CMC). Polyvinyl pyrrolidone (PVP) and hydroxypropylmethyl cellulose (HPMC) could both be used in alcoholic solutions to granulate the therapeutic.

An anti-frictional agent may be included in the formulation of the therapeutic to prevent sticking during the formulation process. Lubricants may be used as a layer between the therapeutic and the die wall, and these can include but are not limited to; stearic acid including its magnesium and calcium salts, polytetrafluoroethylene (PTFE), liquid paraffin, vegetable oils and waxes. Soluble lubricants may also be used such as sodium lauryl sulfate, magnesium lauryl sulfate, polyethylene glycol of various molecular weights, Carbowax 4000 and 6000. Glidants that might improve the flow properties of the drug during formulation and to aid rearrangement during compression might be added. The glidants may include starch, talc, pyrogenic silica and hydrated silicoaluminate.

To aid dissolution of the therapeutic into the aqueous environment a surfactant might be added as a wetting agent. Surfactants may include anionic detergents such as sodium lauryl sulfate, dioctyl sodium sulfosuccinate and dioctyl sodium sulfonate. Cationic detergents might be used and could include benzalkonium chloride or benzethomium chloride. The list of potential non-ionic detergents that could be included in the formulation as surfactants are lauromacrogol 400, polyoxyl 40 stearate, polyoxyethylene hydrogenated castor oil 10, 50 and 60, glycerol monostearate, polysorbate 40, 60, 65 and 80, sucrose fatty acid ester, methyl cellulose and carboxymethyl cellulose. These surfactants could be present in the formulation of the inhibitor or derivative either alone or as a mixture in different ratios.

Pharmaceutical preparations which can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. Microspheres formulated for oral administration may also be used. Such microspheres have been well defined in the art. All formulations for oral administration should be in dosages suitable for such administration.

Kits

The invention also includes kits. The kit has a container housing an inhibitor of the invention and optionally additional containers with other therapeutics such as anti-viral agents or viral vaccines. The kit also includes instructions for administering the component(s) to a subject who has or is at risk of having an enveloped viral infection.

In some aspects of the invention, the kit can include a pharmaceutical preparation vial, a pharmaceutical preparation diluent vial, and inhibitor. The vial containing the diluent for the pharmaceutical preparation is optional. The diluent vial contains a diluent such as physiological saline for diluting what could be a concentrated solution or lyophilized powder of inhibitor. The instructions can include instructions for mixing a particular amount of the diluent with a particular amount of the concentrated pharmaceutical preparation, whereby a final formulation for injection or infusion is prepared. The instructions may include instructions for use in an oral formulation, inhaler, intravenous injection or any other device useful according to the invention. The instructions can include instructions for treating a patient with an effective amount of inhibitor. It also will be understood that the containers containing the preparations, whether the container is a bottle, a vial with a septum, an ampoule with a septum, an infusion bag, and the like, can contain indicia such as conventional markings which change color when the preparation has been autoclaved or otherwise sterilized.

EXAMPLES

Example 1: Syntheses of Exemplary Compounds of the Invention

The compounds of the invention can be synthesized according to the following representative procedures (Methods A, B, C), wherein the substituents are as defined above, except where further noted.

$^1$H NMR spectra were recorded on a Varian Inova 600 MHz spectrometer with chemical shifts reported in parts per million (ppm) relative to an internal standard (trimethylsilane). Coupling constants (J) are reported in hertz (Hz). Standard resolution mass spectra were obtained on an Agilent 1200 Series HPLC (4.6×100 mm, 5 μm Phenomenex C18 reverse-phase column) and a 6130 Series mass spectrometer system; all mass spectra were obtained using electrospray ionization (EI) in positive ion mode. Standard reverse-phase HPLC conditions were as follows: mobile phase A=0.1% formic acid in water; mobile phase B=0.1% formic acid in acetonitrile. Solvents for synthesis were purchased as anhydrous grade and used without further purification. Reagents were purchased from commercial sources and used as received.

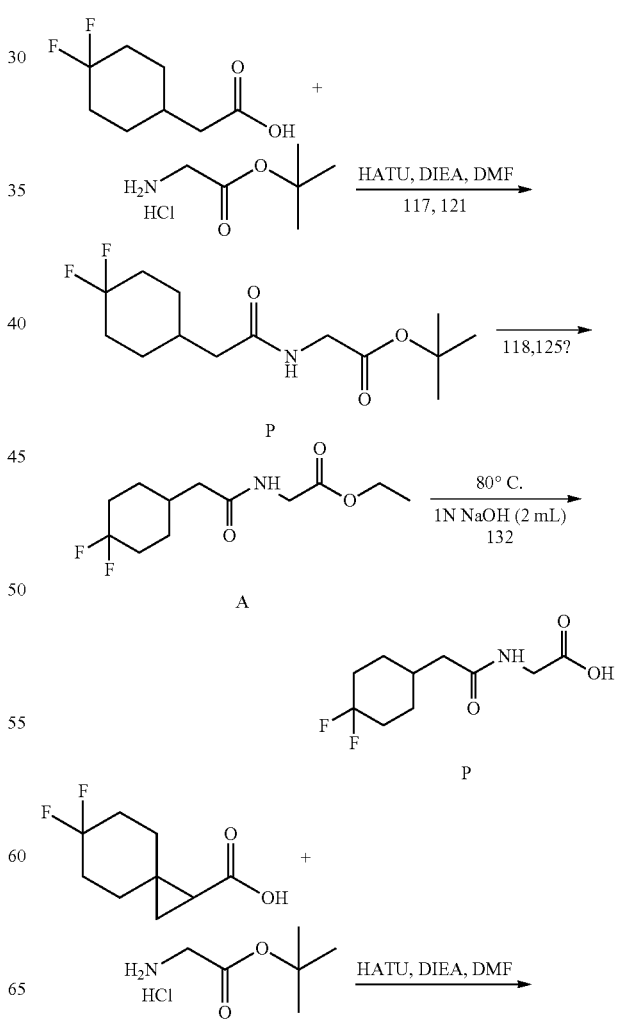

Scheme 1: Synthetic scheme for certain compounds of the invention according to Method A.

133
-continued
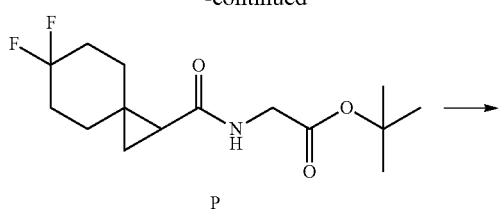
P
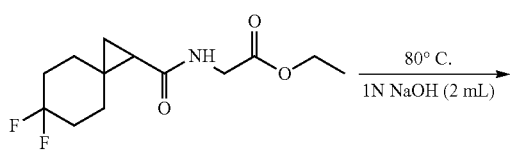
A
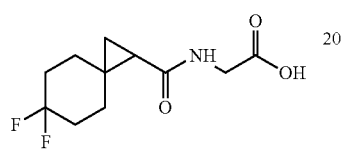
P
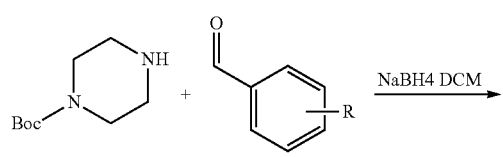
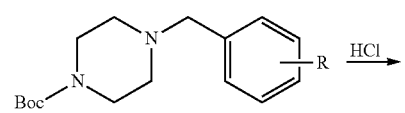
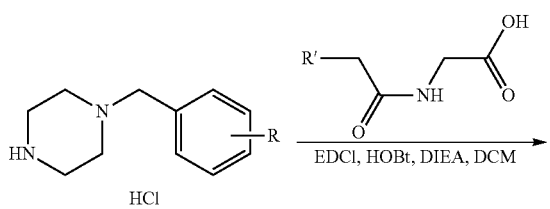
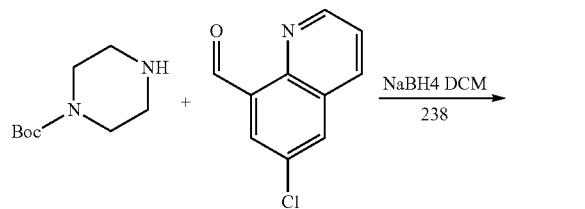
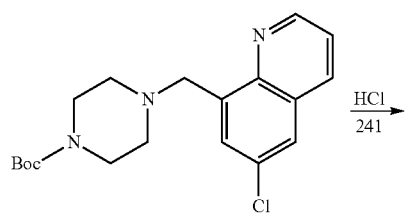
134
-continued
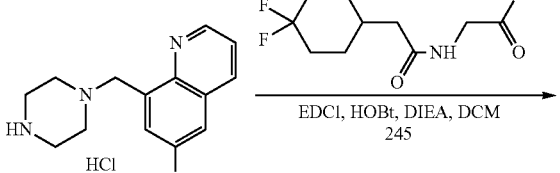
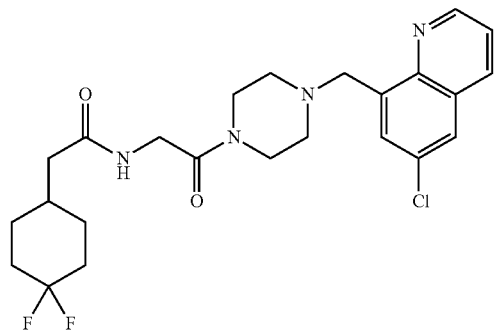
245
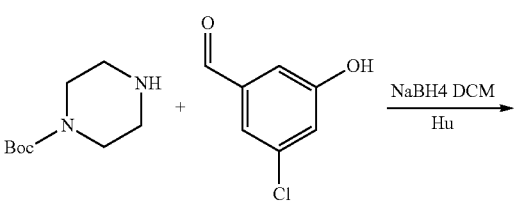
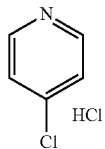
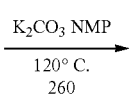
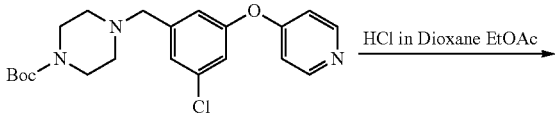
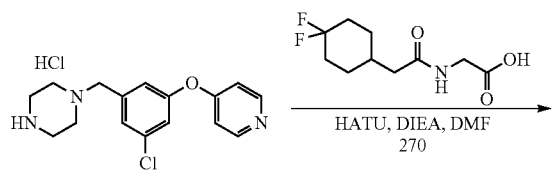
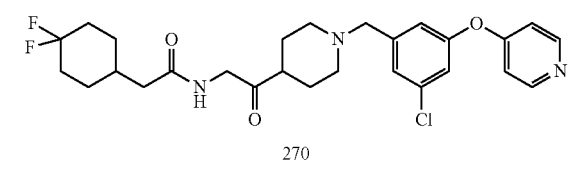
270

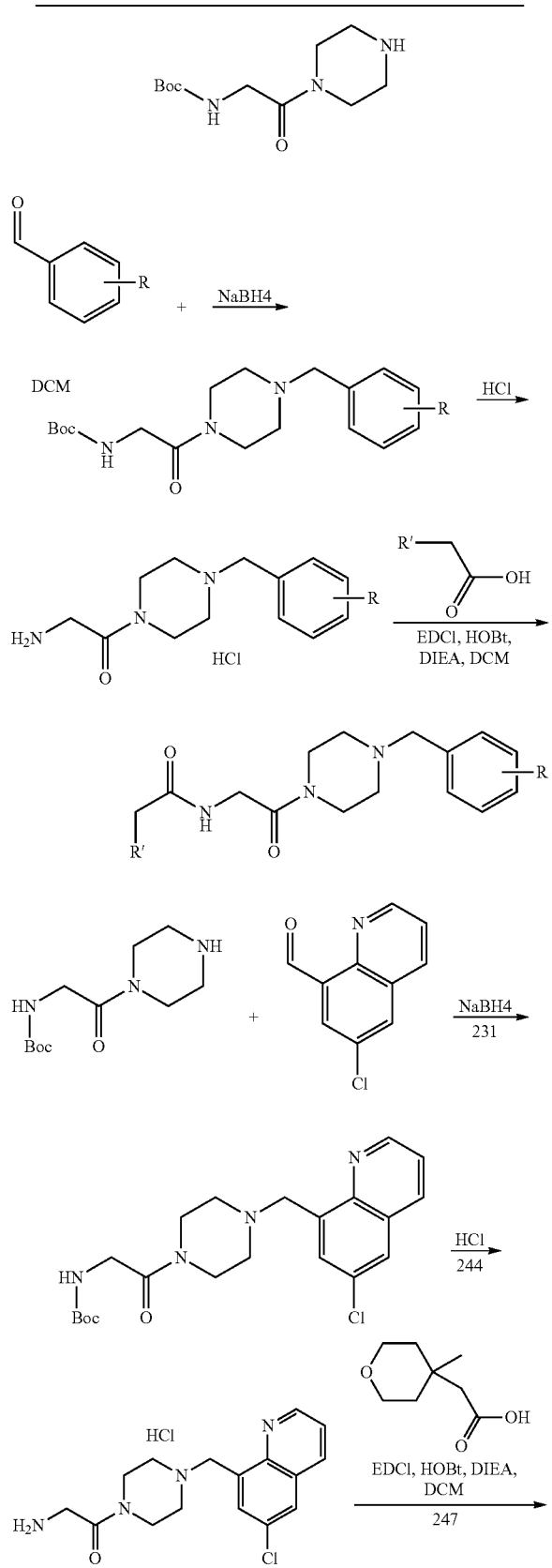
Scheme 2: Synthetic scheme for certain compounds of the invention according to Method B
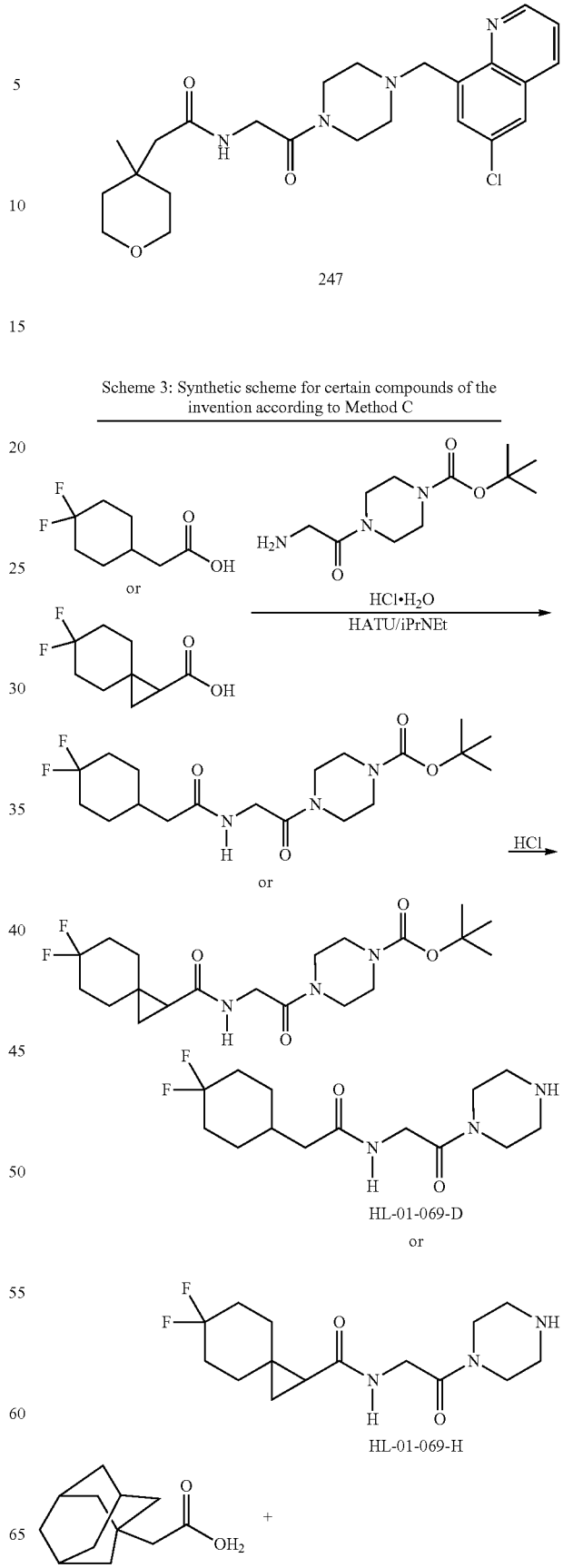
Scheme 3: Synthetic scheme for certain compounds of the invention according to Method C

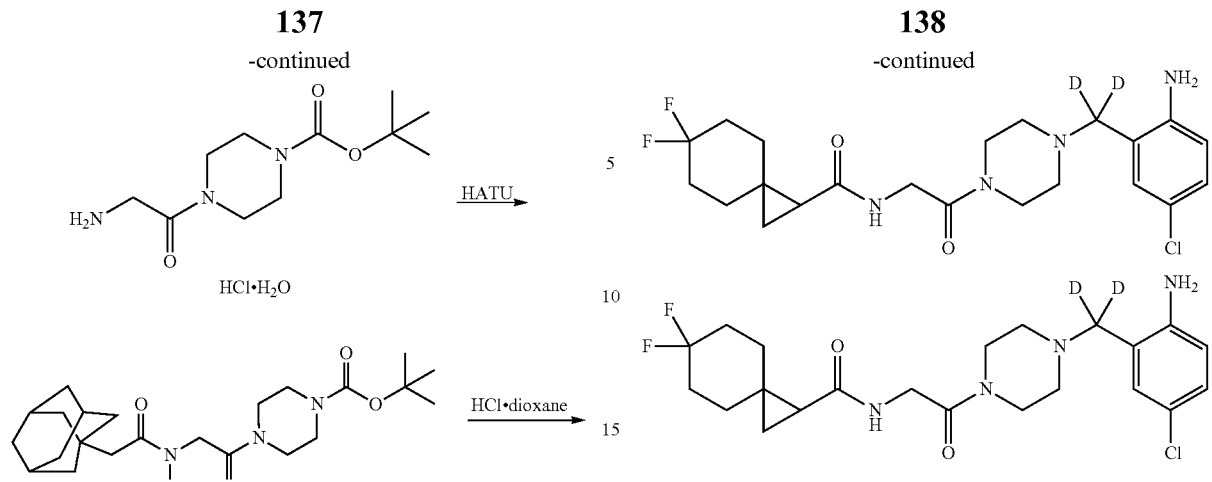

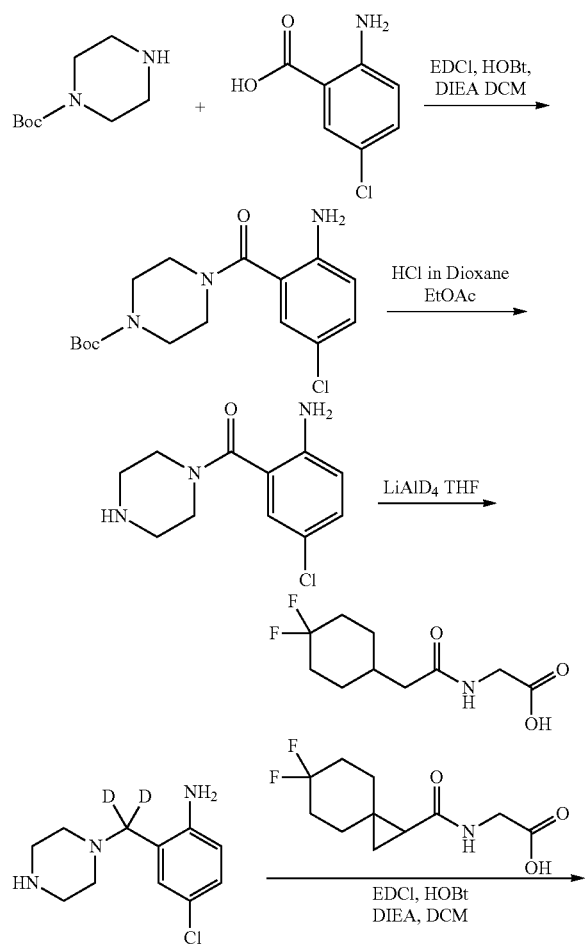

tert-Butyl 4-(2-amino-5-chlorobenzoyl)piperazine-1-carboxylate

To the proper amount of DCM solution Boc-piperazine (1 eq) and 2-amino-5-chlorobenzoic acid (1.2 eq), under the nitrogen flushing, minimum amount of DCM solution of NaBH(Ac)$_3$ (3 eq) was added dropwise. Then the mixture was stirred at room temperature overnight. After the reaction, the solvent was removed by GeneVec. Saturated Na$_2$CO$_3$ aq was added into the mixture, after sonication and centrifugation, the clear water phase was removed and the residues was dissolved in EtOAc and dried by MgSO4. Then the mixture was directly loaded onto a solid phase extraction (SPE) cartridge containing strong ion exchanger (SCX, Ig; UCT, CUBCX1M15). The cartridge was first washed with EtOAc:MeOH (10:1, 12 mL), which was discarded, and then the product was eluted with EtOAc-MeOH-Et3N (20: 2:1, 6 mL) and obtained by concentration. MS m/z: 440.20 (M+1), calc'd for C$_{16}$H$_{22}$ClN$_3$O$_3$: 339.13.

(2-Amino-5-chlorophenyl)(piperazin-1-yl)methanone

In a 5 mL glass vial, the Boc protected piperazine derivative was dissolved in 1 mL of EtOAc and then 1 mL of 4N HCl in Dioxane was added to the solution. Under N2 protection, the mixture was stirred at room temperature overnight. After the reaction the mixture was then concentrated by GeneVec. The pure product was obtained as a solid. MS m/z: 240.10 (M+1), calc'd for C$_{11}$H$_{14}$ClN$_3$O: 239.08.

4-Chloro-2-(piperazin-1-ylmethyl-d2)aniline (2-Amino-5-chlorophenyl)(piperazin-1-yl)methanone and lithium aluminium hydride (6 eq) was dissolved separated in unhydrous THF and was degassed and refilled with N$_2$. Then the solution of amide was added to a stirred suspension of lithium aluminium hydride in unhydrous THF. The reaction was heated to 50° C. for 4 hours and then cooled. The reaction was quenched by adding 6 eq of Sodium sulfate decahydrate portion-wise and stirred at rt for overnight. Then the mixture was filtered and the filtrate was concentrated to afford the product. MS m/z: 228.20 (M+1), calc'd for C$_{11}$H$_{14}$D$_2$ClN$_3$: 227.12.

N-(2-(4-((2-amino-5-chlorophenyl)methyl-d2)piperazin-1-yl)-2-oxoethyl)-2-(4,4-difluorocyclohexyl)acetamide 1412

(2-(4,4-difluorocyclohexyl)acetyl)glycine (1 eq), amine (1 eq), EDCI (1.2 eq) and HOBt (1.5 eq) were dissolved in proper amount of DCM and then DIEA (12 eq) was added to the solution. Under N2 protection, the mixture was stirred at room temperature overnight. After the reaction, the DIEA was evaporated by GeneVec. Water was added into the residue, and some oily or solid substance was appeared. After sonication and centrifugation, the water phase was removed and the residue was dissolved in EtOAc, dried by MgSO4, filtered and concentrated. Pure product was then obtained by productive thin layer chromatography (MeOH: DCM 1:20). $^1$H NMR (400 MHz, CDCl$_3$, ppm): δ 7.06 (dd, J1=2.5, J2=8.4, 1H), 6.95 (d, J=2.5, 1H), 6.58 (d, J=8.4, 1H), 6.55 (br, 1H), 4.05 (d, J=4.0, 2H), 3.63 (t, J=5.0, 2H), 3.39 (t, J=5.0, 2H), 2.43 (t, J=5.0, 4H), 2.18 (d, J=7.0, 2H), 2.10-1.74 (m, 6H), 1.33 (m, 3H). MS m/z: 445.2 (M+1), calc'd for $C_{21}H_{27}D_2ClF_2N_4O_2$: 444.21.

Compound N-(2-(4-((2-amino-5-chlorophenyl)methyl-d2)piperazin-1-yl)-2-oxoethyl)-6,6-difluorospiro[2.5]octane-1-carboxamide 1413 was prepared from (6,6-difluorospiro[2.5]octane-1-carbonyl)glycine in a manner similar to that described for compound 1412 MS m/z: 457.20 (M+1), calc'd for $C_{22}H_{27}D_2ClF_2N_4O_2$: 456.21.

General Procedures for Certain Compounds

Scheme 5: Synthetic scheme for certain compounds of the invention according to Method A1

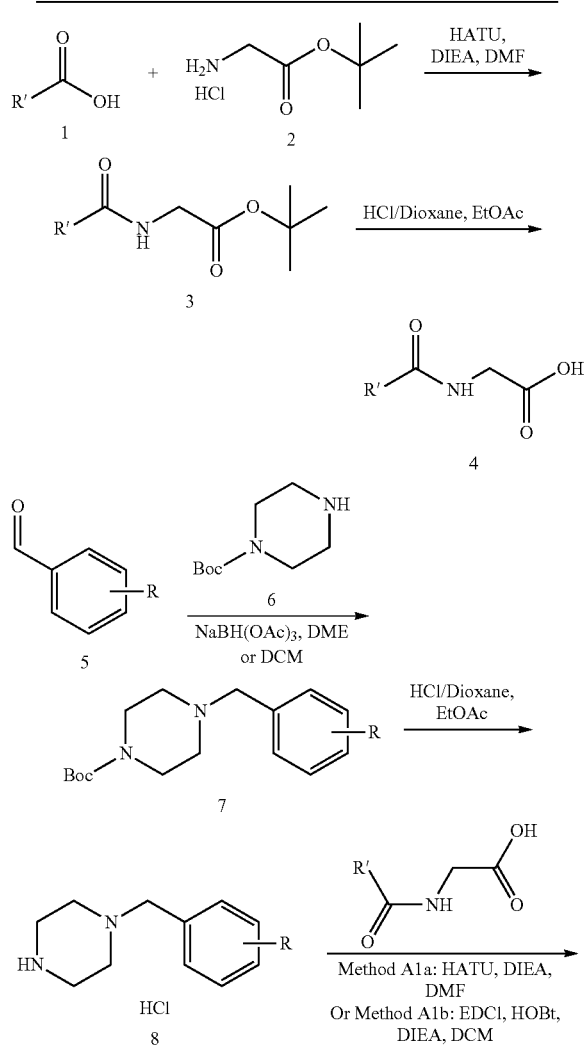

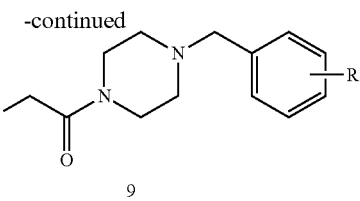

Method A1

To a mixture of the appropriate acid (1, 1 mmol, 1 eq), HATU (1.5 mmol, 1.5 eq), under nitrogen was added 1.4 mL of anhydrous DMF. Under stirring, N, N-diisopropylethylamine (2, 0.3 mL) was added and the reaction stirred for 1 hr, then tert-butyl glycinate hydrochloride (1.2 mmol, 1.2 eq) added in one portion. The reaction was then stirred for overnight at room temperature. The reaction was concentrated in genevec to remove iPr2NEt, water added, and deep brown color precipitation, spinned, washed with water 2×6 mL to afford crude product 3 which were used for next step without further purification.

In a 5 mL glass vial, 3 was dissolved in 1 mL of EtOAc and then 1 mL of 4N HCl in Dioxane was added to the solution. Under nitrogen protection, the mixture was stirred at room temperature overnight. After the reaction the mixture was then concentrated by GeneVec. The pure product acid 4 was obtained as a solid.

In a vial was placed Boc-piperizine (6, 2 mmol, 1.1-3 eq) in 5 mL of anhydrous DME or DCM. Aldehyde 5 (1.85 mmol, 1 eq) was then added, followed by NaBH(OAc)$_3$ (3.7 mmol, 2-4 eq). The reaction stirred for overnight and then was dried to afford an oily crude mixture. To this crude was added sat. aq. Na$_2$CO$_3$, sonicated for 10 minutes, to get a sticky brown color wax/oil. Washed, sonicated with water 2×10 mL. The residue was dried to afford the 7.

In a 5 mL glass vial, the Boc-protected amine 7 was dissolved in 2 mL of EtOAc and then 2 mL of 4N HCl in Dioxane was added to the solution. Under nitrogen protection, the mixture was stirred at room temperature overnight. After the reaction the mixture was then concentrated by GeneVec. The HCl salt of amine 8 was obtained as a solid.

In a glass vial, the appropriate acid (4, 1 eq), amine (8, 1 eq) and HATU (1.2 eq), were dissolved in minimum amount of DMF and then the same amount of DIEA was added to the solution (Method A1a). [Alternative method: Appropriate acid (4, 1 eq), amine (8, 1 eq), EDCI (1.2 eq) and HOBt (1.5 eq) were dissolved in proper amount of DCM and then DIEA (12 eq) was added to the solution (Method A1b).] Under N$_2$ protection, the mixture was stirred at room temperature for overnight. After the reaction, the DIEA was evaporated by GeneVec. Water was added into the residue, and some oily or solid substance was appeared. After sonication and centrifugation, the water phase was removed and the residue was dissolved in EtOAc, dried by MgSO4, filtered and concentrated. Pure product 9 was then obtained by productive thin layer chromatography (5% MeOH/CH$_2$Cl$_2$).

Scheme 6: Synthetic scheme for certain compounds of the invention according to Method A2

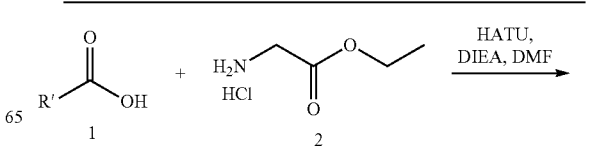

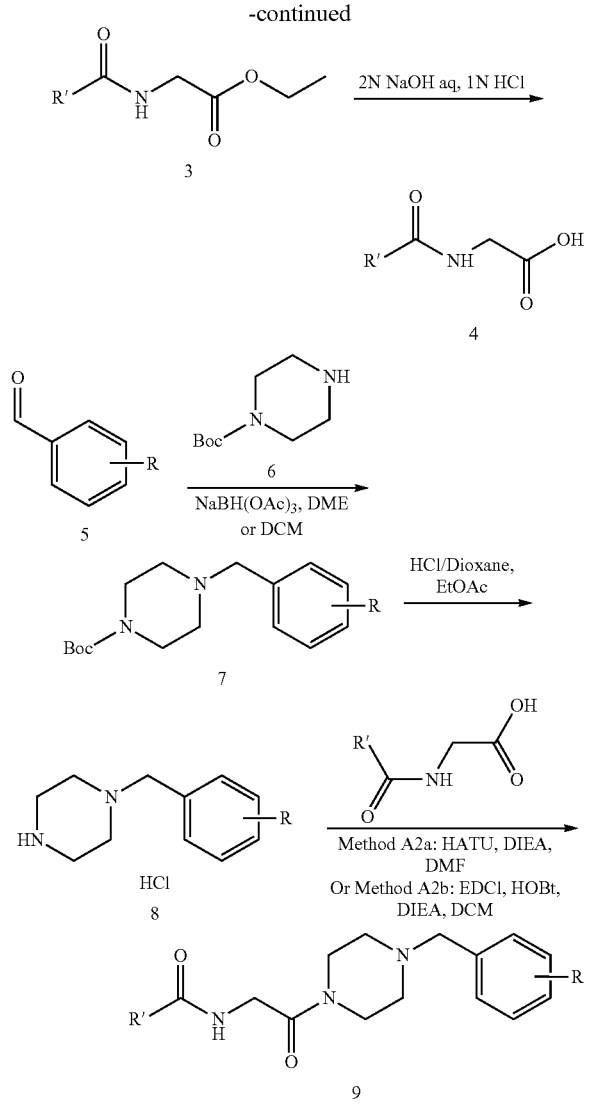

Method A2

To a mixture of the appropriate acid (1, 3.2 mmol, 1 eq), ethyl glycinate hydrochloride (2, 3.9 mmol, 1.2 eq), HATU (4.8 mmol, 1.5 eq), under nitrogen was added 6 mL of anhydrous DMF. Under stirring, N, N-diisopropylethylamine (0.3 mL) was added and the reaction then stirred for overnight at room temperature. To the mixture was added water (30 mL), white wax type precipitation formed. The water was decanted, and the wax washed with 3×30 mL water under sonication to afford 3.

To the wax 3 was added 15 mL of EtOH, and 15 mL of 1N NaOH, stirred at rt for over night. After the MeOH was removed, the mixture was extracted by EtOAc. The water layer is acidified to pH=5 by 1N HCl, and white solid formed, filtered to get 4.

In a vial was placed Boc-piperizine (6, 2 mmol, 1.1-3 eq) in 5 mL of anhydrous DME or DCM. Aldehyde 5 (1.85 mmol, 1 eq) was then added, followed by NaBH(OAc)$_3$ (3.7 mmol, 2-4 eq). The reaction stirred for overnight and then was dried to afford an oily crude mixture. To this crude was added sat. aq. Na$_2$CO$_3$, sonicated for 10 minutes, to get a sticky brown color wax/oil. Washed, sonicated with water 2×10 mL. The residue was dried to afford the 7.

In a 5 mL glass vial, the Boc-protected piperazine 7 was dissolved in 2 mL of EtOAc and then 2 mL of 4N HCl in Dioxane was added to the solution. Under nitrogen protection, the mixture was stirred at room temperature overnight. After the reaction the mixture was then concentrated by GeneVec. The HCl salt of piperazine 8 was obtained as a solid.

In a glass vial, the appropriate acid (4, 1 eq), amine (8, 1 eq) and HATU (1.2 eq), were dissolved in minimum amount of DMF and then the same amount of DIEA was added to the solution (Method A2a). [Alternative method: Appropriate acid (4, 1 eq), amine (8, 1 eq), EDCI (1.2 eq) and HOBt (1.5 eq) were dissolved in proper amount of DCM and then DIEA (12 eq) was added to the solution (Method A2b).] Under N$_2$ protection, the mixture was stirred at room temperature for overnight. After the reaction, the DIEA was evaporated by GeneVec. Water was added into the residue, and some oily or solid substance was appeared. After sonication and centrifugation, the water phase was removed and the residue was dissolved in EtOAc, dried by MgSO4, filtered and concentrated. Pure product 9 was then obtained by productive thin layer chromatography (5% MeOH/ CH$_2$Cl$_2$).

Scheme 7: Synthetic scheme for certain compounds of the invention according to Method B1

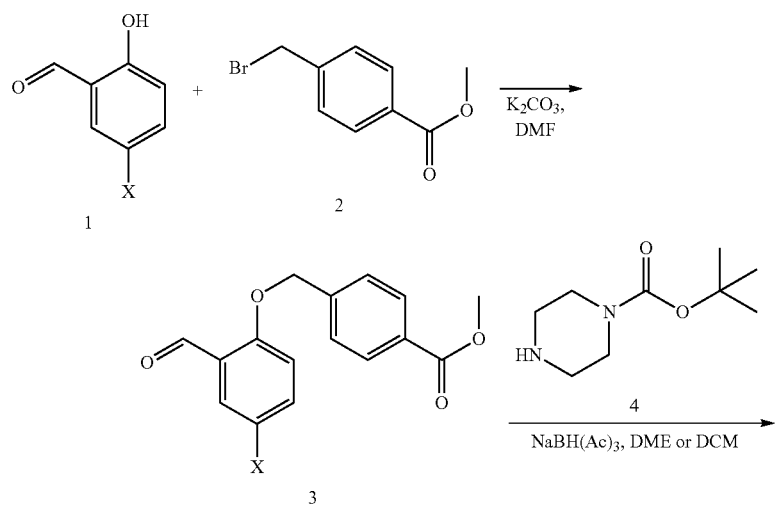

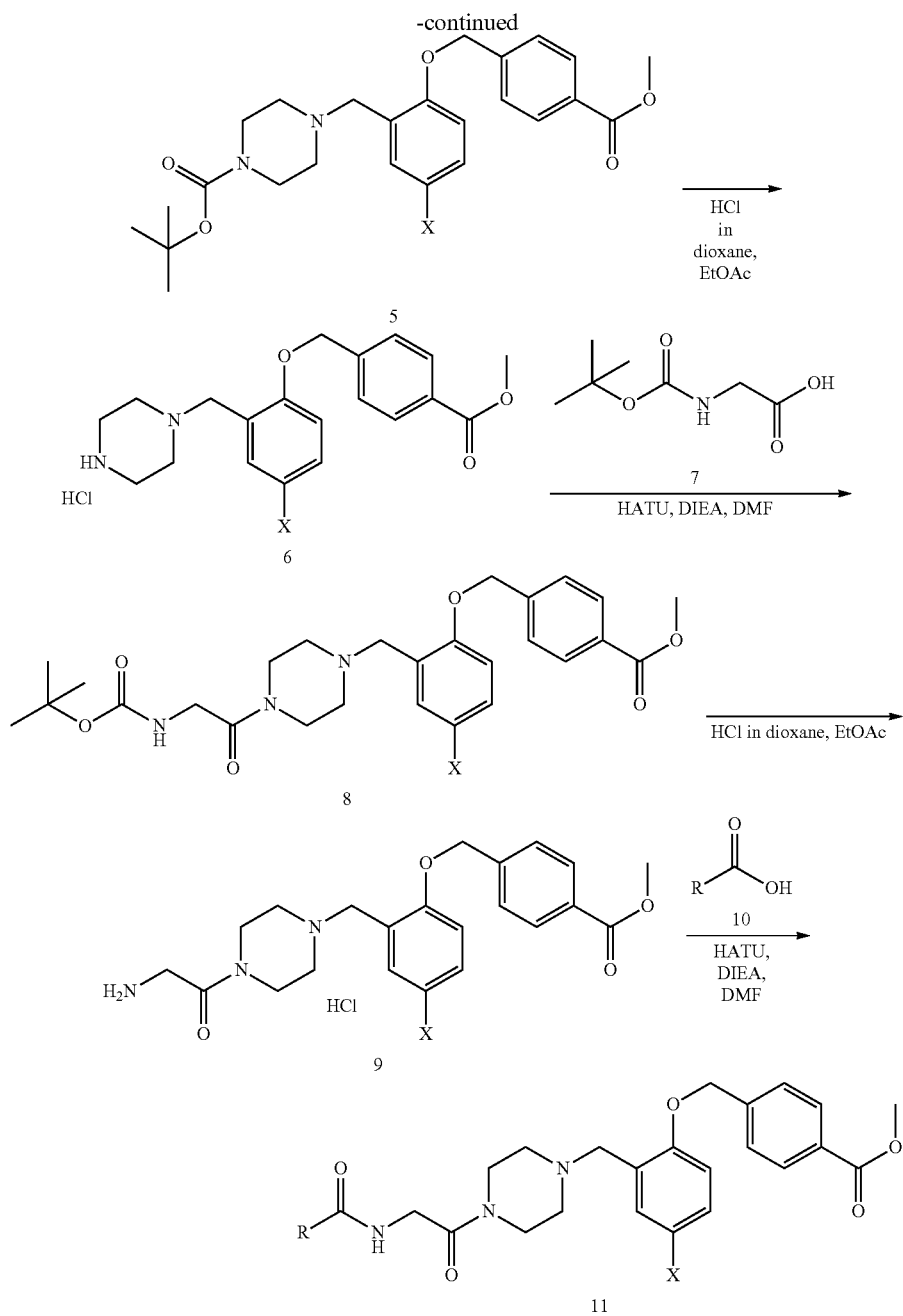

Method B1

To a mixture of proper aldehyde (1, 3.8 mmol, 1eq) and potassium carbonate (11 mmol, 4 eq) in DMF (5 mL) was added methyl 4-(bromomethyl)benzoate (2, 4.0 mmol, 1.05 eq) and the resulting mixture was stirred for 16 h at room temperature. The solvent was removed under reduced pressure and the residue was partitioned between H₂O (20 mL) and EtOAc (15 mL). The organic layer was washed with brine, dried over sodium sulfate, and concentrated under reduced pressure. The residue was purified by flash column chromatography (gradient: 20-100% EtOAc/hexanes) to give 3 as a white solid.

In a vial was placed Boc-piperizine (4, 2 mmol, 1.1-3 eq) in 5 mL of anhydrous DME or DCM. Aldehyde 3 (1.85 mmol, 1 eq) was then added, followed by NaBH(OAc)₃ (3.7 mmol, 2-4 eq). The reaction stirred for overnight and then was dried to afford an oily crude mixture. To this crude was added sat. aq. Na₂CO₃, sonicated for 10 minutes, to get a sticky brown color wax/oil. Washed, sonicated with water 2×10 mL. The residue was dried to afford the 5.

In a 5 mL glass vial, the Boc-protected piperazine 5 (2 mmol) was dissolved in 2 mL of EtOAc and then 2 mL of 4N HCl in Dioxane was added to the solution. Under nitrogen protection, the mixture was stirred at room temperature overnight. After the reaction, the mixture was then concentrated by GeneVec. The HCl salt of piperazine 6 was obtained as a solid.

To a mixture of the (tert-butoxycarbonyl)glycine (7, 1.2 mmol, 1.2 eq), piperazine (1 mmol, 1 eq), HATU (1.5 mmol, 1.5 eq), under nitrogen was added 3 mL of anhydrous DMF.

Under stirring, N, N-diisopropylethylamine (0.2 mL) was added and the reaction then stirred for overnight at room temperature. To the mixture was added water (10 mL), white precipitation formed. After sonication and centrifugation, the water was decanted, and the residue was washed with 10 mL water under sonication one more time to afford 8.

In a 5 mL glass vial, the Boc-protected amine 8 (1 mmol) was dissolved in 1 mL of EtOAc and then 1 mL of 4N HCl in Dioxane was added to the solution. Under nitrogen protection, the mixture was stirred at room temperature overnight. After the reaction, the mixture was then concentrated by GeneVec. The HCl salt of amine 9 was obtained as a solid.

In a glass vial, the appropriate acid (10, 1 eq), amine (9, 1 eq) and HATU (1.2 eq), were dissolved in minimum amount of DMF and then the same amount of DIEA was added to the solution. Under $N_2$ protection, the mixture was stirred at room temperature for overnight. After the reaction, the DIEA was evaporated by GeneVec. Water was added into the residue, and some oily or solid substance was appeared. After sonication and centrifugation, the water phase was removed and the residue was dissolved in EtOAc, dried by MgSO4, filtered and concentrated. Pure product 11 was then obtained by productive thin layer chromatography (5% MeOH/$CH_2Cl_2$).

Scheme 8: Synthetic scheme for certain compounds of the invention according to Method B2

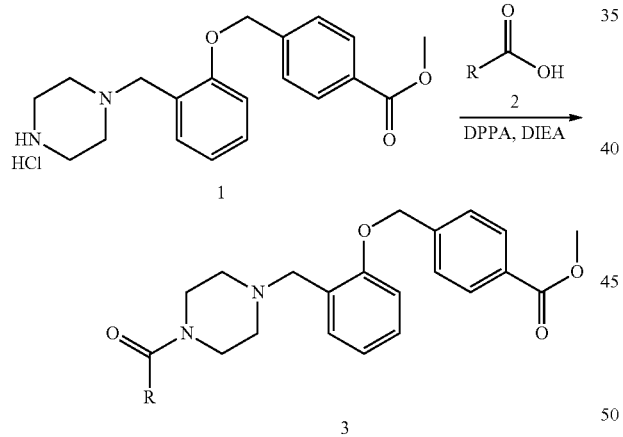

Method B2

In a sealed vial under nitrogen was placed the acid 2 (1.1 eq) in 1 mL of anhydrous DME, DIEA (1.6 eq) added, followed by DPPA (1.2 eq). The reaction was shaken for 2 hrs at rt and then was heated up to 78° C. on a shaker for another 2 h, and then cooled to rt, methyl 4-((2-(piperazin-1-ylmethyl)phenoxy)methyl)benzoate hydrochloride 1 in 0.5 mL of anhydrous DMF added, followed by another 3 eq of DIEA. The mixture shaken for overnight. A mixture of amide and urea were obtained and the pure product of these two derivatives were separated by PTLC (5% MeOH/$CH_2Cl_2$).

Scheme 9: Synthetic scheme for certain compounds of the invention according to Method B3

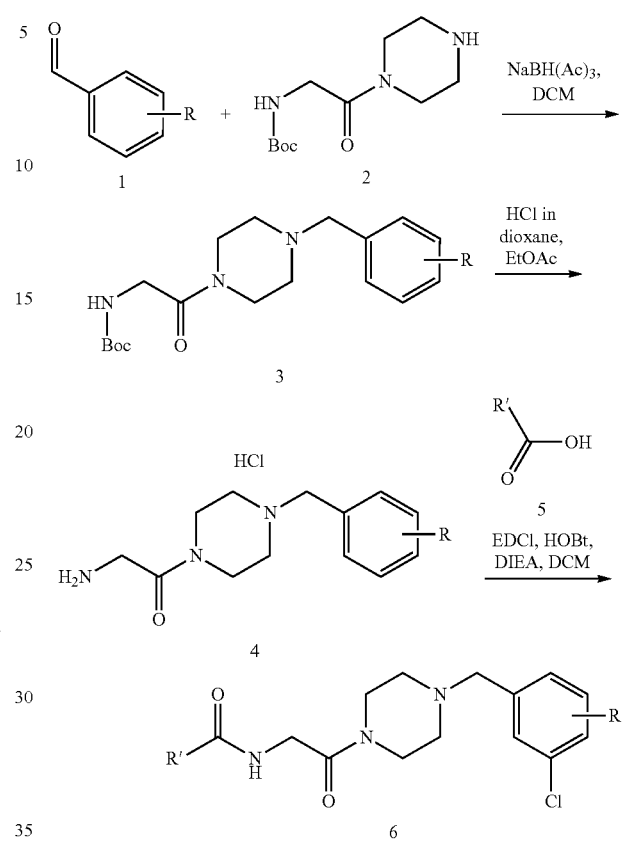

In a vial was placed tert-butyl (2-oxo-2-(piperazin-1-yl)ethyl)carbamate (2, 2 mmol, 1.1-3 eq) in 5 mL of anhydrous DCM. Aldehyde 1 (1.85 mmol, 1 eq) was then added, followed by NaBH(OAc)$_3$ (3.7 mmol, 2-4 eq). The reaction stirred for overnight and then was dried to afford an oily crude mixture. To this crude was added sat. aq. Na$_2$CO$_3$, sonicated for 10 minutes, to get a sticky brown color wax/oil. Washed, sonicated with water 2×10 mL. The residue was dried to afford the 3.

In a 5 mL glass vial, the Boc-protected amine 3 (2 mmol) was dissolved in 2 mL of EtOAc and then 2 mL of 4N HCl in Dioxane was added to the solution. Under nitrogen protection, the mixture was stirred at room temperature overnight. After the reaction, the mixture was then concentrated by GeneVec. The HCl salt of amine 4 was obtained as a solid.

In a glass vial, appropriate acid (5, 1 eq), amine (4, 1 eq), EDCI (1.2 eq) and HOBt (1.5 eq) were dissolved in proper amount of DCM and then DIEA (12 eq) was added to the solution. Under $N_2$ protection, the mixture was stirred at room temperature for overnight. After the reaction, the DIEA was evaporated by GeneVec. Water was added into the residue, and some oily or solid substance was appeared. After sonication and centrifugation, the water phase was removed and the residue was dissolved in EtOAc, dried by MgSO4, filtered and concentrated. Pure product 6 was then obtained by productive thin layer chromatography (5% MeOH/$CH_2Cl_2$).

Scheme 10: Synthetic scheme for certain compounds of the invention according to Method B4

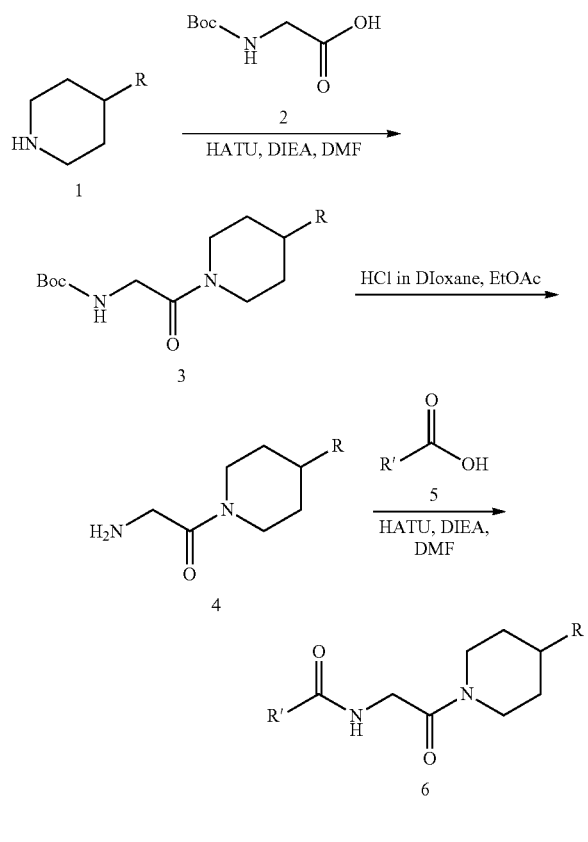

Scheme 11: Synthetic scheme for certain compounds of the invention according to Method C1

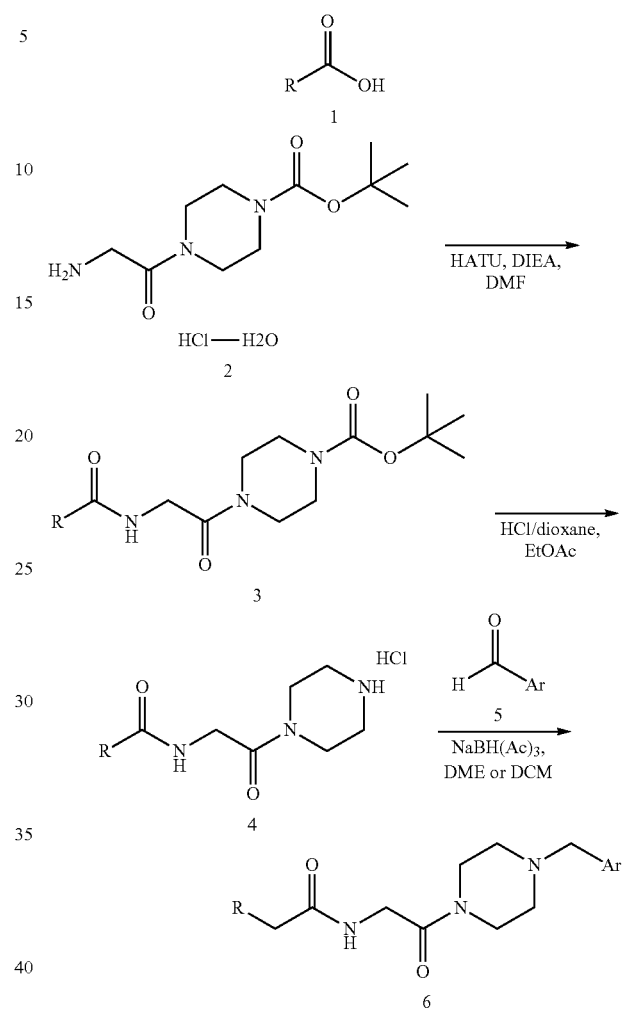

Method B4

In a glass vial, (tert-butoxycarbonyl)glycine (2, 2.2 mmol, 1.1 eq), proper piperidine (1, 2 mmol, 1 eq) and HATU (2.4 mmol, 1.2 eq), were dissolved in minimum amount of DMF and then the same amount of DIEA was added to the solution. Under $N_2$ protection, the mixture was stirred at room temperature for overnight. After the reaction, the DIEA was evaporated by GeneVec. Water was added into the residue, and some oily or solid substance was appeared. After sonication and centrifugation, the water phase was removed and the residue was dissolved in EtOAc, dried by MgSO4, filtered and concentrated to afford crude 3.

In a 5 mL glass vial, the Boc-protected amine 3 (1 mmol) was dissolved in 1 mL of EtOAc and then 1 mL of 4N HCl in Dioxane was added to the solution. Under nitrogen protection, the mixture was stirred at room temperature overnight. After the reaction, the mixture was then concentrated by GeneVec. The HCl salt of amine 4 was obtained as a solid.

In a glass vial, (tert-butoxycarbonyl)glycine (5, 1.2 eq), proper amine (4, 1 eq) and HATU (0.08 mmol, 1.5 eq), were dissolved in minimum amount of DMF and then the same amount of DIEA was added to the solution. Under $N_2$ protection, the mixture was stirred at room temperature for overnight. After the reaction, the DIEA was evaporated by GeneVec. Water was added into the residue, and some oily or solid substance was appeared. After sonication and centrifugation, the water phase was removed and the residue was dissolved in EtOAc, dried by MgSO4, filtered and concentrated to afford crude. Pure product 6 was then obtained by productive thin layer chromatography (5% MeOH/$CH_2Cl_2$).

Method C1

To a mixture of the appropriate acid (1, 2.4 mmol, 1.2 eq), tert-butyl 4-glycylpiperazine-1-carboxylate (2, 2 mmol, 1 eq), HATU (3 mmol, 1.5 eq), under nitrogen was added 4 mL of anhydrous DMF. Under stirring, N, N-diisopropyl-ethylamine (0.3 mL) was added and the reaction then stirred for overnight at room temperature. To the mixture was added water (30 mL), white wax type precipitation formed. The water was decanted, and the residue washed with 3×30 mL water under sonication to afford 3.

In a 5 mL glass vial, the Boc-protected piperazine 3 (1 mmol) was dissolved in 1 mL of EtOAc and then 1 mL of 4N HCl in Dioxane was added to the solution. Under nitrogen protection, the mixture was stirred at room temperature overnight. After the reaction, the mixture was then concentrated by GeneVec. The HCl salt of piperazine 4 was obtained as a solid.

In a vial was placed piperizine (4, 0.06-0.15 mmol, 1.1-3 eq) in 2 mL of anhydrous DME or DCM. Aldehyde 5 (0.05 mmol, 1 eq) was then added, followed by NaBH(OAc)$_3$ (0.1-0.2 mmol, 2-4 eq). The reaction stirred for overnight and then was dried to afford an oily crude mixture. To this crude was added sat. aq. $Na_2CO_3$, sonicated for 10 minutes, to get a sticky brown color wax/oil. Washed, sonicated with water 2×10 mL. The residue was dried to afford the crude. Pure product 6 was then obtained by productive thin layer chromatography (5% MeOH/CH₂Cl₂).

1333 105

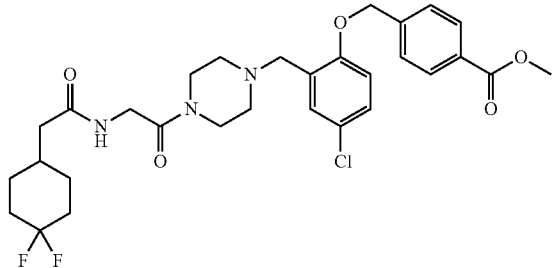

Methyl 4-((4-chloro-2-((4-((2-(4,4-difluorocyclohexyl)acetyl)glycyl)piperazin-1-yl)methyl)phenoxy)methyl)benzoate This compound was prepared according to Method B1 using 5-chloro-2-hydroxybenzaldehyde and 2-(4,4-difluorocyclohexyl)acetic acid. MS m/z: 592.3 (M+1), calc'd for $C_{30}H_{36}ClF_2N_3O_5$: 591.23.

1334 106

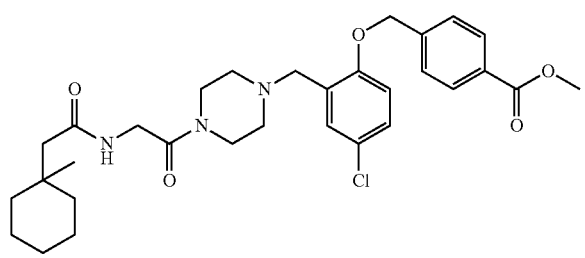 [SMILES: COC(=O)c1ccc(COc2ccc(Cl)cc2CN2CCN(C(=O)CNC(=O)CC3(C)CCCCC3)CC2)cc1]

Methyl 4-((4-chloro-2-((4-((2-(1-methylcyclohexyl)acetyl)glycyl)piperazin-1-yl)methyl)phenoxy)methyl)benzoate This compound was prepared according to Method B1 using 5-chloro-2-hydroxybenzaldehyde and 2-(1-methylcyclohexyl)acetic acid. MS m/z: 570.3 (M+1), calc'd for $C_{31}H_{40}ClN_3O_5$: 569.27.

1335 109

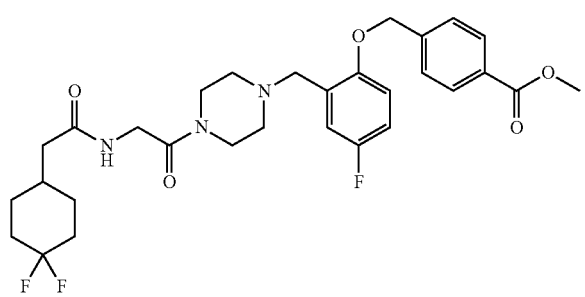 [SMILES: COC(=O)c1ccc(COc2ccc(F)cc2CN2CCN(C(=O)CNC(=O)CC3CCC(F)(F)CC3)CC2)cc1]

Methyl 4-((2-((4-((2-(4,4-difluorocyclohexyl)acetyl)glycyl)piperazin-1-yl)methyl)-4-fluorophenoxy)methyl)benzoate This compound was prepared according to Method B1 using 5-fluoro-2-hydroxybenzaldehyde and 2-(4,4-difluorocyclohexyl)acetic acid. MS m/z: 554.3 (M+1), calc'd for $C_{30}H_{36}F_3N_3O_5$: 553.30.

1336 110

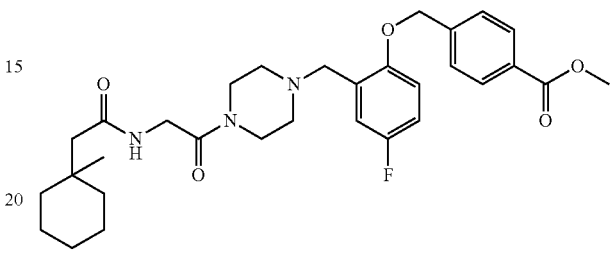

Methyl 4-((4-fluoro-2-((4-((2-(1-methylcyclohexyl)acetyl)glycyl)piperazin-1-yl)methyl)phenoxy)methyl)benzoate This compound was prepared according to Method B1 using 5-fluoro-2-hydroxybenzaldehyde and 2-(1-methylcyclohexyl)acetic acid. MS m/z: 576.3 (M+1), calc'd for $C_{31}H_{40}FN_3O_5$: 575.26.

1342

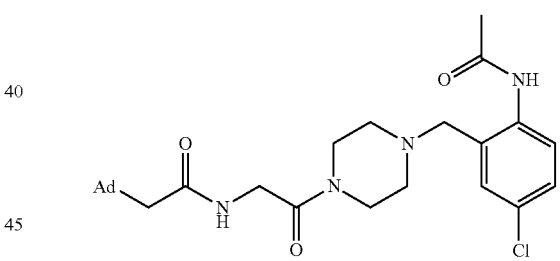

N-(2-(4-(2-Acetamido-5-chlorobenzyl)piperazin-1-yl)-2-oxoethyl)-2-((3s)-adamantan-1-yl)acetamide This compound was prepared according to Method A2a using 2-((1R,3R,5S)-adamantan-1-yl)acetic acid and 2-amino-5-chlorobenzaldehyde with an additional step shown as following. MS: m/z 501.3 (M+1), calc'd for $C_{27}H_{37}ClN_4O_3$: 500.26.

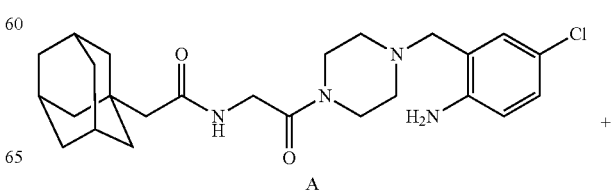

A

-continued

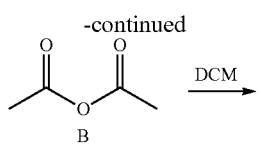

In a glass vial, A (1 eq), B (1.3 eq) were dissolved in 2 mL anhydrous DCM. The reaction was stirred at rt for overnight. Then the mixture was concentrated and the pure product C was obtained by PTCL (5% MeOH/DCM).

13432-120/173

N-(2-(4-(2-Amino-5-chlorobenzyl)piperazin-1-yl)-2-oxoethyl)-2-(4,4-difluorocyclohexyl)acetamide This compound was prepared according to Method A1b using 2-(4,4-difluorocyclohexyl)acetic acid and 2-amino-5-chlorobenzaldehyde. MS m/z: 443.2 (M+1), calc'd for $C_{21}H_{29}ClF_2N_4O_2$: 442.19

1344 119d

Methyl 4-((2-((4-((3,3-difluorobicyclo[3.1.0]hexane-6-carbonyl)glycyl)piperazin-1-yl)methyl)phenoxy)methyl)benzoate This compound was prepared according to Method B1 using 2-hydroxybenzaldehyde and 3,3-difluorobicyclo[3.1.0]hexane-6-carboxylic acid. MS m/z: 542.3 (M+1), calc'd for $C_{29}H_{33}F_2N_3O_5$: 541.24.

1346 123

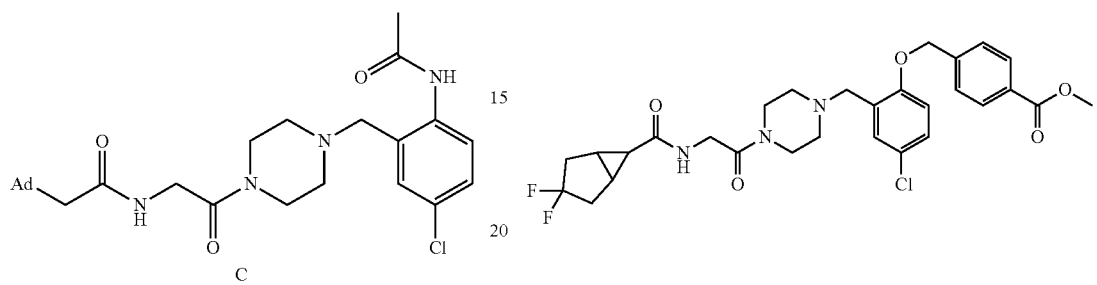

Methyl 4-((4-chloro-2-((4-((3,3-difluorobicyclo[3.1.0]hexane-6-carbonyl)glycyl)piperazin-1-yl)methyl)phenoxy)methyl)benzoate This compound was prepared according to Method B1 using 5-chloro-2-hydroxybenzaldehyde and 3,3-difluorobicyclo[3.1.0]hexane-6-carboxylic acid. MS m/z: 576.2 (M+1), calc'd for $C_{29}H_{32}ClF_2N_3O_5$: 575.20.

1347 124

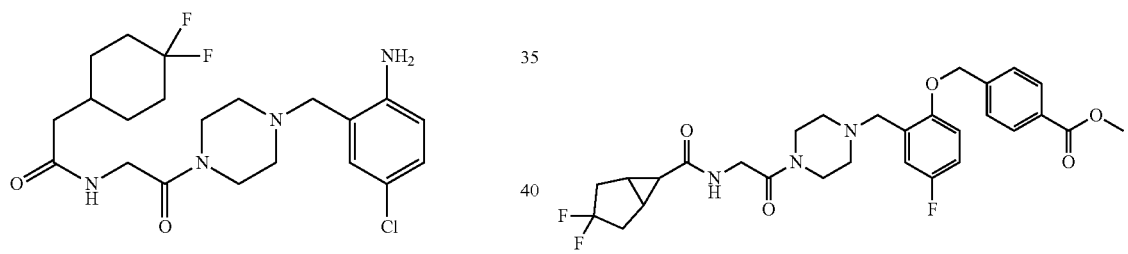

Methyl 4-((2-((4-((3,3-difluorobicyclo[3.1.0]hexane-6-carbonyl)glycyl)piperazin-1-yl)methyl)-4-fluorophenoxy)methyl)benzoate This compound was prepared according to Method B1 using 5-fluoro-2-hydroxybenzaldehyde and 3,3-difluorobicyclo[3.1.0]hexane-6-carboxylic acid. MS m/z: 560.3 (M+1), calc'd for $C_{29}H_{32}F_3N_3O_5$: 559.23.

1355 131m

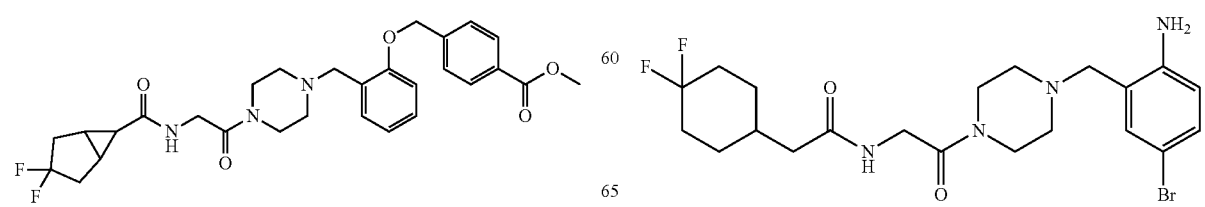

153

N-(2-(4-(2-Amino-5-bromobenzyl)piperazin-1-yl)-2-oxoethyl)-2-(4,4-difluorocyclohexyl)acetamide This compound was prepared according to Method A1b using 2-(4,4-difluorocyclohexyl)acetic acid and 2-amino-5-bromobenzaldehyde. MS m/z: 487.2 (M+1), calc'd for $C_{21}H_{29}BrF_2N_4O_2$: 486.14.

1356 133

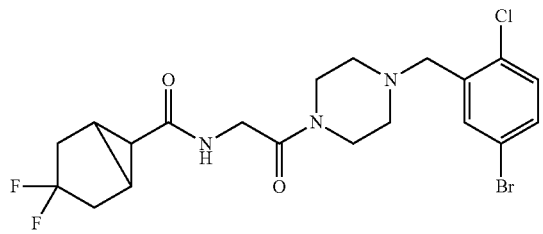 [SMILES: O=C(NCC(=O)N1CCN(Cc2cc(Br)ccc2Cl)CC1)C1C2CC(F)(F)CC21]

N-(2-(4-(5-bromo-2-chlorobenzyl)piperazin-1-yl)-2-oxoethyl)-3,3-difluorobicyclo[3.1.0]hexane-6-carboxamide This compound was prepared according to Method A1a using 3,3-difluorobicyclo[3.1.0]hexane-6-carboxylic acid and 5-bromo-2-chlorobenzaldehyde. MS m/z: 490.1 (M+1), calc'd for $C_{20}H_{23}BrClF_2N_3O_2$: 489.06.

1357 134

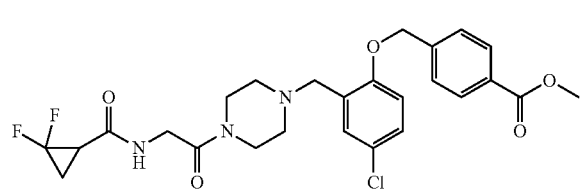 [SMILES: COC(=O)c1ccc(COc2ccc(Cl)cc2CN2CCN(C(=O)CNC(=O)C3CC3(F)F)CC2)cc1]

Methyl 4-((4-chloro-2-((4-((2,2-difluorocyclopropane-1-carbonyl)glycyl)piperazin-1-yl)methyl)phenoxy)methyl)benzoate This compound was prepared according to Method B1 using 5-chloro-2-hydroxybenzaldehyde and 2,2-difluorocyclopropane-1-carboxylic acid. MS m/z: 536.2 (M+1), calc'd for $C_{26}H_{28}ClF_2N_3O_5$: 535.17.

1358 135

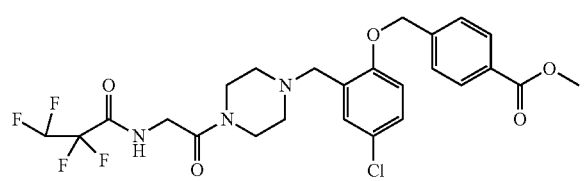 [SMILES: COC(=O)c1ccc(COc2ccc(Cl)cc2CN2CCN(C(=O)CNC(=O)C(F)(F)C(F)F)CC2)cc1]

154

Methyl 4-((4-chloro-2-((4-((2,2,3,3-tetrafluoropropanoyl)glycyl)piperazin-1-yl)methyl)phenoxy)methyl)benzoate This compound was prepared according to Method B1 using 5-chloro-2-hydroxybenzaldehyde and 2,2,3,3-tetrafluoropropanoic acid. MS m/z: 560.2 (M+1), calc'd for $C_{25}H_{26}ClF_4N_3O_5$: 559.15.

1359 143

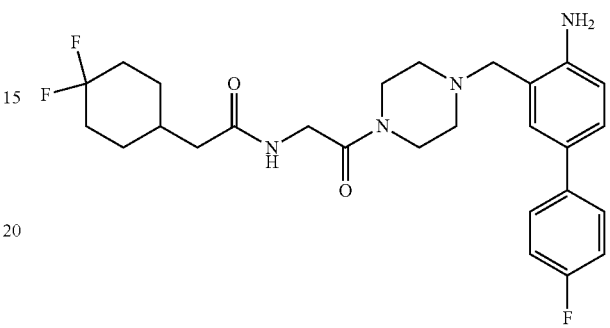

N-(2-(4-((4-Amino-4'-fluoro-[1,1'-biphenyl]-3-yl)methyl)piperazin-1-yl)-2-oxoethyl)-2-(4,4-difluorocyclohexyl)acetamide This compound was prepared according to Method A1a using 2-(4,4-difluorocyclohexyl)acetic acid and 2-amino-5-bromobenzaldehyde with an additional step as following. MS m/z: 503.3 (M+1), calc'd for $C_{27}H_{33}F_3N_4O_2$: 502.26.

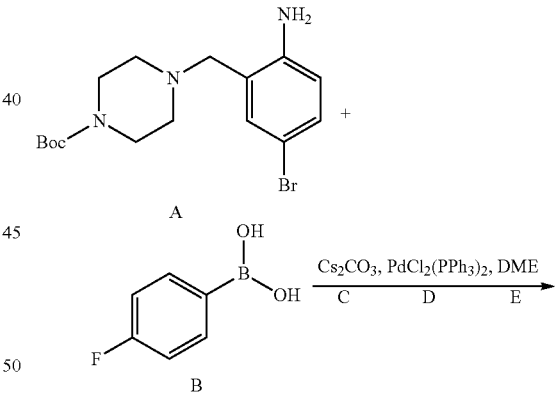

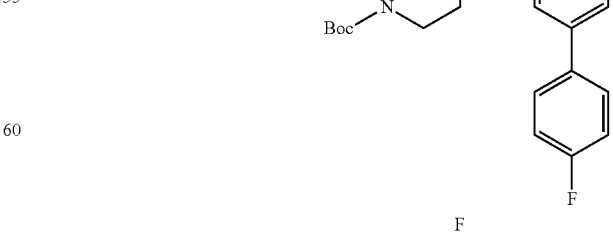

In a glass vial, A (0.2 mmol), B (0.24 mmol), C (0.6 mmol) and D (0.02 mmol) were dissolved in 2 mL of E in a 10 mL pressure vessel. The mixture was stirred, degassed by replacing the air with N2, and placed in an 80° C. oil bath for 18 h. After the reaction, the solvent was removed by reduced pressure evaporation. Then the residue was diluted by water and EtOAc. The organic phase was washed and dried by MgSO4, filtered and loaded onto a solid phase extraction (SPE) cartridge containing strong ion exchanger (SCX, 1 g; UCT, CUBCX1M15). The cartridge was first washed with EtOAc:MeOH (10:1, 12 mL), which was discarded, and then the product was eluted with EtOAc-MeOH-Et3N (20:2:1, 6 mL). The eluent was concentrated in vacuo to yield F as an orange oil.

1360 147

N-(2-(4-(5-Bromo-2-ureidobenzyl)piperazin-1-yl)-2-oxoethyl)-2-(4,4-difluorocyclohexyl)acetamide This compound was prepared according to Method A1a using 2-(4,4-difluorocyclohexyl)acetic acid and 2-amino-5-bromobenzaldehyde with an additional step as following. MS m/z: 530.2 (M+1), calc'd for $C_{22}H_{30}BrF_2N_5O_3$: 529.15.

74 mg A was dissolved in 2 mL of AcOH and then 1 mL of B (17 mg) in water was added to the solution. Under N₂ protection, the mixture was stirred at room temperature overnight. Then the mixture was concentrated by GeneVec. Product C was purified by PTLC (5% MeOH/CH2Cl₂).

1361 148

N-(2-(4-(5-Chloro-2-ureidobenzyl)piperazin-1-yl)-2-oxoethyl)-2-(4,4-difluorocyclohexyl)acetamide This compound was prepared according to Method A1a using 2-(4,4-difluorocyclohexyl)acetic acid and 2-amino-5-chlorobenzaldehyde with an additional step as following. MS m/z: 486.20 Calc'd for C22H30ClF2N5O3: 485.20.

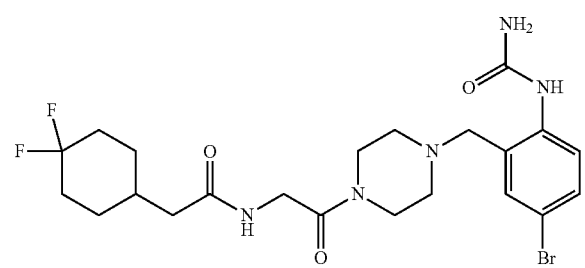 [SMILES: NC(=O)Nc1ccc(Br)cc1CN1CCN(C(=O)CNC(=O)CC2CCC(F)(F)CC2)CC1]

65 mg of A was dissolved in 2 mL of AcOH and then 1 mL of B (17 mg) in water was added to the solution. Under N₂ protection, the mixture was stirred at room temperature overnight. Then the mixture was concentrated by GeneVec. Product C was purified by PTLC (5% MeOH/CH2Cl₂).

1362 152

N-(2-(4-(2-Amino-5-bromobenzyl)piperazin-1-yl)-2-oxoethyl)-3,3-difluorobicyclo[3.1.0]hexane-6-carboxamide

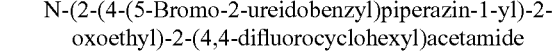

This compound was prepared according to Method A1a using 3,3-difluorobicyclo[3.1.0]hexane-6-carboxylic acid and 2-amino-5-bromobenzaldehyde. MS m/z: 471.2 (M+1), calc'd for $C_{20}H_{25}BrF_2N_4O_2$: 470.11.

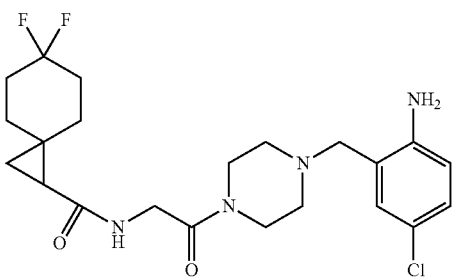 [SMILES: Nc1ccc(Cl)cc1CN1CCN(C(=O)CNC(=O)C2CC23CCC(F)(F)CC3)CC1]

N-(2-(4-(2-Amino-5-chlorobenzyl)piperazin-1-yl)-2-oxoethyl)-6,6-difluorospiro[2.5]octane-1-carboxamide This compound was prepared according to Method 1Ab using 6,6-difluorospiro[2.5]octane-1-carboxylic acid and 2-amino-5-chlorobenzaldehyde. MS m/z: 455.2 (M+1), calc'd for $C_{22}H_{29}ClF_2N_4O_2$: 454.19.

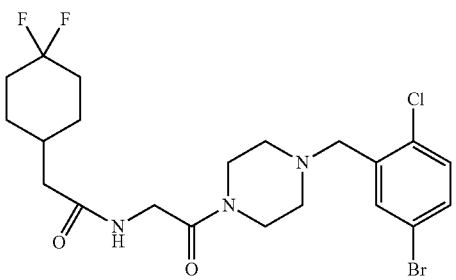 [SMILES: O=C(CC1CCC(F)(F)CC1)NCC(=O)N1CCN(Cc2cc(Br)ccc2Cl)CC1]

N-(2-(4-(5-Bromo-2-chlorobenzyl)piperazin-1-yl)-2-oxoethyl)-2-(4,4-difluorocyclohexyl)acetamide This compound was prepared according to Method A1b using 2-(4,4-difluorocyclohexyl)acetic acid and 5-bromo-2-chlorobenzaldehyde. MS m/z: 506.2 (M+1), calc'd for $C_{21}H_{27}BrClF_2N_3O_2$: 505.09.

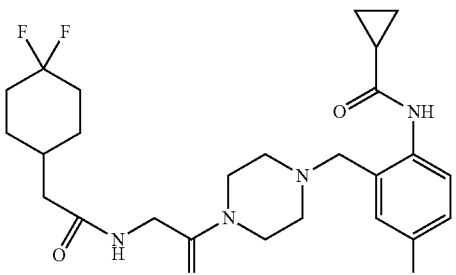

N-(4-Bromo-2-((4-((2-(4,4-difluorocyclohexyl)acetyl)glycyl)piperazin-1-yl)methyl)phenyl)cyclopropanecarboxamide This compound was prepared according to Method A1b using 2-(4,4-difluorocyclohexyl)acetic acid and 2-amino-5-bromobenzaldehyde with an additional step as following. MS m/z: 555.2 (M+1), calc'd for $C_{25}H_{33}BrF_2N_4O_3$: 554.17.

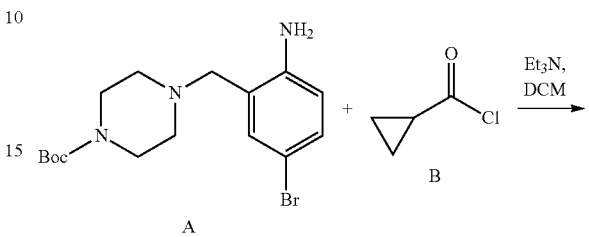

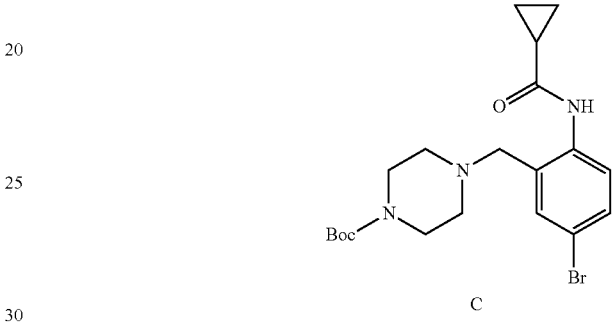

In a glass vial, A (1 eq), B (1.1 eq) were dissolved in 2 mL anhydrous DCM followed by 3 eq of $Et_3N$. The reaction was stirred at rt for overnight. Then the mixture was concentrated and the pure product C was obtained by PTCL (5% MeOH/DCM).

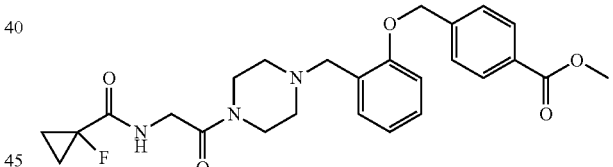

Methyl 4-((2-((4-((1-fluorocyclopropane-1-carbonyl)glycyl)piperazin-1-yl)methyl)phenoxy)methyl)benzoate This compound was prepared according to Method B1 using 2-hydroxybenzaldehyde and 1-fluorocyclopropane-1-carboxylic acid. MS m/z: 484.3 (M+1), calc'd for $C_{26}H_{30}FN_3O_5$: 483.22.

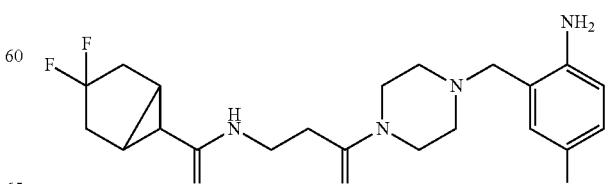

N-(3-(4-(2-Amino-5-chlorobenzyl)piperazin-1-yl)-3-oxopropyl)-3,3-difluorobicyclo[3.1.0]hexane-6-carboxamide This compound was prepared according to Method A2b using 3,3-difluorobicyclo[3.1.0]hexane-6-carboxylic acid, methyl 3-aminopropanoate hydrochloride instead of ethyl glycinate hydrochloride and 2-amino-5-chlorobenzaldehyde. MS m/z: 441.2 (M+1), calc'd for $C_{21}H_{27}ClF_2N_4O_2$: 440.18.

1378 164

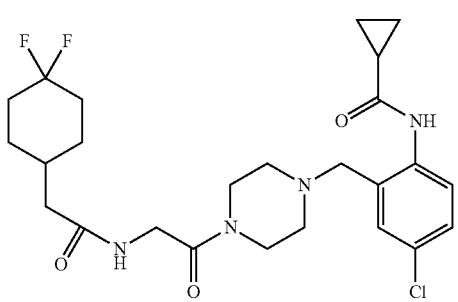 [SMILES: O=C(CC1CCC(F)(F)CC1)NCC(=O)N1CCN(Cc2cc(Cl)ccc2NC(=O)C2CC2)CC1]

N-(4-Chloro-2-((4-((2-(4,4-difluorocyclohexyl)acetyl)glycyl)piperazin-1-yl)methyl)phenyl)cyclopropanecarboxamide This compound was prepared according to Method A1a using 2-(4,4-difluorocyclohexyl)acetic acid and 2-amino-5-chlorobenzaldehyde with an additional step as following. MS m/z: 511.3 (M+1), calc'd for $C_{25}H_{33}ClF_2N_4O_3$: 510.22.

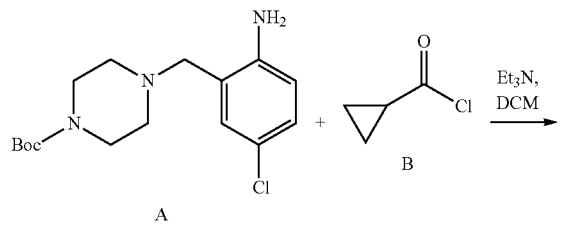

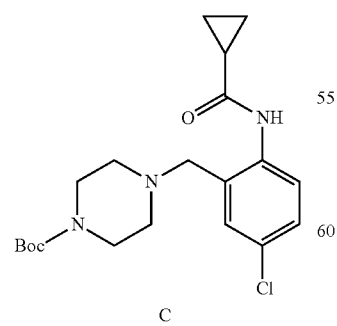

In a glass vial, A (1 eq), B (1.1 eq) were dissolved in 2 mL anhydrous DCM followed by 3 eq of Et$_3$N. The reaction was stirred at rt for overnight. Then the mixture was concentrated and the pure product C was obtained by PTCL (5% MeOH/DCM).

1379 165

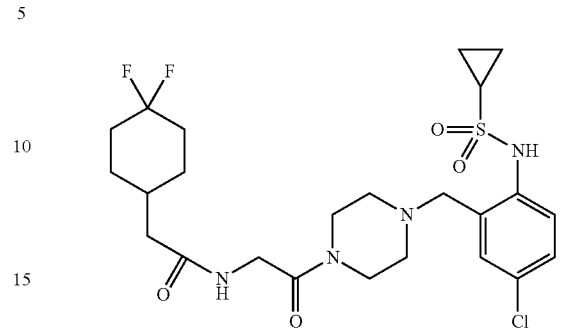

N-(2-(4-(5-Chloro-2-(cyclopropanesulfonamido)benzyl)piperazin-1-yl)-2-oxoethyl)-2-(4,4-difluorocyclohexyl)acetamide This compound was prepared according to Method A1b using 2-(4,4-difluorocyclohexyl)acetic acid and 2-amino-5-chlorobenzaldehyde with an additional step as following. MS m/z: 547.3 (M+1), calc'd for $C_{24}H_{33}ClF_2N_4O_4S$: 546.19.

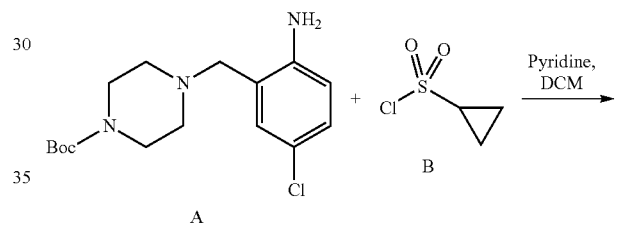

In a glass vial, A (65 mg), B (28 mg) were dissolved in a mixture of 300 uL DCM and 300 uL pyridine. The reaction was stirred at rt for overnight. Then the mixture was concentrated and the pure product C was obtained by PTCL (5% MeOH/DCM).

1385 171

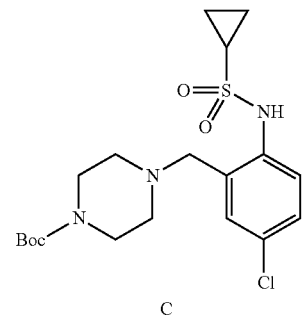

161

N-(2-(4-(3-Amino-5-chlorobenzyl)piperazin-1-yl)-2-oxoethyl)-2-(4,4-difluorocyclohexyl)acetamide

This compound was prepared according to Method A1a using 2-(4,4-difluorocyclohexyl)acetic acid and 3-chloro-5-nitrobenzaldehyde with an additional step as following. MS m/z: 443.3 (M+1), calc'd for $C_{21}H_{29}ClF_2N_4O_2$: 442.19.

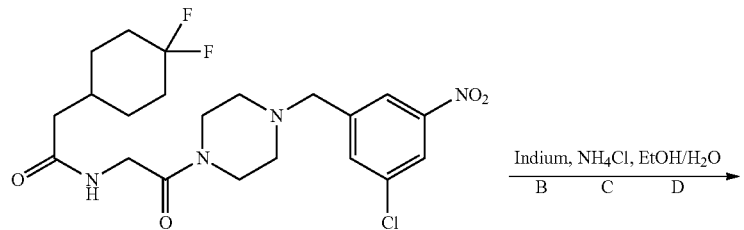

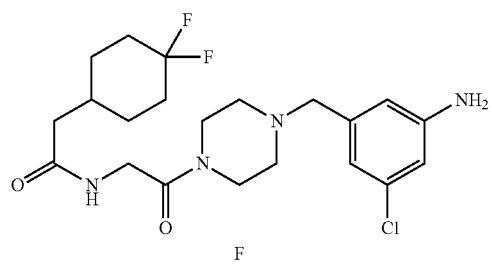

A, B and C were dissolved in 2 mL of EtOH/H2O (1:1). Then the mixture was stirred at 70° C. for overnight. After reaction, the EtOH was removed by GeneVec. The residue was extracted by ETOAc twice. The organic phase was combined, dried by MgSO₄. The solution was concentrated and dissolved again in a few amount of DCM which was loaded to the PTLC and eluted by DCM/MeOH (15:1) to afford the product F.

186 172

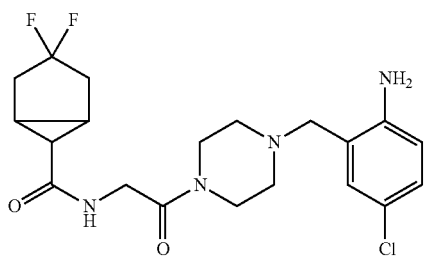

162

(1R,5S,6r)-N-(2-(4-(2-Amino-5-chlorobenzyl)piperazin-1-yl)-2-oxoethyl)-3,3-difluorobicyclo[3.1.0]hexane-6-carboxamide

This compound was prepared according to Method A1a using 3,3-difluorobicyclo[3.1.0]hexane-6-carboxylic acid and 2-amino-5-chlorobenzaldehyde. MS m/z: 427.2 (M+1), calc'd for $C_{20}H_{25}ClF_2N_4O_2$: 426.16.

1387 176

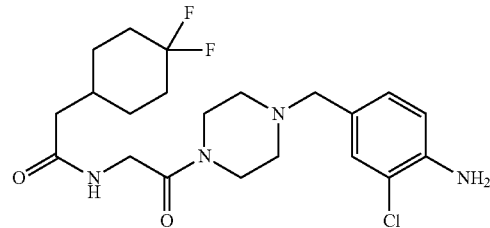 [SMILES: Nc1ccc(CN2CCN(C(=O)CNC(=O)CC3CCC(F)(F)CC3)CC2)cc1Cl]

N-(2-(4-(4-Amino-3-chlorobenzyl)piperazin-1-yl)-2-oxoethyl)-2-(4,4-difluorocyclohexyl)acetamide

This compound was prepared according to Method C1 using 2-(4,4-difluorocyclohexyl)acetic acid and 4-amino-3-chlorobenzaldehyde. MS m/z: 443.2 (M+1), calc'd for $C_{21}H_{29}ClF_2N_4O_2$: 442.19.

1388 180

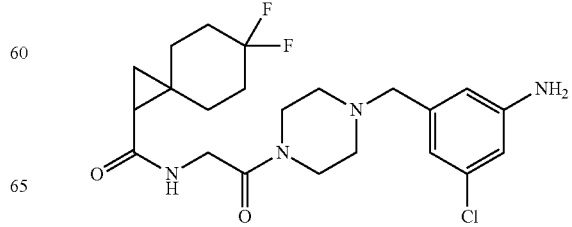

N-(2-(4-(3-Amino-5-chlorobenzyl)piperazin-1-yl)-2-oxoethyl)-6,6-difluorospiro[2.5]octane-1-carboxamide This compound was prepared according to Method Aa using 6,6-difluorospiro[2.5]octane-1-carboxylic acid and 3-chloro-5-nitrobenzaldehyde with an additional step as following. MS m/z: 455.2 (M+1), calc'd for C₂₂H₂₉ClF₂N₄O₂: 454.19.

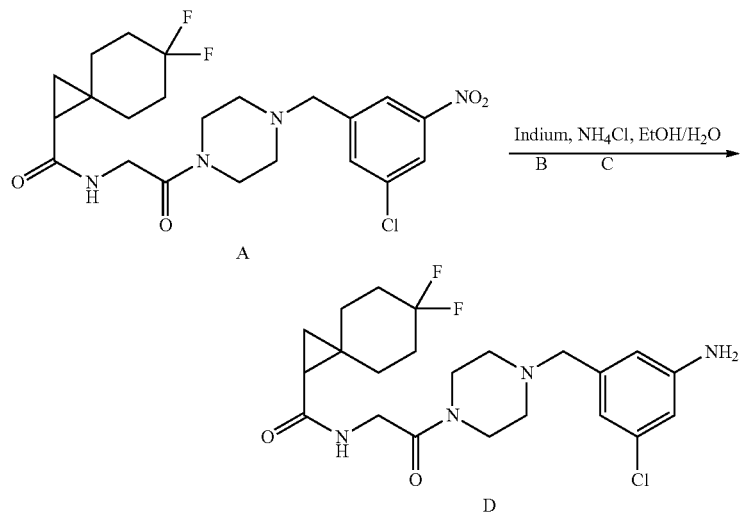

In a glass vial, A (40 mg), B (48 mg) and C (45 mg) were dissolved in 2 mL of EtOH/H2O (1:1). Then the mixture was stirred at 70° C. for overnight. After reaction, the EtOH was removed by GeneVec. The residue was extracted by EtOAc twice. The organic phase was combined, dried by MgSO₄. The solution was concentrated and dissolved again in a few amount of DCM which was loaded to the PTLC and eluted by DCM/MeOH (15:1) to afford the product D.

1389 181

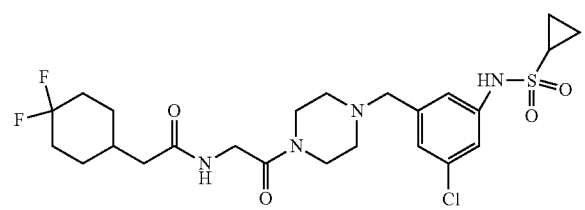 [SMILES: O=C(CC1CCC(F)(F)CC1)NCC(=O)N1CCN(Cc2cc(Cl)cc(NS(=O)(=O)C3CC3)c2)CC1]

4-(3-Chloro-5-(cyclopropanesulfonamido)benzyl)-N-(3-(4,4-difluorocyclohexyl)-2-oxopropyl)piperazine-1-carboxamide This compound was prepared using N-(2-(4-(3-Amino-5-chlorobenzyl)piperazin-1-yl)-2-oxoethyl)-2-(4,4-difluorocyclohexyl)acetamide by one step as following. MS m/z: 547.2 (M+1). Calc'd for C₂₄H₃₃ClF₂N₄O₄S, 546.19.

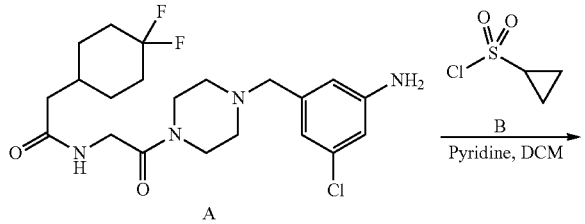

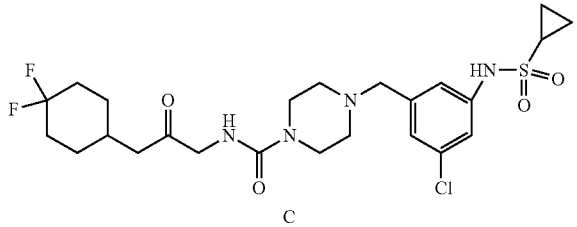

In a glass vial, A (8 mg), B (12.5 mg) were dissolved in a mixture of 300 uL DCM and 300 uL pyridine. The reaction was stirred at rt for overnight. Then the mixture was concentrated and the pure product C was obtained by PTCL (5% MeOH/DCM).

1390 183

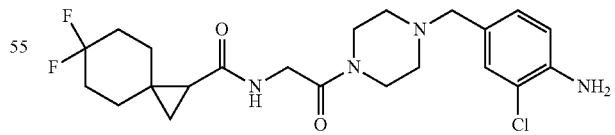

N-(2-(4-(4-Amino-3-chlorobenzyl)piperazin-1-yl)-2-oxoethyl)-6,6-difluorospiro[2.5]octane-1-carboxamide This compound was prepared according to Method B3 using 4-amino-3-chlorobenzaldehyde and 6,6-difluorospiro

[2.5]octane-1-carboxylic acid. MS m/z: 455.2 (M+1), calc'd for $C_{22}H_{29}ClF_2N_4O_2$: 454.19.

1394 194

N-(2-(4-(2-Amino-5-cyclopropylbenzyl)piperazin-1-yl)-2-oxoethyl)-6,6-difluorospiro[2.5]octane-1-carboxamide This compound was prepared according to Method A1b using 6,6-difluorospiro[2.5]octane-1-carboxylic acid and 2-amino-5-chlorobenzaldehyde with an additional step as following. MS m/z: 461.3 (M+1), calc'd for C25H34F2N4O2: 460.26

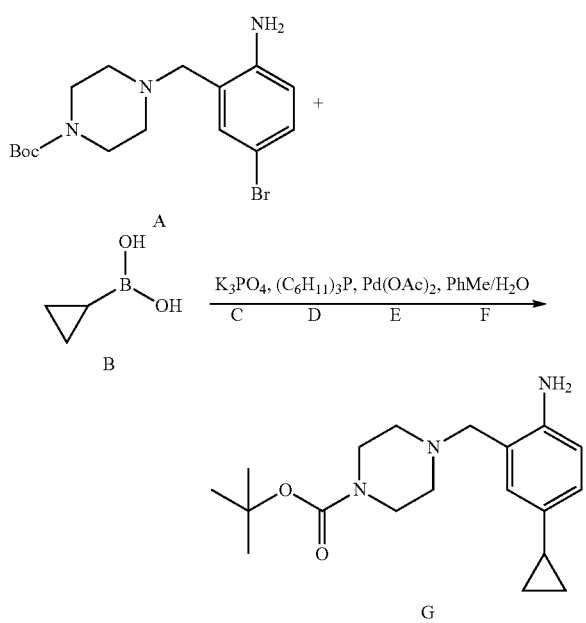

In a glass vial, A (0.2 mmol), B (0.26 mmol), C (0.7 mmol), D (0.2 mmol) and E (0.02 mmol) were dissolved in 2 mL of E (with 0.04 mL water) in a 10 mL pressure vessel. The mixture was stirred, degassed by replacing the air with N2, and placed in an 80° C. oil bath for 18 h. After the reaction, the solvent was removed by reduced pressure evaporation. Then the residue was diluted by water and EtOAc. The organic phase was washed and dried by MgSO4, filtered and loaded onto a solid phase extraction (SPE) cartridge containing strong ion exchanger (SCX, Ig; UCT, CUBCX1M15). The cartridge was first washed with EtOAc:MeOH (10:1, 12 mL), which was discarded, and then the product was eluted with EtOAc-MeOH-Et3N (20: 2:1, 6 mL). The eluent was concentrated in vacuo to yield F as an orange oil.

1398 198

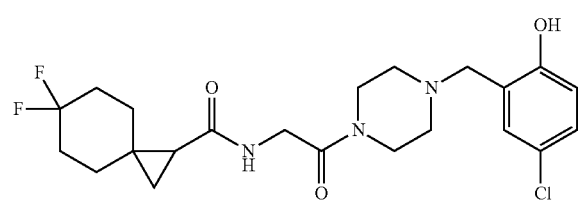 [SMILES: O=C(NCC(=O)N1CCN(Cc2cc(Cl)ccc2O)CC1)C1CC12CCC(F)(F)CC2]

N-(2-(4-(5-Chloro-2-hydroxybenzyl)piperazin-1-yl)-2-oxoethyl)-6,6-difluorospiro[2.5]octane-1-carboxamide This compound was prepared according to Method B3 using 5-chloro-2-hydroxybenzaldehyde and 6,6-difluorospiro[2.5]octane-1-carboxylic acid. MS m/z: 456.2 (M+1), Calc'd for $C_{22}H_{28}ClF_2N_3O_3$: 455.18.

1399 200

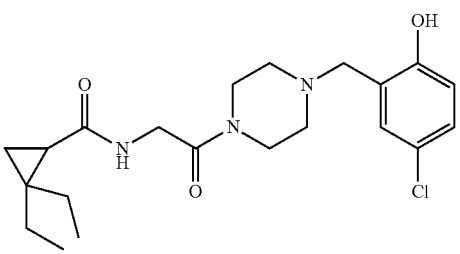 [SMILES: CCC1(CC)CC1C(=O)NCC(=O)N1CCN(Cc2cc(Cl)ccc2O)CC1]

N-(2-(4-(5-Chloro-2-hydroxybenzyl)piperazin-1-yl)-2-oxoethyl)-2,2-diethylcyclopropane-1-carboxamide This compound was prepared according to Method B3 using 5-chloro-2-hydroxybenzaldehyde and 2,2-diethylcyclopropane-1-carboxylic acid. MS m/z: 408.2 (M+1), calc'd for $C_{21}H_{30}ClN_3O_3$: 407.20

1400 202

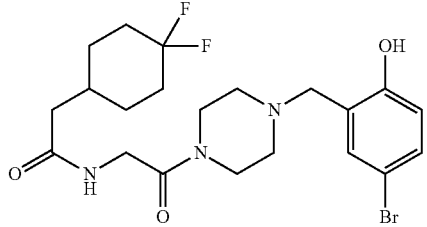 [SMILES: O=C(CC1CCC(F)(F)CC1)NCC(=O)N1CCN(Cc2cc(Br)ccc2O)CC1]

N-(2-(4-(5-Bromo-2-hydroxybenzyl)piperazin-1-yl)-2-oxoethyl)-2-(4,4-difluorocyclohexyl)acetamide This compound was prepared according to Method C1 using 2-(4,4-difluorocyclohexyl)acetic acid and 5-bromo-2-hydroxybenzaldehyde. MS m/z: 488.2 (M+1), calc'd for $C_{21}H_{28}BrF_2N_3O_3$: 487.13.

1401 218

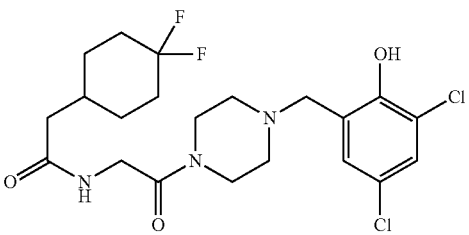 [SMILES: O=C(CC1CCC(F)(F)CC1)NCC(=O)N1CCN(Cc2cc(Cl)cc(Cl)c2O)CC1]

N-(2-(4-(3,5-Dichloro-2-hydroxybenzyl)piperazin-1-yl)-2-oxoethyl)-2-(4,4-difluorocyclohexyl)acetamide This compound was prepared according to Method C1 using 2-(4,4-difluorocyclohexyl)acetic acid and 3,5-dichloro-2-hydroxybenzaldehyde. MS m/z: 478.2 (M+1), calc'd for $C_{21}H_{27}Cl_2F_2N_3O_3$: 477.14.
1402 219

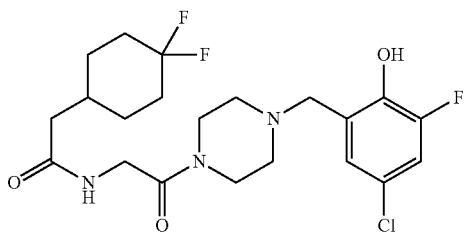 [SMILES: O=C(CC1CCC(F)(F)CC1)NCC(=O)N1CCN(Cc2cc(Cl)cc(F)c2O)CC1]

N-(2-(4-(5-Chloro-3-fluoro-2-hydroxybenzyl)piperazin-1-yl)-2-oxoethyl)-2-(4,4-difluorocyclohexyl)acetamide This compound was prepared according to Method C1 using 2-(4,4-difluorocyclohexyl)acetic acid and 5-chloro-3-fluoro-2-hydroxybenzaldehyde. MS m/z: 462.2 (M+1), calc'd for $C_{21}H_{27}ClF_3N_3O_3$: 461.17.
1403 220

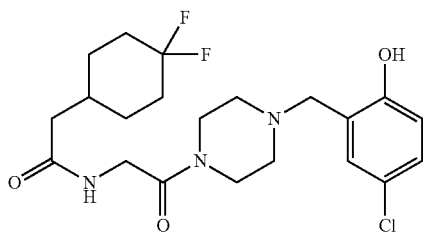 [SMILES: O=C(CC1CCC(F)(F)CC1)NCC(=O)N1CCN(Cc2cc(Cl)ccc2O)CC1]

N-(2-(4-(5-Chloro-2-hydroxybenzyl)piperazin-1-yl)-2-oxoethyl)-2-(4,4-difluorocyclohexyl)acetamide This compound was prepared according to Method C1 using 2-(4,4-difluorocyclohexyl)acetic acid and 5-chloro-2-hydroxybenzaldehyde. $^1$H NMR (400 MHz, CDCl$_3$, ppm): δ 7.15 (dd, J1=2.5, J2=8.4, 1H), 6.95 (d, J=2.5, 1H), 6.77 (d, J=8.4, 1H), 6.53 (br, 1H), 4.05 (d, J=4.0, 2H), 3.68 (s, 4H), 3.48 (t, J=5.0, 2H), 2.57 (s, 4H), 2.18 (d, J=7.0, 2H), 2.10-1.74 (m, 6H), 1.33 (m, 3H). MS m/z: 444.2 (M+1), calc'd for $C_{21}H_{28}ClF_2N_3O_3$: 443.18.
1404 221

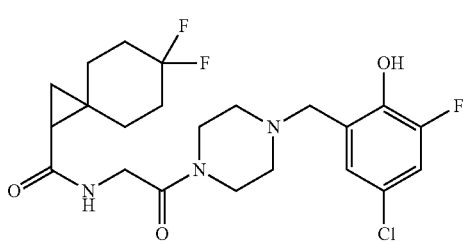 [SMILES: O=C(NCC(=O)N1CCN(Cc2cc(Cl)cc(F)c2O)CC1)C1CC12CCC(F)(F)CC2]

N-(2-(4-(5-chloro-3-fluoro-2-hydroxybenzyl)piperazin-1-yl)-2-oxoethyl)-6,6-difluorospiro[2.5]octane-1-carboxamide This compound was prepared according to Method C1 using 6,6-difluorospiro[2.5]octane-1-carboxylic acid and 5-chloro-3-fluoro-2-hydroxybenzaldehyde. MS m/z: 474.2 (M+1), calc'd for $C_{22}H_{27}ClF_3N_3O_3$: 473.17.
1409 226

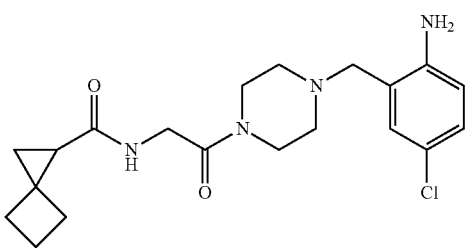 [SMILES: Nc1ccc(Cl)cc1CN1CCN(C(=O)CNC(=O)C2CC23CCC3)CC1]

N-(2-(4-(2-Amino-5-chlorobenzyl)piperazin-1-yl)-2-oxoethyl)spiro[2.3]hexane-1-carboxamide This compound was prepared according to Method B3 using 2-amino-5-chlorobenzaldehyde and spiro[2.3]hexane-1-carboxylic acid. MS m/z: 391.2 (M+1), calc'd for $C_{20}H_{27}ClN_4O_2$: 390.18.
1410 227

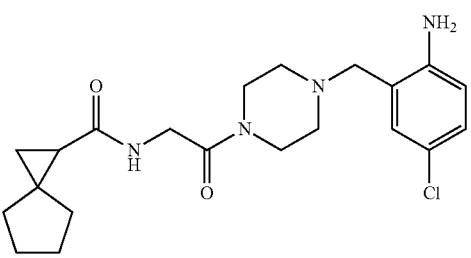 [SMILES: Nc1ccc(Cl)cc1CN1CCN(C(=O)CNC(=O)C2CC23CCCC3)CC1]

N-(2-(4-(2-Amino-5-chlorobenzyl)piperazin-1-yl)-2-oxoethyl)spiro[2.4]heptane-1-carboxamide This compound was prepared according to Method B3 using 2-amino-5-chlorobenzaldehyde and spiro[2.4]heptane-1-carboxylic acid. MS m/z: 405.2 (M+1), calc'd for $C_{21}H_{29}ClN_4O_2$: 404.20.
1411 228

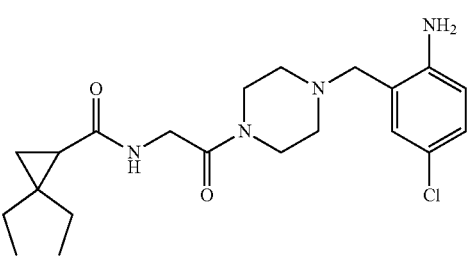 [SMILES: CCC1(CC)CC1C(=O)NCC(=O)N1CCN(Cc2cc(Cl)ccc2N)CC1]

N-(2-(4-(2-amino-5-chlorobenzyl)piperazin-1-yl)-2-oxoethyl)-2,2-diethylcyclopropane-1-carboxamide This compound was prepared according to Method B3 using 2-amino-5-chlorobenzaldehyde and 2,2-diethylcyclopropane-1-carboxylic acid. MS m/z: 407.2 (M+1), calc'd for $C_{21}H_{31}ClN_4O_2$: 406.21.
1412 236

N-(2-(4-((2-amino-5-chlorophenyl)methyl-d2)piperazin-1-yl)-2-oxoethyl)-2-(4,4-difluorocyclohexyl)acetamide See Example: Synthesis of 1412 and 1413
$^1$H NMR (400 MHz, CDCl$_3$, ppm): δ 7.06 (dd, J1=2.5, J2=8.4, 1H), 6.95 (d, J=2.5, 1H), 6.58 (d, J=8.4, 1H), 6.55 (br, 11H), 4.05 (d, J=4.0, 2H), 3.63 (t, J=5.0, 2H), 3.39 (t, J=5.0, 2H), 2.43 (t, J=5.0, 4H), 2.18 (d, J=7.0, 2H), 2.10-1.74 (m, 6H), 1.33 (m, 3H). MS m/z: 445.2 (M+1), calc'd for $C_{21}H_{27}D_2ClF_2N_4O_2$: 444.21.
1413 237

N-(2-(4-((2-amino-5-chlorophenyl)methyl-d2)piperazin-1-yl)-2-oxoethyl)-6,6-difluorospiro[2.5]octane-1-carboxamide See Example: Synthesis of 1412 and 1413
MS m/z: 457.2 (M+1), calc'd for $C_{22}H_{27}D_2ClF_2N_4O_2$: 456.21.
1420 239

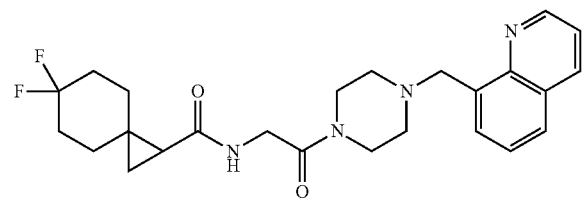 [SMILES: O=C(NCC(=O)N1CCN(Cc2cccc3cccnc23)CC1)C1CC12CCC(F)(F)CC2]

6,6-Difluoro-N-(2-oxo-2-(4-(quinolin-8-ylmethyl)piperazin-1-yl)ethyl)spiro[2.5]octane-1-carboxamide This compound was prepared according to Method C1 using 6,6-difluorospiro[2.5]octane-1-carboxylic acid and quinoline-8-carbaldehyde. MS m/z: 457.3 (M+1), calc'd for $C_{25}H_{30}F_2N_4O_2$: 456.23.
1421 240

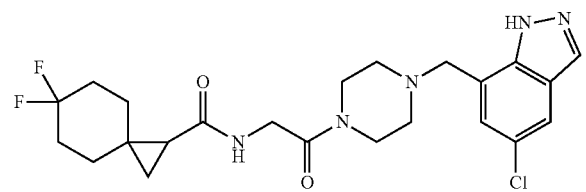 [SMILES: O=C(NCC(=O)N1CCN(Cc2cc(Cl)cc3cn[nH]c23)CC1)C1CC12CCC(F)(F)CC2]

N-(2-(4-((5-Chloro-JH-indazol-7-yl)methyl)piperazin-1-yl)-2-oxoethyl)-6,6-difluorospiro[2.5]octane-1-carboxamide This compound was prepared according to Method C1 using 6,6-difluorospiro[2.5]octane-1-carboxylic acid and 5-chloro-1H-indazole-7-carbaldehyde. MS m/z: 480.2 (M+1), calc'd for $C_{23}H_{28}ClF_2N_5O_2$: 479.19.
1422 245

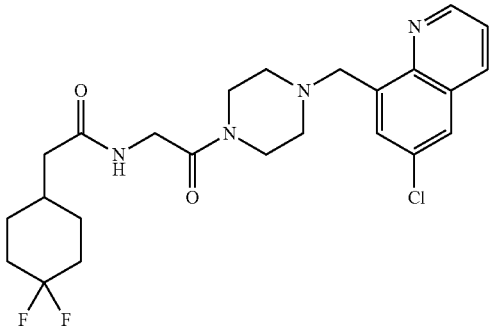 [SMILES: O=C(CC1CCC(F)(F)CC1)NCC(=O)N1CCN(Cc2cc(Cl)cc3cccnc23)CC1]

N-(2-(4-((6-Chloroquinolin-8-yl)methyl)piperazin-1-yl)-2-oxoethyl)-2-(4,4-difluorocyclohexyl)acetamide This compound was prepared according to Method A1a using 2-(4,4-difluorocyclohexyl)acetic acid and 6-chloroquinoline-8-carbaldehyde. $^1$H NMR (400 MHz, CDCl$_3$, ppm): δ 8.90 (dd, J1=1.7, J2=4.2, 1H), 8.09 (dd, J1=1.7, J2=8.3, 11H), 7.83 (d, J=2.2, 1H), 7.73 (d, J=2.2, 1H), 7.44 (dd, J1=4.2, J2=8.3, 1H), 6.58 (br, 1H), 4.28 (s, 2H), 4.05 (d, J=4.0, 2H), 3.72 (t, J=5.0, 2H), 3.47 (t, J=5.0, 2H), 2.62 (t, J=5.0, 4H), 2.18 (d, J=7.0, 2H), 2.10-1.74 (m, 6H), 1.33 (m, 3H). MS m/z: 479.2 (M+1), calc'd for $C_{24}H_{29}ClF_2N_4O_2$: 478.19.
1423 246

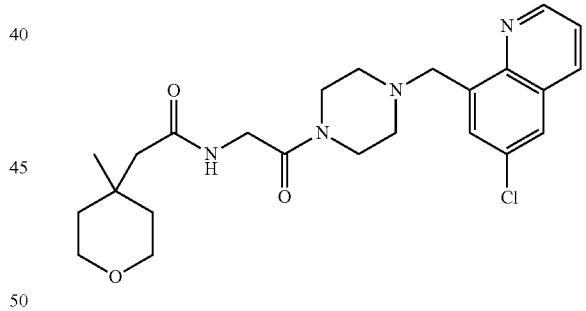

N-(2-(4-((6-Chloroquinolin-8-yl)methyl)piperazin-1-yl)-2-oxoethyl)-2-(4-methyltetrahydro-2H-pyran-4-yl)acetamide This compound was prepared according to Method B3 using 6-chloroquinoline-8-carbaldehyde and 2-(4-methyltetrahydro-2H-pyran-4-yl)acetic acid. $^1$H NMR (400 MHz, CDCl$_3$, ppm): δ 8.90 (dd, J1=1.8, J2=4.2, 11H), 8.08 (dd, J1=1.8, J2=8.3, 1H), 7.82 (d, J=2.4, 11H), 7.73 (d, J=2.4, 1H), 7.44 (dd, J1=4.2, J2=8.3, 11H), 6.54 (br, 1H), 4.28 (s, 2H), 4.05 (d, J=4.0, 2H), 3.67 (m, 6H), 3.47 (t, J=5.0, 2H), 2.63 (t, J=4.9, 4H), 2.23 (s, 2H), 1.66 (m, 2H), 1.45 (m, 2H) 1.15 (s, 3H). MS m/z: 459.2 (M+1), calc'd for C24H31ClN4O3: 458.21.

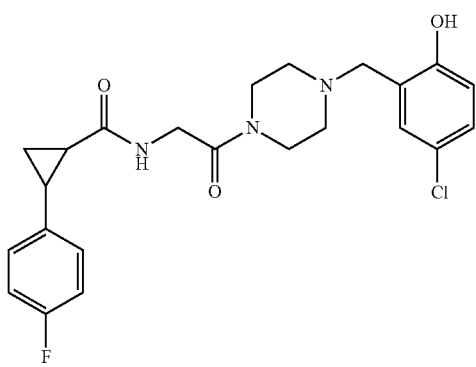 [SMILES: O=C(NCC(=O)N1CCN(Cc2cc(Cl)ccc2O)CC1)C1CC1c1ccc(F)cc1]

N-(2-(4-(5-Chloro-2-hydroxybenzyl)piperazin-1-yl)-2-oxoethyl)-2-(4-fluorophenyl)cyclopropane-1-carboxamide This compound was prepared according to Method B3 using 5-chloro-2-hydroxybenzaldehyde and 2-(4-fluorophenyl)cyclopropane-1-carboxylic acid. MS m/z: 446.2 (M+1), calc'd for $C_{23}H_{25}ClFN_3O_3$: 445.16.

$^1$H NMR (400 MHz, CDCl$_3$, ppm): δ 7.50 (m, 6H), 7.68 (d, J=8.7, 1H), 7.73 (br, 1H), 4.11 (d, J=4.0, 2H), 3.69 (s, 4H), 3.49 (s, 2H), 2.60 (s, 4H).
1426 251

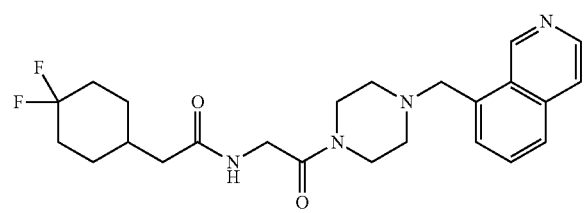 [SMILES: O=C(CC1CCC(F)(F)CC1)NCC(=O)N1CCN(Cc2cccc3ccncc23)CC1]

2-(4,4-Difluorocyclohexyl)-N-(2-(4-(isoquinolin-8-ylmethyl)piperazin-1-yl)-2-oxoethyl)acetamide This compound was prepared according to Method C1 using 2-(4,4-difluorocyclohexyl)acetic acid and isoquinoline-8-carbaldehyde. $^1$H NMR (400 MHz, CDCl$_3$, ppm): δ 8.94 (dd, J1=1.7, J2=4.2, 11H), 8.66 (d, J=5.7, 11H), 7.78 (d, J=8.3, 11H), 7.67 (d, J=5.8, 1H), 7.61 (dd, J1=7, J2=8.3, 11H), 7.46 (d, J=7, 1H), 6.59 (br, 1H), 4.04 (d, J=4.0, 2H), 3.99 (s, 2H), 3.62 (t, J=5.0, 2H), 3.37 (t, J=5.0, 2H), 2.52 (q, J=5.0, 4H), 2.18 (d, J=7.0, 2H), 2.10-1.74 (m, 6H), 1.33 (m, 3H). MS m/z: 445.2 (M+1), calc'd for $C_{24}H_{30}F_2N_4O_2$: 444.23.
1428 255

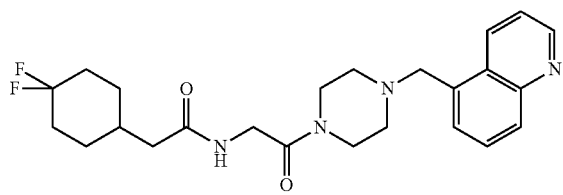 [SMILES: O=C(CC1CCC(F)(F)CC1)NCC(=O)N1CCN(Cc2cccc3ncccc23)CC1]

2-(4,4-Difluorocyclohexyl)-N-(2-oxo-2-(4-(quinolin-5-ylmethyl)piperazin-1-yl)ethyl)acetamide This compound was prepared according to Method C1 using 2-(4,4-difluorocyclohexyl)acetic acid and quinoline-5-carbaldehyde. $^1$H NMR (400 MHz, CDCl$_3$, ppm): δ 8.94 (dd, J1=1.7, J2=4.2, 1H), 8.66 (d, J=8.8, 11H), 8.09 (d, J=8.4, 1H), 7.65 (m, 1H), 7.44 (m, 2H), 6.56 (br, 1H), 4.04 (d, J=4.0, 2H), 3.93 (s, 2H), 3.64 (s, 2H), 3.37 (t, J=5, 2H), 2.64 (q, J=5, 4H), 2.18 (d, J=7.0, 2H), 2.10-1.74 (m, 6H), 1.33 (m, 3H). MS m/z: 445.3 (M+1), calc'd for $C_{24}H_{30}F_2N_4O_2$: 444.23.
1429 256

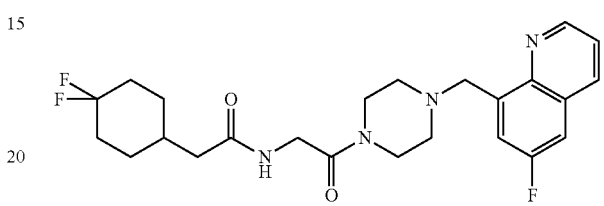

2-(4,4-Difluorocyclohexyl)-N-(2-(4-((6-fluoroquinolin-8-yl)methyl)piperazin-1-yl)-2-oxoethyl)acetamide This compound was prepared according to Method C1 using 2-(4,4-difluorocyclohexyl)acetic acid and 6-fluoroquinoline-8-carbaldehyde. $^1$H NMR (400 MHz, CDCl$_3$, ppm): δ 8.86 (dd, J1=1.7, J2=4.3, 1H), 8.12 (dd, J=1.8, J=8.3, 11H), 7.70 (d, J=9.1, 1H), 7.43 (dd, J1=4.1, J2=8.3, 1H), 7.35 (m, 1H), 6.58 (br, 1H), 4.30 (s, 2H), 4.05 (d, J=4.0, 2H), 3.73 (s, 2H), 3.49 (s, 2H), 2.64 (s, 4H), 2.21 (d, J=7.0, 2H), 2.10-1.74 (m, 6H), 1.33 (m, 3H). MS m/z: 463.3 (M+1), calc'd for $C_{24}H_{29}F_3N_4O_2$: 462.22.
1430 257

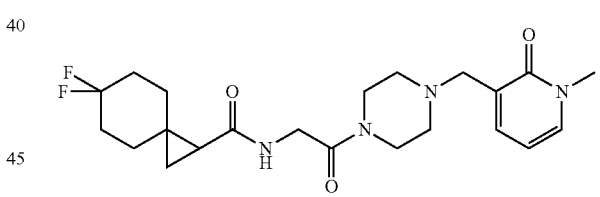

6,6-Difluoro-N-(2-(4-((1-methyl-2-oxo-1,2-dihydropyridin-3-yl)methyl)piperazin-1-yl)-2-oxoethyl)spiro[2.5]octane-1-carboxamide This compound was prepared according to Method C1 using 6,6-difluorospiro[2.5]octane-1-carboxylic acid and 1-methyl-2-oxo-1,2-dihydropyridine-3-carbaldehyde. MS m/z: 437.3 (M+1), calc'd for $C_{22}H_{30}F_2N_4O_3$: 436.23.

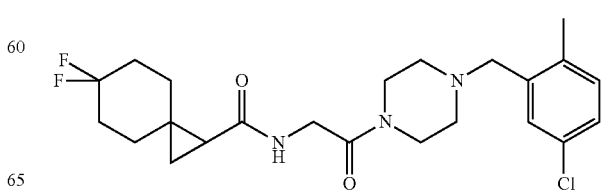

N-(2-(4-(5-Chloro-2-methylbenzyl)piperazin-1-yl)-2-oxoethyl)-6,6-difluorospiro[2.5]octane-1-carboxamide This compound was prepared according to Method C1 using 6,6-difluorospiro[2.5]octane-1-carboxylic acid and 5-chloro-2-methylbenzaldehyde. MS m/z: 454.2 (M+1), calc'd for $C_{23}H_{30}ClF_2N_3O_2$: 453.20.

1432 270

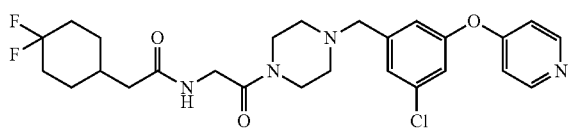 [SMILES: O=C(CC1CCC(F)(F)CC1)NCC(=O)N1CCN(Cc2cc(Cl)cc(Oc3ccncc3)c2)CC1]

N-(2-(4-(3-Chloro-5-(pyridin-4-yloxy)benzyl)piperazin-1-yl)-2-oxoethyl)-2-(4,4-difluorocyclohexyl)acetamide This compound was prepared according to Method A1b using 2-(4,4-difluorocyclohexyl)acetic acid and 3-chloro-5-hydroxybenzaldehyde with an additional step as following. $^1$H NMR (400 MHz, CDCl$_3$, ppm): δ 8.51 (dd, J1=1.7, J2=4.8, 1H), 7.22 (t, J=1.8, 1H), 6.98 (m, 3H), 6.85 (dd, J1=1.6, J2=4.8, 1H), 6.56 (br, 1H), 4.05 (d, J=4.0, 2H), 3.65 (t, J=5.4, 2H), 3.50 (s, 1H), 3.47 (s, 11H), 3.42 (t, J=5.0, 2H), 2.45 (m, 4H), 2.21 (d, J=7.0, 2H), 2.10-1.74 (m, 6H), 1.33 (m, 3H). MS m/z: 521.2 (M+1), calc'd for $C_{26}H_{31}ClF_2N_4O_3$: 520.21.

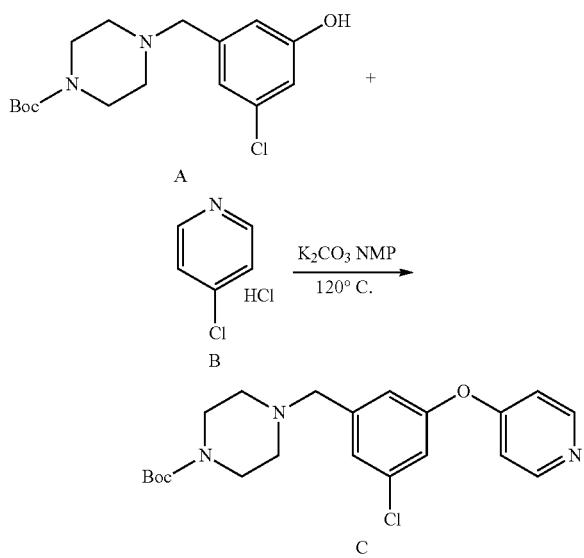

In a glass vial, A (1 eq), B (1.2 eq) and eq of K$_2$CO$_3$ were dissolved in 2 mL anhydrous NMP. The reaction was stirred at 120° C. for overnight. After reaction, water was added into the residue. After sonication and centrifugation, the water phase was removed and the residue was dissolved in EtOAc, dried by MgSO4, filtered and concentrated to afford the crude product C.

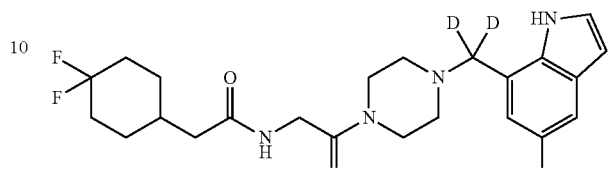

N-(2-(4-((5-Chloro-JH-indol-7-yl)methyl-d2)piperazin-1-yl)-2-oxoethyl)-2-(4,4-difluorocyclohexyl)acetamide This compound was prepared by a similar method of 1412 using 5-chloro-1H-indole-7-carboxylic acid. $^1$H NMR (400 MHz, CDCl$_3$, ppm): δ 9.41 (s, 1H), 7.55 (d, J=2, 1H), 7.24 (t, J=2.8, 1H), 6.96 (d, J=1.9, 1H), 6.54 (br, 11H), 6.50 (dd, J1=2.0, J2=3.0, 1H), 4.05 (d, J=4.0, 2H), 3.68 (t, J=5.4, 2H), 3.44 (t, J=5.4, 2H), 2.50 (m, 4H), 2.19 (d, J=7.0, 2H), 2.10-1.74 (m, 6H), 1.33 (m, 3H). MS: m/z 469.2 (M+1), calc'd for $C_{23}H_{27}D_2ClF_2N_4O_2$: 468.21.

1416 HL-01-091-002

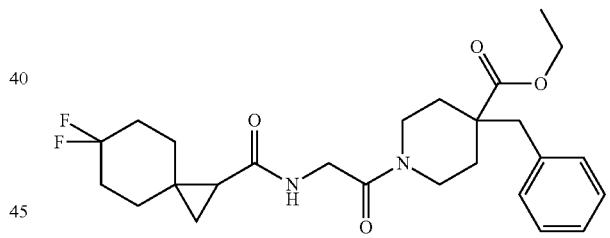

Ethyl 4-benzyl-1-((6,6-difluorospiro[2.5]octane-1-carbonyl)glycyl)piperidine-4-carboxylate This compound was prepared according to Method B4 using ethyl 4-benzylpiperidine-4-carboxylate and 6,6-difluorospiro[2.5]octane-1-carboxylic acid. MS: m/z 477.3 (M+1), calc'd for $C_{26}H_{34}F_2N_2O_4$: 476.25.

1415 HL-01-091-001

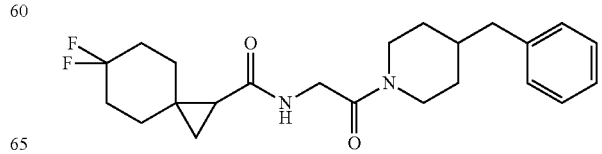

N-(2-(4-Benzylpiperidin-1-yl)-2-oxoethyl)-6,6-difluorospiro[2.5]octane-1-carboxamide This compound was prepared according to Method B4 using 4-benzylpiperidine and 6,6-difluorospiro[2.5]octane-1-carboxylic acid. MS: m/z 405.3 (M+1), calc'd for $C_{23}H_{30}F_2N_2O_2$: 404.23.
1414 HL-01-087-001

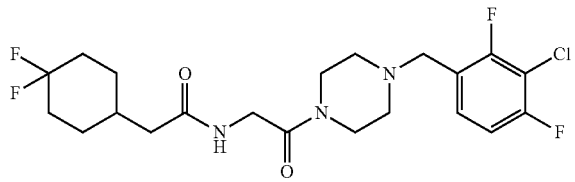 [SMILES: O=C(CC1CCC(F)(F)CC1)NCC(=O)N1CCN(Cc2ccc(F)c(Cl)c2F)CC1]

N-(2-(4-(3-Chloro-2,4-difluorobenzyl)piperazin-1-yl)-2-oxoethyl)-2-(4,4-difluorocyclohexyl)acetamide This compound was prepared according to Method C1 using 2-(4,4-difluorocyclohexyl)acetic acid and 3-chloro-2,4-difluorobenzaldehyde MS: m/z 464.2 (M+1), calc'd for $C_{21}H_{26}ClF_4N_3O_2$: 463.16.
1407 HL-01-085-H

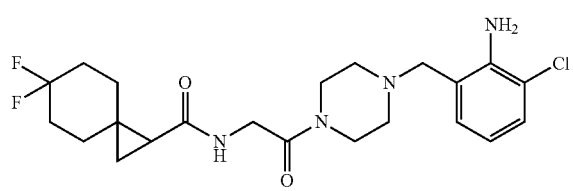 [SMILES: Nc1c(Cl)cccc1CN1CCN(C(=O)CNC(=O)C2CC23CCC(F)(F)CC3)CC1]

N-(2-(4-(2-Amino-3-chlorobenzyl)piperazin-1-yl)-2-oxoethyl)-6,6-difluorospiro[2.5]octane-1-carboxamide This compound was prepared according to Method C1 using 6,6-difluorospiro[2.5]octane-1-carboxylic acid and 2-amino-3-chlorobenzaldehyde. MS: m/z 455.2 (M+1), calc'd for $C_{22}H_{29}ClF_2N_4O_2$: 454.19.
1406 HL-01-085-C

N-(2-(4-((5-Chloro-JH-indazol-7-yl)methyl)piperazin-1-yl)-2-oxoethyl)-2-(4,4-difluorocyclohexyl)acetamide This compound was prepared according to Method C1 using 2-(4,4-difluorocyclohexyl)acetic acid and 5-chloro-1H-indazole-7-carbaldehyde. MS: m/z 468.2 (M+1), calc'd for $C_{22}H_{28}ClF_2N_5O_2$: 467.19.

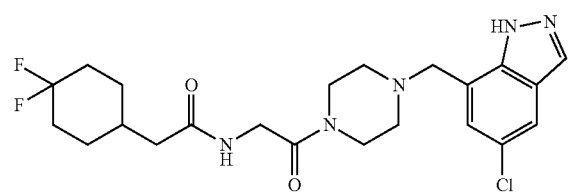 [SMILES: O=C(CC1CCC(F)(F)CC1)NCC(=O)N1CCN(Cc2cc(Cl)cc3cn[nH]c23)CC1]

5-chloro-1H-indazole-7-carbaldehyde was prepared by the following procedures:

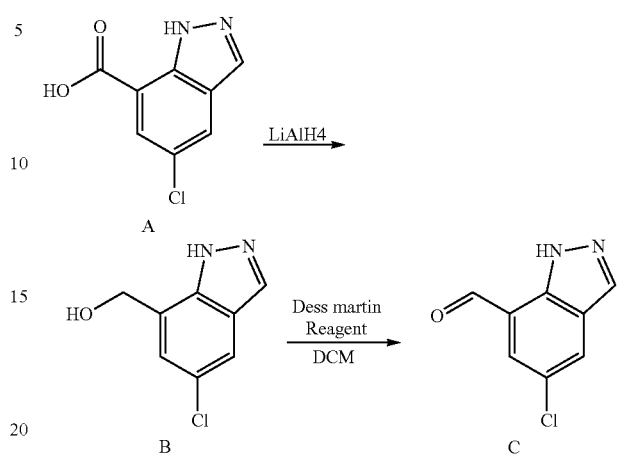

In a flask under nitrogen was placed acid in 2 mL of anhy-THF. Cooled to 0° C., LiAH4 added slowly. The ice bath was then removed, and reaction allowed to warm to rt. Stirred for 6 hrs, after which, $Na_2SO_4$-10$H_2O$ added. The mixture stirred for overnight. The solid was spinned down, washed with EtOAc, and the organic layers concentrated under vacuum.

In a vial under nitrogen was placed alcohol B (17 mg), Dess Martin reagent (47 mg) in 2 mL of anhydrous $CH_2Cl_2$. The reaction stirred for overnight. To the mixture was added 2 drops of MeOH, stirred for 2 more hours, then diluted with EtOAc, filtered, concentrated to afford the crude C.
1405 HL-01-085-B

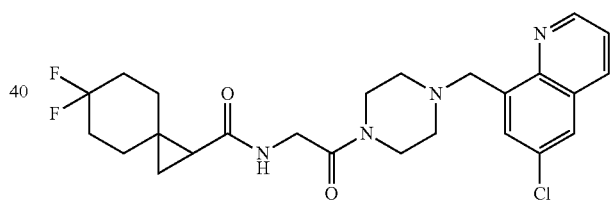

N-(2-(4-((6-Chloroquinolin-8-yl)methyl)piperazin-1-yl)-2-oxoethyl)-6,6-difluorospiro[2.5]octane-1-carboxamide This compound was prepared according to Method C1 using 6,6-difluorospiro[2.5]octane-1-carboxylic acid and 6-chloroquinoline-8-carbaldehyde. MS: m/z 491.2 (M+1), calc'd for $C_{25}H_{29}ClF_2N_4O_2$: 490.19.
1393 HL-01-078-003

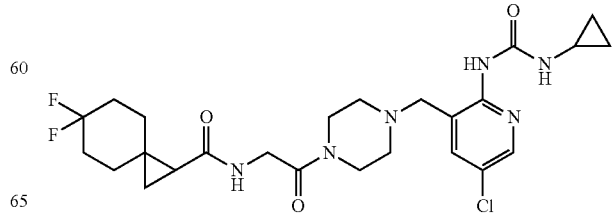

177

N-(2-(4-((5-Chloro-2-(3-cyclopropylureido)pyridin-3-yl)methyl)piperazin-1-yl)-2-oxoethyl)-6,6-difluorospiro[2.5]octane-1-carboxamide This compound was prepared according to Method A1a using 6,6-difluorospiro[2.5]octane-1-carboxylic acid and 2-amino-5-chloronicotinaldehyde with two additional steps as following. MS: m/z 539.3 (M+1), calc'd for $C_{25}H_{33}ClF_2N_6O_3$: 538.23.

178

N-(2-(4-((5-Chloro-2-(3-phenylureido)pyridin-3-yl)methyl)piperazin-1-yl)-2-oxoethyl)-6,6-difluorospiro[2.5]octane-1-carboxamide This compound was prepared according to Method A1a using 6,6-difluorospiro[2.5]octane-1-carboxylic acid and 2-amino-5-chloronicotinaldehyde with two additional steps as following. MS: m/z 575.3 (M+1), calc'd for $C_{28}H_{33}ClF_2N_6O_3$: 574.23.

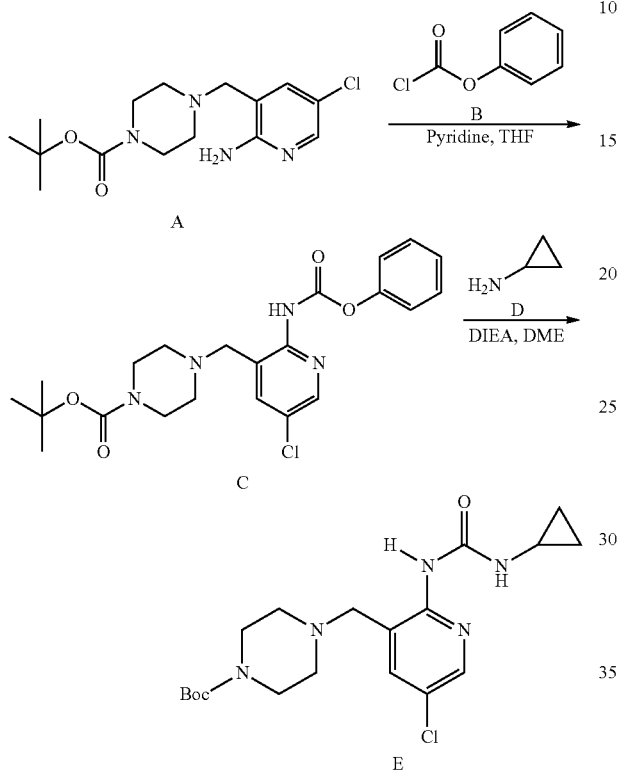

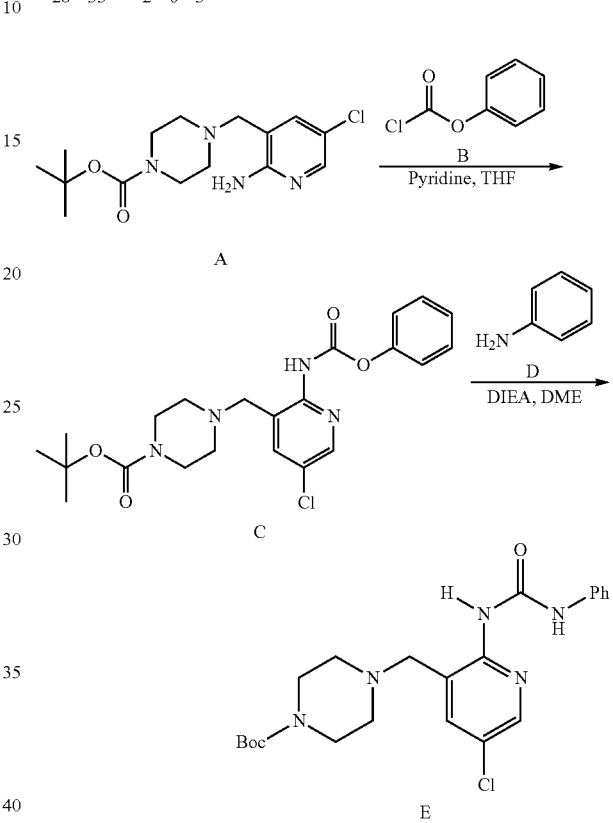

In a glass vial, A (200 mg) was dissolved in tetrahydrofuran (2 ml) under a nitrogen atmosphere. Pyridine (97 mg) was added. Then phenyl chloroformate (191 mg) was added at room temperature, and the cloudy mixture was stirred for 60 minutes. A saturated aqueous solution of sodium hydrogencarbonate (6 ml) was added to the mixture. The mixture was extracted with EtOAc, and combined organic layers dried. The residue was washed with water 2×5 mL, and dried. The crude intermediate was taken to next step directly.

In a microwave vial was placed C (1 eq), D (57 mg, 10 eq) in 2 mL of anhyd. DME, iPr2Net (5 eq) added, and heated to 80° C. for 2 hrs. Cooled to rt, concentrated. The residue was dissolved by minimal amount of MeOH, added with water, and the precipitation spinned, washed, to afford the crude E.
1392 HL-01-078-002

In a glass vial, A (200 mg) was dissolved in tetrahydrofuran (2 ml) under a nitrogen atmosphere. Pyridine (97 mg) was added. Then phenyl chloroformate (191 mg) was added at room temperature, and the cloudy mixture was stirred for 60 minutes. A saturated aqueous solution of sodium hydrogencarbonate (6 ml) was added to the mixture. The mixture was extracted with EtOAc, and combined organic layers dried. The residue was washed with water 2×5 mL, and dried. The crude intermediate was taken to next step directly.

In a microwave vial was placed C (1 eq), D (33 mg, 5 eq) in 2 mL of anhyd. DME, iPr2Net (5 eq) added, and heated to 80° C. for 2 hrs. Cooled to rt, concentrated. The residue was dissolved by minimal amount of MeOH, added with water, and the precipitation spinned, washed, to afford the crude E.
1391 HL-01-078-001

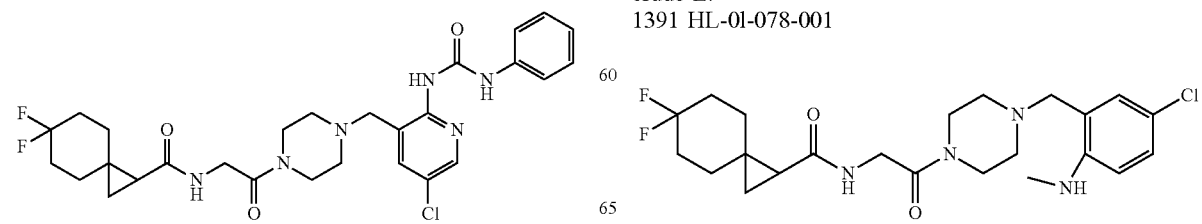

N-(2-(4-(5-Chloro-2-(methylamino)benzyl)piperazin-1-yl)-2-oxoethyl)-6,6-difluorospiro[2.5]octane-1-carboxamide This compound was prepared according to Method A1a using 6,6-difluorospiro[2.5]octane-1-carboxylic acid and 2-amino-5-chlorobenzaldehyde with two additional steps as following. MS: m/z 469.2 (M+1), calc'd for $C_{23}H_{31}ClF_2N_4O_2$: 468.21.

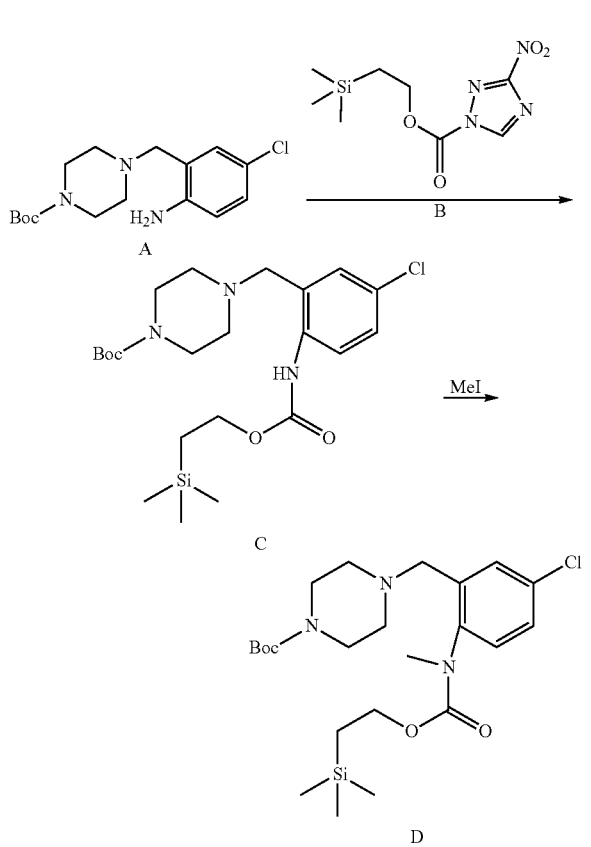

In a vial was placed aniline-A (60 mg), B (50 mg) in 2 mL of anhy DME, iPr2Net (1 eq) was added, and the reaction stirred for overnight. To the reaction was added water, extracted with EtOAc, and the combined organic phases concentrated, taken to the next step directly.

In a uwave vial under nitrogen was placed C (36 mg, 0.077 mmol) in 2 mL of anhyd THF. Cooled to 0° C., and NaHMDS (0.085 mmol) added slowly. After 15 minutes, MeI (0.092 mmol) added slowly, and reaction stirred for 4 more hours, allowed to warm to rt slowly. The reaction was then quenched with sat aq NH4Cl, extraction with EtOAc. The combined organic layers concentrated, taken to the next step directly.
1384 HL-01-074-E

N-(2-(4-(5-Chloro-2-methoxybenzyl)piperazin-1-yl)-2-oxoethyl)-2-(4,4-difluorocyclohexyl)acetamide This compound was prepared according to Method C1 using 2-(4,4-difluorocyclohexyl)acetic acid and 5-chloro-2-methoxybenzaldehyde. MS: m/z 458.2 (M+1), calc'd for $C_{22}H_{30}ClF_2N_3O_3$: 457.19.
1383 HL-01-074-D

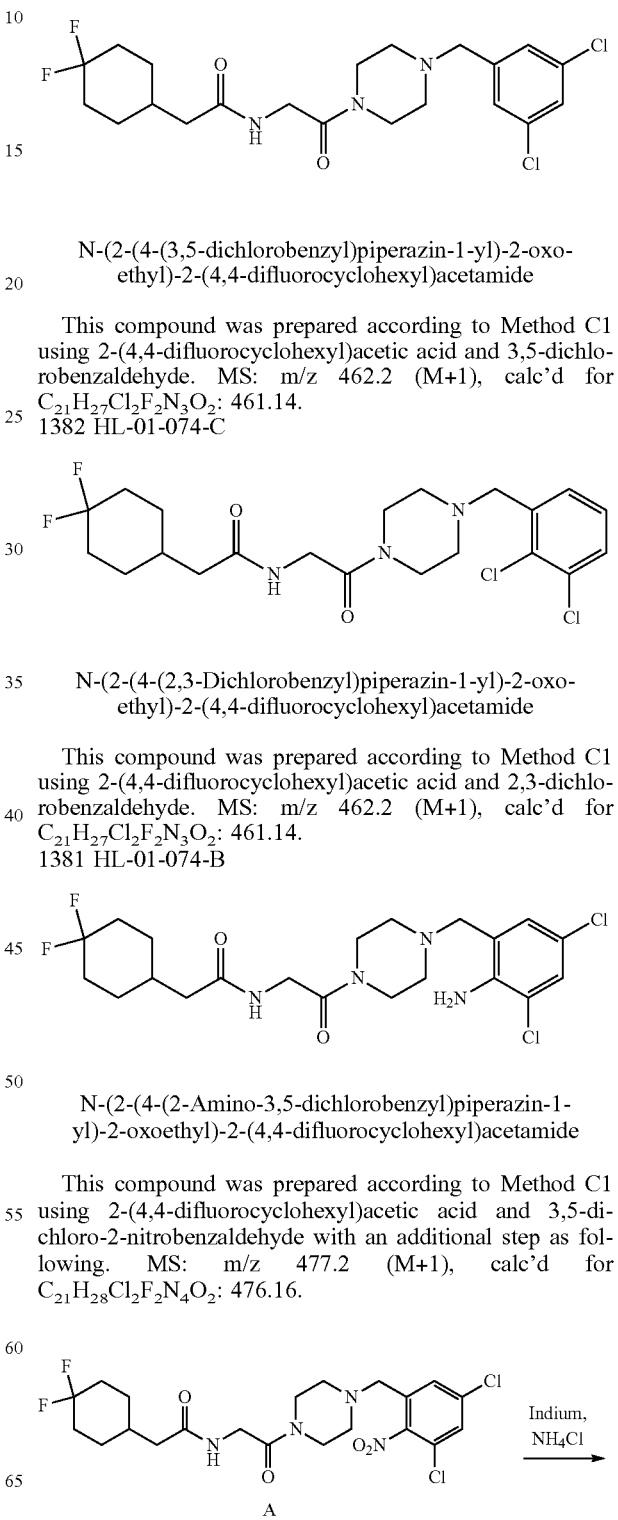

N-(2-(4-(3,5-dichlorobenzyl)piperazin-1-yl)-2-oxoethyl)-2-(4,4-difluorocyclohexyl)acetamide This compound was prepared according to Method C1 using 2-(4,4-difluorocyclohexyl)acetic acid and 3,5-dichlorobenzaldehyde. MS: m/z 462.2 (M+1), calc'd for $C_{21}H_{27}Cl_2F_2N_3O_2$: 461.14.
1382 HL-01-074-C

N-(2-(4-(2,3-Dichlorobenzyl)piperazin-1-yl)-2-oxoethyl)-2-(4,4-difluorocyclohexyl)acetamide This compound was prepared according to Method C1 using 2-(4,4-difluorocyclohexyl)acetic acid and 2,3-dichlorobenzaldehyde. MS: m/z 462.2 (M+1), calc'd for $C_{21}H_{27}Cl_2F_2N_3O_2$: 461.14.
1381 HL-01-074-B

N-(2-(4-(2-Amino-3,5-dichlorobenzyl)piperazin-1-yl)-2-oxoethyl)-2-(4,4-difluorocyclohexyl)acetamide This compound was prepared according to Method C1 using 2-(4,4-difluorocyclohexyl)acetic acid and 3,5-dichloro-2-nitrobenzaldehyde with an additional step as following. MS: m/z 477.2 (M+1), calc'd for $C_{21}H_{28}Cl_2F_2N_4O_2$: 476.16.

181
-continued

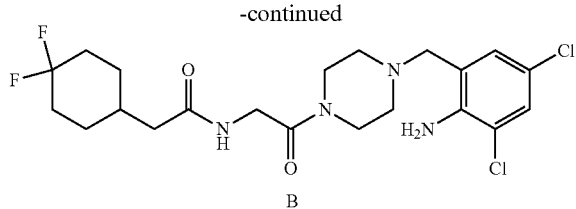

B

In a sealed tube was placed A, 25 mg of Indium (5 eq), 50 mg (10 eq) of NH$_4$Cl, in 1.5 mL EtOH, 1.5 mL of water, heated to 75° C. for 8 hrs. The solid was filtered, and the filtrate was concentrated, diluted with water, extracted with EtOAc. The organic phases concentrated, purified by TLC (3% MeOH/CH2Cl$_2$) to afford B.
1380 HL-01-073-001

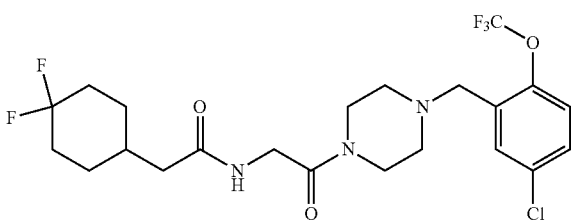 [SMILES: O=C(CC1CCC(F)(F)CC1)NCC(=O)N1CCN(Cc2cc(Cl)ccc2OC(F)(F)F)CC1]

N-(2-(4-(5-Chloro-2-(trifluoromethoxy)benzyl)piperazin-1-yl)-2-oxoethyl)-2-(4,4-difluorocyclohexyl)acetamide This compound was prepared according to Method C1 using 2-(4,4-difluorocyclohexyl)acetic acid and 5-chloro-2-(trifluoromethoxy)benzaldehyde. MS: m/z 512.2 (M+1), calc'd for C$_{22}$H$_{27}$ClF$_5$N$_3$O$_3$: 511.17.
1371 L-01-070-I

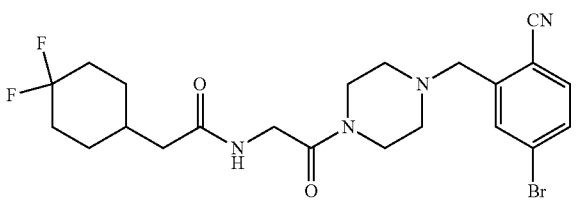 [SMILES: N#Cc1ccc(Br)cc1CN1CCN(C(=O)CNC(=O)CC2CCC(F)(F)CC2)CC1]

N-(2-(4-(5-Bromo-2-cyanobenzyl)piperazin-1-yl)-2-oxoethyl)-2-(4,4-difluorocyclohexyl)acetamide This compound was prepared according to Method C1 using 2-(4,4-difluorocyclohexyl)acetic acid and 4-bromo-2-formylbenzonitrile. MS: m/z 497.2 (M+1), calc'd for C$_{22}$H$_{27}$BrF$_2$N$_4$O$_2$: 496.13.
1370 L-01-070-H

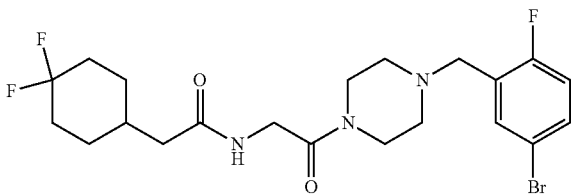 [SMILES: O=C(CC1CCC(F)(F)CC1)NCC(=O)N1CCN(Cc2cc(Br)ccc2F)CC1]

182
N-(2-(4-(5-Bromo-2-fluorobenzyl)piperazin-1-yl)-2-oxoethyl)-2-(4,4-difluorocyclohexyl)acetamide This compound was prepared according to Method C1 using 2-(4,4-difluorocyclohexyl)acetic acid and 5-bromo-2-fluorobenzaldehyde. MS: m/z 490.2 (M+1), calc'd for C$_{21}$H$_{27}$BrF$_3$N$_3$O$_2$: 489.12.
1369 L-01-070-G

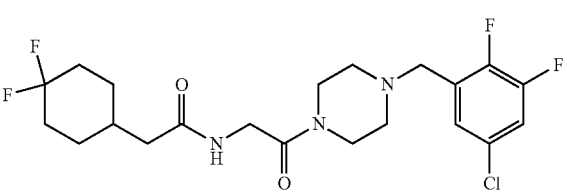 [SMILES: O=C(CC1CCC(F)(F)CC1)NCC(=O)N1CCN(Cc2cc(Cl)cc(F)c2F)CC1]

N-(2-(4-(5-Chloro-2,3-difluorobenzyl)piperazin-1-yl)-2-oxoethyl)-2-(4,4-difluorocyclohexyl)acetamide This compound was prepared according to Method C1 using 2-(4,4-difluorocyclohexyl)acetic acid and 5-chloro-2,3-difluorobenzaldehyde. MS: m/z 464.2 (M+1), calc'd for C$_{21}$H$_{26}$ClF$_4$N$_3$O$_2$: 463.16.
1368 L-01-070-F

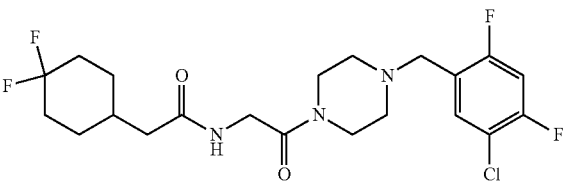 [SMILES: O=C(CC1CCC(F)(F)CC1)NCC(=O)N1CCN(Cc2cc(Cl)c(F)cc2F)CC1]

N-(2-(4-(5-chloro-2,4-difluorobenzyl)piperazin-1-yl)-2-oxoethyl)-2-(4,4-difluorocyclohexyl)acetamide This compound was prepared according to Method C1 using 2-(4,4-difluorocyclohexyl)acetic acid and 2,4-difluorobenzaldehyde. MS: m/z 464.2 (M+1), calc'd for C$_{21}$H$_{26}$ClF$_4$N$_3$O$_2$: 463.16.
1367 L-01-070-D

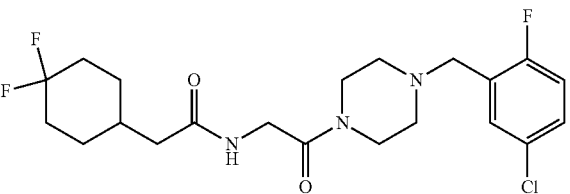 [SMILES: O=C(CC1CCC(F)(F)CC1)NCC(=O)N1CCN(Cc2cc(Cl)ccc2F)CC1]

N-(2-(4-(5-chloro-2-fluorobenzyl)piperazin-1-yl)-2-oxoethyl)-2-(4,4-difluorocyclohexyl)acetamide This compound was prepared according to Method C1 using 2-(4,4-difluorocyclohexyl)acetic acid and 5-chloro-2-fluorobenzaldehyde. MS: m/z 446.2 (M+1), calc'd for $C_{21}H_{27}ClF_3N_3O_2$: 445.17.
1366 L-01-070-C

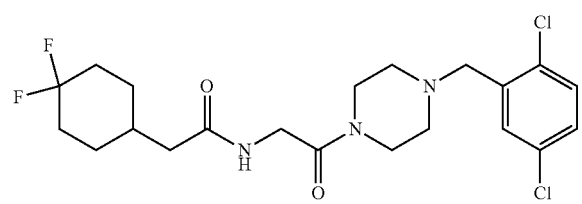 [SMILES: O=C(CC1CCC(F)(F)CC1)NCC(=O)N1CCN(Cc2cc(Cl)ccc2Cl)CC1]

N-(2-(4-(2,5-Dichlorobenzyl)piperazin-1-yl)-2-oxoethyl)-2-(4,4-difluorocyclohexyl)acetamide This compound was prepared according to Method C1 using 2-(4,4-difluorocyclohexyl)acetic acid and 2,5-dichlorobenzaldehyde. MS: m/z 462.2 (M+1), calc'd for $C_{21}H_{27}Cl_2F_2N_3O_2$: 461.14.
1365 HL-01-067-F

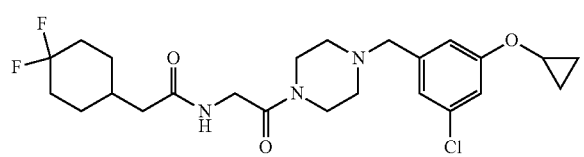 [SMILES: O=C(CC1CCC(F)(F)CC1)NCC(=O)N1CCN(Cc2cc(Cl)cc(OC3CC3)c2)CC1]

N-(2-(4-(3-Chloro-5-cyclopropoxybenzyl)piperazin-1-yl)-2-oxoethyl)-2-(4,4-difluorocyclohexyl)acetamide This compound was prepared according to Method A1a using 2-(4,4-difluorocyclohexyl)acetic acid and 3-chloro-5-hydroxybenzaldehyde with an additional step as following. MS: m/z 484.2 (M+1), calc'd for $C_{24}H_{32}ClF_2N_3O_3$: 483.21.

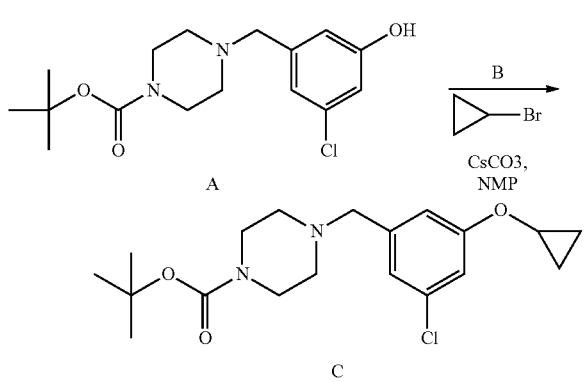

In a sealed tube was placed A, $Cs_2CO_3$ (3 eq) in 1.5 mL of Anhyd NMP. 4 eq of B added, heated at 110° C. for 6 hrs, after which, another 4 eq of B added, heated for O.N. Reaction cooled to rt, diluted with water, extracted with EtOAc. The EtOAc was removed, to the residue (with NMP) was added water, off white precipitation formed. The residue was spinned (emulsion), washed with water, 2×3 mL. get HL-01-067-C as an off-white solid.
1364HL-01-064-003

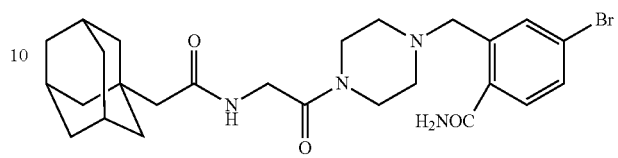

2-((4-((2-(((1R,3R,5S)-Adamantan-1-yl)acetyl)glycyl)piperazin-1-yl)methyl)-4-bromobenzamide This compound was prepared according to Method A2a using 2-((1R,3R,5S)-adamantan-1-yl)acetic acid and 4-bromo-2-formylbenzonitrile with an additional step as following. MS: m/z 531.2 (M+1), calc'd for $C_{26}H_{35}BrN_4O_3$: 530.19.

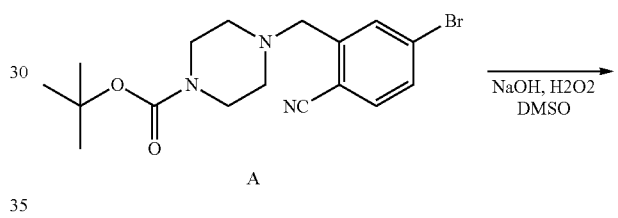

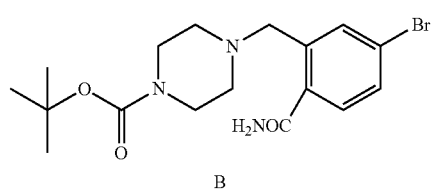

In a vial was placed the cyano compound in 2.5 mL of DMSO. NaOH (2 M) added, followed by H2O2 (50% w/w, diluted by 3×volume of water). The reaction became cloudy at beginning, and sonicated. Stirred at rt for 1 hr, the reaction was diluted with water (8 mL), extracted with EtOAc, concentrated. The DMSO was removed by Genevec to get a white solid.
1363 HL-01-063-C

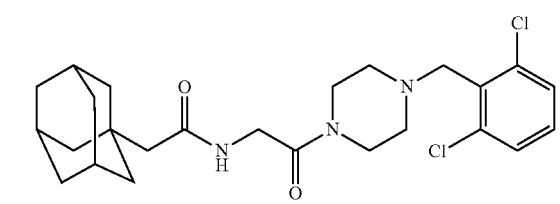 [SMILES: O=C(CC12CC3CC(CC(C3)C1)C2)NCC(=O)N1CCN(Cc2c(Cl)cccc2Cl)CC1]

2-((1R,3R,5S)-Adamantan-1-yl)-N-(2-(4-(2,6-dichlorobenzyl)piperazin-1-yl)-2-oxoethyl)acetamide This compound was prepared according to Method C1 using 2-((1R,3R,5S)-adamantan-1-yl)acetic acid and 2,6-dichlorobenzaldehyde. MS: m/z 478.2 (M+1), calc'd for $C_{25}H_{33}Cl_2N_3O_2$: 477.19.
1354 HL-01-062-F

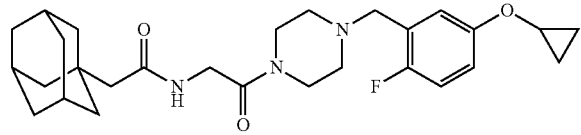 [SMILES: O=C(CC12CC3CC(CC(C3)C1)C2)NCC(=O)N1CCN(Cc2cc(OC3CC3)ccc2F)CC1]

2-((1R,3R,5S)-Adamantan-1-yl)-N-(2-(4-(5-cyclopropoxy-2-fluorobenzyl)piperazin-1-yl)-2-oxoethyl)acetamide This compound was prepared according to Method A2a using 2-((1R,3R,5S)-adamantan-1-yl)acetic acid and 2-fluoro-5-hydroxybenzaldehyde with an additional step as following. MS: m/z 484.3 (M+1), calc'd for $C_{28}H_{38}FN_3O_3$: 483.29.

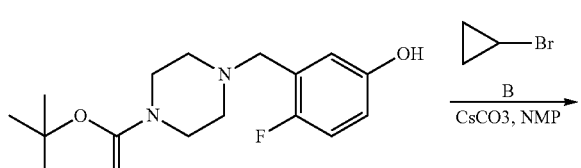

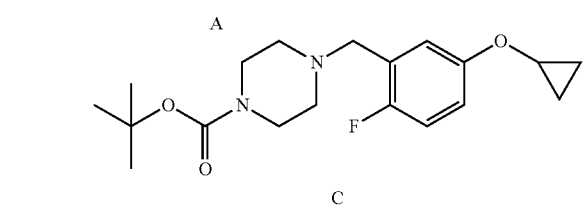

In a sealed tube was placed A, $Cs_2CO_3$ in 1.5 mL of Anhyd NMP. 4 eq of B added, heated at 110° C. for 6 hrs, after which, another 4 eq of B added, heated for O.N. Reaction cooled to rt, diluted with water, extracted with EtOAc. The EtOAc was removed, to the residue (with NMP) was added water, yellow precipitation formed. The residue was spinned, washed with water, 2×3 mL. get crude product as a brown solid.
1353HL-01-063-B

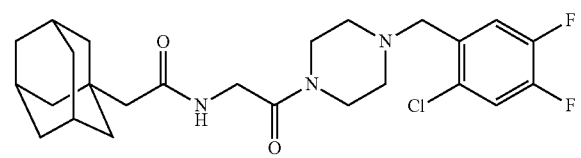 [SMILES: O=C(CC12CC3CC(CC(C3)C1)C2)NCC(=O)N1CCN(Cc2cc(F)c(F)cc2Cl)CC1]

2-((1R,3R,5S)-Adamantan-1-yl)-N-(2-(4-(2-chloro-4,5-difluorobenzyl)piperazin-1-yl)-2-oxoethyl)acetamide This compound was prepared according to Method C1 using 2-((1R,3R,5S)-adamantan-1-yl)acetic acid and 2-chloro-4,5-difluorobenzaldehyde. MS: m/z 480.3 (M+1), calc'd for $C_{25}H_{32}ClF_2N_3O_2$: 479.22.
1352 HL-01-063-A

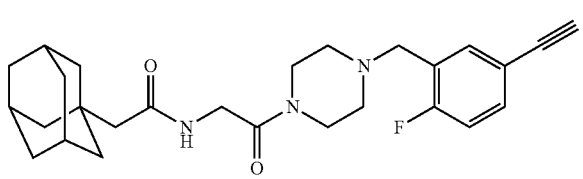 [SMILES: C#Cc1ccc(F)c(CN2CCN(C(=O)CNC(=O)CC34CC5CC(CC(C5)C3)C4)CC2)c1]

2-((1R,3R,5S)-Adamantan-1-yl)-N-(2-(4-(5-ethynyl-2-fluorobenzyl)piperazin-1-yl)-2-oxoethyl)acetamide This compound was prepared according to Method C1 using 2-((1R,3R,5S)-adamantan-1-yl)acetic acid and 5-ethynyl-2-fluorobenzaldehyde. MS: m/z 452.3 (M+1), calc'd for $C_{27}H_{34}FN_3O_2$: 451.26.
1351 HL-01-060-007

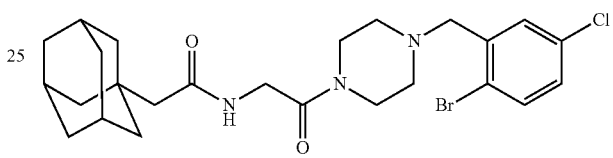

2-((1R,3R,5S)-Adamantan-1-yl)-N-(2-(4-(2-bromo-5-chlorobenzyl)piperazin-1-yl)-2-oxoethyl)acetamide This compound was prepared according to Method C1 using 2-((1R,3R,5S)-adamantan-1-yl)acetic acid and 2-bromo-5-chlorobenzaldehyde. MS: m/z 522.2 (M+1), calc'd for $C_{25}H_{33}BrClN_3O_2$: 521.14.
1350 HL-01-060-006

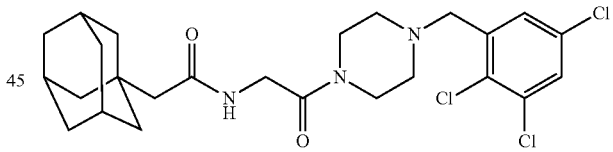

2-((1R,3R,5S)-adamantan-1-yl)-N-(2-oxo-2-(4-(2,3,5-trichlorobenzyl)piperazin-1-yl)ethyl)acetamide This compound was prepared according to Method C1 using 2-((1R,3R,5S)-adamantan-1-yl)acetic acid and 2,3,5-trichlorobenzaldehyde. MS: m/z 512.2 (M+1), calc'd for $C_{25}H_{32}Cl_3N_3O_2$: 511.16.
1349 HL-01-060-005

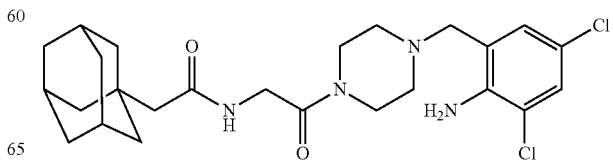

187

2-((1R,3R,5S)-Adamantan-1-yl)-N-(2-(4-(2-amino-3,5-dichlorobenzyl)piperazin-1-yl)-2-oxoethyl)acetamide This compound was prepared according to Method C1 using 2-((1R,3R,5S)-adamantan-1-yl)acetic acid and 3,5-dichloro-2-nitrobenzaldehyde with an additional step shown as following. MS: m/z 493.2 (M+1), calc'd for $C_{25}H_{34}Cl_2N_4O_2$: 492.21.

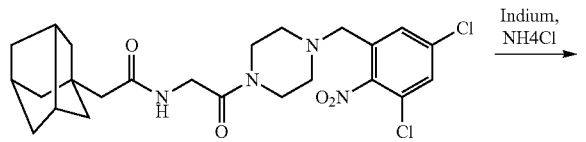

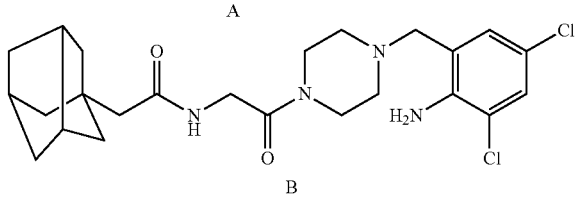

In a sealed tube was placed A, 25 mg of Indium (5 eq), 50 mg of NH$_4$Cl (10 eq), in 1.5 mL EtOH, 1.5 mL of water, heated to 75° C. for 8 hrs. The solid was filtered, and the filtrate was concentrated, diluted with water, extracted with EtOAc. The organic phases concentrated, purified by TLC (3% MeOH/CH2Cl$_2$) to afford B.
1348 HL-01-055-F

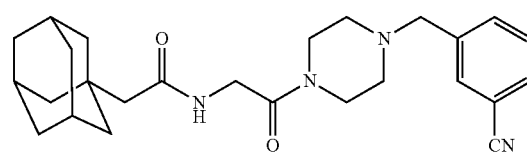

2-((1R,3R,5S)-Adamantan-1-yl)-N-(2-(4-(3-bromo-5-cyanobenzyl)piperazin-1-yl)-2-oxoethyl)acetamide This compound was prepared according to Method C1 using 2-((1R,3R,5S)-adamantan-1-yl)acetic acid and 3-bromo-5-formylbenzonitrile. MS: m/z 513.2 (M+1), calc'd for $C_{26}H_{33}BrN_4O_2$: 512.18.
1341 HL-01-055-002

2-((1R,3R,5S)-Adamantan-1-yl)-N-(2-(4-(3-amino-5-bromobenzyl)piperazin-1-yl)-2-oxoethyl)acetamide This compound was prepared from 2-((1R,3R,5S)-adamantan-1-yl)-N-(2-(4-(3-bromo-5-nitrobenzyl)piperazin-1-yl)-2-oxoethyl)acetamide by following procedures. MS: m/z 503.2 (M+1), calc'd for $C_{25}H_{35}BrN_4O_2$: 502.19.

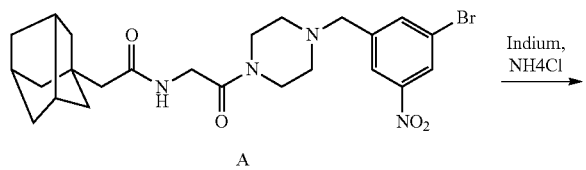

188

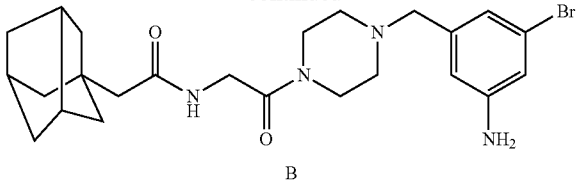

In a sealed tube was placed A, 25 mg of Indium (5 eq), 50 mg (10 eq) of NH$_4$Cl, in 1.5 mL EtOH, 1.5 mL of water, heated to 75° C. for 8 hrs. The solid was filtered, and the filtrate was concentrated, diluted with water, extracted with EtOAc. The organic phases concentrated, purified by TLC (3% MeOH/CH2Cl$_2$) to afford B.
1340 HL-01-055-G

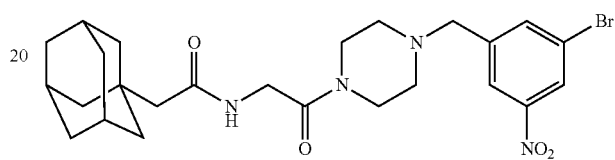

2-((1R,3R,5S)-Adamantan-1-yl)-N-(2-(4-(3-bromo-5-nitrobenzyl)piperazin-1-yl)-2-oxoethyl)acetamide This compound was prepared according to Method C1 using 2-((1R,3R,5S)-adamantan-1-yl)acetic acid and 3-bromo-5-nitrobenzaldehyde. MS: m/z 533.2 (M+1), calc'd for $C_{25}H_{33}BrN_4O_4$: 532.17.
1339 HL-01-055-E

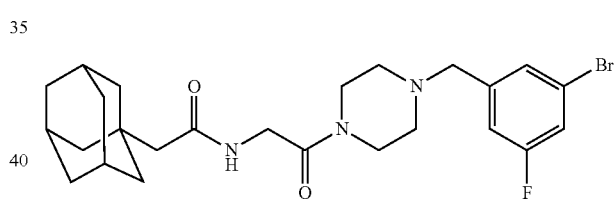

2-((1R,3R,5S)-Adamantan-1-yl)-N-(2-(4-(3-bromo-5-fluorobenzyl)piperazin-1-yl)-2-oxoethyl)acetamide This compound was prepared according to Method C1 using 2-((1R,3R,5S)-adamantan-1-yl)acetic acid and 3-bromo-5-fluorobenzaldehyde. MS: m/z 506.2 (M+1), calc'd for $C_{25}H_{33}BrFN_3O_2$: 505.17.
1338 HL-01-055-D

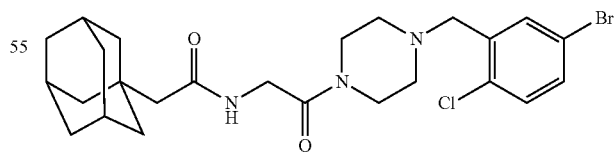

2-((1R,3R,5S)-Adamantan-1-yl)-N-(2-(4-(5-bromo-2-chlorobenzyl)piperazin-1-yl)-2-oxoethyl)acetamide This compound was prepared according to Method C1 using 2-((1R,3R,5S)-adamantan-1-yl)acetic acid and 5-bromo-2-chlorobenzaldehyde. MS: m/z 522.2 (M+1), calc'd for $C_{25}H_{33}BrClN_3O_2$: 521.14.
1337 HL-01-055-C

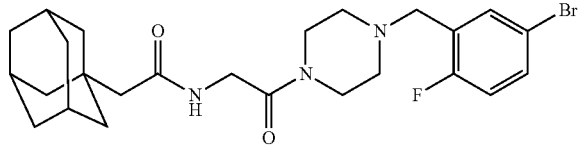 [SMILES: O=C(CC12CC3CC(CC(C3)C1)C2)NCC(=O)N1CCN(Cc2cc(Br)ccc2F)CC1]

2-((1R,3R,5S)-Adamantan-1-yl)-N-(2-(4-(5-bromo-2-fluorobenzyl)piperazin-1-yl)-2-oxoethyl)acetamide This compound was prepared according to Method C1 using 2-((1R,3R,5S)-adamantan-1-yl)acetic acid and 5-bromo-2-fluorobenzaldehyde. MS: m/z 506.2 (M+1), calc'd for $C_{25}H_{33}BrFN_3O_2$: 505.17.
1332 HL-01-050-G

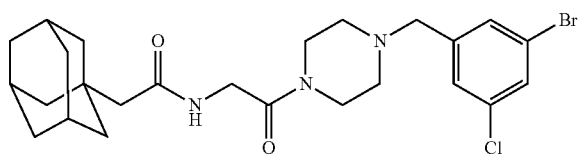 [SMILES: O=C(CC12CC3CC(CC(C3)C1)C2)NCC(=O)N1CCN(Cc2cc(Cl)cc(Br)c2)CC1]

2-((1R,3R,5S)-Adamantan-1-yl)-N-(2-(4-(3-bromo-5-chlorobenzyl)piperazin-1-yl)-2-oxoethyl)acetamide This compound was prepared according to Method A2a using 2-((1R,3R,5S)-adamantan-1-yl)acetic acid and 3-bromo-5-chlorobenzaldehyde. MS: m/z 522.2 (M+1), calc'd for $C_{25}H_{33}BrClN_3O_2$: 521.14.
1331 HL-01-051-I

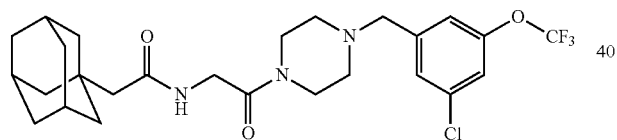

2-((1R,3R,5S)-Adamantan-1-yl)-N-(2-(4-(3-chloro-5-(trifluoromethoxy)benzyl)piperazin-1-yl)-2-oxoethyl)acetamide This compound was prepared according to Method C1 using 2-((1R,3R,5S)-adamantan-1-yl)acetic acid and 3-chloro-5-(trifluoromethoxy)benzaldehyde. MS: m/z 528.3 (M+1), calc'd for $C_{26}H_{33}ClF_3N_3O_3$: 527.22.
1329 HL-01-051-B

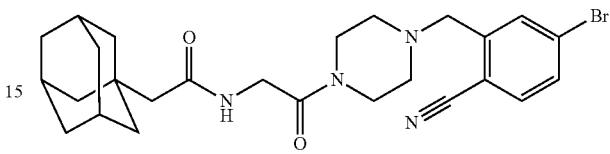

2-((1R,3R,5S)-Adamantan-1-yl)-N-(2-(4-(5-bromo-2-cyanobenzyl)piperazin-1-yl)-2-oxoethyl)acetamide This compound was prepared according to Method C1 using 2-((1R,3R,5S)-adamantan-1-yl)acetic acid and 4-bromo-2-formylbenzonitrile. MS: m/z 513.2 (M+1), calc'd for $C_{26}H_{33}BrN_4O_2$: 512.18.
1328HL-01-041-H

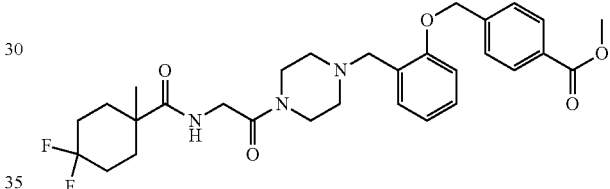

Methyl 4-((2-((4-((4,4-difluoro-1-methylcyclohexane-1-carbonyl)glycyl)piperazin-1-yl)methyl)phenoxy)methyl)benzoate This compound was prepared by a similar manner to Method B1 using 4,4-difluoro-1-methylcyclohexane-1-carbonyl chloride as following. MS: m/z 558.3.2 (M+1), calc'd for $C_{30}H_{37}F_2N_3O_5$: 557.27.

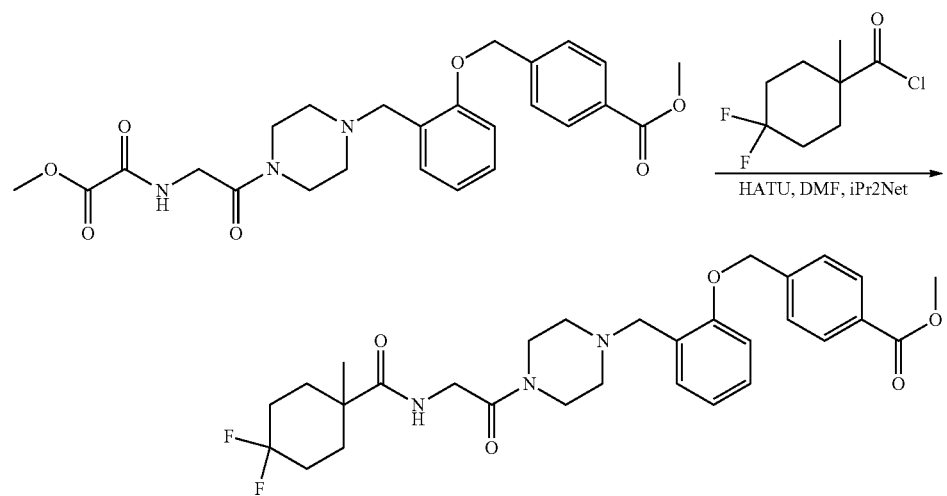

1327 HL-01-051-G

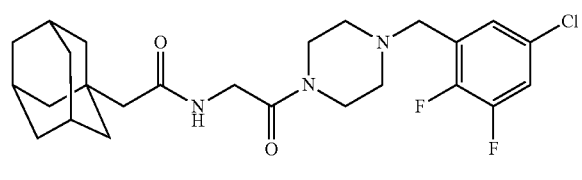

2-((1R,3R,5S)-Adamantan-1-yl)-N-(2-(4-(5-chloro-2,3-difluorobenzyl)piperazin-1-yl)-2-oxoethyl)acetamide This compound was prepared according to Method C1 using 2-((1R,3R,5S)-adamantan-1-yl)acetic acid and 5-chloro-2,3-difluorobenzaldehyde. MS: m/z 480.3 (M+1), calc'd for $C_{25}H_{32}ClF_2N_3O_2$: 479.22.

1326 HL-01-051-F

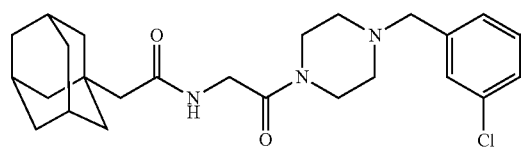

2-((1R,3R,5S)-Adamantan-1-yl)-N-(2-(4-(3-chloro-5-(trifluoromethyl)benzyl)piperazin-1-yl)-2-oxoethyl)acetamide This compound was prepared according to Method C1 using 2-((1R,3R,5S)-adamantan-1-yl)acetic acid and 3-chloro-5-(trifluoromethyl)benzaldehyde. MS: m/z 512.3 (M+1), calc'd for $C_{26}H_{33}ClF_3N_3O_2$: 511.22.

1325 HL-01-051-E

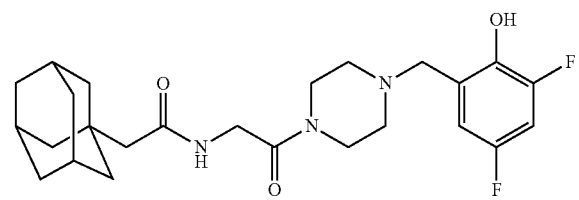 [SMILES: O=C(CC12CC3CC(CC(C3)C1)C2)NCC(=O)N1CCN(Cc2cc(F)cc(F)c2O)CC1]

2-((1R,3R,5S)-Adamantan-1-yl)-N-(2-(4-(3,5-difluoro-2-hydroxybenzyl)piperazin-1-yl)-2-oxoethyl)acetamide This compound was prepared according to Method C1 using 2-((1R,3R,5S)-adamantan-1-yl)acetic acid and 3,5-difluoro-2-hydroxybenzaldehyde. MS: m/z 462.3 (M+1), calc'd for $C_{25}H_{33}F_2N_3O_3$: 461.25.

1324 HL-01-051-C

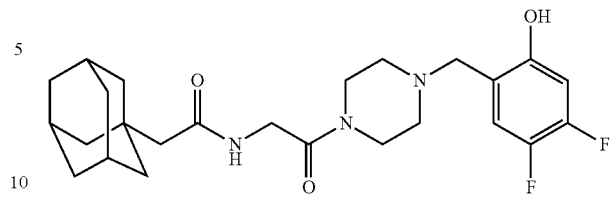

2-((1R,3R,5S)-Adamantan-1-yl)-N-(2-(4-(4,5-difluoro-2-hydroxybenzyl)piperazin-1-yl)-2-oxoethyl)acetamide This compound was prepared according to Method C1 using 2-((1R,3R,5S)-adamantan-1-yl)acetic acid and 4,5-difluoro-2-hydroxybenzaldehyde. MS: m/z 462.3 (M+1), calc'd for $C_{25}H_{33}F_2N_3O_3$: 461.25.

1323 HL-01-050-I

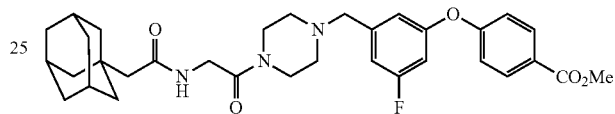

Methyl 4-(3-((4-((2-((1R,3R,5S)-adamantan-1-yl)acetyl)glycyl)piperazin-1-yl)methyl)-5-chlorophenoxy)benzoate This compound was prepared according to Method A2a using 2-((1R,3R,5S)-adamantan-1-yl)acetic acid and 3-chloro-5-hydroxybenzaldehyde with an additional step shown as following. MS: m/z 594.3 (M+1), calc'd for C33H40ClN3O5: 593.27.

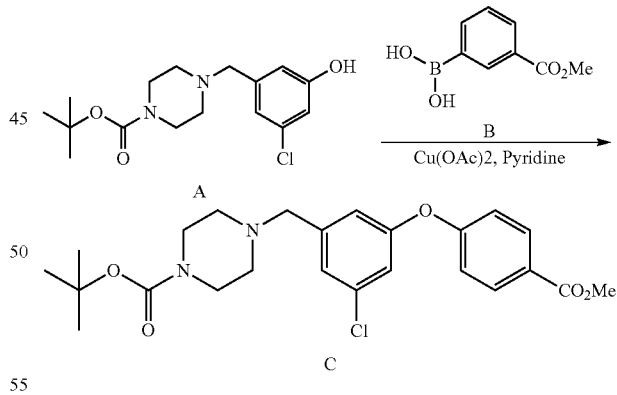

A microwave vial under nitrogen is charged with phenol A (1 eq), Cu(OAc)$_2$ (2 eq), boronic acid (2 eq) in CH$_2$Cl$_2$ (2 mL), followed by pyridine (6 eq). The reaction mixture was stirred at room temperature for overnight. The stirring was stopped, and the blue color suspension is allowed to settle, and then the clear solution transferred by an syringe to a uWave vial under nitrogen, and contains an additional 2 eq of boronic acid, 2 eq Cu(OAc)2. The mixture was stirred at room temperature for another 48 hrs, Reaction diluted with water, extracted with EtOAc. The organic phases dried, and loaded onto Silica bound PhSO3H, basic eluent (EtOAc/MeOH, 10:1, Et3N), get product with reasonable purity.

1322 HL-01-050-H

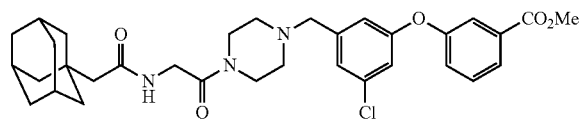 [SMILES: COC(=O)c1cccc(Oc2cc(Cl)cc(CN3CCN(C(=O)CNC(=O)CC45CC6CC(CC(C6)C4)C5)CC3)c2)c1]

Methyl 3-(3-((4-((2-(((1R,3R,5S)-adamantan-1-yl)acetyl)glycyl)piperazin-1-yl)methyl)-5-chlorophenoxy)benzoate This compound was prepared according to Method A2a using 2-((1R,3R,5S)-adamantan-1-yl)acetic acid and 3-chloro-5-hydroxybenzaldehyde with an additional step shown as following. MS: m/z 594.3 (M+1), calc'd for $C_{33}H_{40}ClN_3O_5$: 593.27.

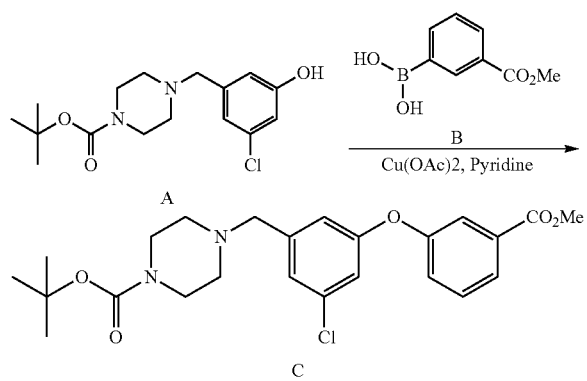

A microwave vial under nitrogen is charged with phenol A (1 eq), Cu(OAc)$_2$ (2 eq), boronic acid (2 eq) in CH$_2$Cl$_2$ (2 mL), followed by pyridine (6 eq). The reaction mixture was stirred at room temperature for overnight. The stirring was stopped, and the blue color suspension is allowed to settle, and then the clear solution transferred by an syringe to a uWave vial under nitrogen, and contains an additional 2 eq of boronic acid, 2 eq Cu(OAc)2. The mixture was stirred at room temperature for another 48 hrs, Reaction diluted with water, extracted with EtOAc. The organic phases dried, and loaded onto Silica bound PhSO3H, basic eluent (EtOAc/MeOH, 10:1, Et3N), get product with reasonable purity.

1321 HL-01-050-F

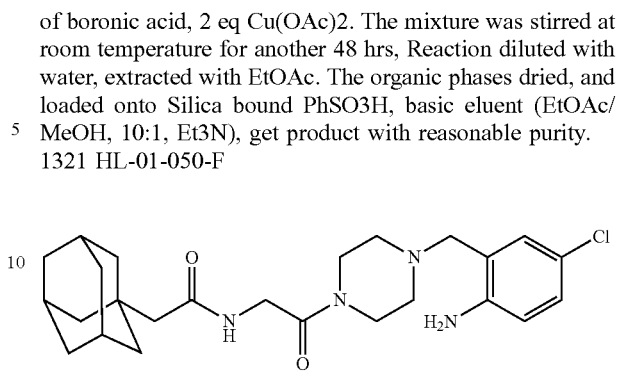

2-((1R,3R,5S)-Adamantan-1-yl)-N-(2-(4-(2-amino-5-chlorobenzyl)piperazin-1-yl)-2-oxoethyl)acetamide This compound was prepared according to Method A2a using 2-((1R,3R,5S)-adamantan-1-yl)acetic acid and 2-amino-5-chlorobenzaldehyde. MS: m/z 459.3 (M+1), calc'd for $C_{25}H_{35}ClN_4O_2$: 458.24.

1320 HL-01-049-002

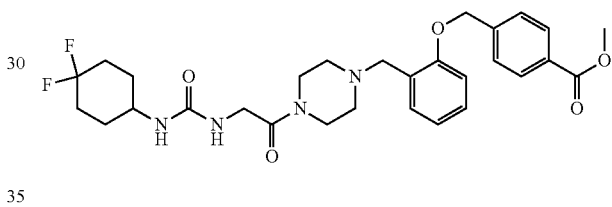

Methyl 4-((2-((4-(((4,4-difluorocyclohexyl)carbamoyl)glycyl)piperazin-1-yl)methyl)phenoxy)methyl)benzoate This compound was prepared from 4,4-difluorocyclohexan-1-ol by following procedures. MS: m/z 559.3 (M+1), calc'd for $C_{29}H_{36}F_2N_4O_5$: 558.27.

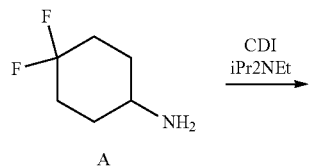

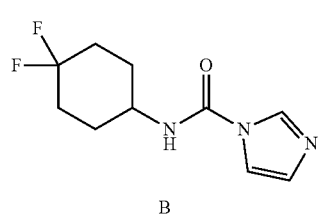

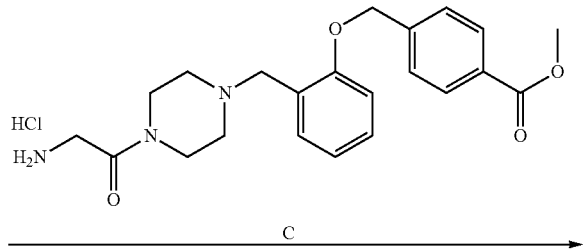

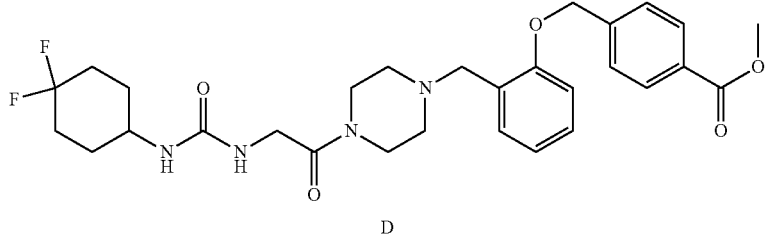

D

In a vial under nitrogen was placed A (43 mg 1 eq), CDI (43 mg, 1.05 eq) in 2 mL of anhyd DMF, iPr2NEt added slowly. The reaction was stirred for 2 hrs, and then added to a solution of C (1.2 eq) in anhyd. DMF. followed by additional iPr2NEt. Reaction stirred for ON. Reaction was precipitated with water, the white solid formed was dried, and purified by Benzene-sulfonic acid silica gel column to afford product D.
1319 HL-01-049-001

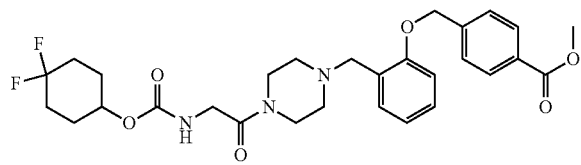 [SMILES: COC(=O)c1ccc(COc2ccccc2CN2CCN(C(=O)CNC(=O)OC3CCC(F)(F)CC3)CC2)cc1]

Methyl 4-((2-((4-(((((4,4-difluorocyclohexyl)oxy) carbonyl)glycyl)piperazin-1-yl)methyl)phenoxy) methyl)benzoate This compound was prepared from 4,4-difluorocyclohexan-1-ol by following procedures. MS: m/z 560.3 (M+1), calc'd for $C_{29}H_{35}F_2N_3O_6$: 559.25.

In a vial under nitrogen was placed triphosgene (34 mg, 0.35 eq) in 1 mL of any THF, and A (45 mg, 1 eq) and iPr2NEt in 1 mL of THF added slowly. The reaction was stirred for 2 hrs, and then was added to a solution of C (1.2 eq) in anhyd. DME, followed by additional iPr2NEt. Reaction stirred for ON. Reaction was dried, sonicated with water, the white solid formed was dried, and purified by Benzene-sulfonic acid silica gel column to afford Product D.
1317 HL-01-041-G

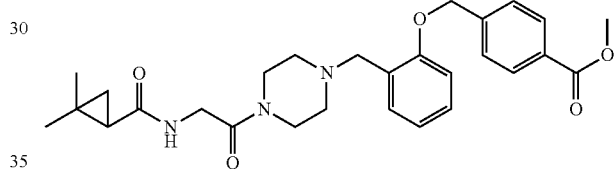

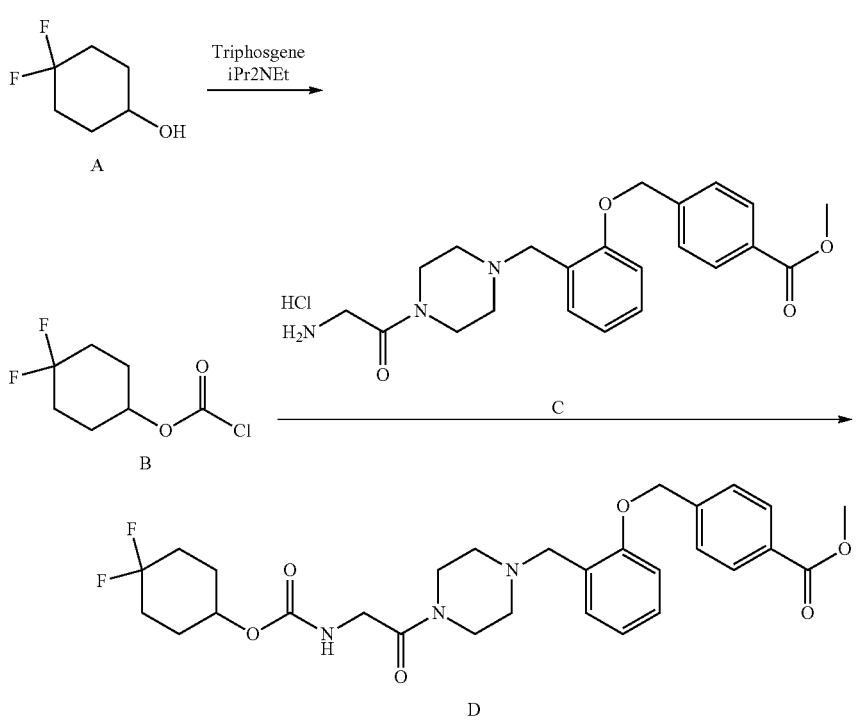

Methyl 4-((2-((4-((2,2-dimethylcyclopropane-1-carbonyl)glycyl)piperazin-1-yl)methyl)phenoxy)methyl)benzoate This compound was prepared according to Method B1 using 2-hydroxybenzaldehyde and 2,2-dimethylcyclopropane-1-carboxylic acid. MS: m/z 494.3 (M+1), calc'd for $C_{28}H_{35}N_3O_5$: 493.26.
1316 HL-01-041-F

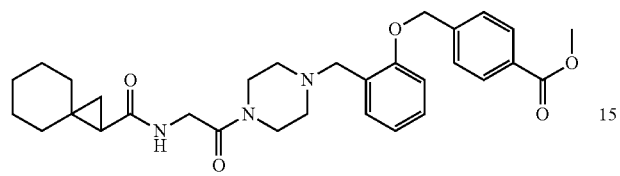

Methyl 4-((2-((4-((spiro[2.5]octane-1-carbonyl)glycyl)piperazin-1-yl)methyl)phenoxy)methyl)benzoate This compound was prepared according to Method B1 using 2-hydroxybenzaldehyde and spiro[2.5]octane-1-carboxylic acid. MS: m/z 534.3 (M+1), calc'd for $C_{31}H_{39}N_3O_5$: 533.29.
1315 HL-01-041-E

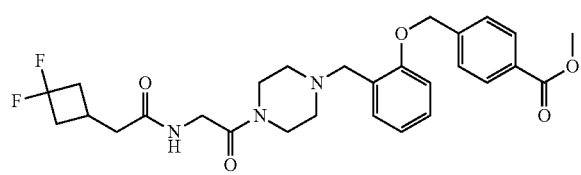 [SMILES: COC(=O)c1ccc(COc2ccccc2CN2CCN(C(=O)CNC(=O)CC3CC(F)(F)C3)CC2)cc1]

Methyl 4-((2-((4-((2-(3,3-difluorocyclobutyl)acetyl)glycyl)piperazin-1-yl)methyl)phenoxy)methyl)benzoate This compound was prepared according to Method B1 using 2-hydroxybenzaldehyde and 2-(3,3-difluorocyclobutyl)acetic acid. MS: m/z 530.3 (M+1), calc'd for $C_{28}H_{33}F_2N_3O_5$: 529.24
1312 HL-01-041-D

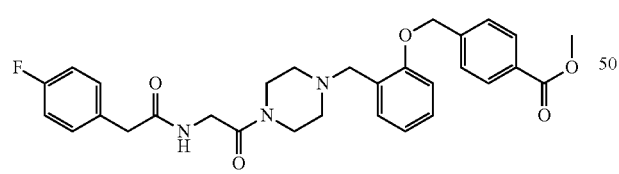

Methyl 4-((2-((4-((2-(4-fluorophenyl)acetyl)glycyl)piperazin-1-yl)methyl)phenoxy)methyl)benzoate This compound was prepared according to Method B1 using 2-hydroxybenzaldehyde and 2-(4-fluorophenyl)acetic acid. MS: m/z 534.3 (M+1), calc'd for $C_{30}H_{32}FN_3O_5$: 533.23.
1311 HL-01-041-B

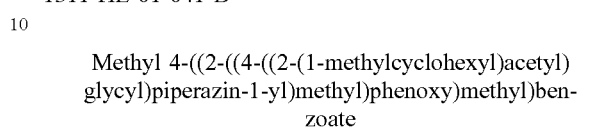

Methyl 4-((2-((4-((2-(1-methylcyclohexyl)acetyl)glycyl)piperazin-1-yl)methyl)phenoxy)methyl)benzoate

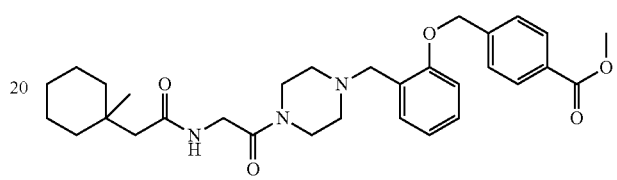

This compound was prepared according to Method B1 using 2-hydroxybenzaldehyde and 2-(1-methylcyclohexyl)acetic acid. MS: m/z 536.3 (M+1), calc'd for $C_{31}H_{41}N_3O_5$: 535.30.
1310 HL-01-044-001

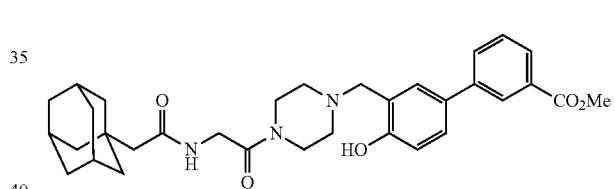

Methyl 3'-((4-((2-((1R,3R,5S)-adamantan-1-yl)acetyl)glycyl)piperazin-1-yl)methyl)-4'-hydroxy-[1,1'-biphenyl]-3-carboxylate This compound was prepared according to Method A2a using 2-((1R,3R,5S)-adamantan-1-yl)acetic acid and 5-chloro-2-hydroxybenzaldehyde with an additional step shown as following. MS: m/z 560.3 (M+1), calc'd for $C_{33}H_{41}N_3O_5$: 559.30.

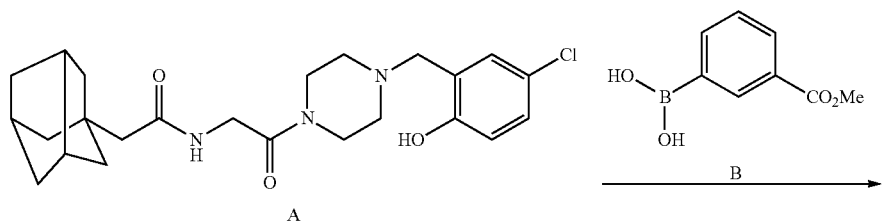

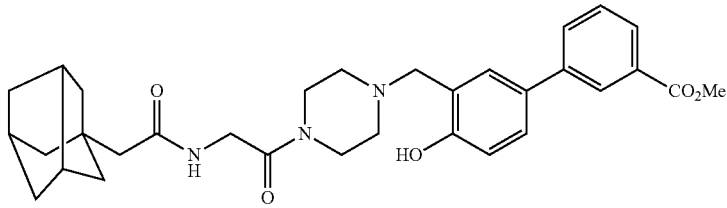

C

An microwave vial under N2, was loaded with A (1.5 eq), B (1 eq), KF (3 eq), Pd(OAc)$_2$ (0.1 eq), and RuPhos (0.2 eq). The system was then evacuated and backfilled twice with N2. 1.5 mL of anhydrous DME added, and the suspension was bubbled with N2, vacuumed, and filled with N2; the process was repeated one more time. The vessel was placed in an oil bath at 65° C. and heated overnight. The dark brown suspension was cooled and filtered. The crude mixture was concentrated, and purified by TLC (4% MeOH/CH$_2$Cl$_2$) to afford the product C.

1309 HL-01-030-I

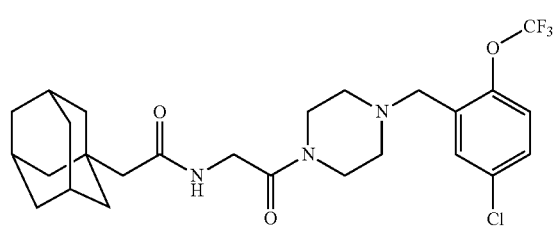 [SMILES: O=C(CC12CC3CC(CC(C3)C1)C2)NCC(=O)N1CCN(Cc2cc(Cl)ccc2OC(F)(F)F)CC1]

2-((1R,3R,5S)-Adamantan-1-yl)-N-(2-(4-(5-chloro-2-(trifluoromethoxy)benzyl)piperazin-1-yl)-2-oxoethyl)acetamide This compound was prepared according to Method C1 using 2-((1R,3R,5S)-adamantan-1-yl)acetic acid and 5-chloro-2-(trifluoromethoxy)benzaldehyde. MS: m/z 528.3 (M+1), calc'd for C$_{26}$H$_{33}$ClF$_3$N$_3$O$_3$: 527.22.

1308 HL-01-030-H

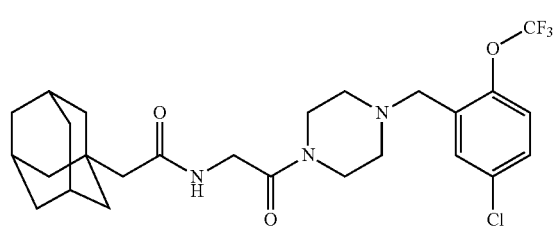 [SMILES: O=C(CC12CC3CC(CC(C3)C1)C2)NCC(=O)N1CCN(Cc2cc(Cl)ccc2OC(F)(F)F)CC1]

2-((1R,3R,5S)-Adamantan-1-yl)-N-(2-(4-(5-chloro-2-(trifluoromethyl)benzyl)piperazin-1-yl)-2-oxoethyl)acetamide This compound was prepared according to Method C1 using 2-((1R,3R,5S)-adamantan-1-yl)acetic acid and 5-chloro-2-(trifluoromethyl)benzaldehyde. MS: m/z 512.3 (M+1), calc'd for C$_{26}$H$_{33}$ClF$_3$N$_3$O$_2$: 511.22.

1307 HL-01-030-F

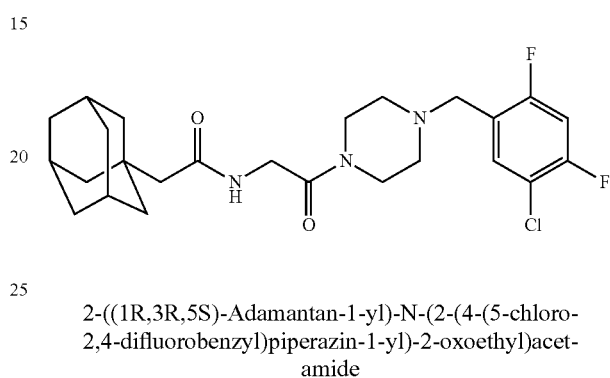

2-((1R,3R,5S)-Adamantan-1-yl)-N-(2-(4-(5-chloro-2,4-difluorobenzyl)piperazin-1-yl)-2-oxoethyl)acetamide This compound was prepared according to Method C1 using 2-((1R,3R,5S)-adamantan-1-yl)acetic acid and 5-chloro-2,4-difluorobenzaldehyde. MS: m/z 480.3 (M+1), calc'd for C$_{25}$H$_{32}$ClF$_2$N$_3$O$_2$: 479.22.

1306 HL-01-030-E

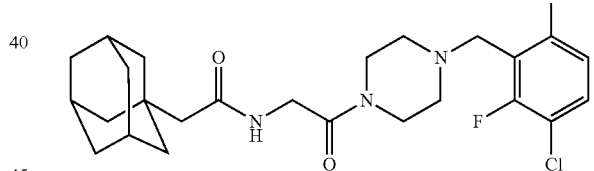

2-((1R,3R,5S)-Adamantan-1-yl)-N-(2-(4-(3-chloro-2,6-difluorobenzyl)piperazin-1-yl)-2-oxoethyl)acetamide This compound was prepared according to Method C1 using 2-((1R,3R,5S)-adamantan-1-yl)acetic acid and 3-chloro-2,6-difluorobenzaldehyde. MS: m/z 480.3 (M+1), calc'd for C$_{25}$H$_{32}$ClF$_2$N$_3$O$_2$: 479.22.

1305 HL-01-030-D

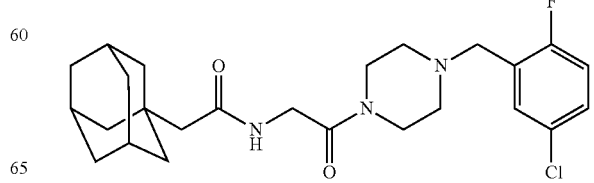

2-((1R,3R,5S)-Adamantan-1-yl)-N-(2-(4-(5-chloro-2-fluorobenzyl)piperazin-1-yl)-2-oxoethyl)acetamide This compound was prepared according to Method C1 using 2-((1R,3R,5S)-adamantan-1-yl)acetic acid and 5-chloro-2-fluorobenzaldehyde. MS: m/z 462.3 (M+1), calc'd for $C_{25}H_{33}ClFN_3O_2$: 461.22.
1304 HL-01-030-C

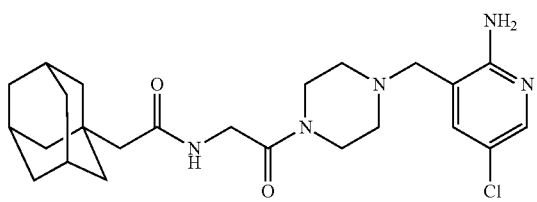 [SMILES: Nc1ncc(Cl)cc1CN1CCN(C(=O)CNC(=O)CC23CC4CC(CC(C4)C2)C3)CC1]

2-((1R,3R,5S)-Adamantan-1-yl)-N-(2-(4-((2-amino-5-chloropyridin-3-yl)methyl)piperazin-1-yl)-2-oxoethyl)acetamide This compound was prepared according to Method C1 using 2-((1R,3R,5S)-adamantan-1-yl)acetic acid and 2-amino-5-chloronicotinaldehyde. MS: m/z 460.3 (M+1), calc'd for $C_{24}H_{34}ClN_5O_2$: 459.24.
1303 HL-01-038-B

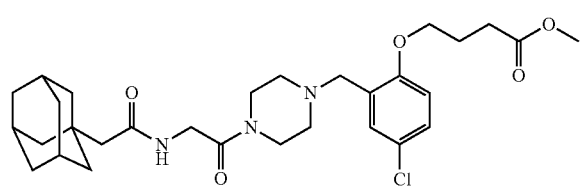 [SMILES: COC(=O)CCCOc1ccc(Cl)cc1CN1CCN(C(=O)CNC(=O)CC23CC4CC(CC(C4)C2)C3)CC1]

Methyl 4-(2-((4-((2-((1R,3R,5S)-Adamantan-1-yl)acetyl)glycyl)piperazin-1-yl)methyl)-4-chlorophenoxy)butanoate This compound was prepared according to Method C1 using 2-((1R,3R,5S)-adamantan-1-yl)acetic acid and methyl 4-(4-chloro-2-formylphenoxy)butanoate. MS: m/z 560.3 (M+1), calc'd for $C_{30}H_{42}ClN_3O_5$: 559.28.
Methyl 4-(4-chloro-2-formylphenoxy)butanoate was prepared by following procedures:

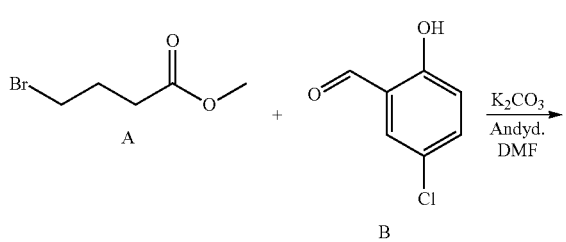

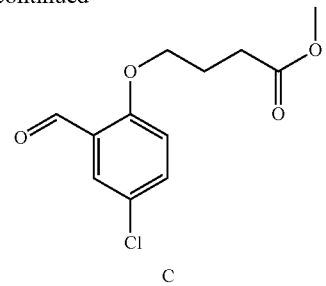

In a sealed vial under $N_2$ was placed the A (103 mg), B (101 mg) in 1.5 mL of anhyd. DMF. Stirred at rt for overnight; diluted with water, extracted with $CH_2Cl_2$, and the organic phase washed with sat $Na_2CO_3$ (2×2 mL). The organic phases were then dried with MgSO4, filtered and concentrated to afford the crude product C.
1302 HL-01-032-D

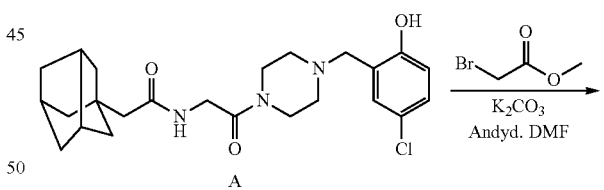

Methyl 2-(2-((4-((2-((1R,3R,5S)-adamantan-1-yl)acetyl)glycyl)piperazin-1-yl)methyl)-4-chlorophenoxy)acetate This compound was prepared from 2-((1R,3R,5S)-Adamantan-1-yl)-N-(2-(4-(5-chloro-2-hydroxybenzyl)piperazin-1-yl)-2-oxoethyl)acetamide by the following procedures. MS: m/z 532.3 (M+1), calc'd for $C_{28}H_{38}ClN_3O_5$: 531.25.

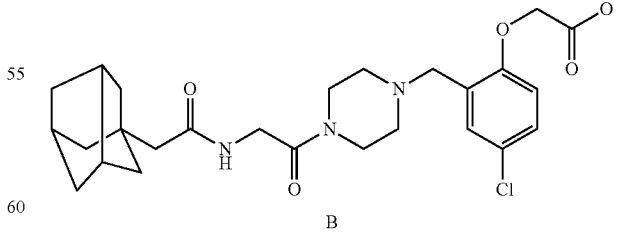

In a sealed vial under $N_2$ was placed the starting materials in 1.5 mL of anhyd. DMF. Stirred at rt for overnight. The reaction was diluted with water, extracted with EtOAc, dried, filtered concentrated and purified by TLC (3% MeOH/$CH_2Cl_2$) to afford B.

1301HL-01-033-001

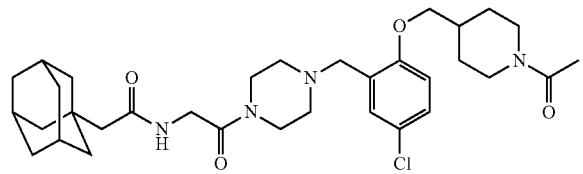 [SMILES: CC(=O)N1CCC(COc2ccc(Cl)cc2CN2CCN(C(=O)CNC(=O)CC34CC5CC(CC(C5)C3)C4)CC2)CC1]

N-(2-(4-(2-((1-acetylpiperidin-4-yl)methoxy)-5-chlorobenzyl)piperazin-1-yl)-2-oxoethyl)-2-((3r,5r,7r)-adamantan-1-yl)acetamide This compound was prepared from 2-((1R,3R,5S)-Adamantan-1-yl)-N-(2-(4-(5-chloro-2-hydroxybenzyl)piperazin-1-yl)-2-oxoethyl)acetamide by the following procedures. MS: m/z 599.4 (M+1), calc'd for $C_{33}H_{47}ClN_4O_4$: 598.33.

In a sealed vial under $N_2$ was placed the A (56 mg, 1 eq), B (60 mg, 1.4 eq), $K_2CO_3$ (3 eq) in 1.5 mL of anhyd. DMF. Stirred at 60° C. for 6 hrs. The reaction was diluted with water, extracted with EtOAc. C was purified by TLC (3% MeOH/$CH_2Cl_2$); The Boc of C was removed under standard conditions mentioned in Method C1, and the HCl/dioxane and EtOAc was removed under vacuum to afford D.

In a vial under nitrogen was placed the D (1 eq) in 1 mL of anhydrous DME. Acetic anhydride (3 eq) added followed by DIEA (8 eq), and the reaction was stirred for overnight. The residue was then concentrated to dryness, E was purified by TLC (6% MeOH/$CH_2Cl_2$).

1300 HL-01-034-C

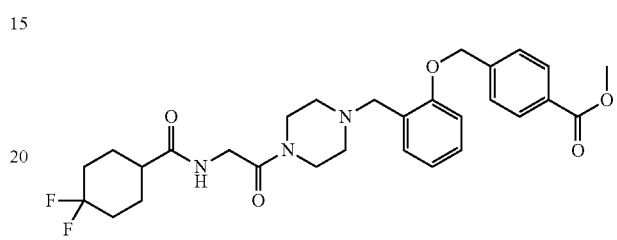

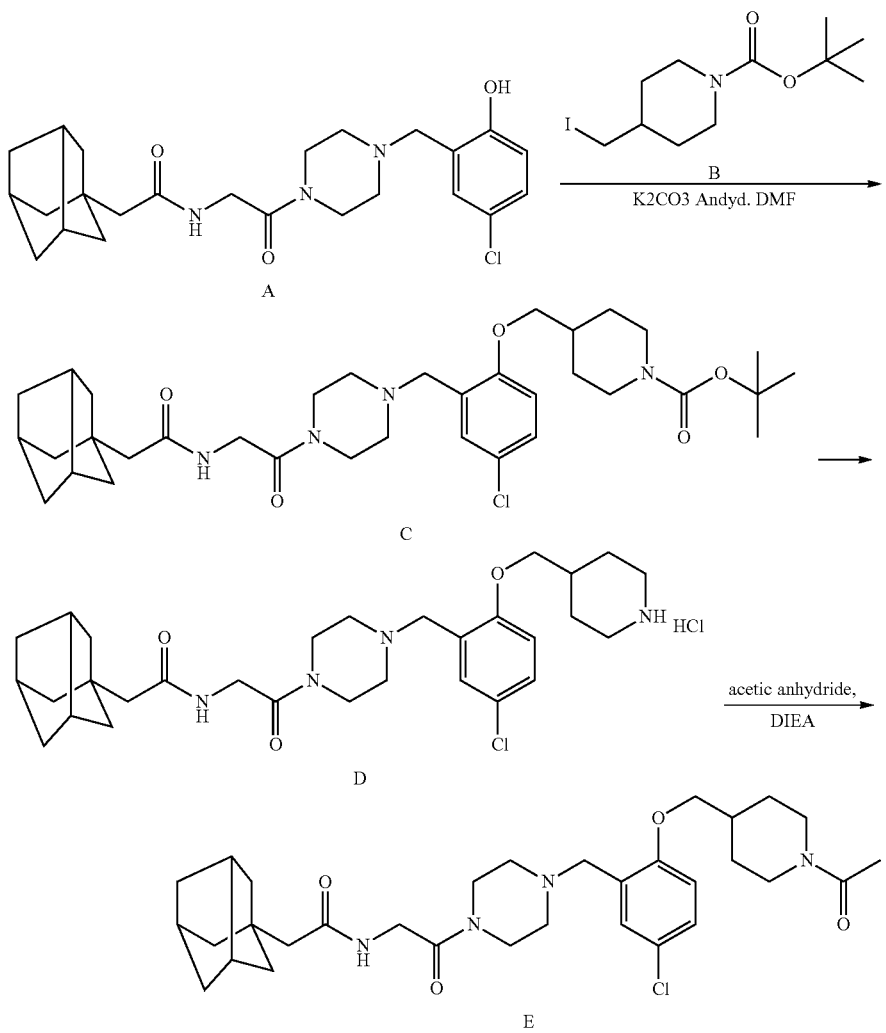

Methyl 4-((2-((4-((4,4-difluorocyclohexane-1-carbonyl)glycyl)piperazin-1-yl)methyl)phenoxy)methyl)benzoate This compound was prepared according to Method B1 using 2-hydroxybenzaldehyde and 4,4-difluorocyclohexane-1-carboxylic acid. MS: m/z 544.3 (M+1), calc'd for $C_{29}H_{35}F_2N_3O_5$: 543.25.
1297 HL-01-035-D

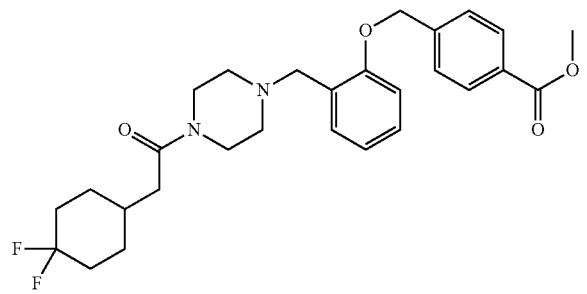 [SMILES: COC(=O)c1ccc(COc2ccccc2CN2CCN(C(=O)CC3CCC(F)(F)CC3)CC2)cc1]

Methyl 4-((2-((4-(2-(4,4-difluorocyclohexyl)acetyl)piperazin-1-yl)methyl)phenoxy)methyl)benzoate This compound was prepared according to Method B2 using 2-(4,4-difluorocyclohexyl)acetic acid. MS: m/z 501.3 (M+1), calc'd for $C_{28}H_{34}F_2N_2O_4$: 500.25.
1296 HL-01-035-C

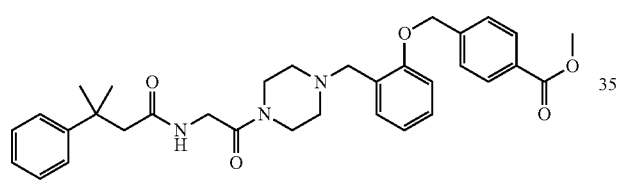

Methyl 4-((2-((4-((3-methyl-3-phenylbutanoyl)glycyl)piperazin-1-yl)methyl)phenoxy)methyl)benzoate This compound was prepared according to Method B1 using 2-hydroxybenzaldehyde and 3-methyl-3-phenylbutanoic acid. MS: m/z 558.3 (M+1), calc'd for $C_{33}H_{39}N_3O_5$: 557.29.
1278 HL-01-019-002

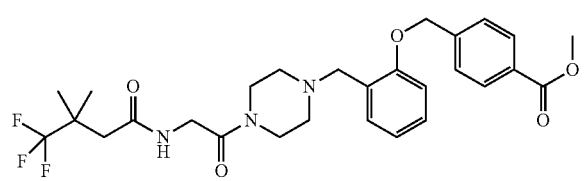 [SMILES: COC(=O)c1ccc(COc2ccccc2CN2CCN(C(=O)CNC(=O)CC(C)(C)C(F)(F)F)CC2)cc1]

Methyl 4-((2-((4-((4,4,4-trifluoro-3,3-dimethylbutanoyl)glycyl)piperazin-1-yl)methyl)phenoxy)methyl)benzoate This compound was prepared according to Method B1 using 2-hydroxybenzaldehyde and 4,4,4-trifluoro-3,3-dimethylbutanoic acid. MS: m/z 550.3 (M+1), calc'd for $C_{28}H_{34}F_3N_3O_5$: 549.25.

1277 HL-01-019-001

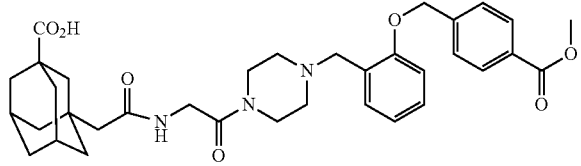 [SMILES: COC(=O)c1ccc(COc2ccccc2CN2CCN(C(=O)CNC(=O)CC34CC5CC(C3)CC(C(=O)O)(C5)C4)CC2)cc1]

(1s,3r,5R,7S)-3-(2-((2-(4-(2-((4-(Methoxycarbonyl)benzyl)oxy)benzyl)piperazin-1-yl)-2-oxoethyl)amino)-2-oxoethyl)adamantane-1-carboxylic acid This compound was prepared according to Method B1 using 2-hydroxybenzaldehyde and (1s,3r,5R,7S)-3-(carboxymethyl)adamantane-1-carboxylic acid. MS: m/z 618.3 (M+1), calc'd for $C_{35}H_{43}N_3O_7$: 617.31.
1275HL-01-017-002

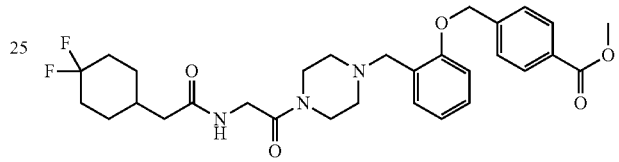

Methyl 4-((2-((4-((2-(4,4-difluorocyclohexyl)acetyl)glycyl)piperazin-1-yl)methyl)phenoxy)methyl)benzoate This compound was prepared according to Method B1 using 2-hydroxybenzaldehyde and 2-(4,4-difluorocyclohexyl)acetic acid. MS: m/z 558.3 (M+1), calc'd for $C_{30}H_{37}F_2N_3O_5$: 557.27.
1249 YT-A-1/HL-01-031-001

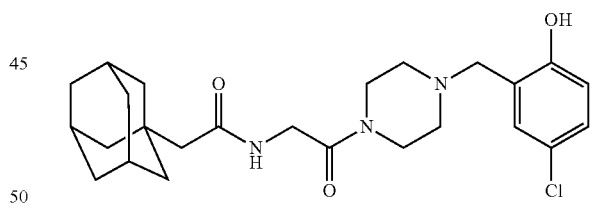

2-((1R,3R,5S)-Adamantan-1-yl)-N-(2-(4-(5-chloro-2-hydroxybenzyl)piperazin-1-yl)-2-oxoethyl)acetamide This compound was prepared according to Method C1 using 2-((1R,3R,5S)-adamantan-1-yl)acetic acid and 5-chloro-2-hydroxybenzaldehyde. MS: m/z 460.3 (M+1), calc'd for $C_{25}H_{34}ClN_3O_3$: 459.23.

6,6-Difluoro-spiro[2.5]octane-1-carboxylic acid (2-{4-[5-chloro-2-(5-cyano-pyridin-2-ylmethoxy)-benzyl]-piperazin-1-yl)-2-oxo-ethyl)-amide (1622)

This compound was prepared according to Method B1. MS m/z: 572.2 (M+1), calc'd: 571.22 (M).

6,6-Difluoro-spiro[2.5]octane-1-carboxylic acid (2-{4-[5-chloro-2-(5-methanesulfonyl-pyridin-2-ylmethoxy)-benzyl]-piperazin-1-yl}-2-oxo-ethyl)-amide (1621)

This compound was prepared according to Method B1. MS m/z: 625.2 (M+1), calc'd: 624.20 (M).

6,6-Difluoro-spiro[2.5]octane-1-carboxylic acid [2-(4-{5-chloro-2-[(5-methanesulfonyl-pyridin-2-ylmethyl)-amino]-phenyl}-di-deutero-methyl}-piperazin-1-yl)-2-oxo-ethyl]-amide (1586)

This compound was prepared from 1466 and the corresponding aldehyde using the reductive amination conditions described in Method A1. MS m/z: 626.2 (M+1), calc'd: 625.23 (M).

6,6-Difluoro-spiro[2.5]octane-1-carboxylic acid [2-(4-{5-chloro-2-[(5-cyano-pyridin-2-ylmethyl)-amino]-phenyl}-di-deutero-methyl}-piperazin-1-yl)-2-oxo-ethyl]-amide (1584)

This compound was prepared from 1466 and the corresponding aldehyde using the reductive amination conditions described in Method A1. MS m/z: 573.2 (M+1), calc'd: 572.24 (M).

6,6-Difluoro-spiro[2.5]octane-1-carboxylic acid [2-(4-{5-chloro-2-[(5-fluoro-pyridin-2-ylmethyl)-amino]-phenyl}-di-deutero-methyl}-piperazin-1-yl)-2-oxo-ethyl]-amide (1582)

This compound was prepared from 1466 and the corresponding aldehyde using the reductive amination conditions described in Method A1. MS m/z: 566.2 (M+1), calc'd: 565.24 (M).

5-{[4-Chloro-2-(4-{2-[(6,6-difluoro-spiro[2.5]octane-1-carbonyl)-amino]-acetyl}-piperazin-1-yl-di-deutero-methyl)-phenylamino]-methyl}-pyridine-2-carboxylic acid methyl ester (1549)

This compound was prepared from 1413 and the corresponding aldehyde using the reductive amination conditions described in Method A1. MS m/z: 606.2 (M+1), calc'd: 605.25 (M).

6-{[4-Chloro-2-(4-{2-[(6,6-difluoro-spiro[2.5]octane-1-carbonyl)-amino]-acetyl}-piperazin-1-yl-di-deutero-methyl)-phenylamino]-methyl}-nicotinic acid methyl ester (1548)

This compound was prepared from 1413 and the corresponding aldehyde using the reductive amination conditions described in Method A1. MS m/z: 606.2 (M+1), calc'd: 605.25 (M).

6,6-Difluoro-spiro[2.5]octane-1-carboxylic acid [2-(4-{5-chloro-2-[(pyrimidin-2-ylmethyl)-amino]-phenyl}-di-deutero-methyl}-piperazin-1-yl)-2-oxo-ethyl]-amide (1580)

This compound was prepared from 1466 and the corresponding aldehyde using the reductive amination conditions described in Method A1. MS m/z: 549.2 (M+1), calc'd: 548.24 (M).

6,6-Difluoro-spiro[2.5]octane-1-carboxylic acid [2-(4-{5-chloro-2-[(oxazol-5-ylmethyl)-amino]-phenyl}-di-deutero-methyl}-piperazin-1-yl)-2-oxo-ethyl]-amide (1587)

This compound was prepared from 1466 and the corresponding aldehyde using the reductive amination conditions described in Method A1. MS m/z: 538.2 (M+1), calc'd: 537.23 (M).

6,6-Difluoro-spiro[2.5]octane-1-carboxylic acid [2-(4-{5-chloro-2-[(oxazol-2-ylmethyl)-amino]-phenyl}-di-deutero-methyl}-piperazin-1-yl)-2-oxo-ethyl]-amide (1585)

This compound was prepared from 1466 and the corresponding aldehyde using the reductive amination conditions described in Method A1. MS m/z: 538.2 (M+1), calc'd: 537.23 (M).

6,6-Difluoro-spiro[2.5]octane-1-carboxylic acid [2-(4-{5-chloro-2-[(oxazol-4-ylmethyl)-amino]-phenyl}-di-deutero-methyl}-piperazin-1-yl)-2-oxo-ethyl]-amide (1583)

This compound was prepared from 1466 and the corresponding aldehyde using the reductive amination conditions described in Method A1. MS m/z: 538.2 (M+1), calc'd: 537.23 (M).

6,6-Difluoro-spiro[2.5]octane-1-carboxylic acid [2-(4-{5-chloro-2-[(isoxazol-3-ylmethyl)-amino]-phenyl}-di-deutero-methyl}-piperazin-1-yl)-2-oxo-ethyl]-amide (1581)

This compound was prepared from 1466 and the corresponding aldehyde using the reductive amination conditions described in Method A1. MS m/z: 538.2 (M+1), calc'd: 537.23 (M).

6,6-Difluoro-spiro[2.5]octane-1-carboxylic acid [2-(4-{5-chloro-2-[(oxazol-5-ylmethyl)-amino]-phenyl}-di-deutero-methyl}-piperazin-1-yl)-2-oxo-ethyl]-amide (1560)

This compound was prepared from 1413 and the corresponding aldehyde using the reductive amination conditions described in Method A1. MS m/z: 538.2 (M+1), calc'd: 537.23 (M).

6,6-Difluoro-spiro[2.5]octane-1-carboxylic acid (2-{4-[5-chloro-2-(2-fluoro-4-methanesulfonyl-benzylamino)-phenyl}-di-deutero-methyl]-piperazin-1-yl}-2-oxo-ethyl)-amide (1562)

This compound was prepared from 1466 and the corresponding aldehyde using the reductive amination conditions described in Method A1. MS m/z: 643.2 (M+1), calc'd: 642.22 (M).

6,6-Difluoro-spiro[2.5]octane-1-carboxylic acid (2-{4-[5-chloro-2-(3-fluoro-4-methanesulfonyl-benzylamino)-phenyl}-di-deutero-methyl]-piperazin-1-yl}-2-oxo-ethyl)-amide (1561)

This compound was prepared from 1466 and the corresponding aldehyde using the reductive amination conditions described in Method A1. MS m/z: 643.2 (M+1), calc'd: 642.22 (M).

Spiro[2.5]octane-1-carboxylic acid (2-{4-[5-chloro-2-(4-methanesulfonyl-benzyloxy)-benzyl]-piperazin-1-yl}-2-oxo-ethyl)-amide (1539)

This compound was prepared according to Method B1. MS m/z: 588.2 (M+1), calc'd: 587.22 (M).

6,6-Difluoro-spiro[2.5]octane-1-carboxylic acid {2-[4-(5-chloro-2-ethylamino-phenyl]-di-deutero-methyl)-piperazin-1-yl]-2-oxo-ethyl}-amide (1534)

This compound was prepared similarly as 1391. MS m/z: 485.2 (M+1), calc'd: 484.24 (M).

2-((3r,5r,7r)-Adamantan-1-yl)-N-(2-(4-(2-((4-(oxazol-2-yl)benzyl)oxy)benzyl)piperazin-1-yl)-2-oxoethyl)acetamide (1803)

Yield: 42.1%. $^1$H NMR (400 MHz, Chloroform-d, ppm) δ: 8.08 (s, 1H), 7.79-7.21 (m, 7H), 7.00-6.92 (m, 2H), 6.50 (d, J=3.8 Hz, 1H), 5.17 (s, 2H), 4.02 (d, J=4.0 Hz, 2H), 3.62 (s, 4H), 3.40 (t, J=4.9 Hz, 2H), 2.47-2.42 (m, 4H), 2.01 (s, 2H), 1.97 (s, 3H), 1.74-1.60 (m, 12H). MS: m/z 583.30 [M+H]$^+$, calc'd for $C_{35}H_{43}N_4O_4$: 583.33.

(1s,3r,5R,7S)—N-(2-(4-(2-((4-bromobenzyl)oxy)benzyl)piperazin-1-yl)-2-oxoethyl)-3-(4-hydroxy-3-nitrophenyl)adamantane-1-carboxamide (1805)

Yield: 42.3%. $^1$H NMR (400 MHz, Chloroform-d, ppm) δ: 10.47 (s, 1H), 8.03 (t, J=2.2 Hz, 1H), 7.63 (dt, 11=8.8 Hz, J2=2.1 Hz, 1H), 7.51 (d, J=6.8 Hz, 2H), 7.37-7.22 (m, 4H), 7.12-7.09 (d, J=8.8 Hz, 11H), 6.97 (t, J=7.2 Hz, 1H), 6.91 (d, J=8.0 Hz, 11H), 6.84 (s, 1H), 5.03 (s, 2H), 4.02 (dd, J=4.1, 1.6 Hz, 2H), 3.64 (d, J=5.6 Hz, 4H), 3.41 (s, 2H), 2.49 (d, J=5.2 Hz, 4H), 2.30 (s, 2H), 1.99-1.87 (m, 9H), 1.27 (s, 2H). MS m/z: 717.30 [M+H]$^+$, calc'd for $C_{37}H_{42}BrN_4O_6$: 717.23.

N-(2-(4-(2-Amino-5-chlorobenzyl)piperazin-1-yl)-2-oxoethyl)spiro[2.4]heptane-1-carboxamide (1806)

Yield: 10.4%. $^1$H NMR (400 MHz, Chloroform-d, ppm) δ: 7.06 (dd, J=8.4, 2.5 Hz, 1H), 6.95 (d, J=2.5 Hz, 1H), 6.61 (s, 1H), 6.58 (d, J=8.5 Hz, 1H), 4.60 (br, 2H), 4.07 (d, J=4.1 Hz, 2H), 3.63 (t, J=5.1 Hz, 2H), 3.48 (s, 2H), 3.39 (t, J=5.1 Hz, 2H), 2.43 (t, J=5.1 Hz, 4H), 1.65-1.51 (m, 8H), 1.35 (t, J=7.3 Hz, 1H), 1.24-1.21 (m, 1H), 0.93 (dd, J1=8.2 Hz, J2=4.2 Hz, 1H). MS m/z: 405.20 [M+H]$^+$, calc'd for $C_{21}H_{30}ClN_4O_2$: 405.21.

N-(2-(4-(2-Amino-5-chlorobenzyl)piperazin-1-yl)-2-oxoethyl)spiro[2.3]hexane-1-carboxamide (1807)

Yield: 11.9%. $^1$H NMR (400 MHz, Chloroform-d, ppm) δ: 7.06 (dd, J1=8.5 Hz, J2=2.5 Hz, 11H), 6.96 (d, J=2.5 Hz, 1H), 6.58 (d, J=8.4 Hz, 11H), 4.62 (br, 2H), 4.10-4.05 (m, 2H), 3.64 (t, J=5.1 Hz, 2H), 3.48 (s, 2H), 3.39 (t, J=5.1 Hz, 2H), 2.43 (t, J=5.1 Hz, 4H), 2.23-1.98 (m, 4H), 1.45 (dd, J=8.4, 5.3 Hz, 1H), 1.38 (t, J=7.3 Hz, 1H), 1.23-1.09 (m, 1H), 0.97-0.84 (m, 2H). MS m/z: 391.20 [M+H]$^+$, calc'd for $C_{20}H_{28}ClN_4O_2$: 391.19.

N-(2-(4-(2-Amino-5-chlorobenzoyl)piperazin-1-yl)-2-oxoethyl)-6,6-difluorospiro[2.5]octane-1-carboxamide (1808)

Yield: 38.4%. $^1$H NMR (400 MHz, Chloroform-d, ppm) δ: 7.15 (dd, J=8.6, 2.4 Hz, 11H), 7.04 (d, J=2.4 Hz, 11H), 6.67 (d, J=8.6 Hz, 2H), 4.32 (s, 2H), 4.10 (dd, J=7.4, 3.5 Hz, 2H), 3.75-3.58 (m, 6H), 3.50-3.42 (m, 2H), 2.02-1.80 (m, 6H), 1.57-1.43 (m, 3H), 1.21 (t, J=4.9 Hz, 11H), 0.86 (dd, J=8.0, 4.5 Hz, 1H). MS m/z: 469.20 [M+H]$^+$, calc'd for $C_{22}H_{28}ClF_2N_4O_3$: 469.18.

Example 2: Biological Assays

The following assay methods were used to identify and evaluate compounds of Formula (I) and Formula (II).

Solubility.

Kinetic solubility was tested from a 10 mM DMSO stock solution by spiking into pre-warmed pH 7.4 phosphate buffered saline in a 96-well plate. The final concentration was 100 μM (1% DMSO). The plate was maintained at ambient temperature for 24 hours on an orbital shaker. Samples were centrifuged through a Millipore Multiscreen Solvinter 0.45 micron low binding PTFE hydrophilic filter plate and were analyzed by HPLC or LC-MS/MS if additional sensitivity was required. Peak area was compared to standards of known concentration.

Plasma Protein Binding.

Plasma protein binding was determined using equilibrium dialysis using ThermoScientific™ RED Device. The plate was incubated with shaking at 37° C. for 6 hours. The concentration of drug in the plasma vs buffer compartments were determined by LC-MS/MS. The fraction bound was calculated as ([plasma]−[buffer])/[plasma].

Plasma Stability.

Plasma stability was evaluated by incubating 10 μM test compound with undiluted plasma at 37° C. with aliquots removed at multiple time points out to four hours. Aliquots were added to acetonitrile (5×, v:v) to stop any enzymatic activity and held on ice. Samples were centrifuged through a Millipore Multiscreen Solvinter 0.45 micron low binding PTFE hydrophilic filter plate and analyzed by LC-MS/MS.

Hepatic Microsomal Stability.

Microsome stability was evaluated by incubating 1 μM test compound with 1 mg/mL hepatic microsomes in 100 mM KPi, at pH 7.4. The reaction was initiated by adding NADPH (1 mM final concentration). Aliquots were removed at 0, 5, 10, 20, 40, and 60 minutes and added to acetonitrile (5×, v:v) to stop the reaction and precipitate the protein. NADPH dependence of the reaction was evaluated by setting up incubations without NADPH. At the end of the assay, the samples were centrifuged through a Millipore Multiscreen Solvinter 0.45 micron low binding PTFE hydrophilic filter plate and analyzed by LC-MS/MS. Data were log transformed and represented as half-life.

Pharmacokinetics.

Pharmacokinetics of the compounds were assessed in C57Bl/6 or BALB/c mice. Blood was collected at representative time points e.g. 0.08, 0.25, 0.5, 1, 2, 4, 8, 12 and 24 hours and pharmacokinetic parameters were calculated using Phoenix WinNonlin® to determine peak plasma concentration (Cmax), oral bioavailability (% F), exposure (AUC), half-life (t1/2), clearance (CL), and volume of distribution (Vd). Compounds were dosed intravenously via the tail vein or by oral gavage. In some cases, co-formulation with Ritonavir was used as a boosting strategy. All procedures are approved by the Scripps Florida IACUC and Scripps vivarium is fully AAALAC accredited.

Cell Lines

Vero, 293T, HeLa (ATCC) and human fibroblasts (Coriell) were maintained in DMEM (Invitrogen) supplemented with 5% FetalPlex, 5% FBS (Gemini) or 10% FBS (HeLa, human fibroblasts). All CHO derived cell lines were grown as previously described. Millard, E. E. et al. *J. Biol. Chem.* 280, 28581-28590 (2005); Millard, E. E. et al., *J. Biol. Chem.* 275, 38445-38451 (2000).

Production and Purification of Pseudotyped Virions

VSV-ΔG pseudotyped viruses were created as described previously. Chandran, K. et al., *Science* 308, 1643-1645 (2005). LacZ-encoding retroviral pseudotypes bearing the designated envelope glycoproteins were prepared as previously described. Soneoka, Y. et al. *Nucleic Acids Res.* 23, 628-633 (1995).

Infection Assays with Pseudotyped Virus

VSV pseudotyped viruses expressing GFP were added to cells in serial tenfold dilutions and assayed using fluorescence microscopy. An infectious unit (i.u.) is defined as one GFP-expressing cell within a range where the change in GFP-positive cells is directly proportional to the virus dilution. For VSV expressing the luciferase reporter, pseudotyped virus was added to cells and luciferase activity was assayed 6-20 h post-infection using the firefly luciferase kit (Promega). Signal was measured in relative luminescence units (RLU) using an EnVison plate reader (Perkin Elmer). In experiments involving inhibitors, stock solutions of the compounds of the invention in DMSO were diluted to a final concentration of 1% DMSO in media. Inhibitory activity was stable in the media of cultured cells for more than 72 h as assessed using a single cycle entry assay.

Ebola Virus Infections under BSL-4 Conditions

Vero cells or CHO cells were seeded to 96-well plates and exposed to EboV-GFP. Vero cells were incubated with the compounds of the invention, ??E-64-d (150 μM) or 1% DMSO 90 min before the addition of virus (m.o.i.=0.1). Virus was added to CHO cells at m.o.i. of 1 as measured on Vero cells. Virus-encoded GFP fluorescence was determined using a SpectraMax M5 plate reader (Molecular Devices) at excitation 485 nm, emission 515 nm, cutoff 495 nm at 22.5, 42, 71 and 97 h post-infection. An additional inhibitor experiment was performed using the compounds of the invention. Vero cells were treated with the compounds of the invention (20 μM) or 1% DMSO alone for 4 h, and then infected with EBOV Zaire-1995 (m.o.i.=0.1). After 1 h, the virus inoculum was removed, cells were washed, and fresh media containing the compounds of the invention or DMSO was added. Cell supernatant was collected at 0, 24, 48, 72, or 91 h post-infection. RNA was isolated from the supernatant using Virus RNA Extraction kits (Qiagen) and EboV NP RNA was measured using a real-time RT-PCR assay. Virus titre was calculated using

TABLE 3

Data for Compound 1466

| | |
|---|---|
| EBOV G-A82 (Hela) $EC_{50}$: | 0.37 μM |
| EBOV Kikwit(Hela) $EC_{50}$: | 2.49 μM |
| EBOV Makona (Hela) $EC_{50}$: | 2.19 μM |
| EBOV Maiynga) (Hela) $EC_{50}$: | 4.28 μM |
| Molecular Weight: | 457 |
| cLogP: | 287 |
| m-μsome $T_{1/2}$: | 3 min |
| m-μsome $T_{1/2}$ (with 3 μM of Ritonavir) | 91 min |
| m-plasma stability | stable |
| m-plasma protein binding: | 88% |
| m-PK P.O. dose: | 50 mpk of 1466 and 50 mpk of Ritonavir |
| AUC: | 121 μM*hr |
| $C_{max}$ | 19.5 μM |
| $C_{@12\ hr}$ | 2 μM |
| $T_{1/2}$: | 3.2 h |

TABLE 4

Data for Compound 1476

| | |
|---|---|
| EBOV G-A82 (Hela) $EC_{50}$: | <0.08 μM |
| EBOV Kikwit(Hela) $EC_{50}$: | 0.21 μM |
| EBOV Makona (Hela) $EC_{50}$: | 0.14 μM |
| EBOV Maiynga) (Hela) $EC_{50}$: | 0.42 μM |
| Molecular Weight: | 623 |
| cLogP: | 3.82 |
| m-μsome $T_{1/2}$ (with 3 μM of Ritonavir) | 170 min |
| m-plasma stability | stable |
| m-plasma protein binding: | 98.7% |
| m-PK P.O. dose: | 75 mpk of 1476 and 50 mpk of Ritonavir |
| AUC: | 314 μM*hr |
| $C_{max}$ | 23 μM |
| $C_{@12\ hr}$ | 14 μM |
| $T_{1/2}$: | 6.1 h |

TABLE 5

Data for Compound 1477

| | |
|---|---|
| EBOV Kikwit(Hela) $EC_{50}$: | 0.012 μM |
| EBOV Makona (Hela) $EC_{50}$: | 0.052 μM |
| EBOV Maiynga) (Hela) $EC_{50}$: | 0.033 μM |
| Molecular Weight: | 610 |
| cLogP: | 3.55 |
| m-μsome $T_{1/2}$ (with 3 μM of Ritonavir) | 90 min |
| m-plasma stability | stable |
| m-plasma protein binding: | 99.9% |

TABLE 6

Data for Compound 1478

| | |
|---|---|
| EBOV Kikwit(Hela) $EC_{50}$: | 0.009 μM |
| EBOV Makona (Hela) $EC_{50}$: | 0.017 μM |
| EBOV Maiynga) (Hela) $EC_{50}$: | 0.035 μM |
| Molecular Weight: | 622 |
| cLogP: | 3.24 |
| m-μsome$T_{1/2}$ (with 3 μM of Ritonavir) | 128 min |
| m-plasma stability | stable |
| m-plasma protein binding: | 99.9% |

Pharmacokinetic Properties of Certain Compounds of the Invention

Figure 8:
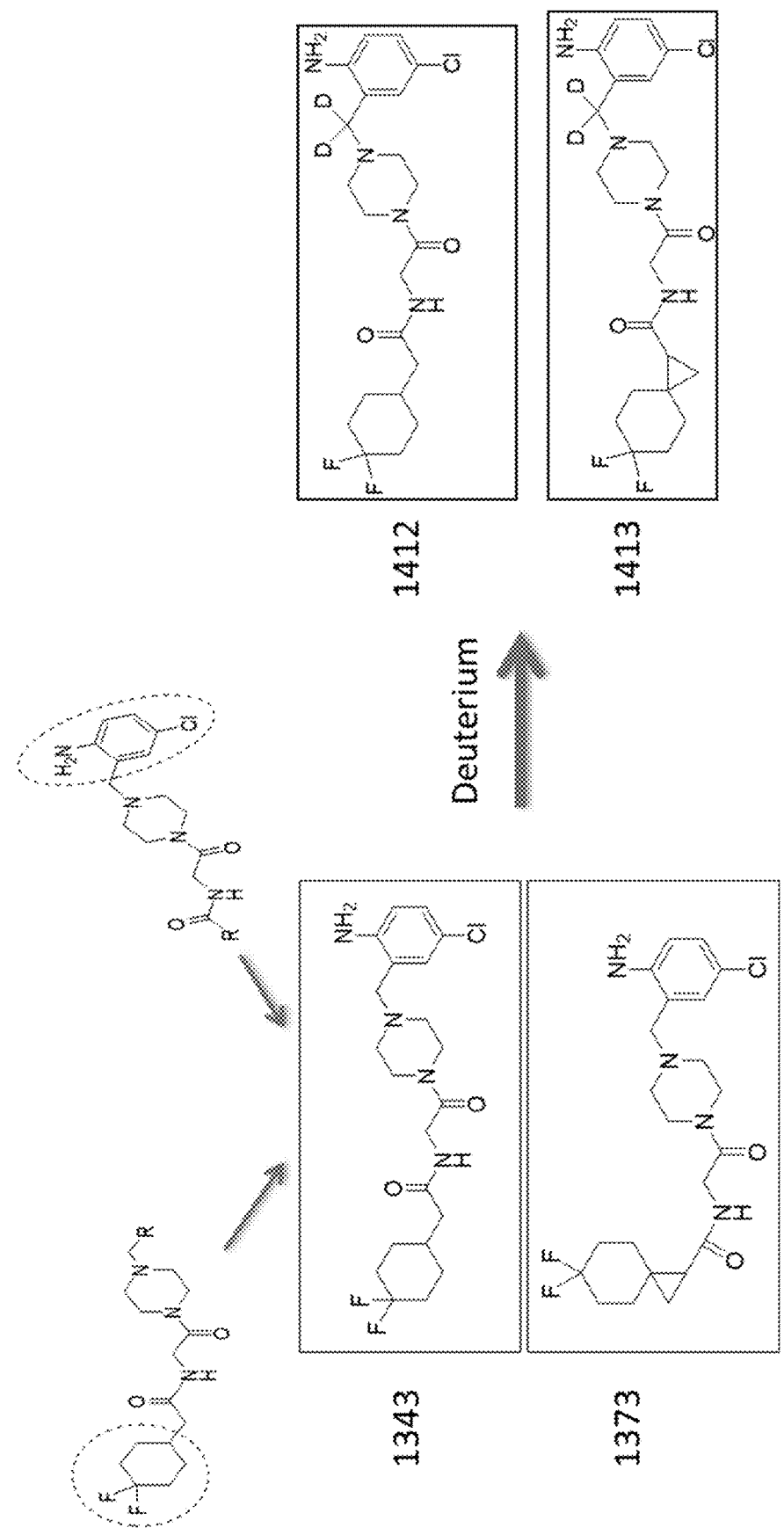
FIG. 8 depicts a scheme showing the effects of structural changes on the pharmacokinetic properties of compounds disclosed herein.

The effect of structure changes on the pharmacokinetic properties of certain compounds is highlighted in FIG. 8 and Table 7.

TABLE 7

Effect changes on PK properties.

| Cpd: | $IC_{50}$(mM) | MW | clogP | Sol(mM) | $T_{1/2}$(min) |
|---|---|---|---|---|---|
| 1343 | 0.25 | 442.9 | 2.94 | >100 | 8.7 |
| 1373 | 0.12 | 454.9 | 3.15 | | 1.3 |
| 1412 | 0.13 | 444.9 | 2.94 | >100 | 13 |
| 1413 | 0.068 | 456.9 | 3.15 | | 2.0 |

Figure 9:
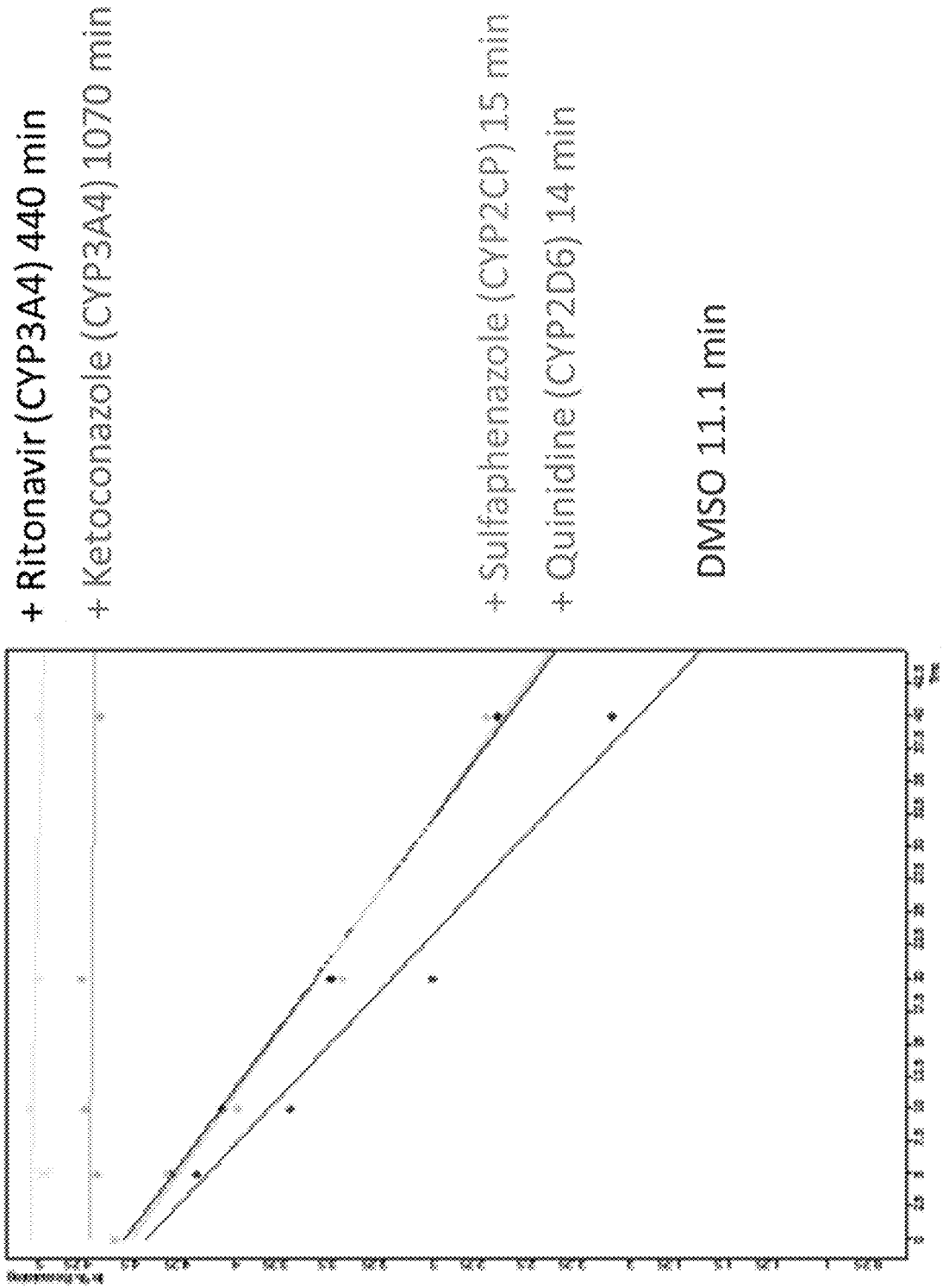
FIG. 9 depicts a plot showing CYP3A4 inhibition improves the $T_{1/2}$ of compound 1412.

Additionally, FIG. 9 illustrates that CYP3A4 inhibition (e.g., Ritonavir, Ketoconazole, Sulphaenazole, Quidine) improves the half-life of compound 1412.

TABLE 8

| | | Improved T½ with ritonavir | |
| Compound | IC50 (nM) | $T_{1/2}$ −/+− ritonavir (min) | PPB % |
| --- | --- | --- | --- |
| 1412 | 68 | 1.4/144 | 94 |
| 1413 | 130 | 13/215 | 86 |

Additional pharmacokinetic properties of certain compounds disclosed herein are highlighted in Tables 9 and 10.

TABLE 9

PK properties of compound 1412

$IC_{50}$: 130 nM
MW: 444.95 daltons
CLogP: 2.94
Kinetic solubility: >100 μM
Plasma protein binding: 86%
Plasma stability: Stable
Microsome $T_{1/2}$: 8.7-13 min - with ritonavir: 215 min

TABLE 10

PK properties of compound 1413

$IC_{50}$: 68 nM
MW: 456.96 daltons
CLogP: 3.15
Kinetic solubility: >100 μM
Plasma protein binding: 94%
Plasma stability: Stable
Microsome $T_{1/2}$: 1.4-2.0 min - with ritonavir: 144 min

Example 3: Comparison of In Vitro ADME Properties

The impact of replacement of the adamantane and other changes that decreased hydrophobicity on the in vitro ADME (absorption, distribution, metabolism, and excretion) properties of 1343 (c log P=2.94), 1412 (c log P=2.94), the (−)-enantiomer of 1413 (also referred to herein as compound 14199) (c log P=2.87), 1458 (c log P=4.10), the (−)-enatantiomer of 1476 (c log P=3.82) and the (−)-enatantiomer of 1503 (c log P=3.24) was examined (Table 11). Although inhibitors (−)-1476 and (−)-1503 are very potent, they are less soluble and bind more extensively to mouse plasma proteins (plasma protein binding, PPB=97.6% and 99.8%, respectively) than smaller compounds such as 1343, and (−)-1413 (PPB=86.9% and 87.9%, respectively). The stability of each compound in plasma is determined by factors such as the molecular weight and steric hindrance around the amide bond. Lower molecular weight compounds, such as 1343, 1412 and (−)-1413, are stable in mouse plasma (>86% remained after four hours) regardless of the left hand acetamide structures. However, the larger compound 1458, which has the less sterically hindered di-fluorocyclohexane acetamide, was unstable in mouse plasma (30% remained after four hours). By comparison, compound (−)-1476, in which the α-carbon of the acetamide is blocked by the methylene of the cyclopropane ring, is more stable (69% remained after four hours).

The stability of these compounds in mouse liver microsomes (MLM) remained suboptimal and in particular, deuteride blocking at the benzylic position of 1343 ($T_{1/2}$=9 min) had minimal impact on the microsomal stability (1412, $T_{1/2}$=11 min). To better understand the oxidative metabolic pathways in mice, we carried out additional studies of mouse liver microsomes that revealed 3A4 as the major P450 cytochrome isoform responsible for metabolism of these compounds (data not shown). Consistent with this finding, the presence of the CYP3A4 inhibitor ritonavir (3 μM), which is approved for clinical use as a booster of anti-HIV drugs,[22] increased the stabilities of 1412 ($T_{1/2}$>120 min) and (−)-1413 ($T_{1/2}$=91 min) in mouse liver microsomes by 10- to 30-fold. The salutary effect of ritonavir was also conferred on derivatives such as (−)-1476 and (−)-1503 that contain the benzyl moiety. Ritonavir does not inhibit VSV EBOV infection ($IC_{50}$>25 μM), and thus is not expected to confound the evaluation of lead NPC1 inhibitors as anti-EBOV agents. As with 3.47, (racemic)-1476, 1477 and (racemic)-1503, the concentration of each of these inhibitors required to reduce cell viability by 50% exceeded 10 μM.

TABLE 11

In vitro ADME properties of selected compounds.

| No. | Kinetic solubility (μM) | Mouse PPB (% bound) | Mouse plasma stability (% at 4 hours) | MLM T½ (min) | MLM, T½ (min) (ritonavir 3 μM) | HLM T½ (min) |
|---|---|---|---|---|---|---|
| 1803 | 5 | 99.7 | 37 | 1 | — | — |
| 1254 | — | — | — | 1 | — | — |
| 1343 | >100 | 86.9 | 94 | 9 | — | 27 |
| 1412 | 93 | — | 86 | 11 | >120 | 32 |
| (−)-1413 | 78 | 87.9 | 88 | 3 | 91 | 16 |
| 1458 | — | — | 30 | — | >120 | — |
| (−)-1476 | 10 | 97.6 | 69 | — | >120 | — |
| (−)-1503 | 4 | 99.8 | 72 | 2 | 87 | 1 |

Example 4—Pharmacokinetic Profile of Exemplary Compounds

At this stage, whether the in vitro optimization of 3.47 along with the protective effect of ritonavir would translate into an acceptable pharmacokinetic profile in vivo was investigated. Oral pharmacokinetic properties for selected compounds were obtained in mice (Table 12).

TABLE 12

Oral pharmacokinetic parameters for selected compounds in mice.

| No. | Dose | $T_{max}$ (hr) | $C_{max}$ (μM) | C@12 hr (μM) | $AUC_{last}$ (μM · hr) | $T_{1/2}$ (hr) | Cl_obs (mL/min/Kg) |
|---|---|---|---|---|---|---|---|
| 1412 | 25 mg/kg | 0.6 | 7.2 | 0.2 | 19.9 | 2.3 | 49.0 |
| 1412/ ritonavir | 25 mg/kg/ 20 mg/kg | 1.3 | 12.0 | 1.7 | 76.8 | 2.3 | 12.3 |
| (−)-1413/ ritonavir | 50 mg/kg/ 50 mg/kg | 1.7 | 19.5 | 2.0 | 120.9 | 3.2 | 15.5 |

TABLE 12-continued

Oral pharmacokinetic parameters for selected compounds in mice.

| No. | Dose | $T_{max}$ (hr) | $C_{max}$ (μM) | C@12 hr (μM) | $AUC_{last}$ (μM · hr) | $T_{1/2}$ (hr) | Cl_obs (mL/min/Kg) |
|---|---|---|---|---|---|---|---|
| (−)-1476/ ritonavir | 50 mg/kg/ 50 mg/kg | 4.0 | 10.4 | 4.7 | 116.4 | 2.2 | 11.9 |
| (−)-1503/ ritonavir | 50 mg/kg/ 50 mg/kg | 7.3 | 7.4 | 5.7 | 107.5 | 1.7 | 12.5 |

After administration to mice by gavage, the inhibitor 1412 was rapidly absorbed and reached a $C_{max}$ of 7.2 μM but was nearly completely cleared in 12 hours. Co-administration of ritonavir (20 mpk) increased the AUC and decreased the clearance of 1412 by nearly 4-fold. As a result, the plasma concentration of 1412 after 12 hours increased to 1.7 μM. The pharmacokinetics of a single 50 mpk dose of (−)-1413, (−)-1476 and (−)-1503 co-administered with ritonavir (50 mpk) was also studied. The plasma concentrations of (−)-1476 (4.7 μM) and (−)-1503 (5.7 μM) after 12 hours were 50-fold greater than the in vitro $IC_{50}$s of these compounds measured against rVSV EBOV infection in 50% human serum. When the concentration of ritonavir decreased after 12 hours, the plasma concentration of the inhibitors declined more rapidly. These findings suggest that an oral b.i.d dosing regimen that delivers an effective concentration of EBOV inhibitors (−)-1476 and (−)-1503 can be achieved in mice.

INCORPORATION BY REFERENCE

All publications and patents mentioned herein are hereby incorporated by reference in their entirety as if each individual publication or patent was specifically and individually indicated to be incorporated by reference. In case of conflict, the present application, including any definitions herein, will control.

EQUIVALENTS

While specific embodiments of the subject invention have been discussed, the above specification is illustrative and not restrictive. Many variations of the invention will become apparent to those skilled in the art upon review of this specification. The appended claims are not intended to claim all such embodiments and variations, and the full scope of the invention should be determined by reference to the claims, along with their full scope of equivalents, and the specification, along with such variations.

We claim:

1. A compound represented by formula (I):

I or a pharmaceutically acceptable salt, solvate, hydrate, prodrug, chemically-protected form, enantiomer or stereoisomer thereof; wherein, independently for each occurrence, A is N or $CR^8$;

Z is

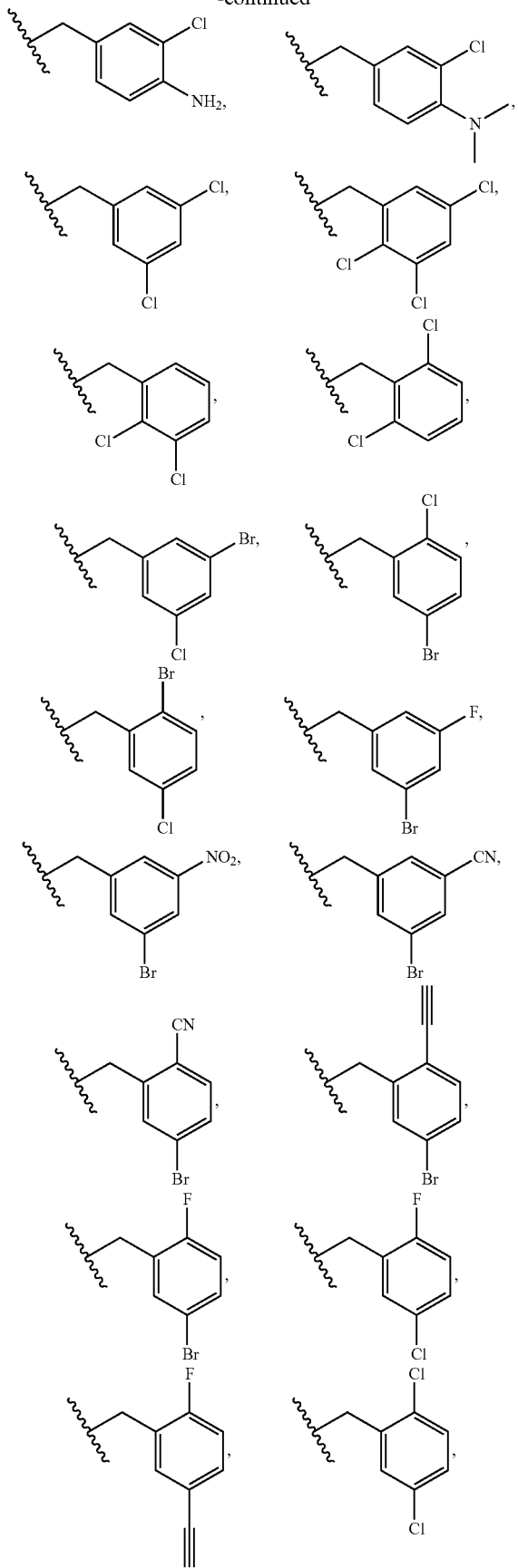
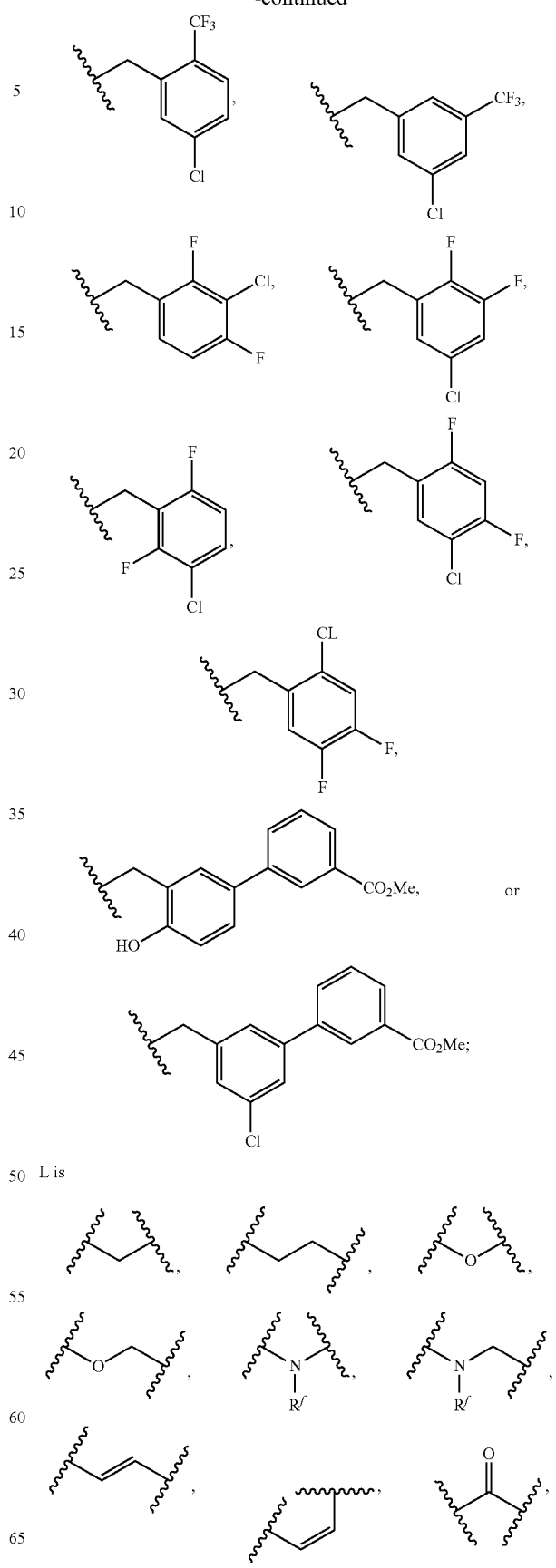

-continued

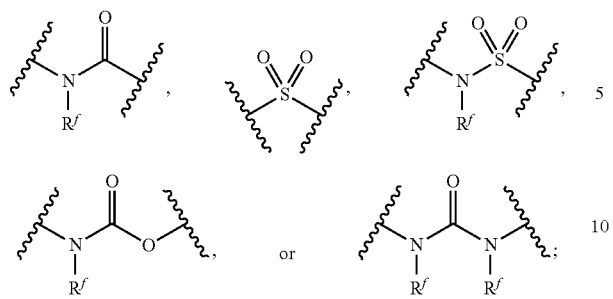

$R^f$ are each independently selected from H, alkyl, and cycloalkyl $R^9$ is selected from H, optionally substituted alkyl, amino, cycloalkyl, heterocyclyl, aryl, and heteroaryl;

n is an integer selected from 0, 1 or 2;

$R^{51}$ is independently selected from deutero, halo, cyano, azido, alkyl, haloalkyl, fluoroalkyl, cycloalkyl, hydroxyl, alkoxy, haloalkoxy, carbocyclylalkoxy, heterocyclylalkoxy, aryloxy, heteroaryloxy, amino, alkylamino, carbocyclylamino, heterocyclylamino, arylamino, heteroarylamino, amido, alkenyl, alkynyl, carbocyclyl, aryl, heteroaryl, and carbocyclylalkoxy;

E is selected from optionally substituted cycloalkyl, arylalkyl, cycloalkylalkyl, amino, alkoxy, cycloalkyloxy, and cycloalkylamino, or E is

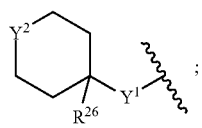

$Y^1$ is selected from O, $NR^{27}$, and $CR^{28}R^{29}$;

$Y^2$ is selected from O, $NR^{30}$, and $CR^{31}R^{32}$;

$R^{26}$, $R^{28}$, $R^{29}$, $R^{31}$, and $R^{32}$ are each independently H, halo, optionally substituted alkyl or haloalkyl, or $R^{26}$ and $R^{29}$ combine to form a 3-, 4-, or 5-membered ring;

$R^{27}$ is selected from H and alkyl;

$R^{30}$ is selected from H,

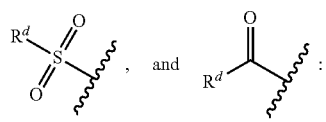

$R^d$ is selected from alkyl, cycloalkyl, heterocyclyl, aryl, or heteroaryl;

$R^2$ and $R^3$ are independently selected from H, deutero, optionally substituted alkyl, haloalkyl, or $R^2$ and $R^3$, together with the carbon to which they are bound, combine to form a carbonyl; and $R^8$ is selected from H, deutero, halo, hydroxyl, cyano, amino, alkyl, alkoxy, carboxy, alkoxycarbonyl, and aminocarbonyl;

provided that E is not

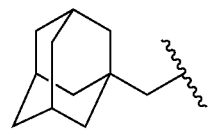

2. The compound of claim 1, wherein A is N.

3. The compound of claim 1, wherein E is

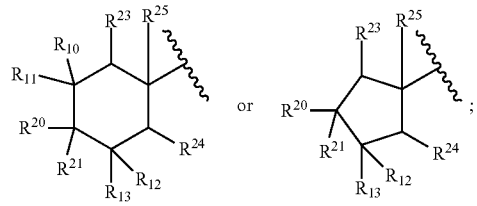

$R^{10}$, $R^{11}$, $R^{12}$, $R^{13}$, and $R^{14}$ are each independently H or halo; or $R^{10}$ and $R^{12}$ combine to form a 3-, 4-, or 5-membered ring; and $R^{20}$, $R^{21}$, $R^{23}$, $R^{24}$, and $R^{25}$ are each independently H, halo, or alkyl; or $R^{23}$ and $R^{24}$ combine to form a 3-, 4-, or 5-membered ring.

4. The compound of claim 1, wherein $R^d$ is methyl.

5. The compound of claim 1, wherein $R^{26}$ and $R^{29}$ combine to form a 3-membered ring.

6. The compound of claim 1, wherein $R^{31}$ and $R^{32}$ are each halo.

7. The compound of claim 6, wherein $R^{31}$ and $R^{32}$ are each F.

8. The compound of claim 1, wherein E is

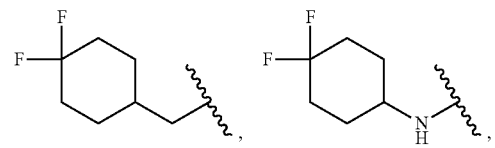

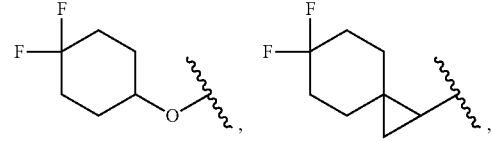

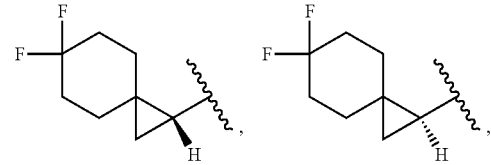

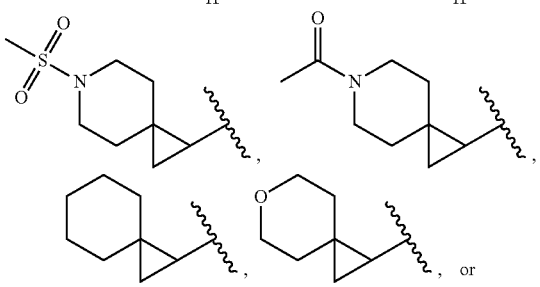

-continued

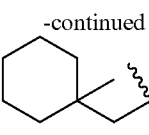

9. The compound of claim 1, wherein Z is

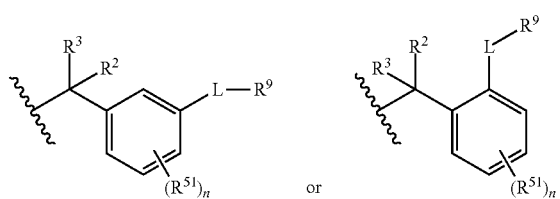

10. The compound of claim 9, wherein $R^9$ is phenyl or pyridinyl optionally substituted with deutero, alkyl, alkenyl, alkynyl, halo, haloalkyl, fluoroalkyl, hydroxy, alkoxy, alkenyloxy, alkynyloxy, carbocyclyloxy, heterocyclyloxy, haloalkoxy, hydroxyalkyl, aminoalkyl fluoroalkyloxy, sulfhydryl, alkylthio, haloalkylthio, fluoroalkylthio, alkenylthio, alkynylthio, sulfonic acid, alkylsulfonyl, haloalkylsulfonyl, arylsulfonyl, fluoroalkylsulfonyl, alkenylsulfonyl, alkynylsulfonyl, alkoxysulfonyl, haloalkoxysulfonyl, fluoroalkoxysulfonyl, alkenyloxysulfonyl, alkynyloxysulfony, aminosulfonyl, alkylaminosulfonyl, arylaminosulfonyl, heteroarylaminosulfonyl, aralkylaminosulfonyl, N-alkyl-N-arylaminosulfonyl, N-aralkyl-N-alkylamino sulfonyl, sulfinic acid, alkylsulfinyl, haloalkylsulfinyl, fluoroalkylsulfinyl, alkenylsulfinyl, alkynylsulfinyl, alkoxysulfinyl, haloalkoxysulfinyl, fluoroalkoxysulfinyl alkenyloxysulfinyl, alkynyloxysulfinyl, aminosulfinyl, formyl, alkylcarbonyl, haloalkylcarbonyl, fluoroalkylcarbonyl, alkenylcarbonyl, alkynylcarbonyl, carboxy, alkoxycarbonyl, haloalkoxycarbonyl, fluoroalkoxycarbonyl, alkenyloxycarbonyl, alkynyloxycarbonyl, alkylcarbonyloxy, haloalkylcarbonyloxy, fluoroalkylcarbonyloxy, alkenylcarbonyloxy, alkynylcarbonyloxy, alkylsulfonyloxy, haloalkylsulfonyloxy, fluoroalkylsulfonyloxy, alkenylsulfonyloxy, alkynylsulfonyloxy, haloalkoxysulfonyloxy, fluoroalkoxysulfonyloxy, alkenyloxysulfonyloxy, alkynyloxysulfonyloxy, alkylsulfinyloxy, haloalkylsulfinyloxy, fluoroalkylsulfinyloxy, alkenylsulfinyloxy, alkynylsulfinyloxy, alkoxysulfinyloxy, haloalkoxysulfinyloxy, fluoroalkoxysulfinyloxy, alkenyloxysulfinyloxy, alkynyloxysulfinyloxy, aminosulfinyloxy, amino, alkylsulfonylamino, arylsulfonylamino, heteroarylsulfonylamino, aralkylsulfonylamino, alkylcarbonylamino, arylcarbonylamino, heteroarylcarbonylamino, aralkylcarbonylamino, aminocarbonyl, alkylaminocarbonyl, arylaminocarbonyl, heteroarylaminocarbonyl, aralkylaminocarbonyl, N-alkyl-N-arylaminocarbonyl, N-aralkyl-N-alkylamino carbonyl cyano, nitro, azido, phosphinyl, phosphoryl including phosphine oxide and phosphonate, silyl, silyloxy, cyclic acetal, aryl, heteroaryl.

11. The compound of claim 9, wherein $R^9$ is phenyl or pyridinyl optionally substituted with halo, amino, amide, cyano, carboxy, alkoxycarbonyl, lower cycloalkyl, sulfanamide, phosphine oxide, phosphoryl, sulfoxide, sulfone, alkyl, or lower cycloalkyl.

12. The compound of claim 9, wherein $R^9$ is phenyl.

13. The compound of claim 9, wherein $R^9$ is

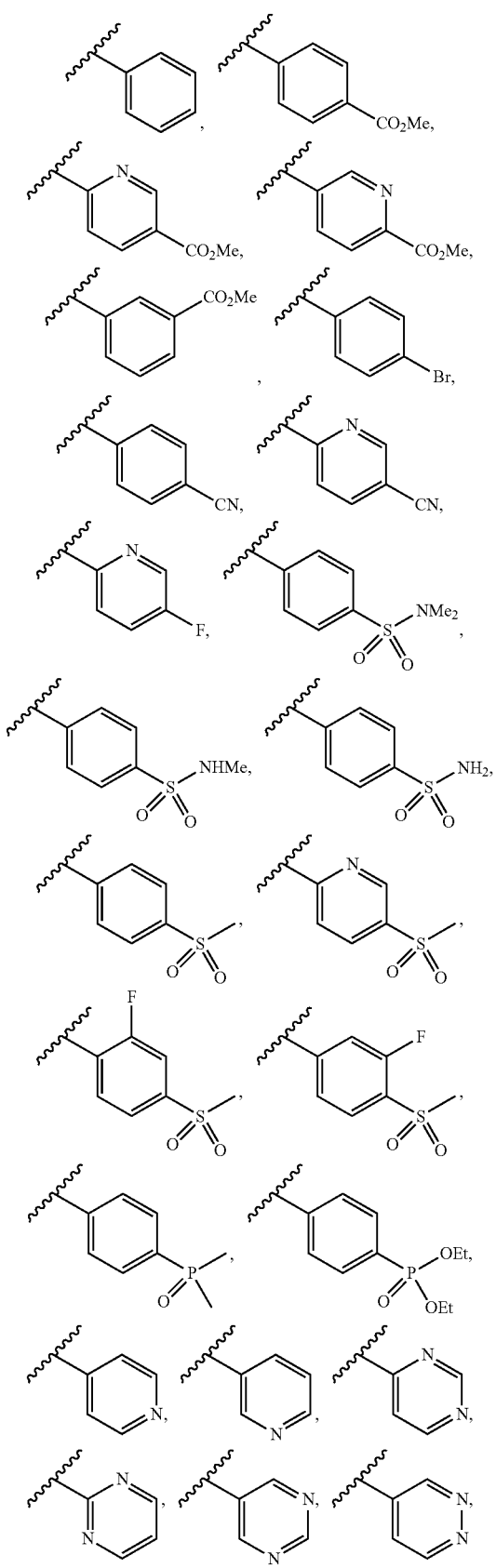

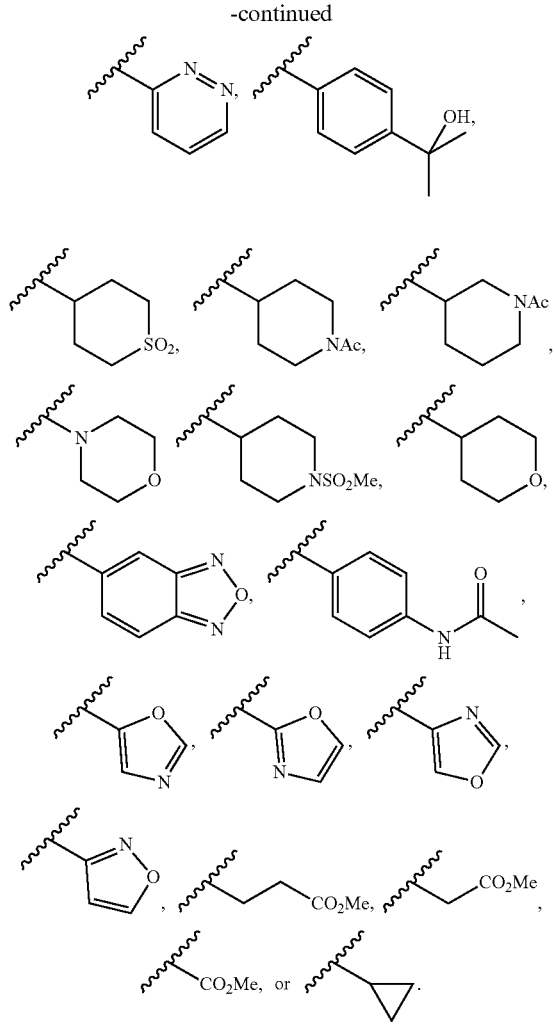
14. The compound of claim 1, wherein Z is
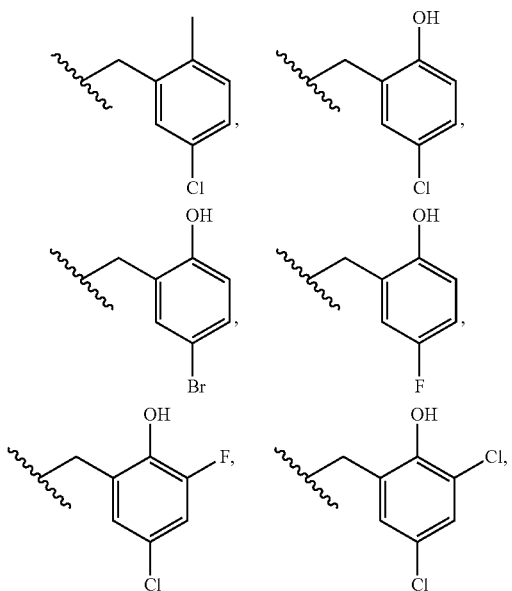
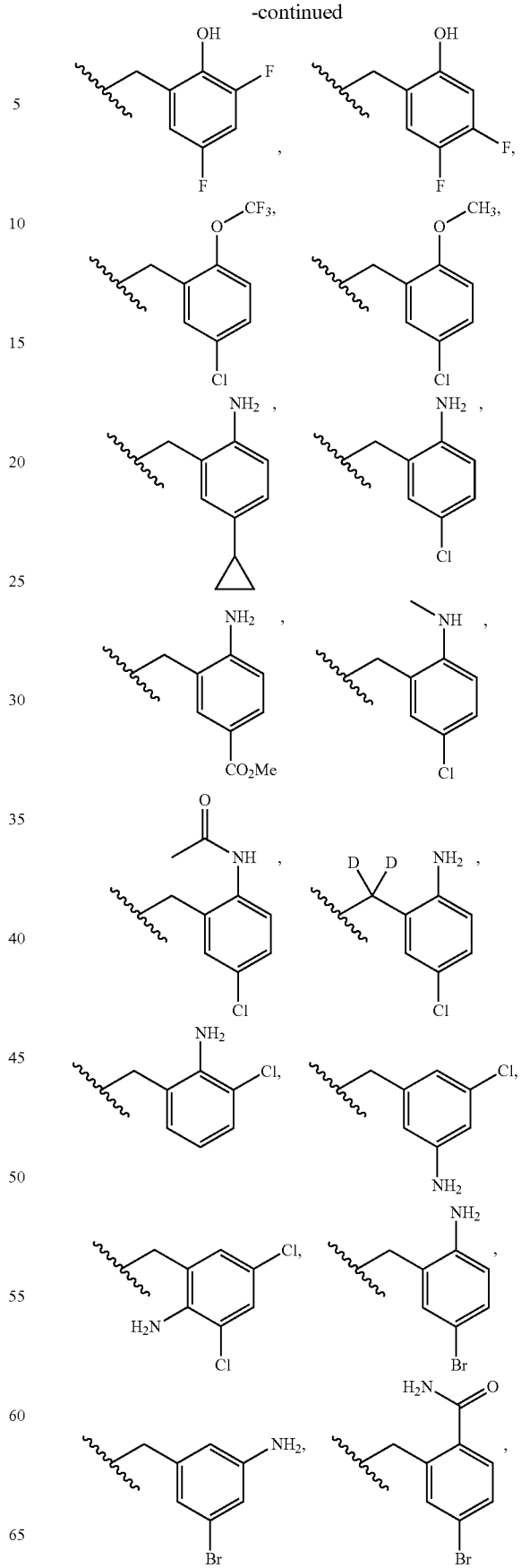

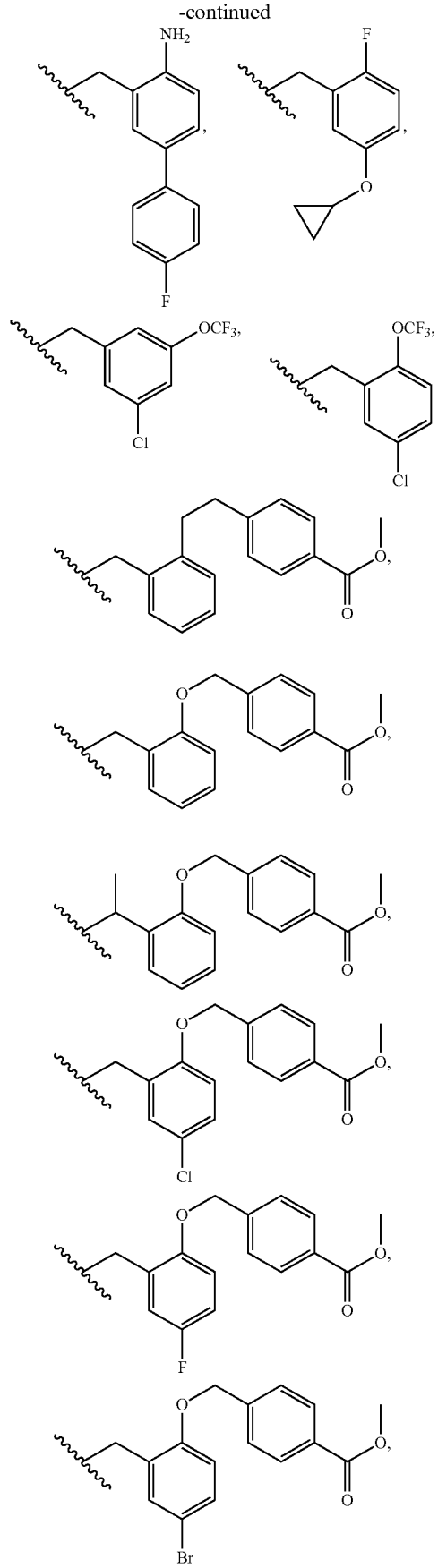
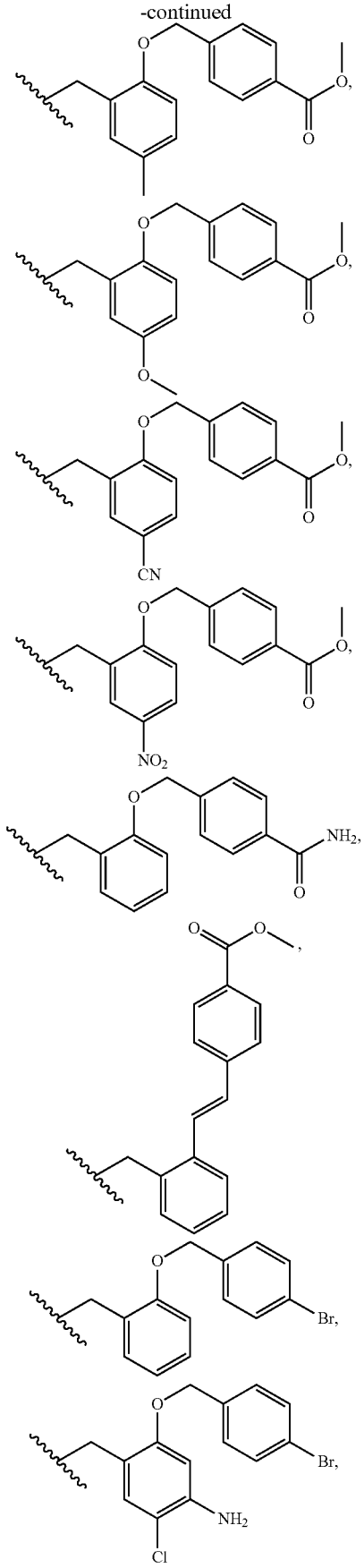

227
-continued
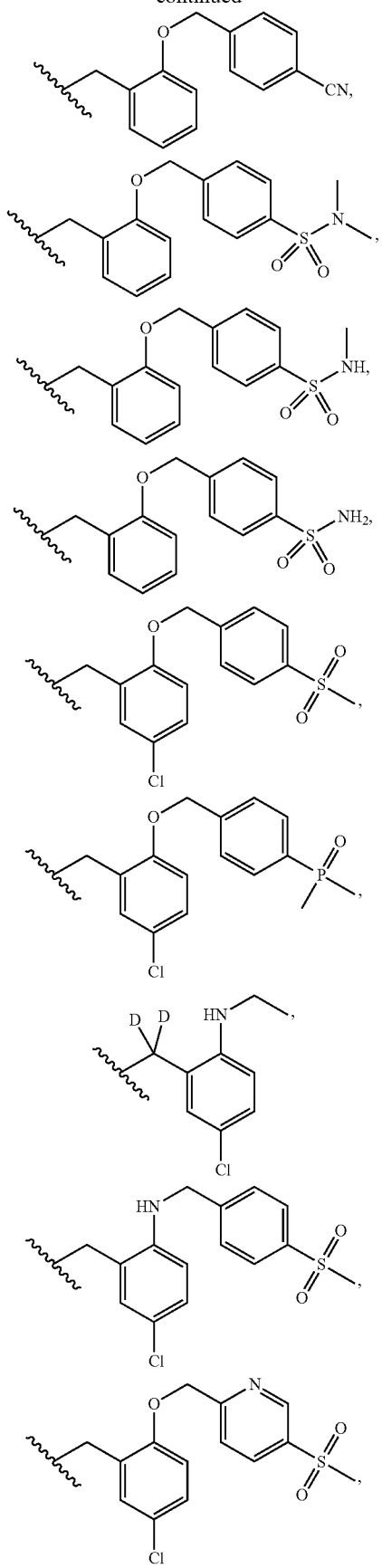
228
-continued
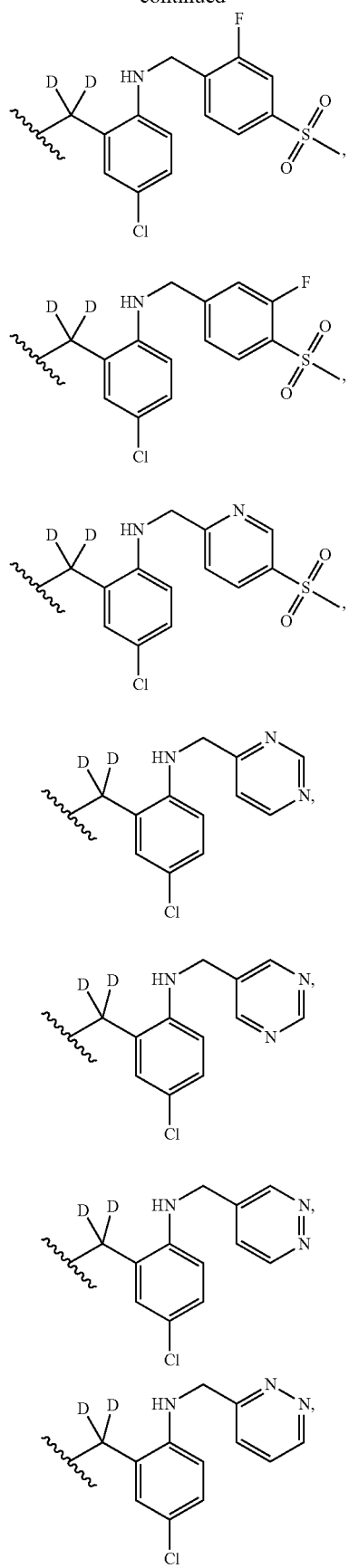

229
-continued
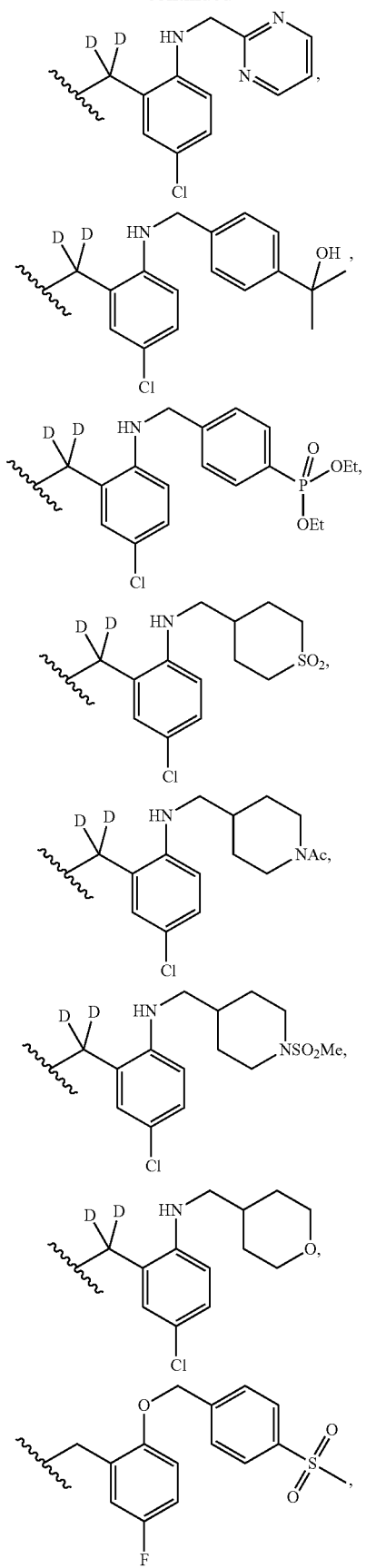
230
-continued
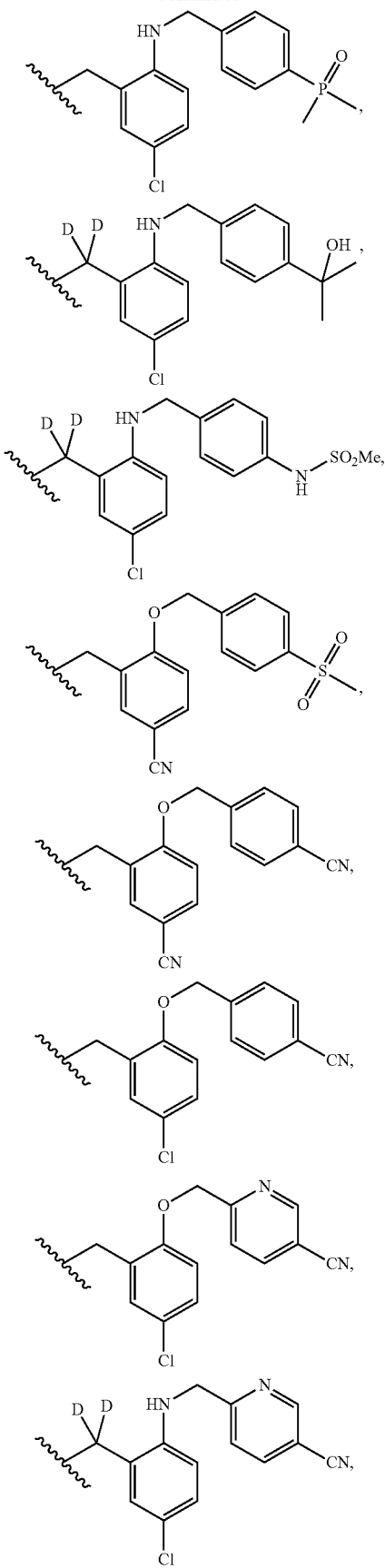

231
-continued
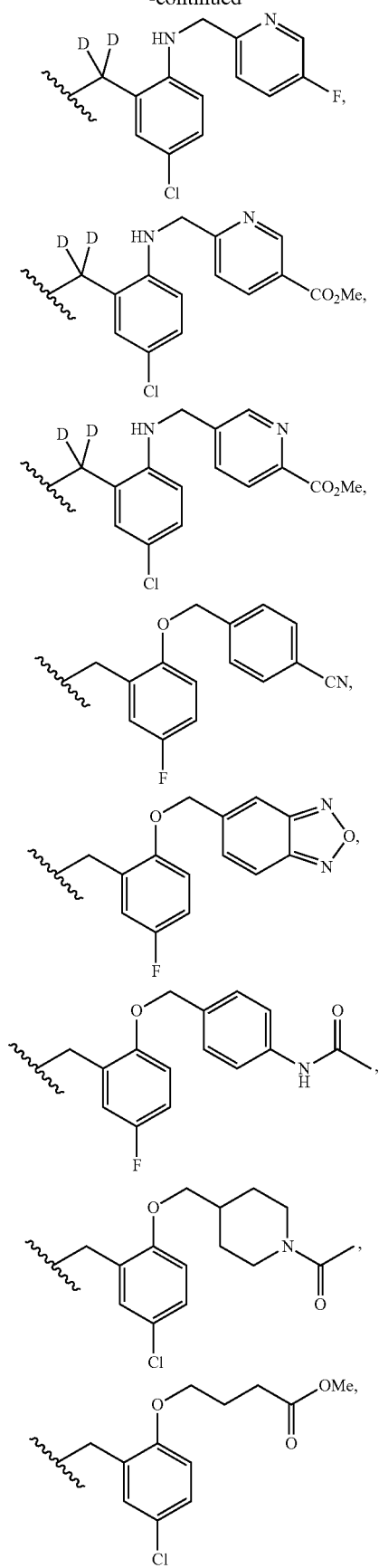
232
-continued
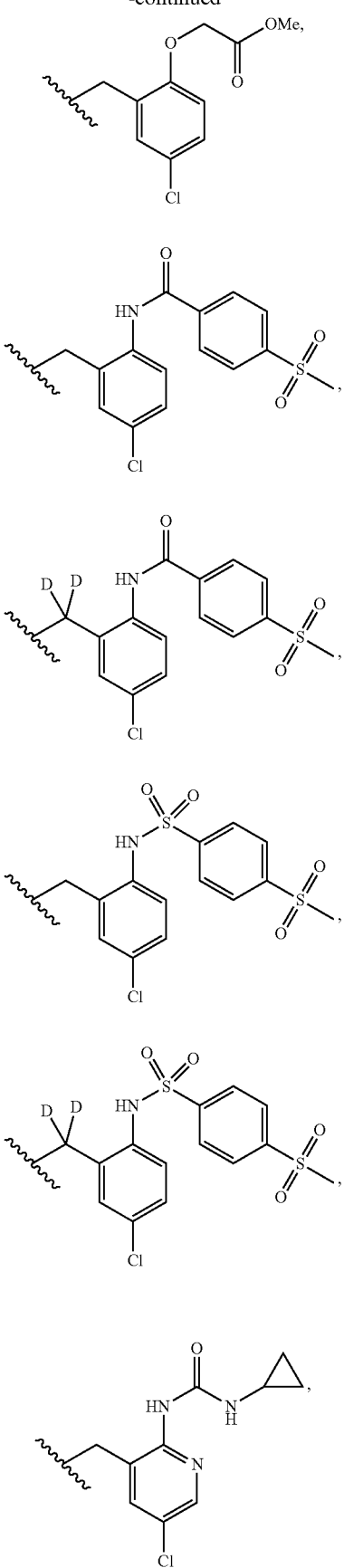

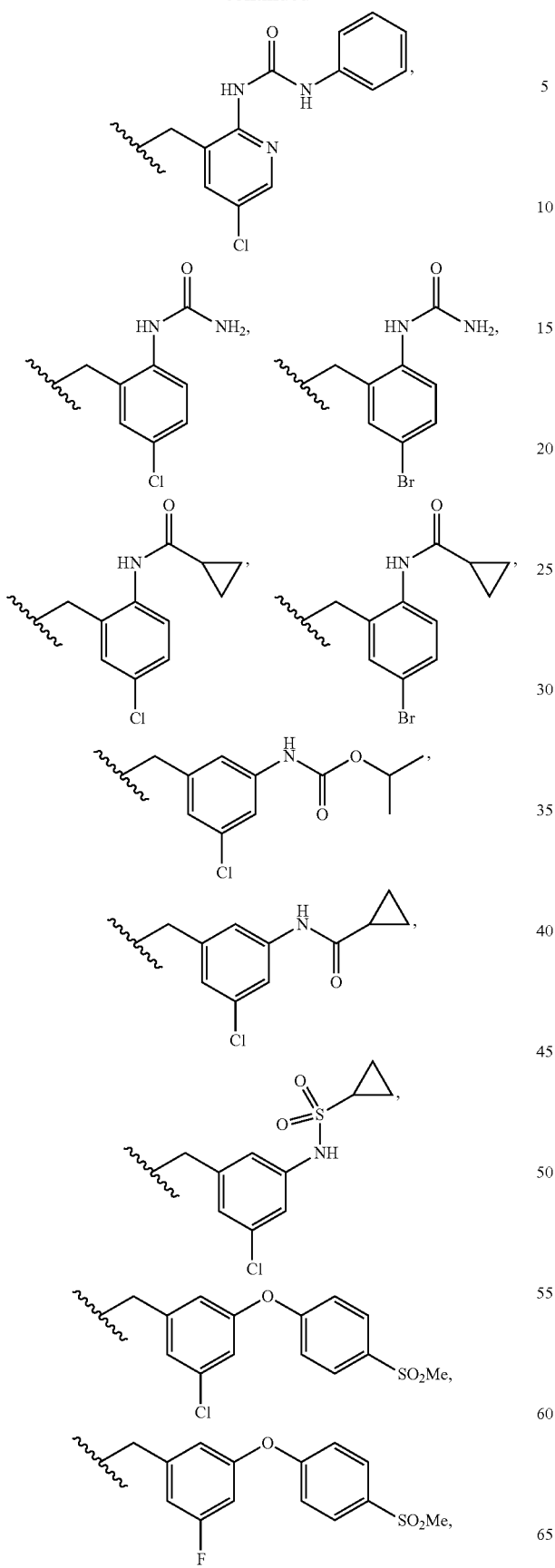
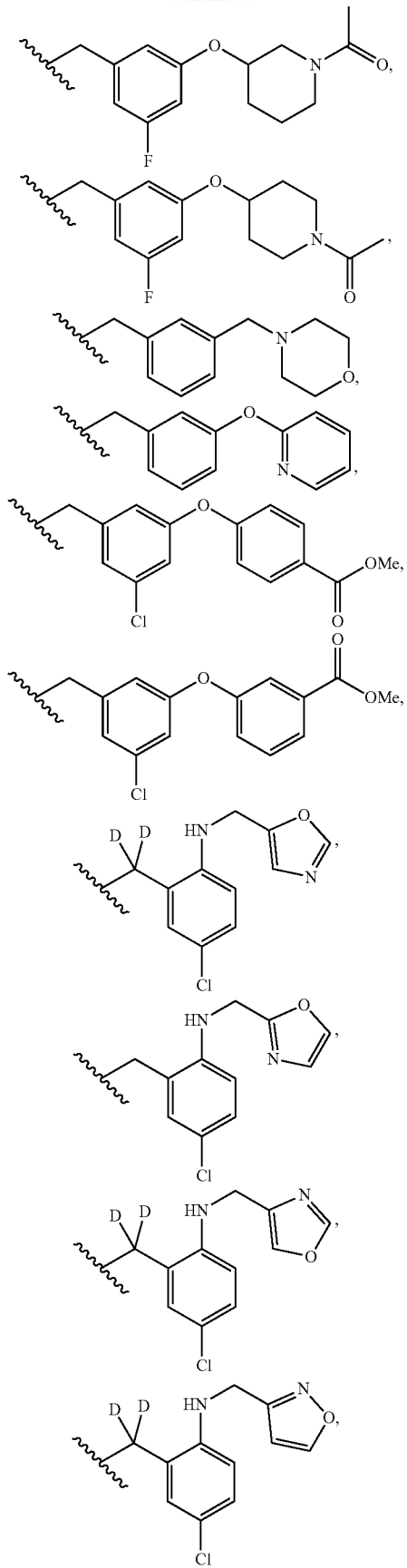

-continued

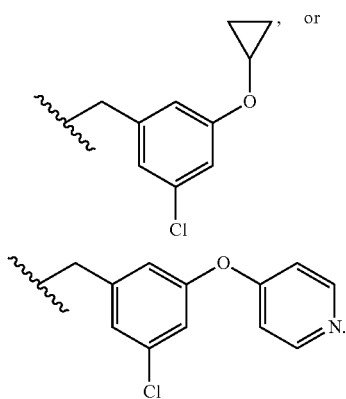

15. A compound represented by formula (II)

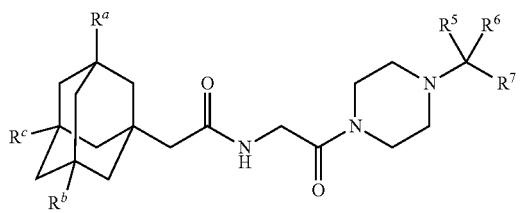

or a pharmaceutically acceptable salt, solvate, hydrate, prodrug, chemically-protected form, enantiomer or stereoisomer thereof; wherein, independently for each occurrence, wherein $R^a$, $R^b$, and $R^c$ are independently selected from H, halo, hydroxy, optionally substituted alkyl, optionally substituted alkoxy, optionally substituted aryl, and optionally substituted heteroaryl;

$R^5$ and $R^6$ are independently selected from H, deutero, and alkyl, or $R^5$ and $R^6$, together with the carbon to which they are bound, combine to form a carbonyl; and $R^7$ is

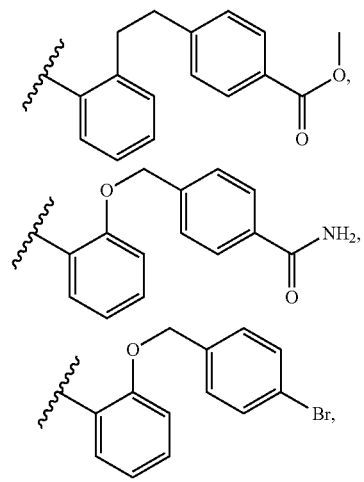

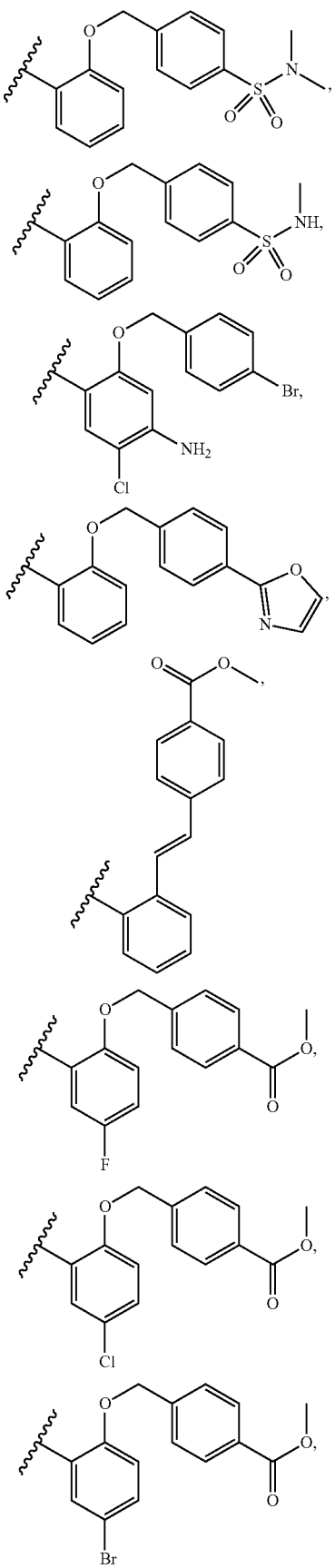

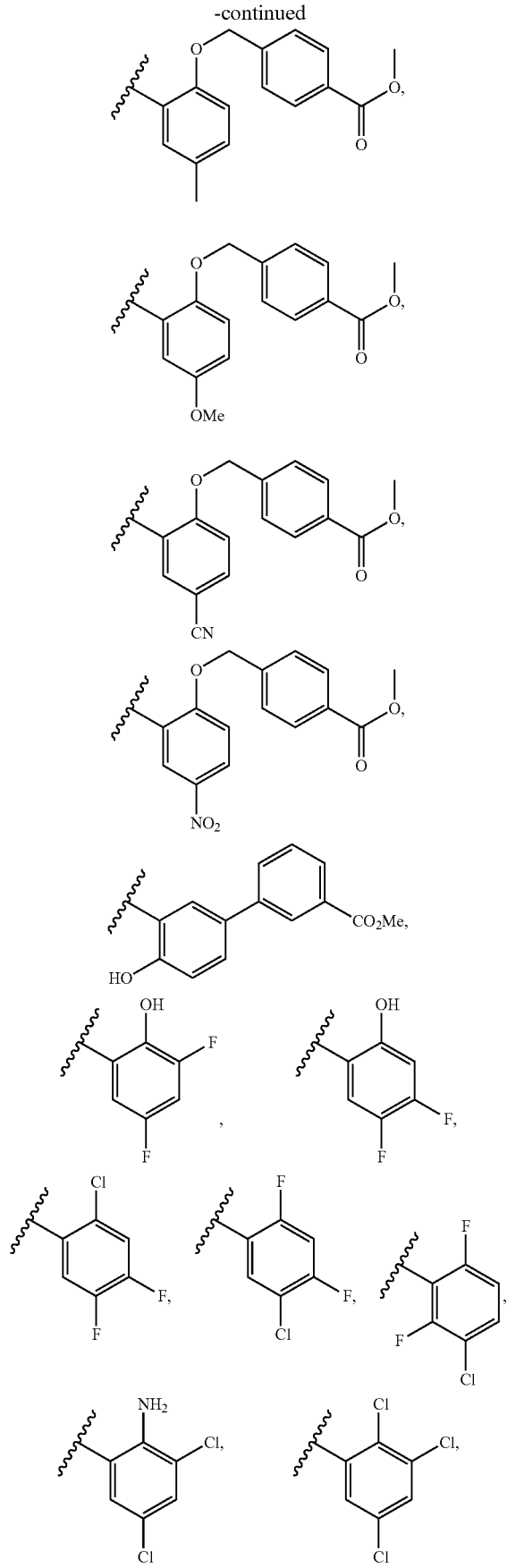
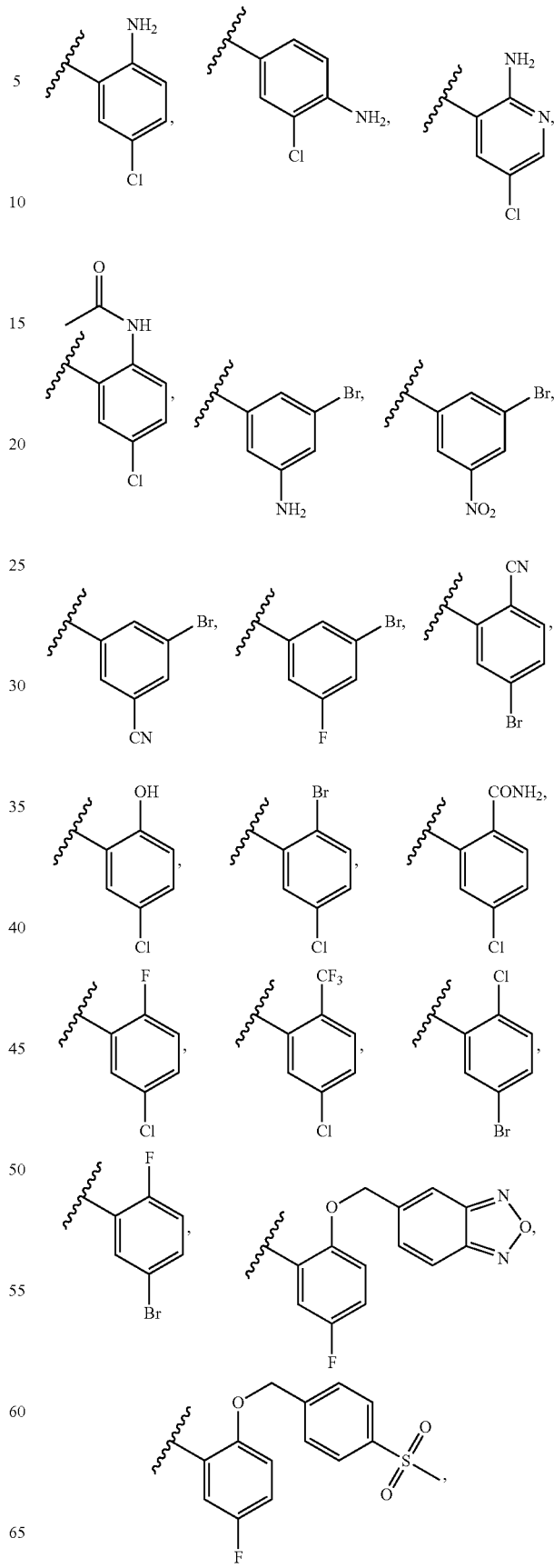

-continued

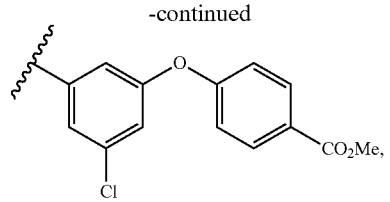

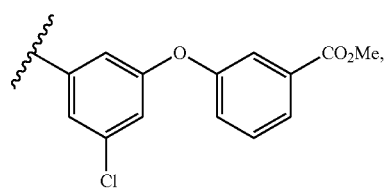

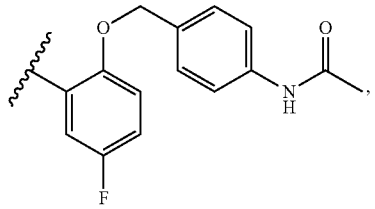

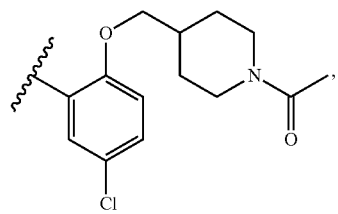

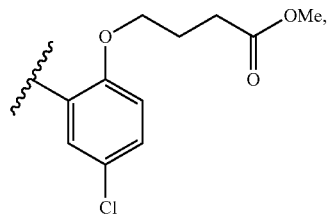

-continued

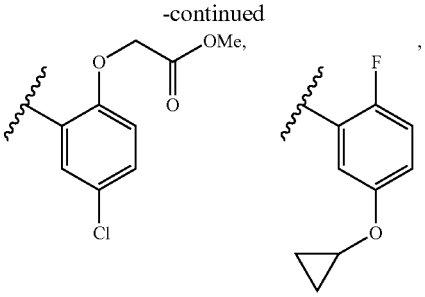

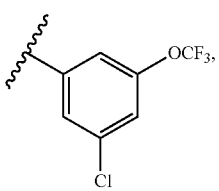   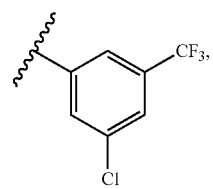

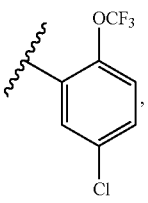   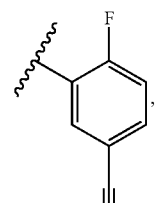

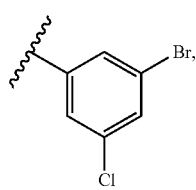   or   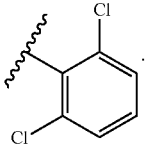

16. A pharmaceutical composition comprising a compound of claim 1 and a pharmaceutically acceptable carrier.

17. A method of treating a viral infection in a subject comprising administering to the subject a therapeutically effective amount of a compound of claim 1.

18. The method of claim 17, wherein the viral infection is caused by HIV.

19. A compound or a pharmaceutically acceptable salt thereof, selected from:

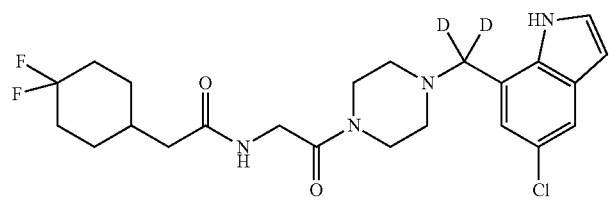

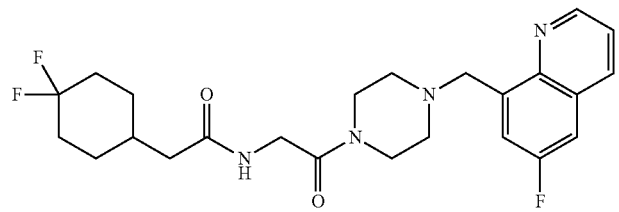

-continued
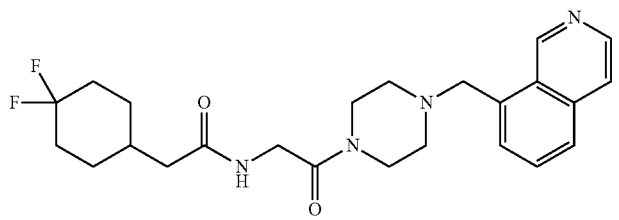
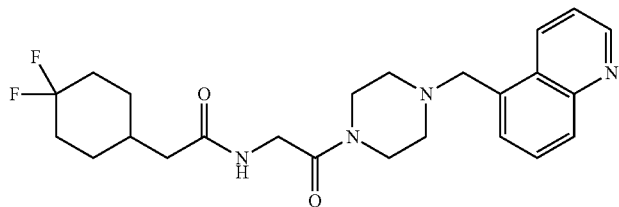
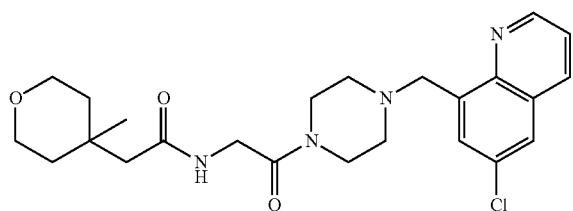
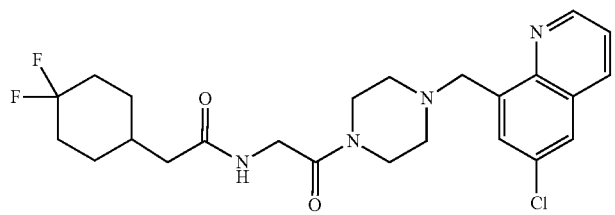
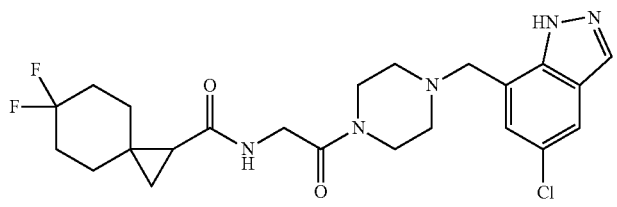
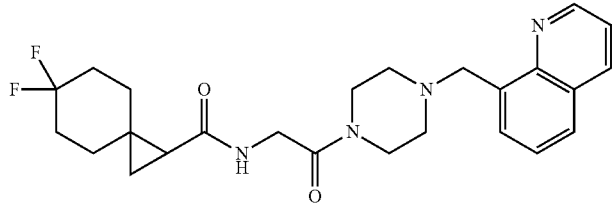
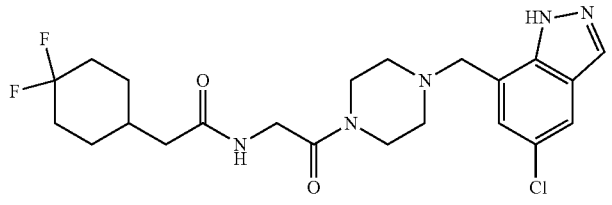
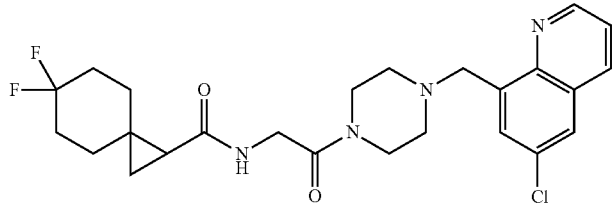
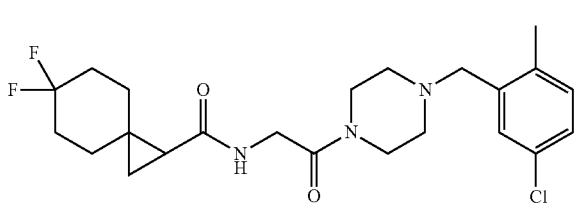
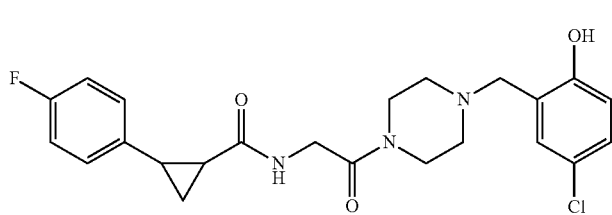
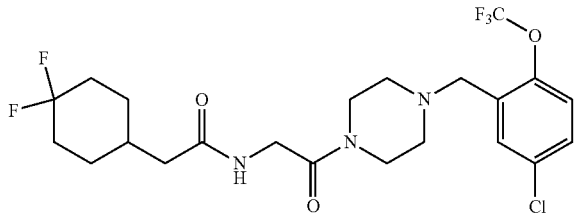

-continued
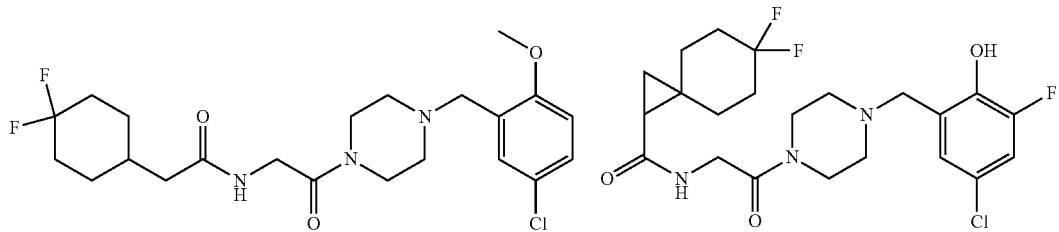
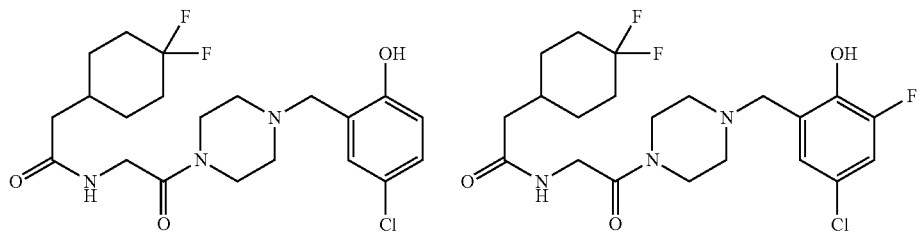
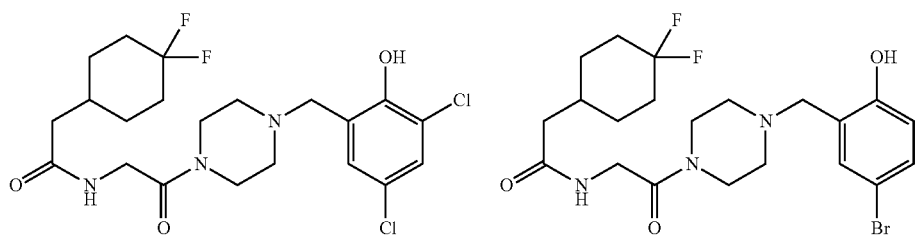
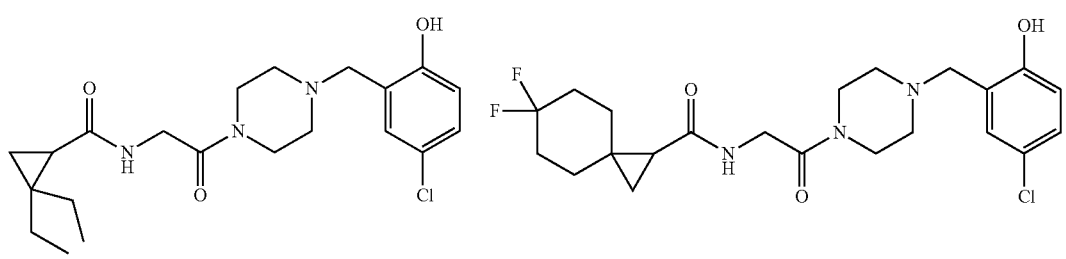
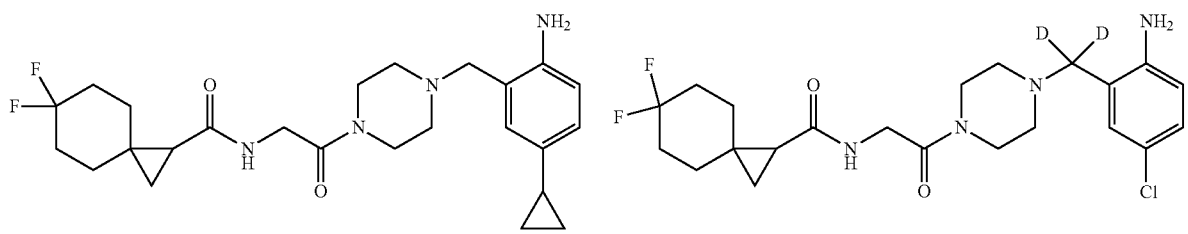
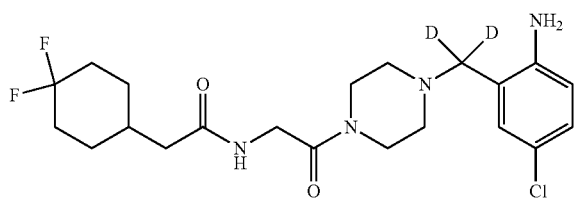
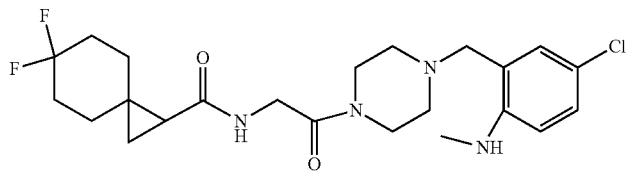

-continued
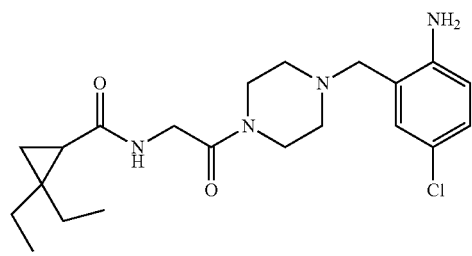
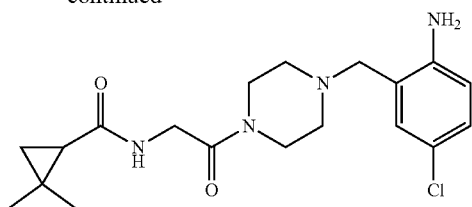
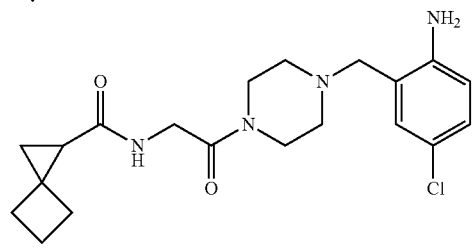
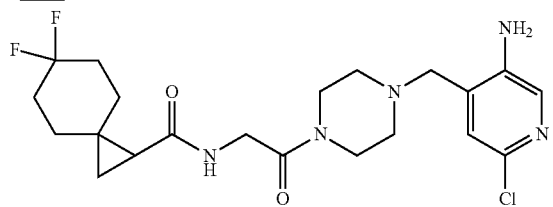
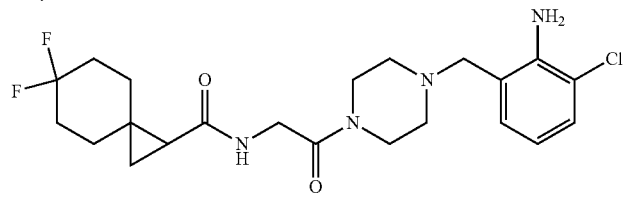
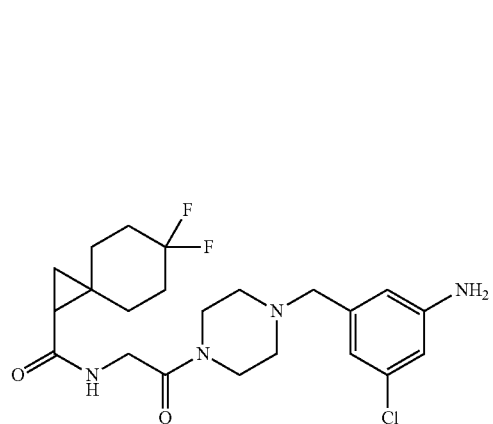
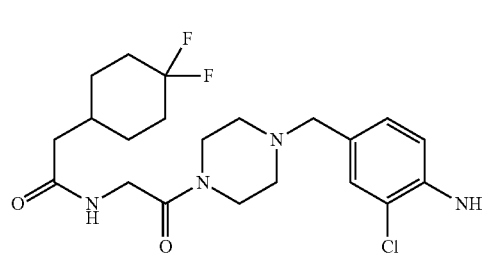
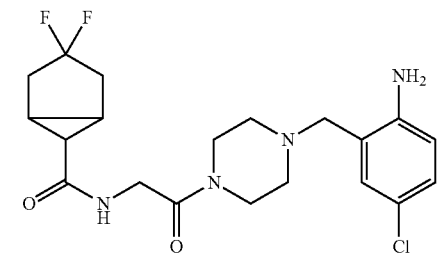
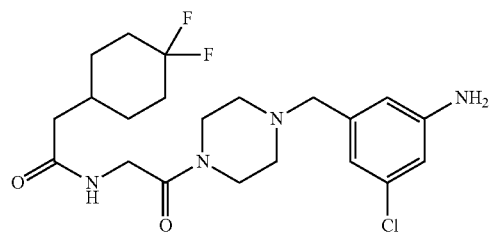
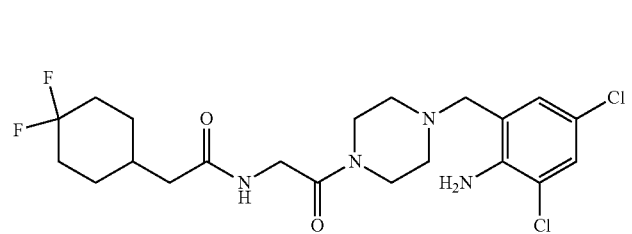
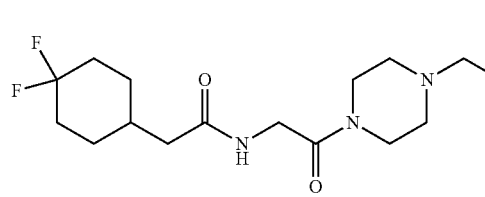
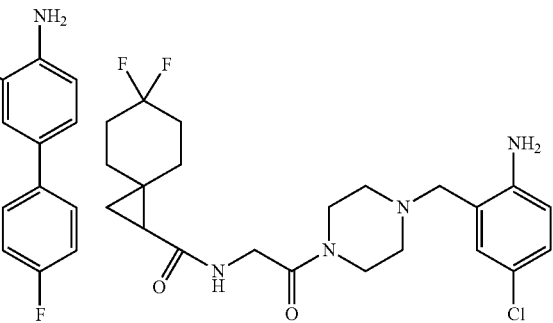

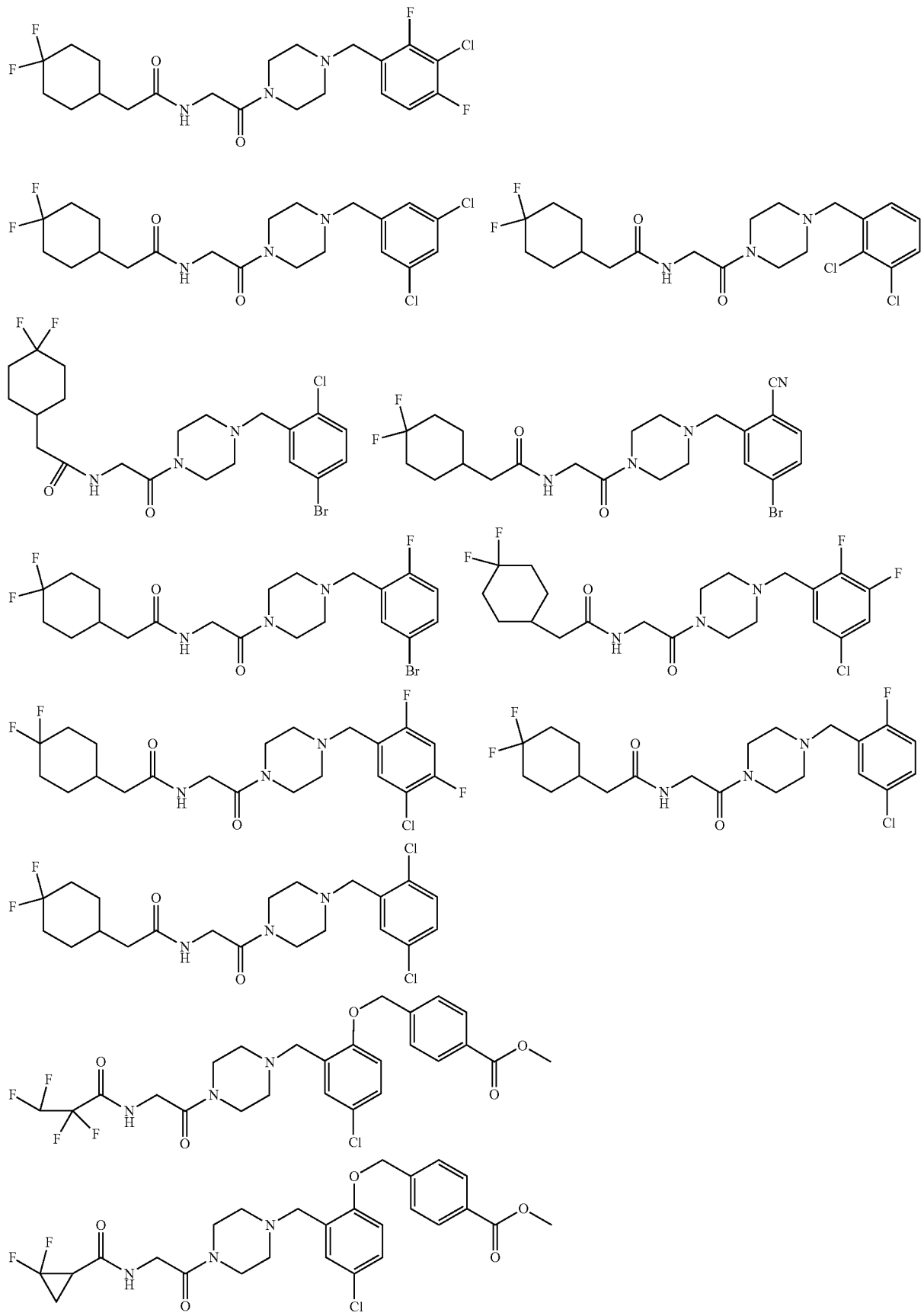

-continued
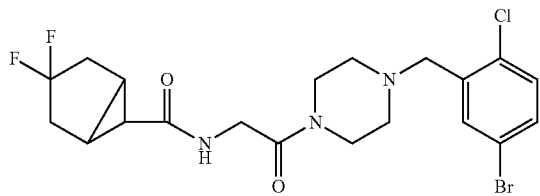
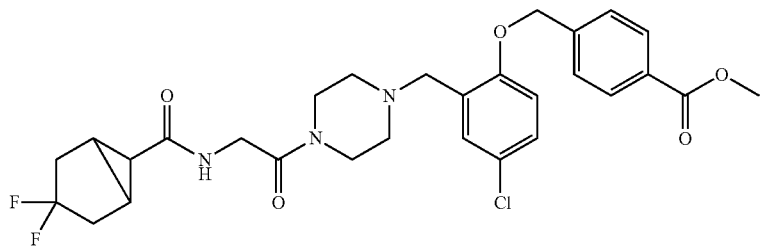
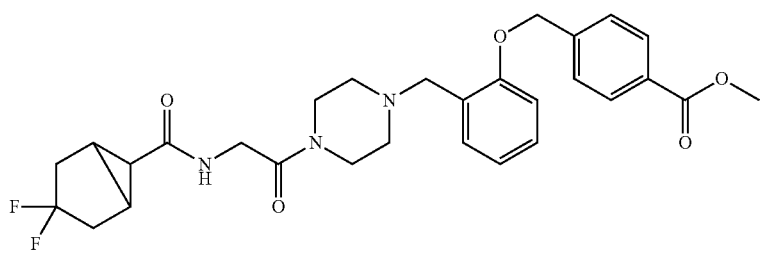
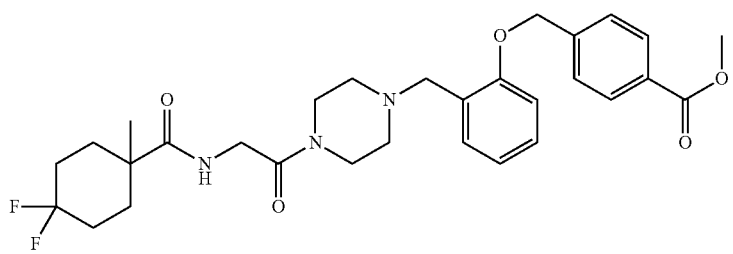
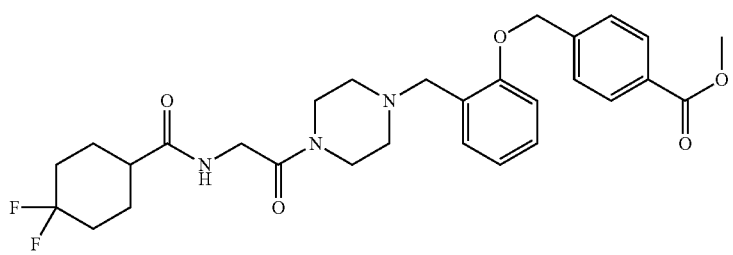
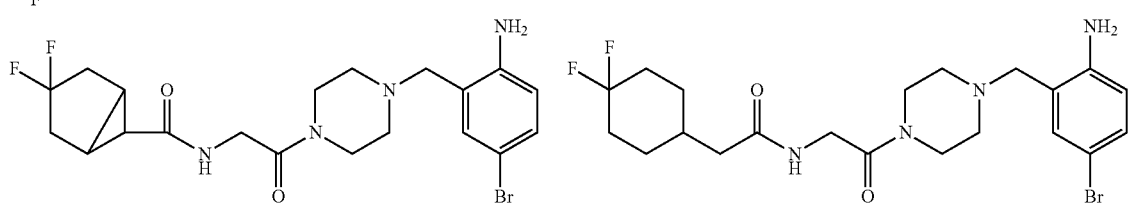
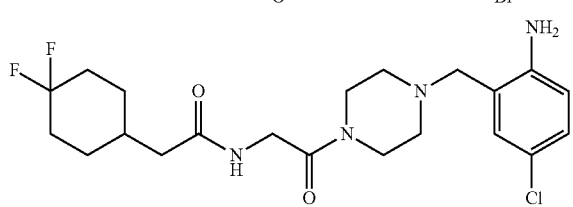

-continued
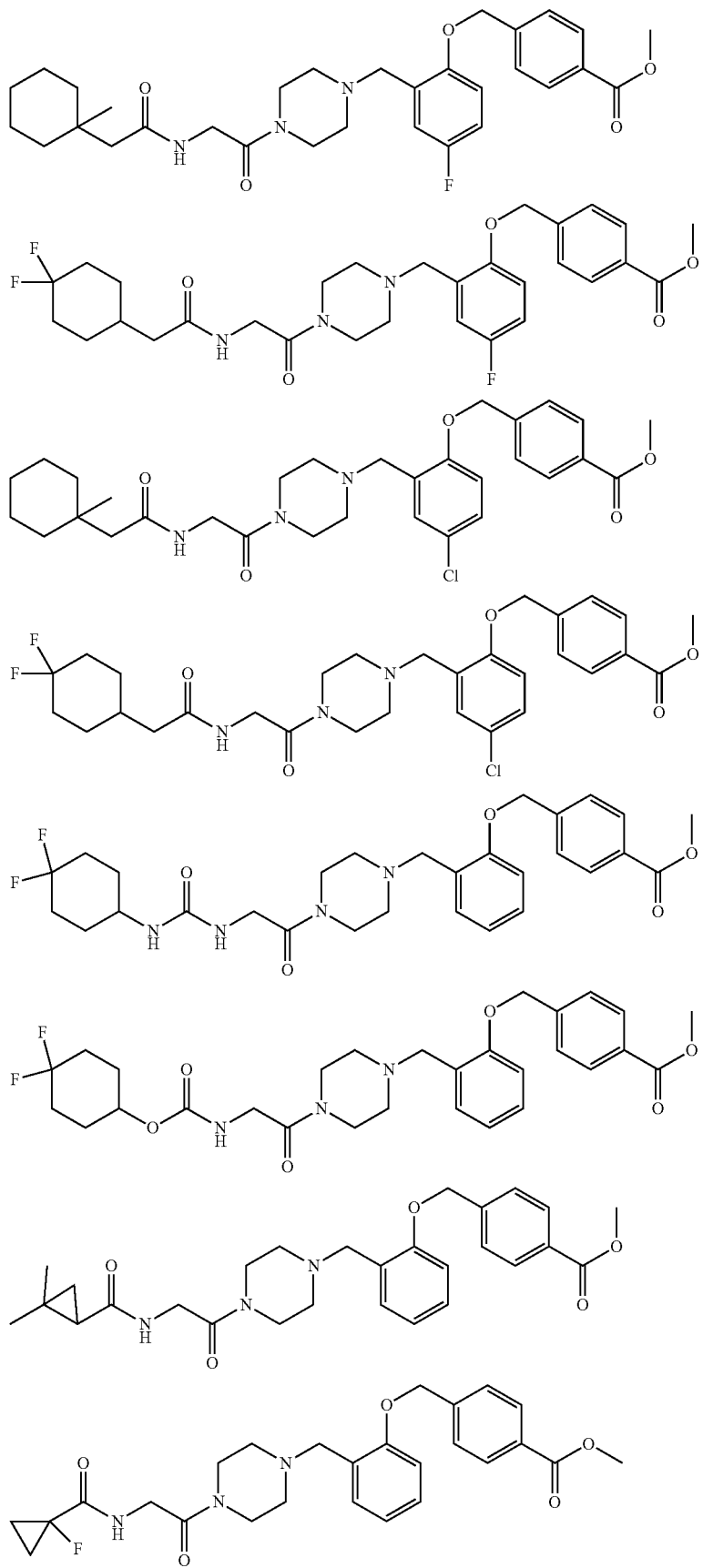

-continued
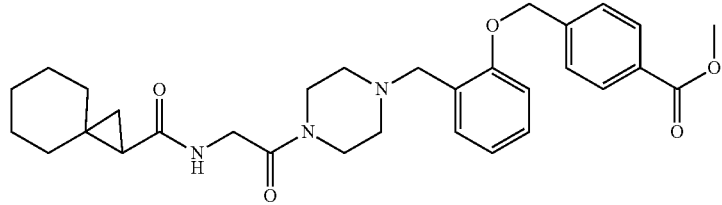
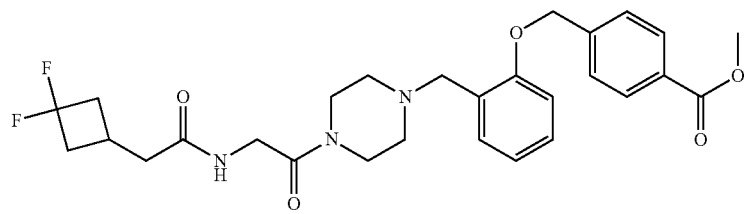
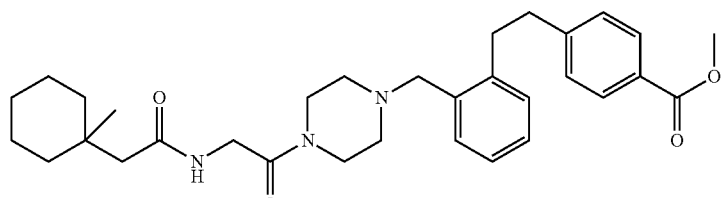
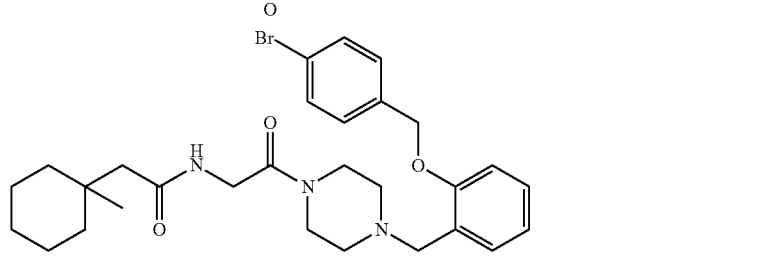
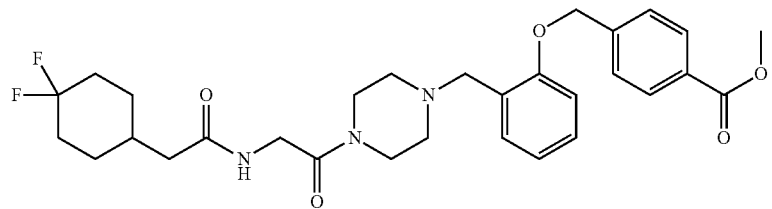
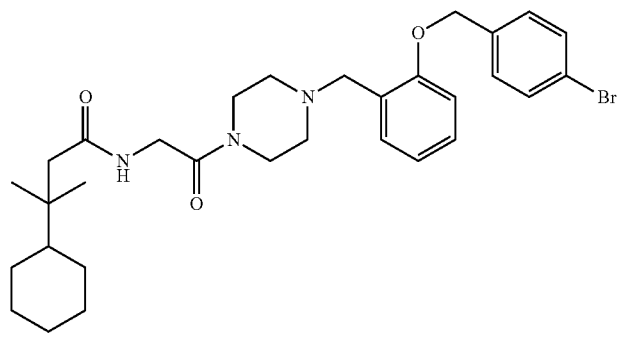
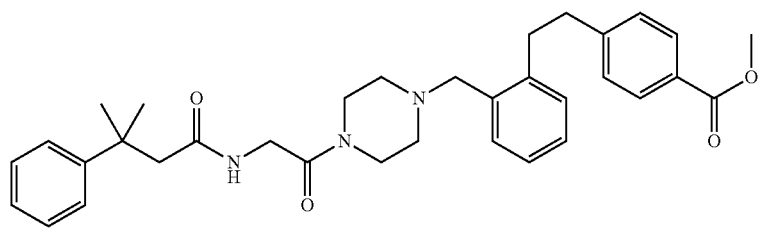

-continued
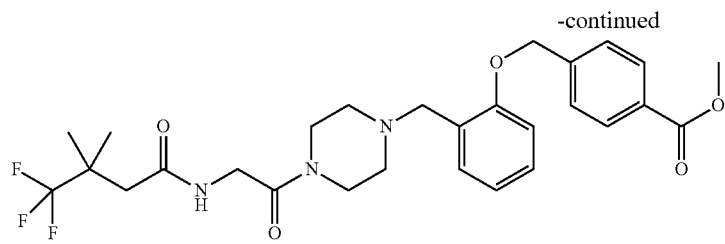
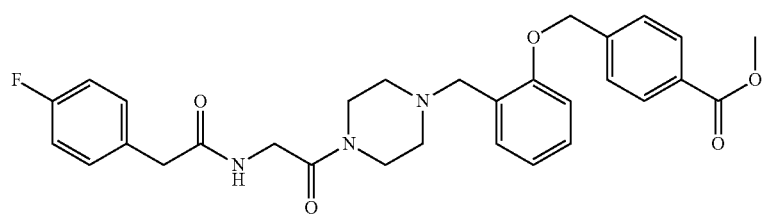
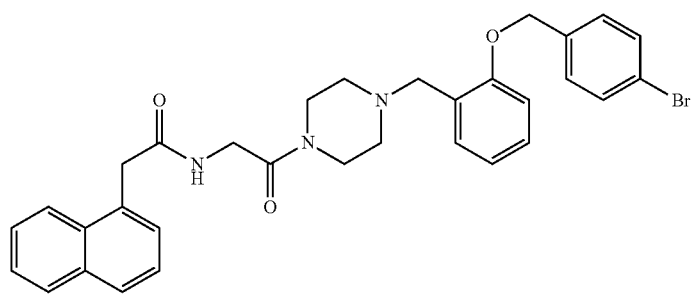
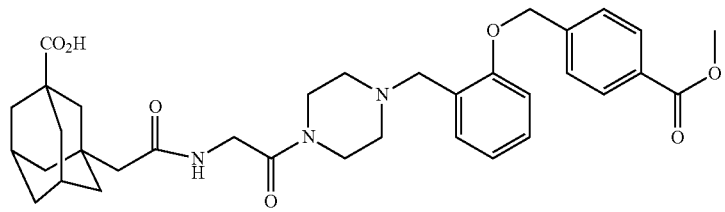
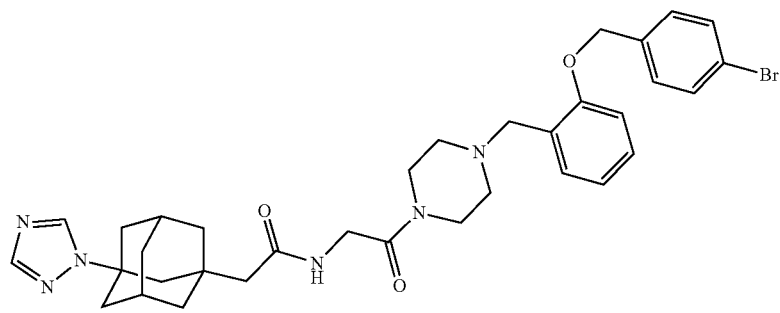
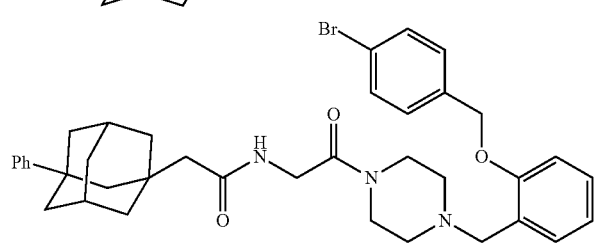

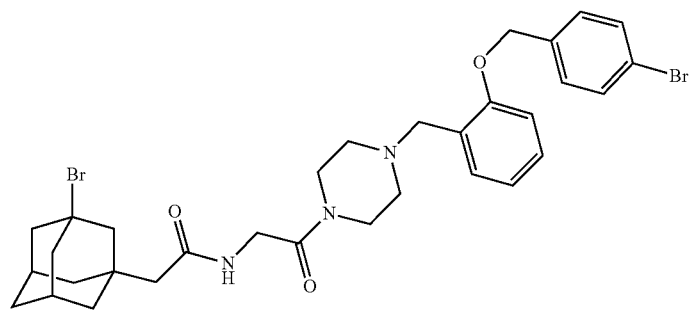
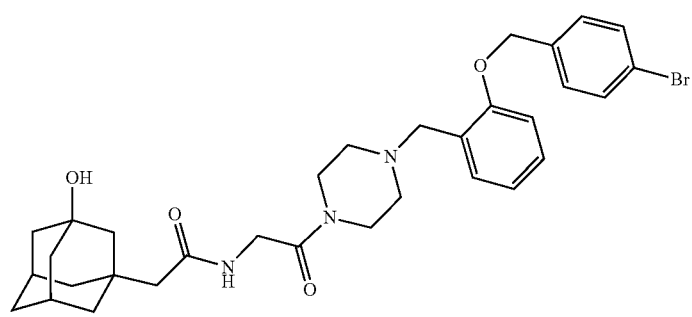
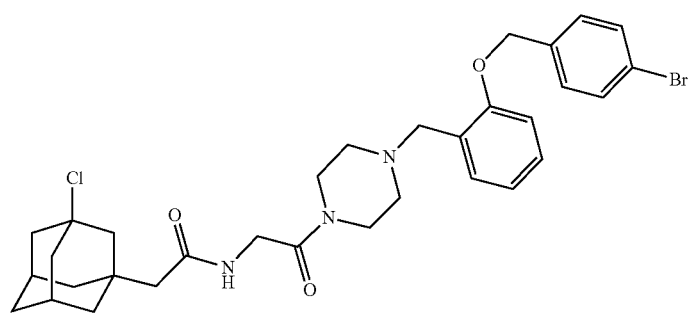
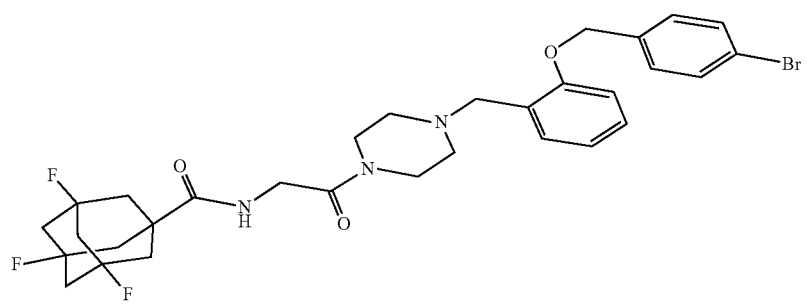
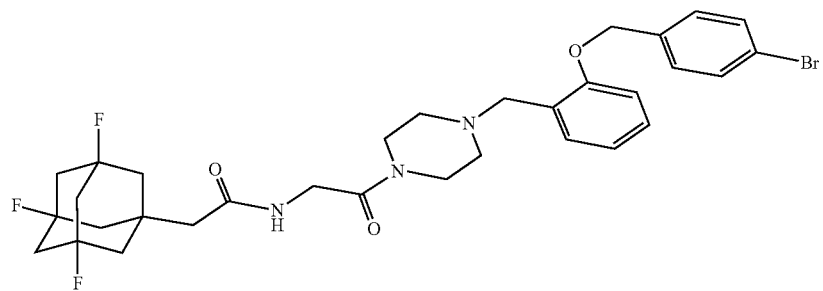

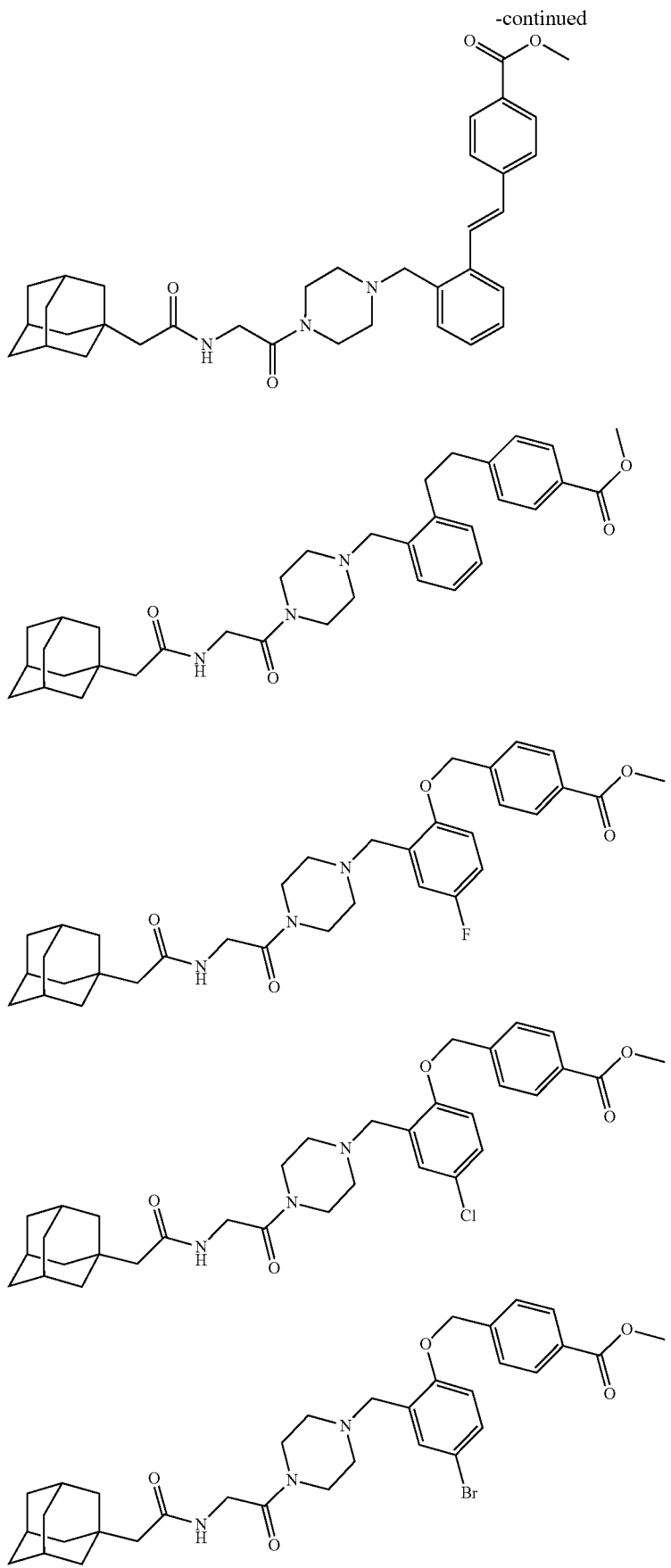

-continued
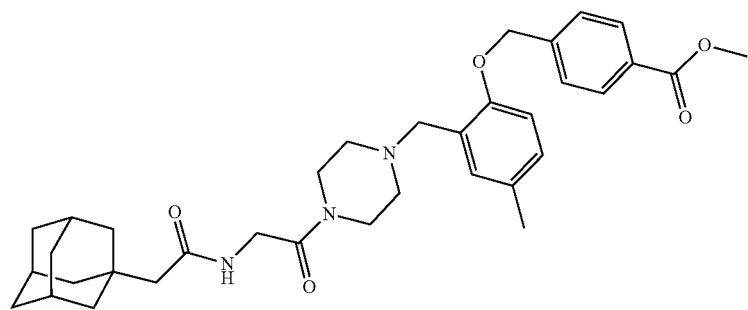
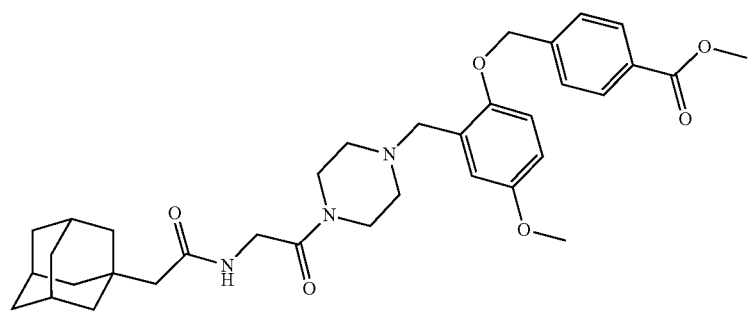
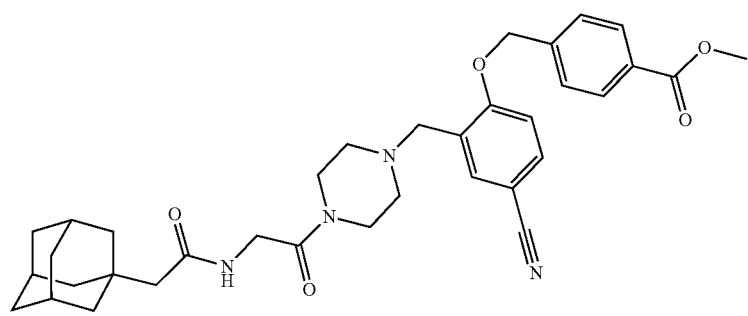
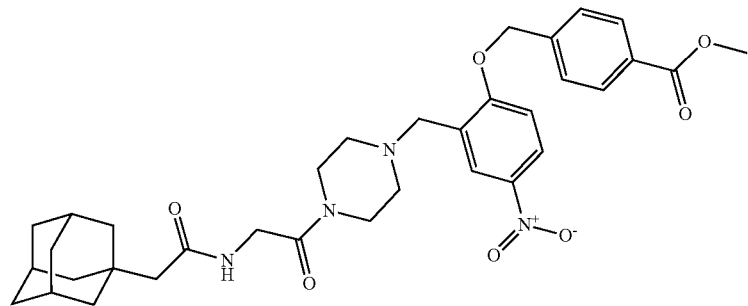
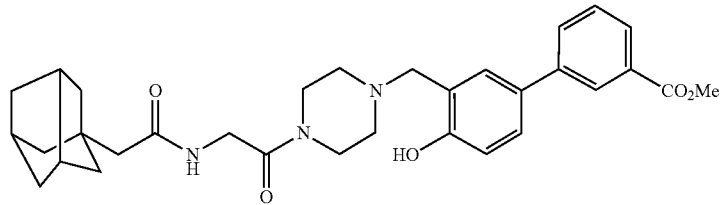
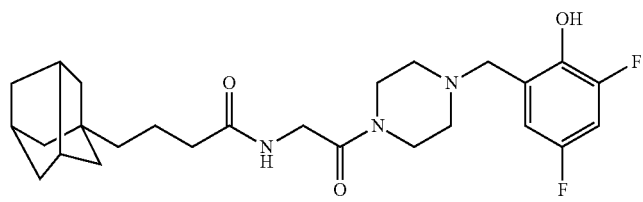

263 264
-continued
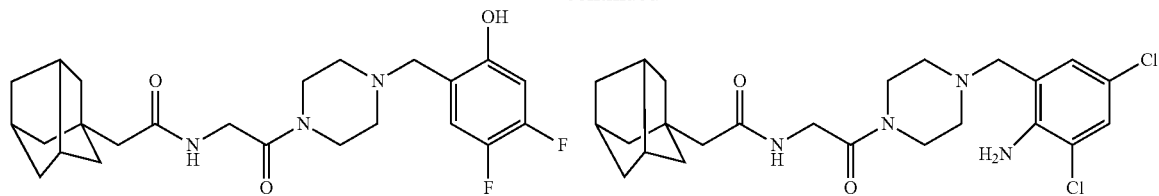
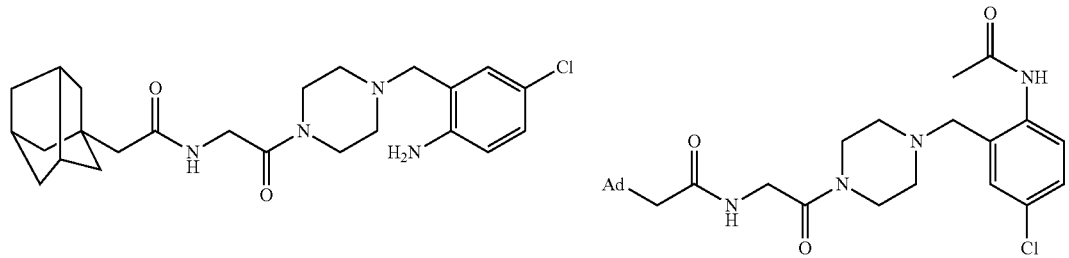
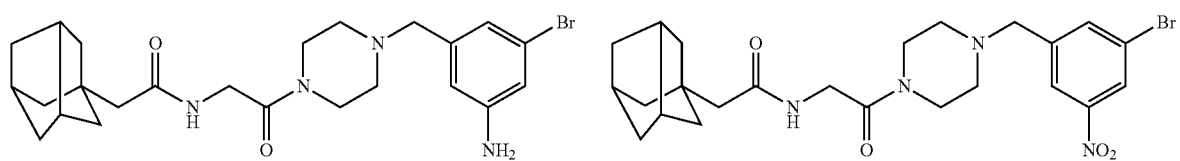
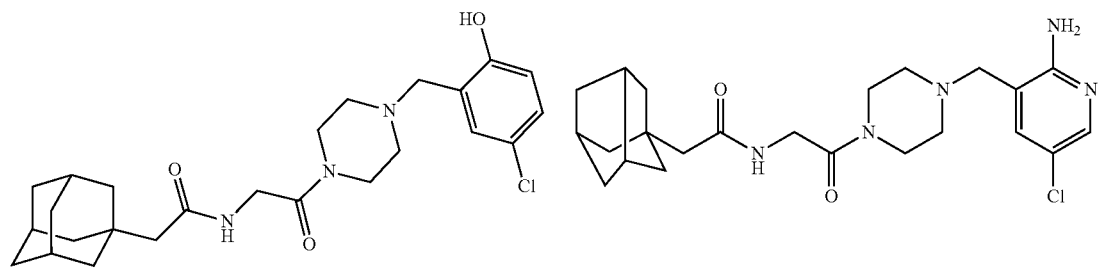
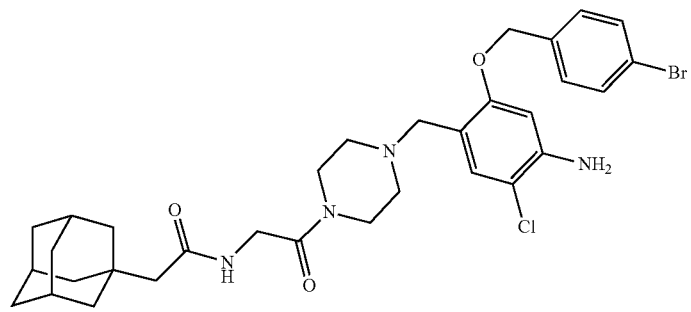
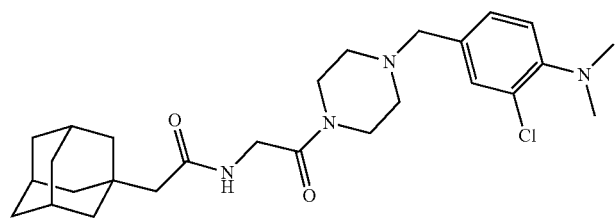
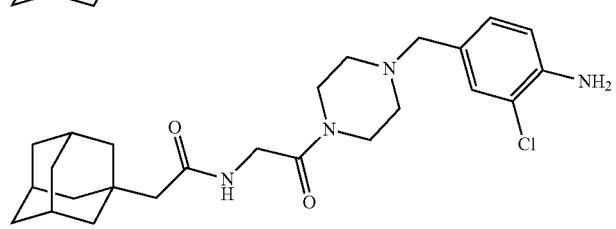

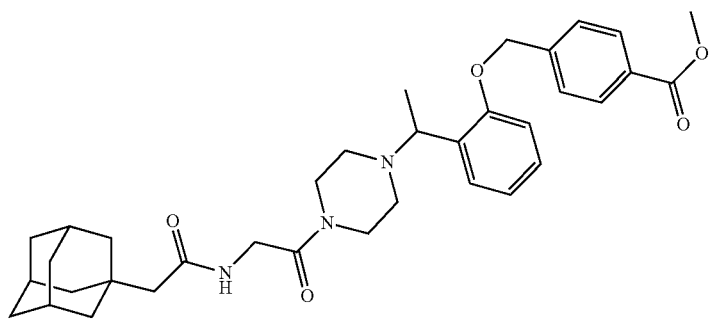
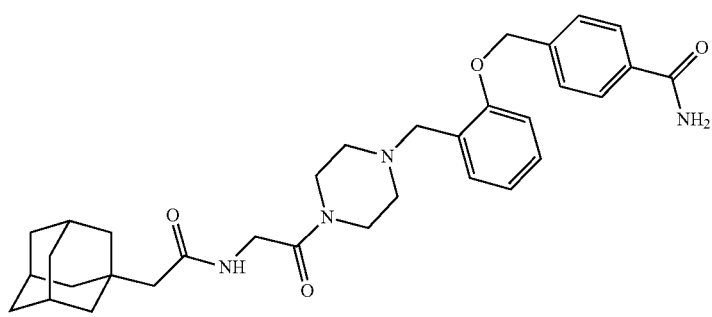
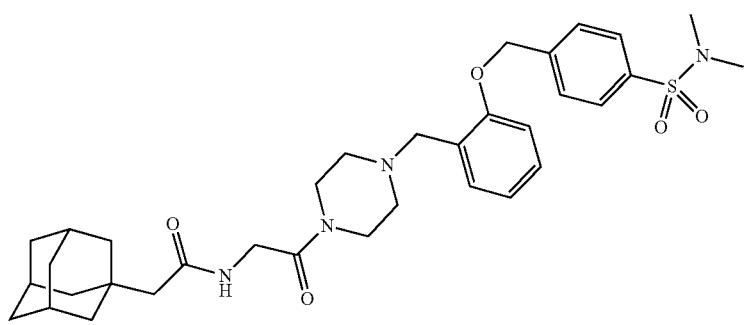
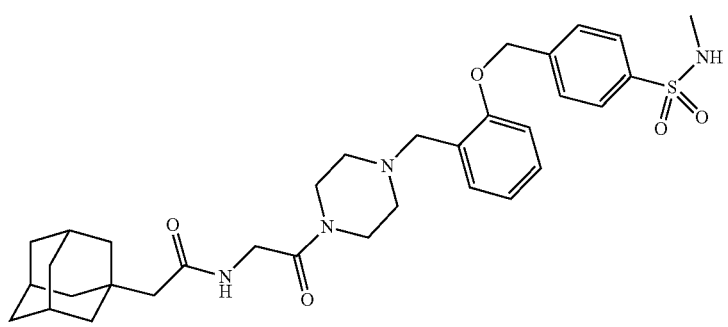
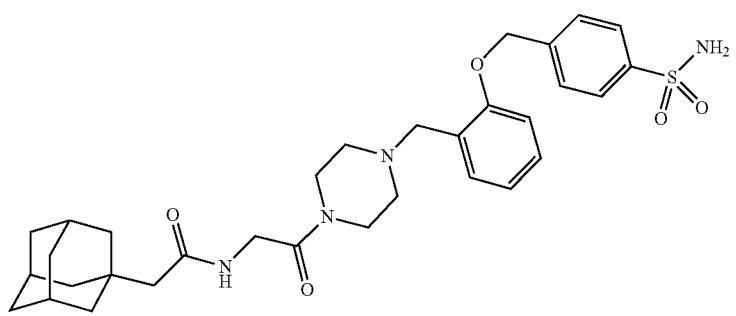

-continued
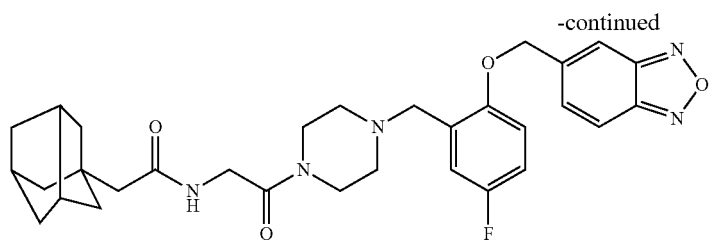
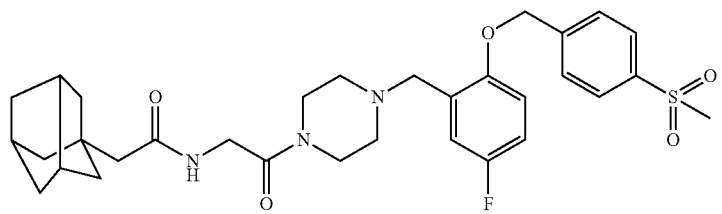
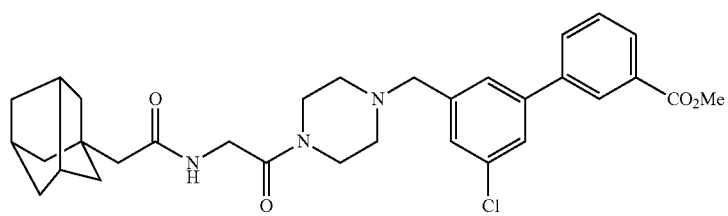
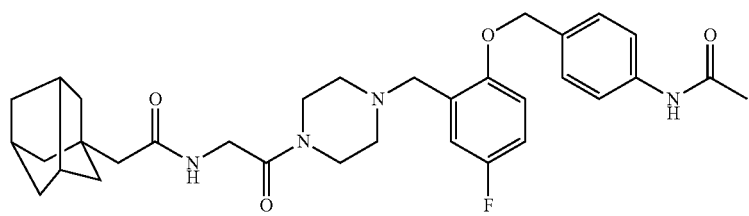
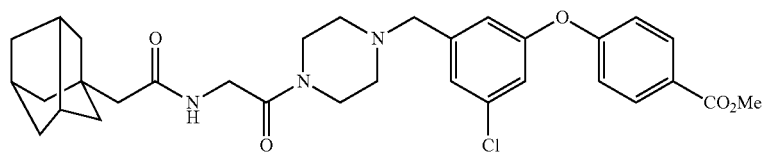
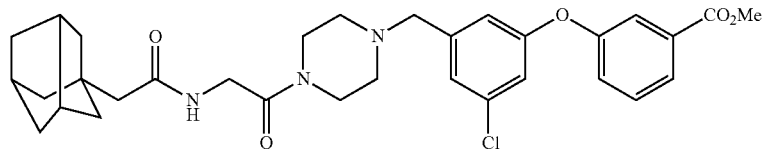
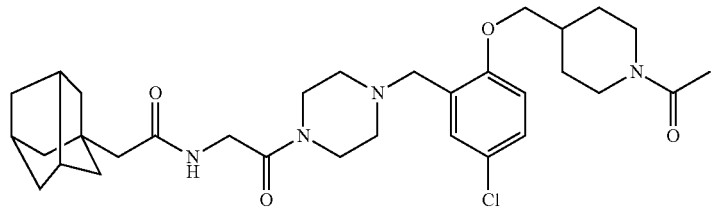
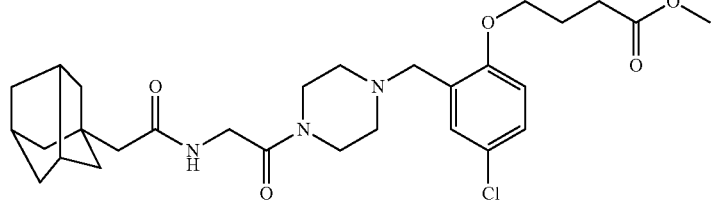

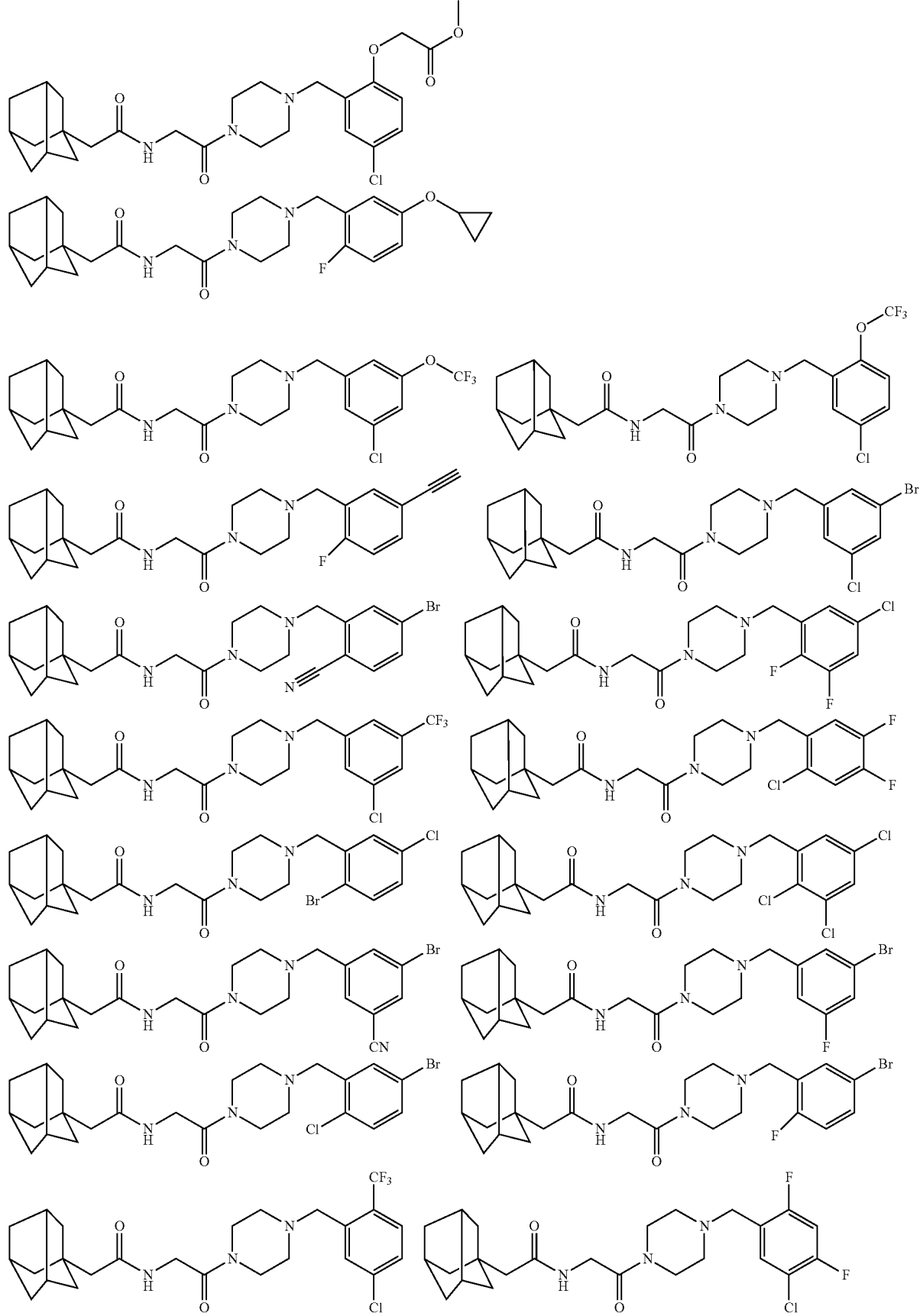
-continued

-continued
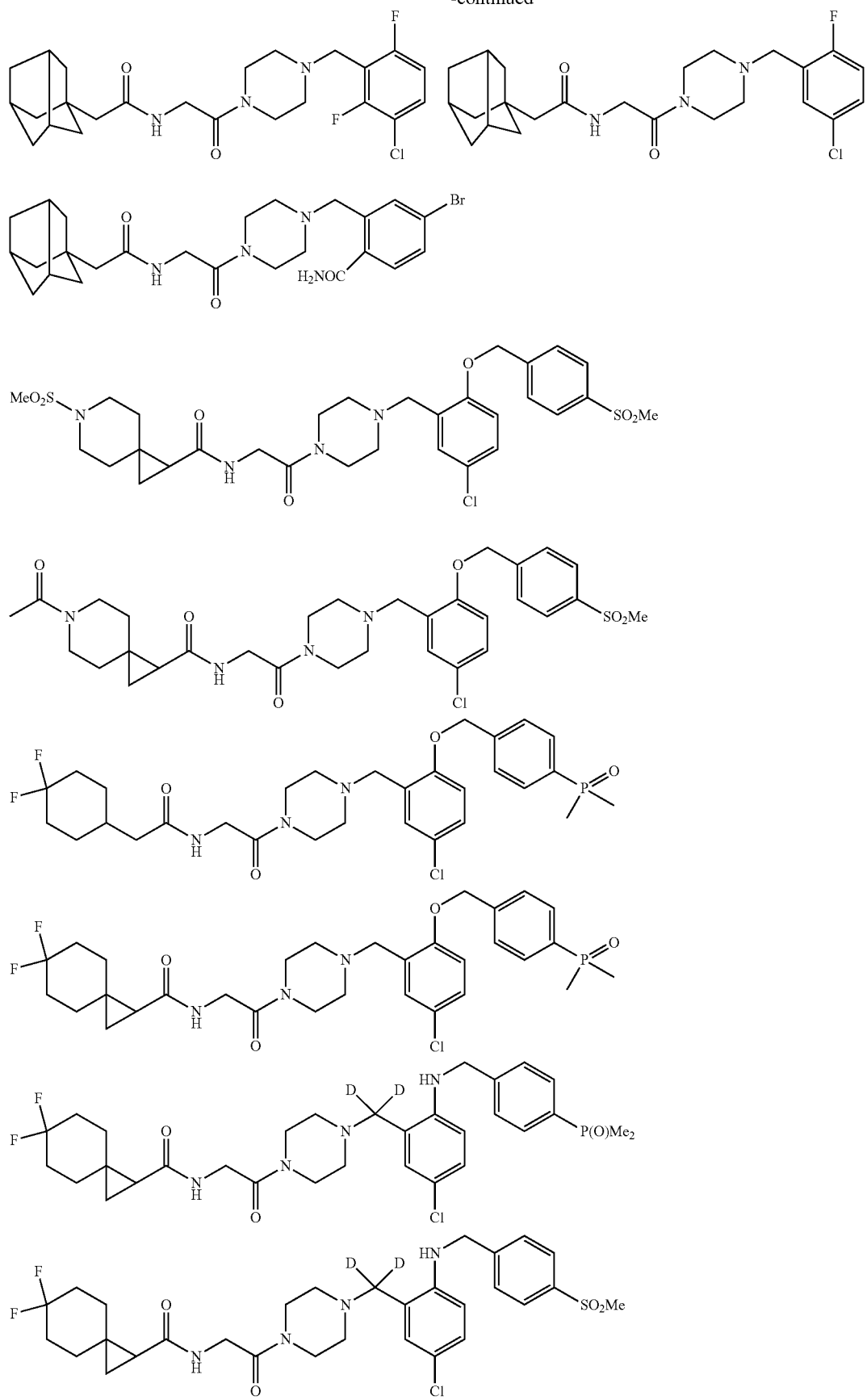

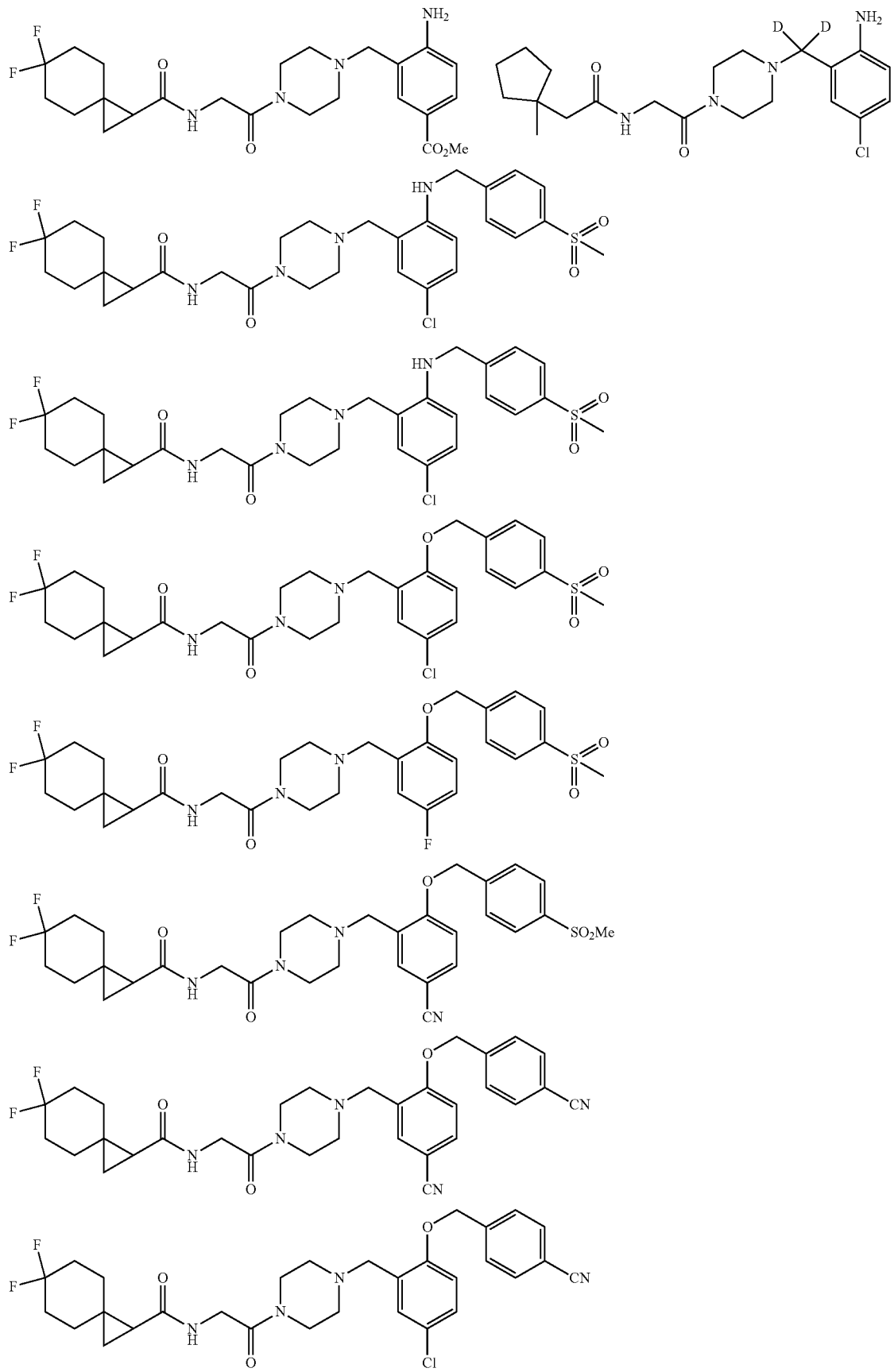

-continued
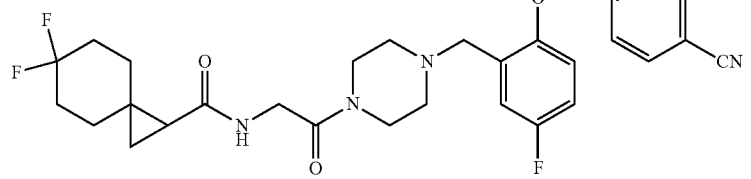
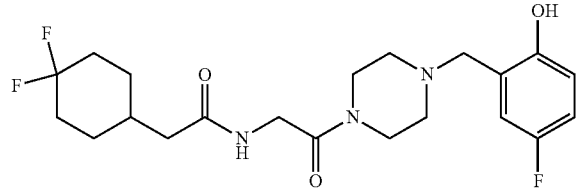
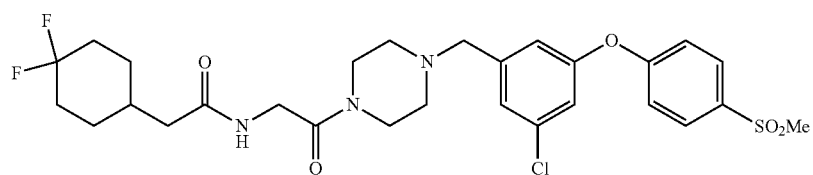
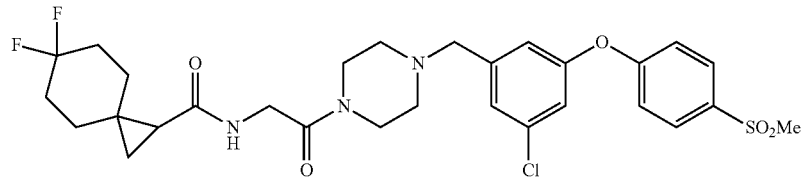
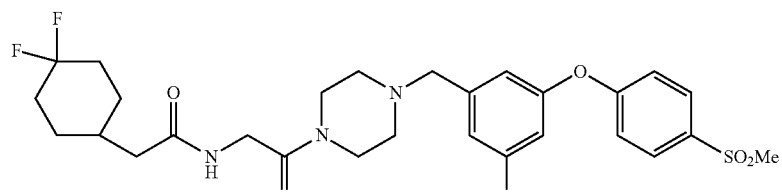
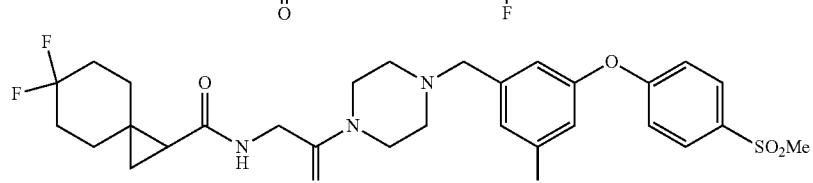
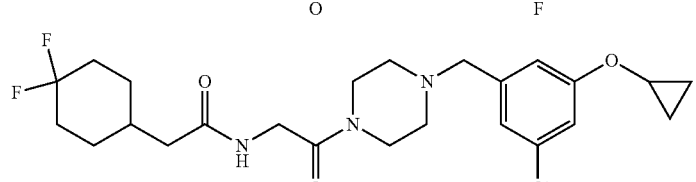
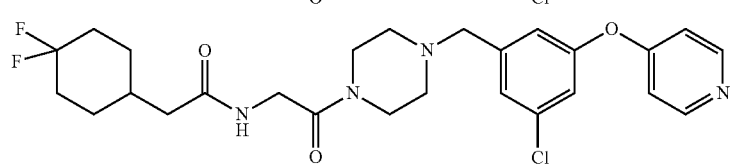
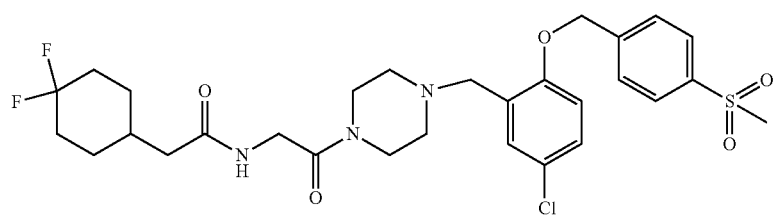

-continued
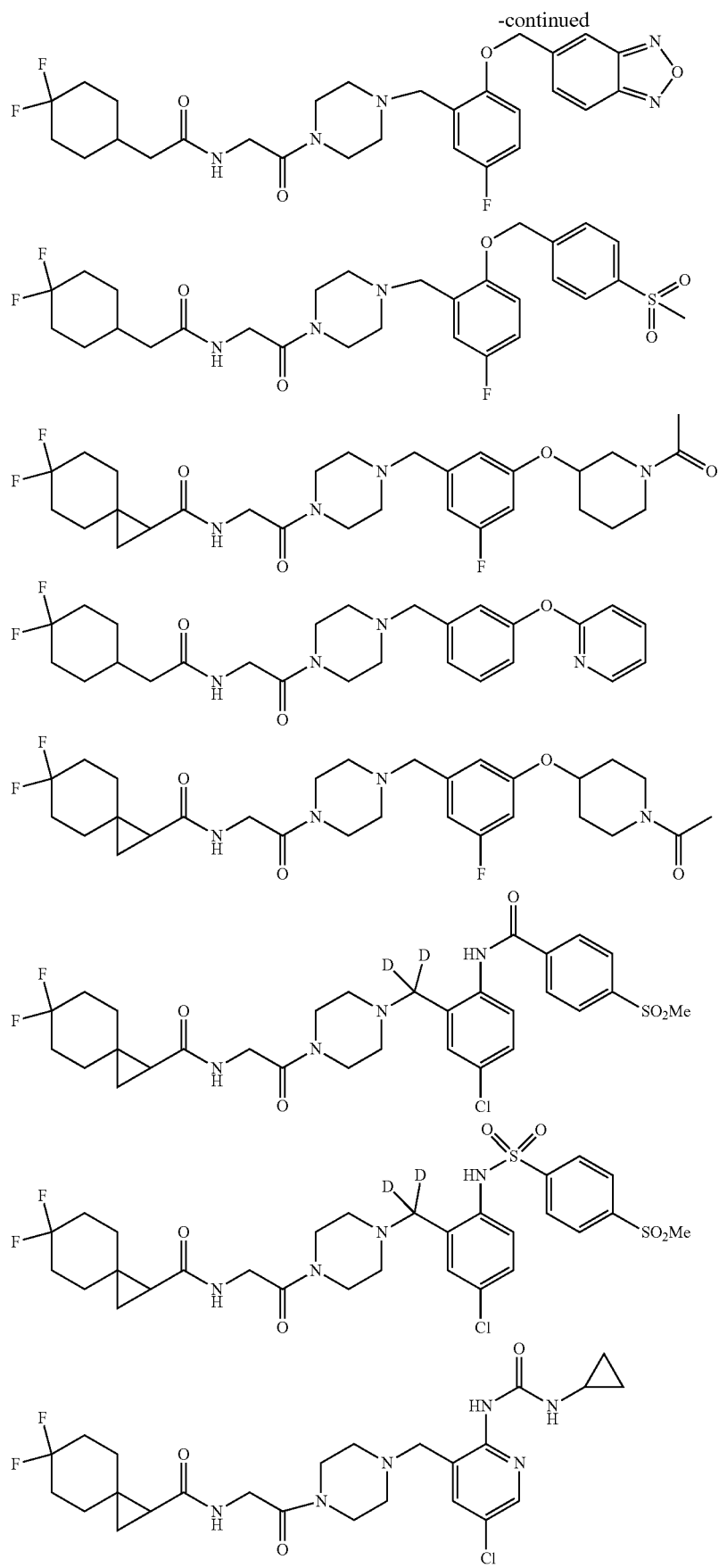

-continued
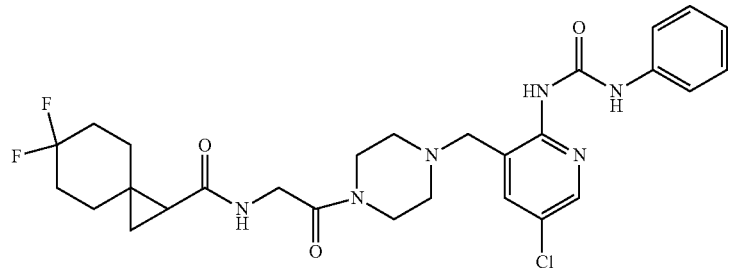
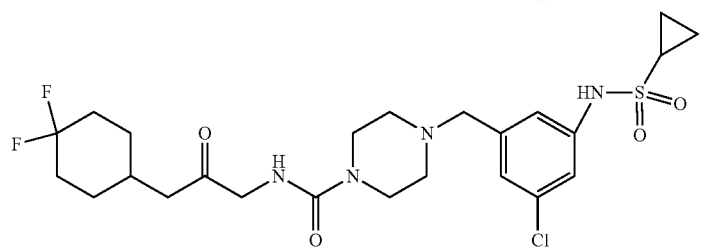
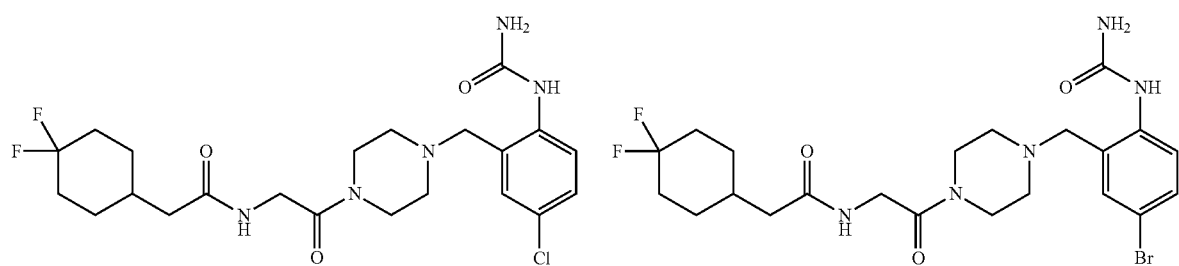
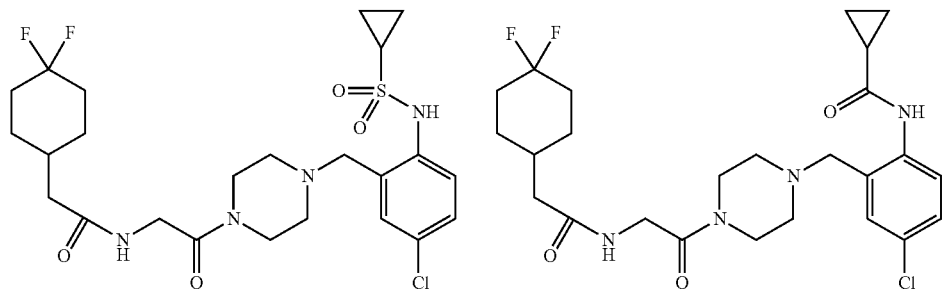
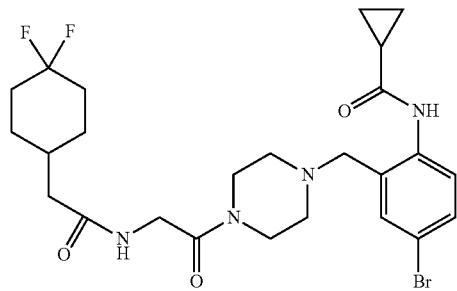
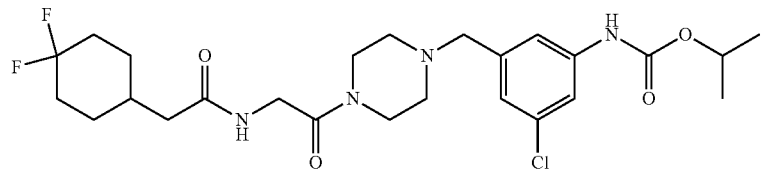
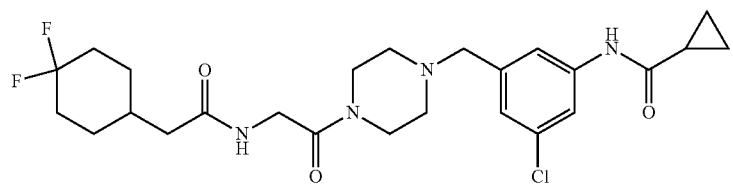

-continued
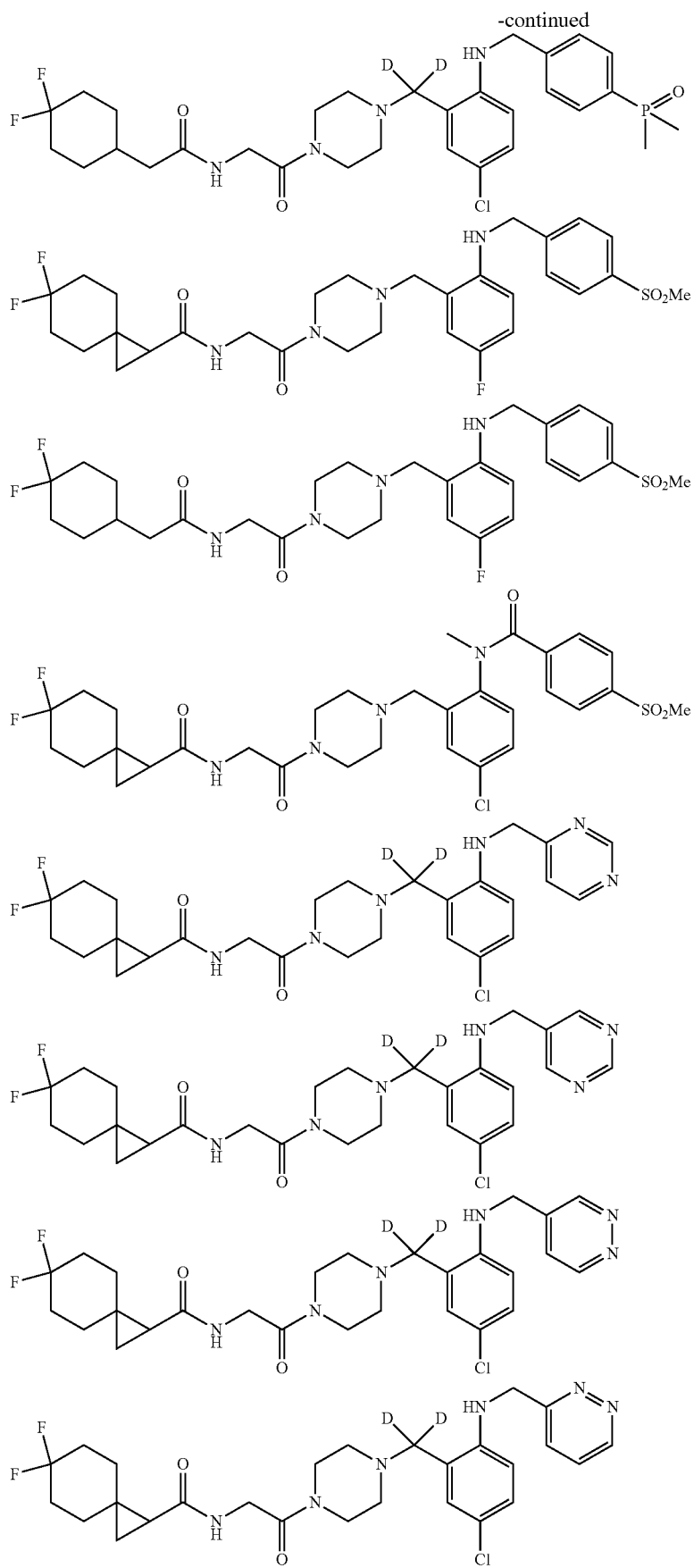

-continued
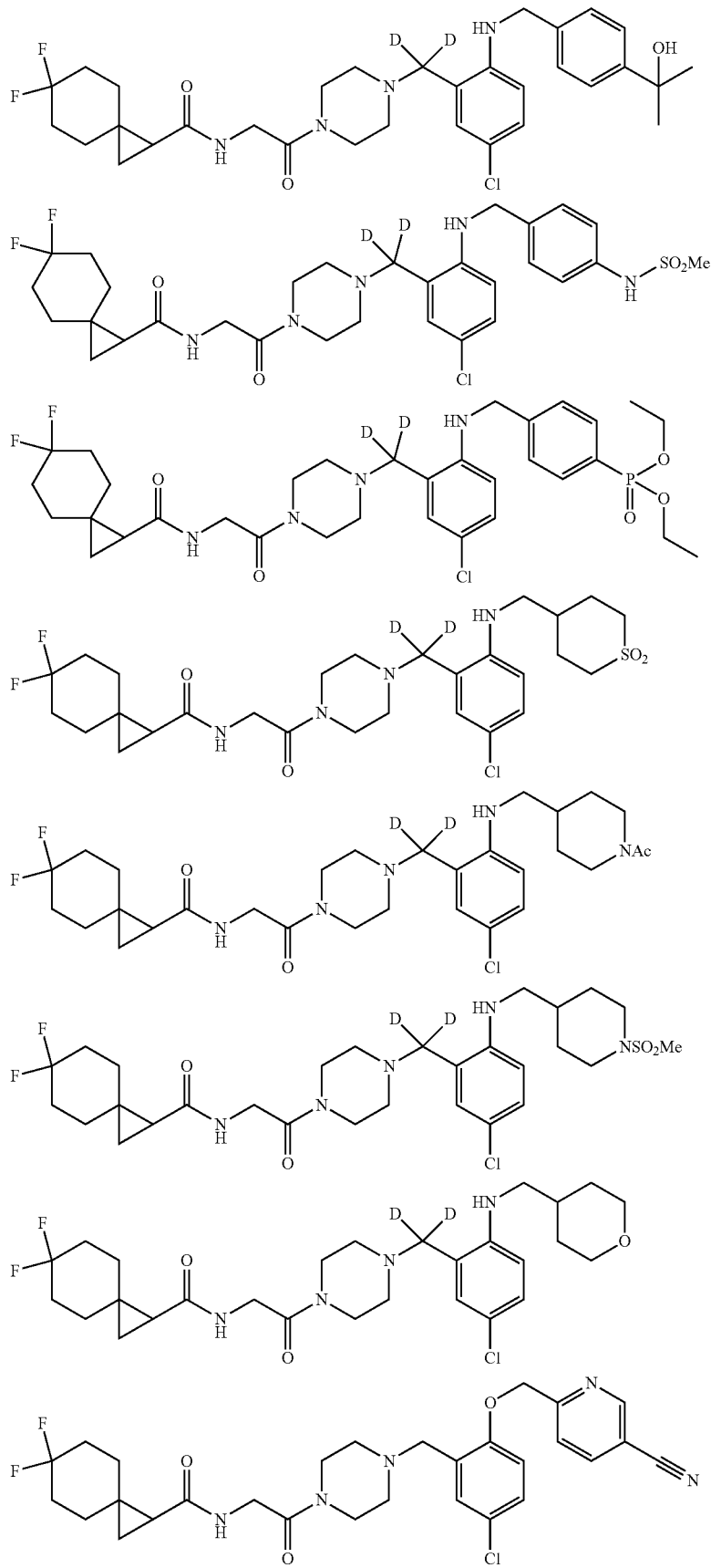

-continued
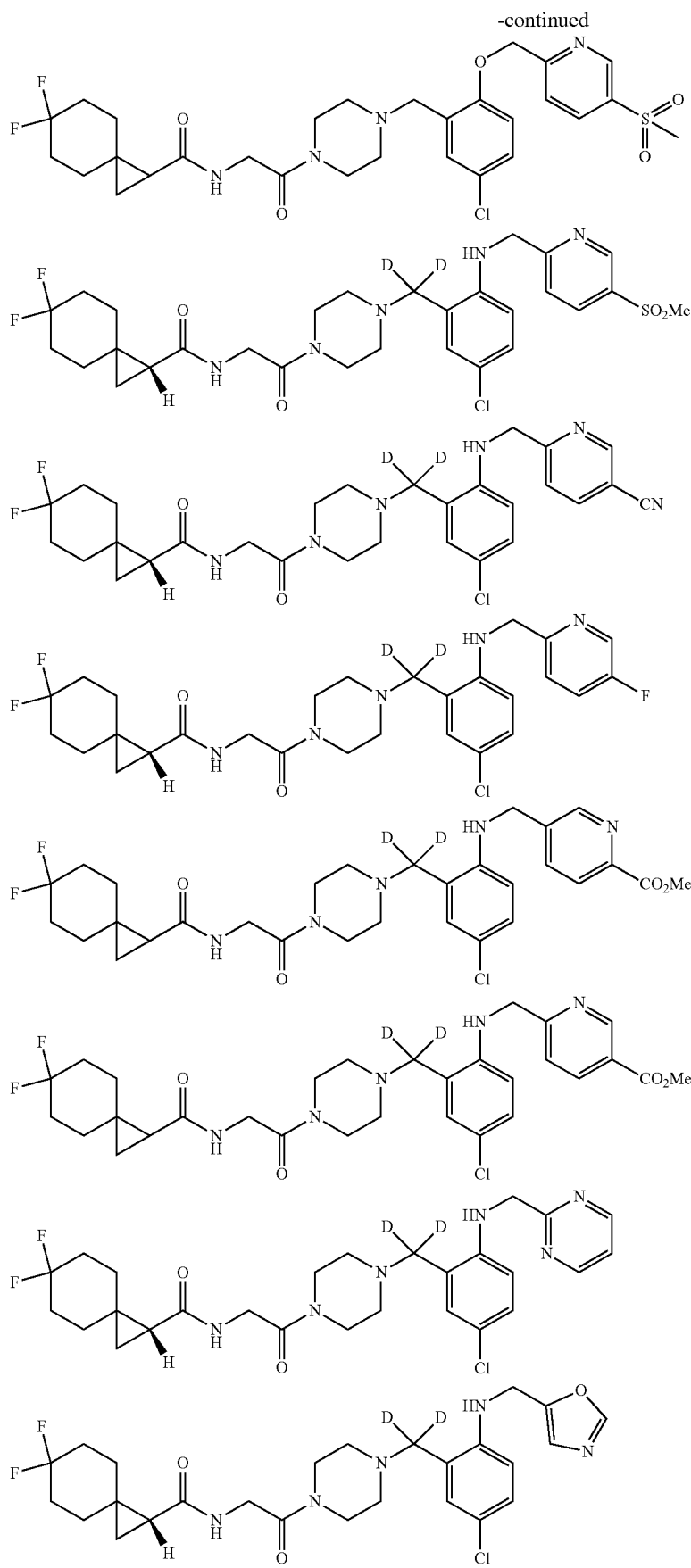

-continued
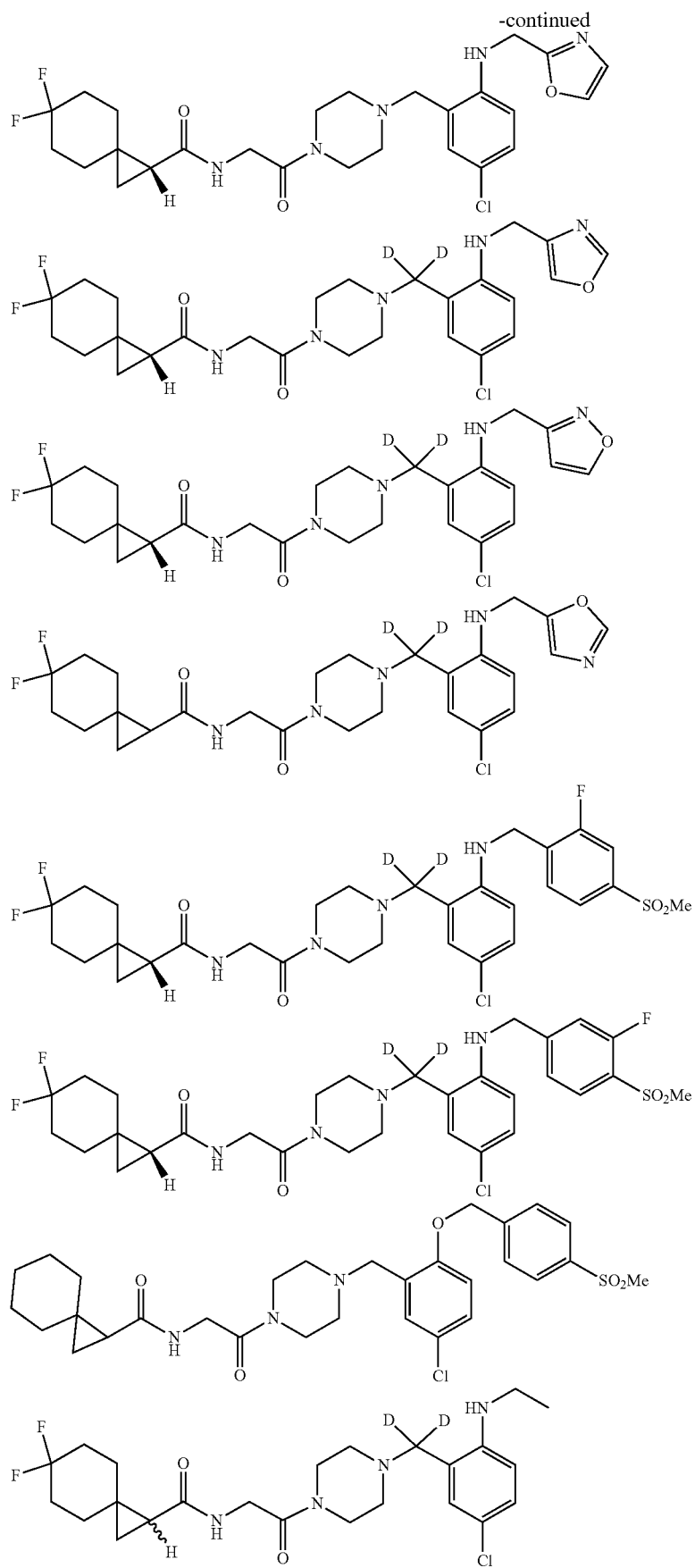

-continued
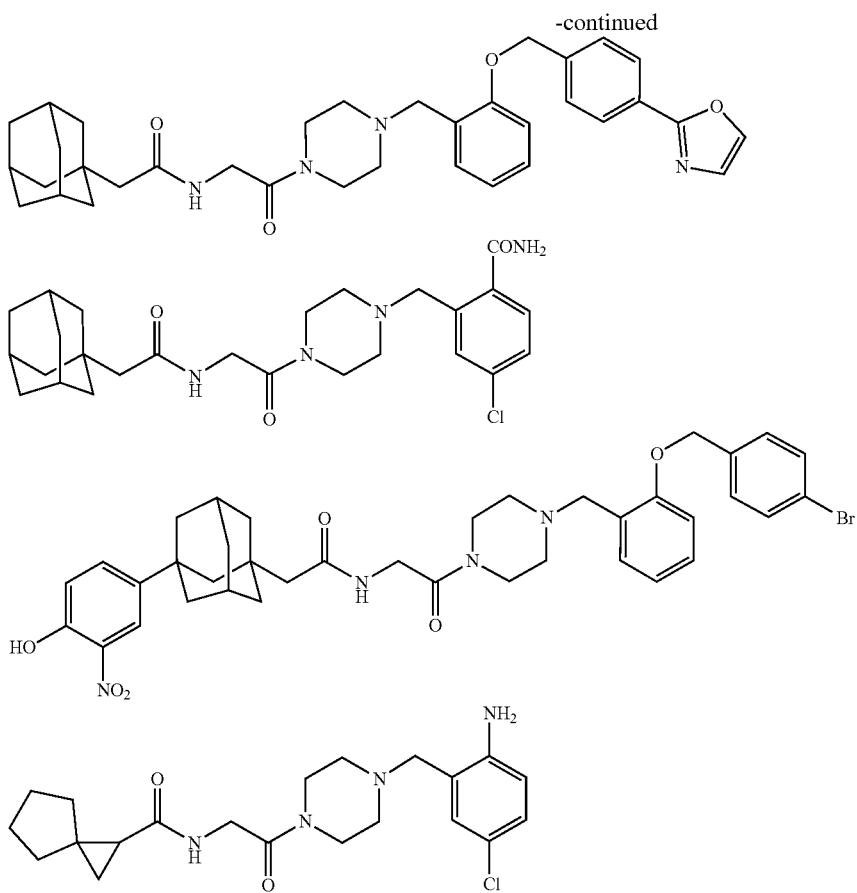
20. The compound of claim 1, wherein the compound has the structure:
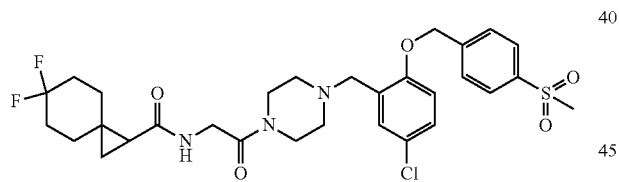
or a pharmaceutically acceptable salt thereof.
* * * * *